US012441037B2

(12) United States Patent
Pearsall et al.

(10) Patent No.: US 12,441,037 B2
(45) Date of Patent: Oct. 14, 2025

(54) DELIVERY DEVICE APPARATUSES, SYSTEMS, AND METHODS

(71) Applicant: DEKA Products Limited Partnership, Manchester, NH (US)

(72) Inventors: Edward J. Pearsall, Manchester, NH (US); Eitan C. Zeira, Hollis, NH (US); Hans E. Johnson, Salem, NH (US); Lee A. Batchelder, Auburn, NH (US); Daniel F. Cote, Jr., New Boston, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 19/229,092

(22) Filed: Jun. 5, 2025

(65) Prior Publication Data

US 2025/0296270 A1 Sep. 25, 2025

Related U.S. Application Data

(63) Continuation of application No. 18/971,815, filed on Dec. 6, 2024.

(Continued)

(51) Int. Cl.
*B29C 45/14* (2006.01)
*B29C 45/26* (2006.01)
(Continued)

(52) U.S. Cl.
CPC .... *B29C 45/14819* (2013.01); *B29C 45/2673* (2013.01); *B29C 45/2703* (2013.01);
(Continued)

(58) Field of Classification Search
CPC .. A61M 2037/0053; A61M 2037/0046; A61M 2037/0015; B29C 45/14844; B29C 45/14418; B29C 45/14336
See application file for complete search history.

(56) References Cited

U.S. PATENT DOCUMENTS

2011/0172609 A1 7/2011 Moga et al.
2020/0054869 A1 2/2020 Liu et al.
(Continued)

FOREIGN PATENT DOCUMENTS

CN 101856538 B 10/2010
FR 3130167 A1 6/2023

OTHER PUBLICATIONS

International Search Report and Written Opinion mailed Apr. 24, 2025 received in International patent application PCT/US2024/058889 from the European Patent Office as International Searching Authority, European Patent Office, P. B. 5818 Patentlaan 2 NL-2280 HV Rijswijk (pp. 1-18).

(Continued)

*Primary Examiner* — Thu Khanh T. Nguyen
(74) *Attorney, Agent, or Firm* — Toohey Law Group LLC; Kevin D. Mandro

(57) ABSTRACT

An example medical agent filling system may comprise a container having an exterior housing formed by a rigid wall and a removable lid. The system may further comprise a fluid introduction port. The system may further comprise a fluid bus extending from the fluid introduction port to a plurality of dispensing sharps. The system may further comprise a plurality of reservoir assemblies each having a main interior volume sealed by a septum. Each of the septa may be in a punctured state with a respective dispensing sharp of the plurality of dispensing sharps extending therethrough. The fluid bus and main interior volumes of the reservoir assemblies may form an isolated fill environment.

16 Claims, 102 Drawing Sheets

Related U.S. Application Data

(60) Provisional application No. 63/727,877, filed on Dec. 4, 2024, provisional application No. 63/686,316, filed on Aug. 23, 2024, provisional application No. 63/686,331, filed on Aug. 23, 2024, provisional application No. 63/686,325, filed on Aug. 23, 2024, provisional application No. 63/551,596, filed on Feb. 9, 2024, provisional application No. 63/551,600, filed on Feb. 9, 2024, provisional application No. 63/551,628, filed on Feb. 9, 2024.

(51) Int. Cl.

| | |
|---|---|
| ***B29C 45/27*** | (2006.01) |
| ***B29C 45/40*** | (2006.01) |
| *A61M 37/00* | (2006.01) |
| *B29C 45/66* | (2006.01) |
| *B29L 31/00* | (2006.01) |

(52) U.S. Cl.
CPC . *B29C 45/4005* (2013.01); *A61M 2037/0053* (2013.01); *B29C 2045/14122* (2013.01); *B29C 2045/664* (2013.01); *B29L 2031/7544* (2013.01)

(56) References Cited

U.S. PATENT DOCUMENTS

| | | | | |
|---|---|---|---|---|
| 2022/0273924 | A1 | 9/2022 | Kamen et al. | |
| 2022/0273925 | A1* | 9/2022 | Zeira | A61M 5/155 |
| 2023/0264006 | A1 | 8/2023 | Kamen et al. | |

OTHER PUBLICATIONS

U.S. Appl. No. 18/971,815, filed Dec. 6, 2024.
U.S. Appl. No. 18/971,881, filed Dec. 6, 2024.

* cited by examiner

DELIVERY DEVICE APPARATUSES, SYSTEMS, AND METHODS

CROSS-REFERENCE TO RELATED APPLICATIONS

The present application is a continuation of U.S. patent application Ser. No. 18/971,815, entitled Delivery Devices Apparatuses, Systems, and Methods, Filed Dec. 6, 2024, and claims the benefit of U.S. Provisional Application Ser. No. 63/551,596, entitled Delivery Device Apparatuses, Systems, and Methods, filed Feb. 9, 2024, and claims the benefit of U.S. Provisional Application Ser. No. 63/551,628, entitled Delivery Device Apparatuses, Systems, and Methods, filed Feb. 9, 2024, and claims the benefit of U.S. Provisional Application Ser. No. 63/551,600, entitled Medical Agent Reconstituting Devices and Related Methods, filed Feb. 9, 2024, and claims the benefit of U.S. Provisional Application Ser. No. 63/686,325, entitled Delivery Device Apparatuses, Systems, and Methods, filed Aug. 23, 2024, and claims the benefit of U.S. Provisional Application Ser. No. 63/686,316, entitled Delivery Device Apparatuses, Systems, and Methods, filed Aug. 23, 2024, and claims the benefit of U.S. Provisional Application Ser. No. 63/686,331, entitled Delivery Device Apparatuses, Systems, and Methods, filed Aug. 23, 2024, and also claims the benefit of U.S. Provisional Application Ser. No. 63/727,877, entitled Components and Methods for Use in Production of Fluid Delivery Devices, filed Dec. 4, 2024.

STATEMENT REGARDING FEDERALLY SPONSORED RESEARCH OR DEVELOPMENT

This invention was made with Government support under Agreement W911NF-17-3-0003-CLIN 0008, awarded by ACC-APG-RTP. The Government has certain rights in the invention.

This invention was made with Government support under Agreement W911NF-17-3-0003-CLIN 0010, awarded by ACC-APG-RTP. The Government has certain rights in the invention.

BACKGROUND

Field of Disclosure

This disclosure relates to medical agent delivery. More specifically, this disclosure relates to delivery devices for therapeutic and other medical agents and the provisioning thereof.

Description of Related Art

Novel pathogens present a variety of public health challenges which are not simple to quickly overcome. From the medical perspective, existing preventive medicine infrastructure has not been and is not well suited to novel pathogens such as SARS, MERS, Zika, and COVID-19. Other pathogens for which herd immunity does not exist (e.g. Ebola), or highly dangerous pathogens which mutate quickly may present similar challenges. Vaccines typically take years to create and once a vaccine does exist, the prospect of rapidly generating billions of doses would almost certainly exceed current vaccine production capabilities. Without vaccination, other preventative measures such as, testing, contact tracing, and personal protective equipment (PPE) are of elevated importance. Again, however, these preventative measures can only provide as much benefit as relevant supply chains allow. Shortages of PPE and testing kits have plagued medical systems in the United States and elsewhere across the globe as they struggled to address the COVID-19 pandemic. In turn, this hampered the potential to perform effective contact tracing which was already a vast undertaking due to the scale of the COVID-19 pandemic. Additionally, novel pathogens may refocus medical systems away from their typical functions. Secondary impacts often result when the medical community's attention is demanded by a widespread pandemic. This can take the form of delayed surgeries, elective procedures, routine doctor's office visits, etc., but secondary impacts can also be much worse. As has been pointed out by the Chief of Immunizations at UNICEF, for example, during efforts to control an Ebola outbreak in the Democratic Republic of the Congo in 2019 the number of deaths due to measles was double the death toll from Ebola.

Novel pathogens also present challenges that are more psychological in nature. Put simply, such pathogens scare people. Without readily available PPE and testing, people may elect to avoid visiting medical facilities or clinics for fear of exposure to disease. Even with readily available PPE, certain individuals, such as populations in high risk demographics for a particular pathogen, may still have misgivings about visiting such facilities. Additionally, as has been the case in the United States, some may fiercely object to usage of PPE for various reasons. This presents a further public health challenge to systems attempting to deal with pandemics. Solutions to novel pathogens should seek to address and work around these challenges in order to be effective.

SUMMARY

In accordance with an embodiment of the present disclosure an example medical agent filling system may comprise a container having an exterior housing formed by a rigid wall and a removable lid. The system may further comprise a fluid introduction port. The system may further comprise a fluid bus extending from the fluid introduction port to a plurality of dispensing sharps. The system may further comprise a plurality of reservoir assemblies each having a main interior volume sealed by a septum. Each of the septa may be in a punctured state with a respective dispensing sharp of the plurality of dispensing sharps extending therethrough. The fluid bus and main interior volumes of the reservoir assemblies may form an isolated fill environment.

In some embodiments, the container may further include a cover tray intermediate the lid and the plurality of reservoir assemblies. The cover tray may include a depression in which a filling implement is disposed. In some embodiments, the filling implement may include a sharp and the fluid introduction port may include a fluid introduction septum. In some embodiments, the filling implement may include a fluid coupling and the fluid introduction port includes a cooperating fluid coupling. In some embodiments, the container may further comprise a locating tray intermediate the fluid bus and at least a portion of each of the plurality of reservoir assemblies. In some embodiments, the locating tray may include a plurality of locating receptacles having spiking apertures. Each spiking aperture may be in line with a respective dispensing sharp of the plurality of dispensing sharps. Each of the septa may be at least partially disposed on the fluid bus containing side of the locating tray. In some embodiments, each of the reservoir assemblies may be disposed within in a respective package. In some embodiments, each of the reservoir assemblies may be included in a respective delivery device. In some embodiments, each of the delivery devices may be included within a respective package. In some embodiments, each of the delivery devices may comprise a central region from which a number of petal members extend. The central region may include a depressible section which, upon application of pressure, flips from a protruding state to a depressed state. Each delivery device may further comprise a bias member disposed intermediate the depressible section and a flexible wall of the main interior volume of a respective reservoir assembly. In some embodiments, each reservoir assembly may include a rigid portion having a stage to which an array of microneedles are coupled. Each reservoir assembly may also include a flexible portion defining a displaceable wall of the main interior volume of that reservoir assembly. The displaceable wall may be preformed such that the main interior volume is in a collapsed state. In some embodiments, the preformed displaceable wall may include at least one undulation for facilitating displacement of the displaceable wall without stretching of the displaceable wall as the main interior volume is transitioned from the collapsed state to a filled state. In some embodiments, the fluid introduction port may be included in the rigid wall of the container. In some embodiments, the fluid introduction port may be disposed entirely within the interior volume of the container. In some embodiments, the fluid bus may include at least one hydrophobic filter vent disposed at a terminal end of the fluid bus opposite the fluid introduction port. In some embodiments, each reservoir assembly may include a hydrophobic filter vent in fluid communication with the main interior volume of the respective reservoir assembly.

In accordance with an embodiment of the present disclosure an example medical agent filling system may comprise a container having an exterior housing formed by a rigid wall and a removable lid. The system may further comprise a fluid introduction septum surrounded by a winged port. The system may further comprise a guide extending at least partially around the winged port. The system may further comprise a plurality of reservoir assemblies each having a main interior volume sealed by a septum. The system may further comprise an isolated fill environment formed from the main interior volume of each of the reservoir assemblies and a fluid bus extending from the winged port to a plurality of dispensing sharps each piercing the septum of a respective reservoir assembly.

In some embodiments, the container may further include a cover tray intermediate the lid and the plurality of reservoir assemblies. The cover tray may include a depression in which a filling aid is disposed. In some embodiments, the filling aid may comprise a vented medicament container dock in fluid communication with a filling implement receptacle. The fill aid may also comprise an outlet sharp in fluid communication with the filling implement receptacle. In some embodiments, the filling aid may include a first check valve inhibiting flow toward the medicament container dock from the filling implement receptacle and a check valve inhibiting flow toward the filling implement from the outlet sharp. In some embodiments, the filling aid may include a recess from which two slots extend. The outlet sharp may be at least partially disposed with the recess. The recess and two slots may define a negative version of at least part of the winged port. In some embodiments, the system may further comprise a locating tray intermediate the fluid bus and at least a portion of each of the plurality of reservoir assemblies. The locating tray may define a plurality of spiking apertures. Each spiking aperture may be in line with a respective dispensing sharp of the plurality of dispensing sharps. Each of the septa may be at least partially disposed on the fluid bus containing side of the locating tray. In some embodiments, each of the reservoir assemblies may be disposed within in a respective package. In some embodiments, each of the reservoir assemblies may be included in a respective delivery device. In some embodiments, each of the delivery devices may be included within a respective package. In some embodiments, each of the delivery devices may comprise a central region from which a number of petal members extend. The central region may include a depressible section which, upon application of pressure, flips from a protruding state to a depressed state. Each delivery device further comprising a bias member disposed intermediate the depressible section and a flexible wall of the main interior volume of a respective reservoir assembly. In some embodiments, each reservoir assembly may include a rigid portion coupled to a flexible portion defining a wall preformed with a set of undulations. The main interior volume may be in a substantially collapsed state and defined partially by the rigid portion and partially by the wall. In some embodiments, each reservoir assembly may include a rigid portion having an array of microneedles coupled thereto. In some embodiments, the fluid bus may include at least one hydrophobic filter vent disposed at a terminal end of the fluid bus opposite the fluid introduction port. In some embodiments, each of the plurality of reservoir assemblies may include a vent for the main interior volume including a hydrophobic filter membrane.

In accordance with another embodiment of the present disclosure, an exemplary medical agent filling system may comprise a container having an exterior housing formed by a rigid wall and a removable lid. The system may further comprise a fluid introduction port. The system may further comprise a plurality of reservoir assemblies each having a main interior volume sealed by a septum. The system may further comprise an isolated fill environment comprising a plurality of access members each in communication with the main interior volume of a reservoir assembly of the plurality of reservoir assemblies via the septum of that reservoir assembly and at least one fluid bus.

In some embodiments, the septum sealing the main interior volume of each reservoir assembly may be a split septum and each of the access members may be a blunt cannula. In some embodiments, each reservoir assembly may include a rigid portion coupled to a flexible portion defining a wall preformed with a set of undulations. The main interior volume may be in a substantially collapsed state and defined partially by the rigid portion and partially by the wall. In some embodiments, each reservoir assembly may include a rigid portion and a flexible portion defining a displaceable wall of the main interior volume. There may be an array of microneedles coupled to each rigid portion. In some embodiments, each of the plurality of reservoir assemblies may include a vent for the main interior volume including a hydrophobic filter membrane. In some embodiments, each access member may include multiple lumens. A first lumen of each access member may be in fluid communication with the filling bus of the at least one fluid bus. A second lumen of each access member may be in fluid communication with a venting bus of the at least one fluid bus, the venting bus having a venting filter at a terminal region thereof. In some embodiments, the access members comprise dispensing access members and venting access members, there being one dispensing access member and one venting access member in fluid communication with the main interior volume of each of the plurality of reservoir assemblies. In some embodiments, each dispensing sharp may be in fluid communication with a filling bus of the at least one fluid bus which extends from the fluid introduction port and each venting sharp may be in fluid communication with a venting bus of the at least one fluid bus. In some embodiments, each of the plurality of reservoir assemblies may be included in a delivery device. In some embodiments, each of the delivery devices may comprise a central region from which a number of petal members extend. The central region may include a depressible section which, upon application of pressure, flips from a protruding state to a depressed state. Each delivery device may further comprise a bias member disposed intermediate the depressible section and a flexible wall of the main interior volume of a respective reservoir assembly. In some embodiments, each of the delivery devices may be disposed within a package for protecting the delivery device after removal from the container.

In accordance with another embodiment of the present disclosure an exemplary method of filling a number of reservoir assemblies may comprise opening a container housing the reservoir assemblies. The method may further comprise accessing an isolated fill environment within the container with a filling implement. The method may further comprise transferring agent from the filling implement into a main interior volume of each of the reservoir assemblies via dispensing members on a fluid bus within the container which each extend through a septum of a respective reservoir assembly. The method may further comprise venting gas in the isolated fill environment via at least one hydrophobic filter.

In some embodiments, opening the container may comprise removing a peelable lid from the container and extracting a cover tray intermediate the peelable lid and the reservoir assemblies. In some embodiments, each of the reservoir assemblies may be included within a delivery device comprising a central region from which a number of petal members extend. The central region may include a depressible section which, upon application of pressure, flips from a protruding state to a depressed state. Each delivery device may further comprise a bias member disposed intermediate the depressible section and a flexible wall of the main interior volume of a respective reservoir assembly. In some embodiments, each of the reservoir assemblies may be included within a delivery device and each delivery device may be disposed within a package. In some embodiments, accessing the isolated fill environment may comprise piercing an agent introduction septum via a side wall of the container with the filling implement. In some embodiments, accessing the isolated fill environment may comprise piercing through an agent introduction septum disposed on the interior of the container with the filling implement after opening the container. In some embodiments, the method may further comprise docking a medicament container and a filling implement onto a filling aid and withdrawing a volume of agent from the medicament container into the filling implement. In some embodiments, accessing the isolated fill environment may comprise displacing the filling aid into a guide and receiving a fluid introduction port having a fluid introduction septum with a recess surrounding an outlet spike of the filling aid. In some embodiments, transferring agent into the main interior volume of each of the reservoir assemblies may comprise displacing a flexible wall of the main interior volume of each of the reservoir assemblies from a collapsed position to a filled position. In some embodiments, transferring agent into the main interior volume of each of the reservoir assemblies may comprise maintaining a volume of gas within the main interior volume of each of the reservoir assemblies. The volume of gas may fill less than 25% of the main interior volume when the main interior volume is unpressurized. In some embodiments, each of the reservoir assemblies may include a hydrophobic filter of the at least one hydrophobic filter and venting gas in the isolated fill environment may comprise driving the gas from the main interior volume of each of the reservoir assemblies through the hydrophobic filter of each of the reservoir assemblies. In some embodiments, each of the at least one hydrophobic filter may be disposed at a terminal region of the fluid bus and venting gas from isolated fill environment may comprise displacing gas in the isolated fill environment out of the at least one hydrophobic filter as agent is transferred through the fluid bus. In some embodiments, each of the at least one hydrophobic filter may be disposed on a venting bus within the container. The venting bus may include a plurality of venting sharps each in communication with the main interior volume of a respective one of the reservoir assemblies via the septum of that reservoir assembly. Venting of gas in the isolated fill environment may comprise driving gas in the filling bus and main interior volume of each reservoir assembly out of the at least one hydrophobic filter via the venting sharps and venting bus.

In accordance with another example embodiment of the present disclosure an example medical agent filling system may comprise a filling portion. The filling portion may comprise a container. The filling portion may further comprise a fluid introduction port coupled to the container. The filling portion may further comprise a plurality of reservoir assemblies each having a main interior volume sealed by a septum. The filling portion may further comprise an isolated fill environment formed from the main interior volume of each of the reservoir assemblies and a fluid bus extending from the fluid introduction port to a plurality of dispensing sharps each piercing the septum of a respective reservoir assembly. The system may further comprise a pumping portion. The pumping portion may comprise a fluid handling set including an inlet spike and an outlet spike. The pumping portion may further comprise a pump. The pumping portion may further comprise a pump housing. The pumping portion may further comprise a medicament container holster.

In some embodiments, each of the reservoir assemblies may be included within a delivery device comprising a central region from which a number of petal members extend. The central region may include a depressible section which, upon application of pressure, flips from a protruding state to a depressed state. Each delivery device may further comprise a bias member disposed intermediate the depressible section and a flexible wall of the main interior volume of a respective reservoir assembly. In some embodiments, the system may further comprise a locating tray intermediate the fluid bus and at least a portion of each of the plurality of reservoir assemblies. The locating tray may define a plurality of spiking apertures each in line with a respective dispensing sharp of the plurality of dispensing sharps. Each of the septa may be at least partially disposed on the fluid bus containing side of the locating tray. In some embodiments, each reservoir assembly may include a rigid portion coupled to a flexible portion defining a wall preformed with a set of undulations. The main interior volume of each reservoir assembly may be in a substantially collapsed state and defined partially by the rigid portion and partially by the wall. In some embodiments, each reservoir assembly may include a rigid portion having an array of microneedles coupled thereto. In some embodiments, each of the plurality of reservoir assemblies may include a vent for the main interior volume including a hydrophobic filter membrane. In some embodiments, the pump may be selected from a group consisting of a syringe pump, a peristaltic pump, a diaphragm pump, and a cassette based pump. In some embodiments, the fluid handling set may include a pumping cassette intermediate the inlet spike and the outlet spike and the pumping portion further comprises a pneumatic distribution assembly configured to actuate valves and a pump chamber of the pumping cassette when the pumping cassette is installed in a cassette receptacle of the pump housing. In some embodiments, the pump may be a syringe pump and the fluid handling set may include a syringe. There may be first check valve upstream of the syringe and a second check valve downstream of the syringe, the first and second check valve inhibiting flow in a direction from the outlet spike to the inlet spike. In some embodiments, the medicament container hostler includes an inlet spike receptacle for retaining and supporting the inlet spike of the fluid handling set. In some embodiments, the container may include a fiducial disposed in a known position relative the fluid introduction portion. The pumping portion may further comprise a spiking assembly comprising an imager, a sled with a cradle for the outlet spike, and a sled actuation assembly including at least one linear actuator. In some embodiments, the system may further comprise a datum tray disposed in a known position relative the pumping portion. The datum tray may be configured to receive the container. In some embodiments, the system may further comprise a controller configured to command capture of an image of the fiducial with the imager and analyze the image to determine a position of the fluid introduction port relative the cradle. The controller may be configured to determine target port spiking position and orchestrate displacement of the sled via the sled actuation assembly to the target port spiking position. In some embodiments, the pumping portion may be included in a handheld assembly.

In accordance with another embodiment of the present disclosure an example delivery device for delivery of medical agent to a barrier may comprise a main body including a central region defining a receptacle and a peripheral region defined by a number of petal members. The delivery device may further comprise a reservoir assembly including a rigid reservoir portion and flexible reservoir portion together defining a collapsed a main interior volume. The reservoir assembly may further comprise a septum in communication with the main interior volume. The reservoir assembly may further comprise a sharp bearing body including at least one delivery sharp each defined on all sides by sidewalls and each having a footprint inboard of the periphery of the sharp bearing body. The rigid portion may be overmolded onto at least one step in the sidewall of the sharp bearing body. The delivery device may further comprise an adhesive pad coupled to at least the petal members. The delivery device may further comprise at least one bias member positioned within the receptacle between the flexible reservoir portion and a wall of the receptacle.

In some embodiments, the at least one delivery sharp may be a row of microneedles. In some embodiments, the flexible reservoir portion may include a displaceable wall including at least one preformed undulation. In some embodiments, the septum may be disposed within a bay defined in the rigid reservoir portion. In some embodiments, the bay may be recessed into a protruding body extending from the rigid portion. The rigid portion may define a ported backstop in communication with the bay intermediate the main interior volume and the septum. In some embodiments, the bay may be disposed outside of the footprint of the flexible reservoir portion. In some embodiments, the main body may include a port extending therethrough. The rigid reservoir portion may include a protruding body in which the septum is disposed. The protruding body may extend through the port. In some embodiments, one of the petal members may include an aperture in line with the port. The aperture may be surrounded at least partially by raised ribs. In some embodiments, each of the petal members may be separated by a slit. There may be a widened slit continuous with the walls of the port separating two of the petal members. In some embodiments, the septum may include a septum axis oriented in an outwardly extending direction with respect to the rigid reservoir portion. In some embodiments, the rigid reservoir portion may include a rigid reservoir portion axis. The sharp being body may be overmolded into a stage projection of the rigid reservoir portion. The at least one delivery sharp may be tilted about a tilt axis such that the at least one delivery sharp extends in a direction other than parallel to the rigid reservoir portion axis. In some embodiments, the septum may include a septum axis oriented parallel to the tilt axis. In some embodiments, the septum may be disposed within a septum housing coupled to the remainder of the reservoir assembly via a span of tubing. In some embodiments, the delivery device may include a bias member with a reservoir interface surface. The septum may be accommodated within a thickened region of the rigid reservoir portion spaced outside of the footprint of the reservoir interface surface.

In accordance with another example embodiment of the present disclosure an example reservoir assembly for a shallow destination medicament delivery device may comprise a rigid portion having an axial dimension. The reservoir assembly may further comprise a flexible reservoir portion together with the rigid portion defining a collapsed a main interior volume. The reservoir assembly may further comprise a sharp bearing body including at least one microneedle. Each of the at least one microneedle may be defined on all sides by sidewalls and each may have a footprint inboard of the periphery of the sharp bearing body. The rigid portion may be overmolded onto at least one step in the sidewall of the sharp bearing body. The sharp bearing body may be tilted about a tilt axis such that each of the at least one microneedle extends in a direction other than parallel to the axial dimension of the rigid portion. The reservoir assembly may further comprise a septum in communication with main interior volume and disposed within a bay defined in the rigid portion. The septum may have a septum axis extending parallel to the tilt axis.

In some embodiments, the main interior volume may be defined in part by a displaceable wall of the flexible portion which is preformed with a set of undulations. In some embodiments, the rigid portion may include a stage projection projecting from a disk body. The stage projection may be the section of the rigid portion overmolded onto the at least one step in the sidewall of the sharp bearing body. In some embodiments, the sharp bearing body may be tilted about the tilt axis such that each of the at least one microneedle extends 15-25° off the axial dimension of the rigid portion. In some embodiments, the bay may be disposed outside of the footprint of the flexible portion. In some embodiments, the bay may be in fluid communication with a ported backstop. The ported backstop may be disposed intermediate the main interior volume and the septum. In some embodiments, the septum may be retained in the bay via material swaged over an exteriorly accessible face of the septum. In some embodiments, the septum may be disposed within a thickened region of the rigid portion. The flexible portion may be preformed with a thickened region receptacle which dimensioned to accept the thickened region. In some embodiments, the rigid portion may include a set of ribs. Each rib of the set of ribs may surround the main interior volume. The flexible portion may be heat staked at least to the set of ribs of the rigid portion. In some embodiments, the walls of the bay may define a nub which protrudes from a side of the reservoir assembly from which the microneedles project. In some embodiments, the main interior volume may be divided into a first portion and a second portion by a flow restrictor. The second portion may be downstream of the first portion with relative to the septum. In some embodiments, the rigid portion may include a set of recesses configured to interlock with cleats of mold ejector pins.

In accordance with another embodiment of the present disclosure an example reservoir assembly for a shallow destination medicament delivery device may comprise a rigid portion having an axial dimension. The reservoir assembly may further comprise a flexible reservoir portion which, together with the rigid portion, may define a collapsed a main interior volume. The reservoir assembly may further comprise a sharp bearing body including at least one microneedle. Each of the at least one microneedle may be defined on all sides by sidewalls and each may have a footprint inboard of the periphery of the sharp bearing body. The rigid portion may be overmolded onto at least one step in the sidewall of the sharp bearing body. The sharp bearing body may be tilted about a tilt axis such that each of the at least one microneedle extends in a direction other than parallel to the axial dimension of the rigid portion. The reservoir assembly may further comprise a septum in communication with main interior volume and disposed within a bay defined in the rigid portion. The septum may have a septum axis extending parallel to sharp bearing face of the sharp bearing body.

In some embodiments, the main interior volume may be defined in part by a displaceable wall of the flexible portion which is preformed with a set of undulations. In some embodiments, the rigid portion may include a stage projection projecting from a disk body. The stage projection may be the section of the rigid portion overmolded onto the at least one step in the sidewall of the sharp bearing body. In some embodiments, the sharp bearing body may be tilted about the tilt axis such that each of the at least one microneedle extends 15-25° off the axial dimension of the rigid portion. In some embodiments, the bay may be disposed at least partially outside of the footprint of the flexible portion. In some embodiments, the bay may be in fluid communication with a ported backstop. The ported backstop may be disposed intermediate the main interior volume and the septum. In some embodiments, the septum may be retained in the bay via material swaged over an exteriorly accessible face of the septum. In some embodiments, the septum may be disposed within a thickened region of the rigid portion. The flexible portion may be preformed with a thickened region receptacle which is dimensioned to accept the thickened region. In some embodiments, the rigid portion may include a set of ribs. Each rib of the set of ribs may surround the main interior volume. The flexible portion may be heat staked at least to the set of ribs of the rigid portion. In some embodiments, the main interior volume may be divided into a first portion and a second portion by a flow restrictor. The second portion may be downstream of the first portion relative to the septum. In some embodiments, the rigid portion may include a set of recesses configured to interlock with cleats of mold ejector pins.

In accordance with another embodiment of the present disclosure an example method of overmolding a component to a sharp bearing body from which at least one microneedle projects may comprise depositing each of the at least one microneedle in a respective pocket defined in a first shut-off of a mold. Each of the at least one microneedle may be self-centered by the geometry of the respective pockets as the microneedles are deposited. The method may further comprise enclosing the sharp bearing body within first and second blocks of a mold. The method may further comprise clamping the sharp bearing body, with a resting clamping force, between the first shut-off and a second shut-off of the mold with a sharp bearing face of the sharp bearing body disposed normal to the force of gravity. The method may further comprise exerting pressure against the mold with clamping platens in a direction normal to the sharp bearing face. The method may further comprise forming the component with an axial dimension which extends in a direction other than normal to the sharp bearing face while overmolding material to a sidewall around the periphery of the sharp bearing body and a portion of the face of the sharp bearing body opposite the sharp bearing face. The method may further comprise venting gas through vents abreast an interface between the sidewall and overmolded material. The method may further comprise retaining the second block of the mold against a base during orchestration of a portion of an ejection sequence in which the first block and component are ejected from the mold.

In some embodiments, the method may further comprise embedding cleats of ejector pins for the component in the material injected into the cavity. In some embodiments, clamping the sharp bearing body may comprise attracting the first block of the mold to the second block via magnets. In some embodiments, retaining the second block against the base may comprise attracting the second block to the base with magnets disposed in the second block. In some embodiments, the method further may comprise displacing a knockout subassembly including a number of part side ejector pins with a set of hydraulically driven ejector pins. In some embodiments, the method may further comprise returning the knockout subassembly to a home state with at least one bias member. In some embodiments, the method may further comprise automatically degating the component by ejecting a runner plate of the mold. In some embodiments, the method may further comprise holding the component and sharp bearing body against the first block as the first block is disassociated from the first block along an ejection axis. In some embodiments, overmolding material to the side wall may comprise overmolding material over at least one step in the sidewall. In some embodiments, overmolding material to the sidewall may comprise encasing a tier formed in the sidewall in overmolded material. In some embodiments, overmolding material to the sidewall may comprise encasing at least one constant cross-section portion of the sharp bearing body and at least part of a chamfered section of the sidewall of the sharp bearing body in overmolded material. In some embodiments, overmolding material to the portion of the face of the sharp bearing body opposite the sharp bearing face may comprise blocking flow of the overmolded material to lumen associated with each of the at least one microneedle with the second shut-off. In some embodiments, the method may further comprise inhibiting contact of kerf regions associated with each of the at least microneedle with the first shut-off. In some embodiments, inhibiting contact of the kerf regions associated with each of the at least one microneedle with the first shut-off may comprise self-centering each of the at least one microneedle before the kerf regions are advanced into the respective pockets. In some embodiments, depositing each of the at least one microneedle in a respective pocket may comprise guiding each of the at least one microneedle via tapered sidewalls of the respective pocket. In some embodiments, depositing each of the at least one microneedle in a respective pocket may comprise contacting a sloped face of each of the at least one microneedle with a ramped sidewall section of the respective pocket.

In accordance with an embodiment of the present disclosure an example method of overmolding a component to a sharp bearing body from which at least one microneedle projects may comprise enclosing the sharp bearing body within first and second blocks of a mold. The method may further comprise clamping the sharp bearing body, with a resting clamping force, between a first and second shut-off of the mold with each of the at least one microneedle surrounded by a sharp pocket in the second shut-off and a sharp bearing face of the sharp bearing body disposed normal to the force of gravity. The method may further comprise exerting pressure against the mold with clamping platens in a direction normal to the sharp bearing face. The method may further comprise forming the component with an axial dimension which extends in a direction other than normal to the sharp bearing face while overmolding material to a sidewall around the periphery of the sharp bearing body. The method may further comprise venting gas through vents abreast an interface between the sidewall and overmolded material. The method may further comprise retaining the second block of the mold against a base during orchestration of a portion of an ejection sequence in which the first block and component are ejected from the mold.

In some embodiments, the method may further comprise embedding cleats of ejector pins for the component in the material injected into the cavity. In some embodiments, clamping the sharp bearing body may comprise attracting the first block of the mold to the second block via magnets. In some embodiments, retaining the second block against the base may comprise attracting the second block to the base with magnets disposed in the second block. In some embodiments, the method may further comprise displacing a knockout subassembly including a number of part side ejector pins with a set of hydraulically driven ejector pins. In some embodiments, the method may further comprise returning the knockout subassembly to a home state with at least one bias member. In some embodiments, the method may further comprise automatically degating the component by ejecting a runner plate of the mold. In some embodiments, the method further may comprise holding the component and sharp bearing body against the first block as the first block is disassociated from the first block along an ejection axis. In some embodiments, overmolding material to the sidewall may comprise overmolding material over at least one step in the sidewall. In some embodiments, overmolding material to the sidewall may comprise encasing a tier formed in the sidewall in overmolded material. In some embodiments, overmolding material to the sidewall may comprise encasing at least one constant cross-section portion of the sharp bearing body and at least part of a chamfered section of the sidewall of the sharp bearing body in overmolded material.

In accordance with another example embodiment of the present disclosure an example method of overmolding a component to a sharp bearing body from which at least one microneedle projects may comprise closing first and second blocks of a mold along a stepped parting line. The method may further comprise applying a resting clamping force to the sharp bearing body via contact faces of a first and second shut-off with each of the at least one microneedle surrounded by a sharp pocket in the second shut-off. A sharp bearing face of the sharp bearing body may be disposed normal to the force of gravity. The contact faces may be parallel to the sharp bearing face. The method may further comprise exerting pressure against the mold with clamping platens in a direction normal to the sharp bearing face. The method may further comprise forming the component with an axial dimension which extends in a direction other than normal to the sharp bearing face while overmolding material to a sidewall of the sharp bearing body. The method may further comprise venting gas through vents directly outboard an interface between the sidewall and overmolded material. The method may further comprise retaining the second block of the mold against a base during orchestration of a portion of an ejection sequence in which the first block and component are ejected from the mold.

In some embodiments, the method may further comprise embedding cleats of ejector pins for the component when forming the component. In some embodiments, applying the resting clamping force may comprise attracting the first block of the mold to the second block via magnets. In some embodiments, applying the resting clamping force may comprise magnetically attracting the first and second block against one another. In some embodiments, retaining the second block against the base may comprise attracting the second block to the base with magnets. In some embodiments, the method may further comprise displacing a knockout subassembly including a number of part side ejector pins with a set of hydraulically driven ejector pins. In some embodiments, the method may further comprise returning the knockout subassembly to a home state with at least one bias member. In some embodiments, the method may further comprise automatically degating the component by ejecting a runner plate of the mold. In some embodiments, the method may further comprise holding the component and sharp bearing body against the first block as the first block is disassociated from the first block along an ejection axis. In some embodiments, overmolding material to the sidewall may comprise overmolding material over at least one step in the sidewall. In some embodiments, overmolding material to the sidewall may comprise encasing a tier formed in the sidewall in overmolded material. In some embodiments, overmolding material to the sidewall may comprise encasing at least one constant cross-section portion of the sharp bearing body and at least part of a chamfered section of the sidewall of the sharp bearing body in overmolded material.

In accordance with an embodiment of the present disclosure an example method of forming sharp bearing bodies having at least one microneedle projecting therefrom may comprise etching microneedles for a plurality of sharp bearing bodies on a silicon wafer. The method may further comprise defining a final footprint of each microneedle by removing a shortest portion of each microneedle in at least one first material remove operation. The method may further comprise forming a first section of the sidewalls of each of the sharp bearing bodies in at least one second material removal operation. The method may further comprise singulating each sharp bearing body from the wafer in at least one third material removal operation which completes formation of the sidewalls of each of the sharp bearing bodies. The final footprint of each microneedle may be surrounded on all sides by a portion of a sharp bearing face of each sharp bearing body.

In some embodiments, each of the at least one first material removal operation may be a dicing cut. In some embodiments, etching the microneedles may comprise creating microneedles with a height of at least 600 microns. In some embodiments, one of the at least one second material removal operation and third material removal operation may be a deep reactive ion etch. In some embodiments, one of the at least one second material removal operation and third material removal operation may be a dicing cut. In some embodiments, the sidewalls of each of the sharp bearing bodies may be tiered. In some embodiments, the sidewalls of each of the sharp bearing bodies may include a first segment where the cross-sectional area of each respective sharp bearing body is variable and a second segment where the cross-section area of each respective sharp bearing body is constant. In some embodiments, the method may further comprise partially defining the sidewalls of each of the sharp bearing bodies in at least one forth material removal operation. In some embodiments, the at least one forth material removal operation may be completed before the at least one third material removal operation. In some embodiments, the at least one forth material removal operation may define a portion of the sidewall of each respective sharp bearing body where the cross-sectional area of the sharp bearing body is variable. In some embodiments, the forth material removal operation may be a deep reactive ion etch.

In accordance with another example embodiment of the present disclosure an exemplary silicon microneedle array may comprise at least one microneedle. Each of the at least one microneedle may have a base footprint and a sloped face opposite the base footprint with microneedle sidewalls extending from the entire outline of the base footprint to sloped face. The microneedle array may further comprise a sharp bearing body with a sharp bearing face from which each of the at least one microneedle projects. The sharp bearing body may have a peripheral sidewall with a first and second constant cross-section region. The first constant cross-section region may be disposed most distal the sharp bearing face and have a larger cross-sectional area than the second constant cross-section region. The base footprint of each microneedle may be surrounded entirely by a portion of the sharp bearing face of the sharp bearing body.

In some embodiments, each microneedle may have a height of at least 600 microns. In some embodiments, the sharp bearing body may include a variable cross-section region intermediate the first and second constant cross-section regions. In some embodiments, the at least one microneedle may comprise two microneedles. In some embodiments, the at least one microneedle array may comprise at least three microneedles disposed in a row. In some embodiments at least a portion of the peripheral sidewall forming one of the first and second constant cross-sectional regions may be formed by an anisotropic etching process. In some embodiments, the remainder of the peripheral sidewall may be formed by dicing the microneedle array from a silicon wafer. In some embodiments, at least a portion of the microneedle sidewalls of each of the at least one microneedle may be formed by a dicing cut. In some embodiments, the peripheral sidewall of the sharp bearing body may be tiered. In some embodiments, the sidewall forming one of the first and second constant cross-section regions is entirely formed by an anisotropic etching process.

In accordance with an embodiment of the present disclosure an example delivery device package may comprise a delivery device having a main body and a reservoir portion with a main interior volume, an array of microneedles, a septum, and venting filter. The septum, main interior volume, and filter may be fluid communication via filling flow paths. The package may further comprise a float disposed in a fill indicator portion of the filling flow paths and displaceable from a first to a second end of the fill indicator portion. The package may further comprise a packet. The packet may comprise an inner shell at least partially surrounding the delivery device. The packet may further comprise a sleeve at least partially surrounding the inner shell. The packet may further comprise a window positioned over a second end of the fill indicator portion. The float may be configured to displace into alignment with the window when the fill indicator portion is loaded with agent and the second end is positioned above the first end.

In some embodiments, the filling indicator portion may be defined by a filter receptacle of the reservoir assembly into which the venting filter is coupled. In some embodiments, the filter receptacle may be defined in a protruding body extending in a direction outward from a main section of the reservoir assembly. In some embodiments, the septum and filter may be disposed in a septum housing coupled to the remainder of the reservoir assembly via tubing. In some embodiments, the filling indicator portion may be defined by a filter receptacle in the septum housing into which the venting filter is coupled. In some embodiments, the filling indicator portion may be downstream of the main interior volume relative to the septum. In some embodiments, the delivery device comprises a central region from which a number of petal members extend, the central region including a depressible section which, upon application of pressure, flips from a protruding state to a depressed state. The delivery device may further comprise a bias member disposed intermediate the depressible section and a flexible wall partially defining the main interior volume of the reservoir assembly. In some embodiments, the central region may be disposed within a rigid dome of the inner shell. In some embodiments, the inner shell may be a clamshell. In some embodiments, the packet may include a septum access formed by an opening in the inner shell and sleeve. The septum may be disposed within the septum access.

In accordance with an embodiment of the present disclosure, an example reservoir assembly for a shallow destination medicament delivery device may comprise a rigid portion with a domed region. The domed region may have a first concave side and a second convex side, the concave side may have a central basin. The rigid portion may have a protruding body with a bay. The reservoir assembly may further comprise a flow restrictor coupled to the central basin. The reservoir assembly may further comprise a flexible portion coupled to a peripheral rim of the domed region. The flexible portion may overlay the first side and may have a domed preform mimicking the concave surface of the concave side. The flexible portion and the first concave side of the rigid portion may form a main interior volume of the reservoir assembly. The reservoir assembly may further comprise a sharp bearing body including at least one microneedle. The reservoir assembly may further comprise a septum disposed in the bay. An end of the protruding body may cover at least a portion of an end face of the septum.

In some embodiments, the end of the protruding body may be swaged over at least the portion of the end face of the septum. In some embodiments, the flow restrictor may be an orifice plate. In some embodiments, the sharp bearing body may be coupled to a stage projection extending from the second convex side of the domed region of the rigid portion. In some embodiments, the stage projection may be overmolded onto the sharp bearing body. In some embodiments, the sharp bearing body may be coupled to the rigid portion via overmolding. In some embodiments, the rigid portion may include a sharp receiving volume in communication with the bay and the main interior volume. An axis of the bay and sharp receiving volume may extend through a wall of the rigid portion before passing into the main interior volume. In some embodiments, the flexible portion may be displaceable from the domed preformed shape to an inverted version of the domed preformed shape. The flexible portion may have a bias toward the nearest of the domed preformed shape and the inverted version of the domed preformed shape. In some embodiments, the reservoir assembly may further comprise a cap surrounding the sharp bearing body and forming an environmental seal around the sharp bearing body. In some embodiments, the main interior volume may have a target fill volume. The flexible portion may displace nearer the inverted version of the domed preform shape than the domed preform shape, but not into the inverted version of the domed preformed shape when the target volume is loaded into the reservoir. The main interior volume may be at a slight negative pressure due to the bias toward the inverted version of the domed preformed shape. In some embodiments, at least one rocker member may project from the second convex side of the rigid portion. In some embodiments, the rigid portion may include a brim. The peripheral rim of the domed region may be intermediate the brim and the domed region. In some embodiments, the peripheral rim may be substantially flat. In some embodiments, the bay of the protruding body may have an axis. The axis may extend parallel to a sharp bearing face of the sharp bearing body, the microneedle extending proud of the sharp bearing face. In some embodiments, the sharp bearing body may be coupled to the rigid portion in an orientation in which the microneedle extends in a direction other than parallel to an axial dimension of the rigid portion. In some embodiments, the direction other than parallel to the axial dimension of the rigid portion may be a direction at a 5-25° angle to the axial dimension of the rigid portion.

In accordance with another example embodiment of the present disclosure an example method of filling a reservoir assembly for a shallow destination medicament delivery device may comprise piercing, with a dispensing sharp, a septum in a bay of a protruding body extending outwardly from a rigid potion of the reservoir assembly. The method may further comprise disposing a tip of the dispensing sharp in a receiving volume of the reservoir assembly. The method may further comprise loading fluid into a sealed main interior volume of the reservoir assembly. The main interior volume may be defined by a flexible portion and a concave surface of the rigid portion. The flexible portion may be displaced from a first preferred shape in which it conforms to the concave surface toward but not into a second preferred shape. The method may further comprise establishing a slight negative pressure in the main interior volume due to a bias of the flexible portion toward the second preferred shape.

In some embodiments, the flexible portion may be preformed with one of the first and second preferred shape. In some embodiments, the second preferred shape may be an inverted version of the first preferred shape. In some embodiments, the method may further comprise removing a cap of the reservoir assembly and allowing the flexible portion to displace to the second preferred shape. In some embodiments, loading fluid into the sealed interior volume may comprise loading a vaccine into the main interior volume. In some embodiments, loading fluid into the main interior volume may comprise loading a target volume of fluid into the main interior volume. In some embodiments, the method may further comprise coupling the reservoir assembly to the delivery device. In some embodiments, the method may further comprise coupling the flexible portion to the rigid portion at a rim surrounding the concave surface. In some embodiments, the piercing the septum may comprise advancing a dispensing sharp through the septum in a direction substantially parallel to a shape bearing face of a sharp bearing body coupled to the rigid portion.

In accordance with another example embodiment of the present disclosure an example reservoir assembly for a shallow destination medicament delivery device may comprise a rigid portion having first face having a concave surface and a second face having a convex surface. The rigid portion may have a protruding body with a bay. The reservoir assembly may further comprise a septum retained within the bay. The reservoir assembly may further comprise a flexible portion coupled to an attachment surface surrounding the concave surface. The flexible portion and the concave surface may form a main interior volume of the reservoir assembly. The flexible portion may have a first preferred shape mimicking the concave surface and a second preferred shape. The reservoir assembly may further comprise a sharp bearing body including at least one microneedle.

In some embodiments, an end of the protruding body may be swaged over at least a portion of an end face of the septum. In some embodiments, the rigid portion may include a central basin defined in the concave surface. A flow restrictor may be coupled to the basin. In some embodiments, the sharp bearing body may be coupled to a stage projection extending from the second face of the rigid portion. In some embodiments, the stage projection may be overmolded onto the sharp bearing body. In some embodiments, the sharp bearing body may be coupled to the rigid portion via overmolding. In some embodiments, the rigid portion may include a sharp receiving volume in communication with the bay and the main interior volume. An axis of the bay and sharp receiving volume may extend through a wall of the rigid portion before passing into the main interior volume. In some embodiments, the second preferred shape may be an inverted version of the first preferred shape. In some embodiments, the flexible portion may be preformed to have one of the first preferred shape and the second preferred shape. In some embodiments, flexible portion may be a bias toward the nearest of the first and second preferred shapes. In some embodiments, the reservoir assembly may further comprise a cap surrounding the sharp bearing body and forming an environmental seal around the sharp bearing body. In some embodiments, the main interior volume may have a target fill volume. The flexible portion may displace nearer the second preferred shape than the first preferred shape, but not into the second preferred shape when the target volume is loaded into the reservoir. The main interior volume may be sealed by a removable cap and at a slight negative pressure due to a bias of the flexible portion toward the second preferred shape. In some embodiments, at least one rocker member map project from the second face of the rigid portion. In some embodiments, the rigid portion may include a brim. The attachment surface may be intermediate the brim and the concave surface. In some embodiments, the attachment surface may be substantially flat. In some embodiments, the bay of the protruding body may have an axis. The axis may extend parallel to a sharp bearing face of the sharp bearing body. The microneedle may extend proud of the sharp bearing face. In some embodiments, the sharp bearing body may be coupled to the rigid portion in an orientation in which the microneedle extends in a direction other than parallel to an axial dimension of the rigid portion. In some embodiments, the direction other than parallel to the axial dimension of the rigid portion may be a direction at a 5-25° angle to the axial dimension of the rigid portion.

In accordance with an embodiment of the present disclosure an example delivery device for delivery of a medicament to a shallow delivery destination of a patient may comprise a main body having a central region forming a receptacle and a peripheral region formed of a plurality of petal members surrounding the central region. The delivery device may further comprise a platform coupled to the receptacle. The delivery device may further comprise a sharp bearing body coupled to the receptacle. The delivery device may further comprise a reservoir assembly outboard from the main body and coupled to the platform via a bridge. A main interior volume of the reservoir assembly may be in fluid communication with the sharp bearing body via a flow path defined at least partially by the bridge and platform. The delivery device may further comprise a septum retained within a bay of the reservoir assembly.

In some embodiments, the platform may include a stage projection. The sharp bearing body may be coupled to the stage projection. In some embodiments, the platform may be overmolded to the sharp bearing body. In some embodiments, the sharp bearing body may include at least one microneedle. In some embodiments, the bridge may extend through an interrupt region between two of the plurality of petal members. In some embodiments, the bridge may extend through an aperture in the main body. In some embodiments, the reservoir assembly may include a base portion with a flexible portion coupled thereto. The reservoir assembly may include a guide. The reservoir assembly may include an actuator body. The base portion and the flexible portion may together define the main interior volume of the reservoir assembly. In some embodiments, the guide may define a displacement path of the actuator body between a first position in which the actuator body is out of contact with the flexible portion and a second position. In some embodiments, the flexible portion may displace from a collapsed state to a raised state when the main interior volume is filled with fluid. The second position of the actuator body may be a position in which the actuator body holds the flexible portion in the collapsed state. In some embodiments, a bias member may be disposed intermediate the flexible portion and the actuator body. In some embodiments, a reservoir interface member may be disposed intermediate the bias member and the flexible portion. In some embodiments, the actuator body may include at least one retention interface. The retention interface may be engaged with a cooperating retention interface of the guide when the actuator body is in the second position. In some embodiments, the shape of the end of the actuator body most proximal the section of the base portion defining the main interior volume may be shaped to mimic a shape of the section of the base portion defining the main interior volume. In some embodiments, a sharp receiving volume may be disposed intermediate the main interior volume and an interior face of the septum. The receiving volume may be in fluid communication with the main interior volume via a filling channel. The filling channel may extend along a path which is not coaxial with the septum.

In accordance with another embodiment of the present disclosure an example delivery device for delivery of a medicament to a shallow delivery destination of a patient may comprise a main body having a receptacle surrounded by a peripheral region formed of a plurality of petal members. The delivery device may further comprise a platform coupled to the receptacle. The delivery device may further comprise a sharp bearing body coupled to the receptacle and having a set of microneedles projecting therefrom at an angle other than parallel to an axial dimension of the platform. The delivery device may further comprise a reservoir assembly outboard from the main body and coupled to the platform via a flow path. A main interior volume of the reservoir assembly may be fluid communication with the sharp through the flow path. The delivery device may further comprise a septum retained within a bay of the reservoir assembly.

In some embodiments, the platform may include a stage projection. The sharp bearing body may be coupled to the stage projection. In some embodiments, the platform may be overmolded to the sharp bearing body. In some embodiments, the bridge may extend through an interrupt region between two of the plurality of petal members. In some embodiments, the platform an at least a portion of the reservoir assembly may be monolithically formed and connected by a bridge. In some embodiments, the reservoir assembly may include a base portion with a flexible portion coupled thereto. The reservoir assembly may include a guide. The reservoir portion may include an actuator body. The base portion and the flexible portion may together define the main interior volume of the reservoir assembly. In some embodiments, the guide may define a displacement path of the actuator body between a first position in which the actuator body is out of contact with the flexible portion and a second position. In some embodiments, the flexible portion may displace from a collapsed state to a raised state when the main interior volume is filled with fluid. The second position of the actuator body may be a position in which the actuator body holds the flexible portion in the collapsed state. In some embodiments, a bias member may be disposed intermediate the flexible portion and the actuator body. In some embodiments, a reservoir interface member may be disposed intermediate the bias member and the flexible portion. In some embodiments, the actuator body may include at least one retention interface. The retention interface may be engaged with a cooperating retention interface of the guide when the actuator body is in the second position. In some embodiments, the shape of the end of the actuator body most proximal the section of the base portion may defining the main interior volume may be shaped to mimic a shape of the section of the base portion defining the main interior volume. In some embodiments, a sharp receiving volume may be disposed intermediate the main interior volume and an interior face of the septum. The receiving volume may be fluid communication with the main interior volume via a fill channel. The fill channel may extend along a path which is not coaxial with the septum.

In accordance with another embodiment of the present disclosure a method of delivering a dose of medicament to a patient with a delivery device may comprise piercing a septum of a reservoir assembly and dispensing medicament into a main interior volume of the reservoir assembly with a filling implement. The method may further comprise adhering petal members of a main body of the delivery device to a delivery site. The method may further comprise pressing a central region of the main body toward the delivery site and generating a spreading displacement of the petal members. The method may further comprise penetrating into the delivery site with at least one microneedle coupled to a platform disposed within a receptacle of the main body. The method may further comprise expelling fluid from the main interior volume of the reservoir assembly through a flow path extending through the wall of the main body and out of the at least one microneedle.

In some embodiments, piercing the septum may comprise advancing a dispensing sharp through the septum and into a receiving volume intermediate the septum and the main interior volume. There may be a fill path extending in a direction other than parallel to an axial dimension of the septum fluidically coupling the receiving volume with the main interior volume. In some embodiments, dispensing medicament into the main interior volume may comprise dispensing at least one vaccine into the main interior volume. In some embodiments, penetrating into the delivery site may comprise advancing the at least one microneedle into the delivery site in an orientation where the lumen of each of the at least one microneedle is at an angle other than perpendicular to a surface of the delivery site. In some embodiments, expelling fluid from the main interior volume may comprise applying a force to an actuator body of the reservoir assembly and displacing it from a first position to a second position. In some embodiments, displacing the actuator body may comprise driving the actuator body along the guide and displacing a flexible member partially defining the main interior volume against a rigid portion of the reservoir assembly which partially defines the main interior volume. In some embodiments, displacing the actuator body may comprise compressing a bias member intermediate the actuator body and a flexible member partially defining the main interior volume. In some embodiments, displacing actuator body may comprise compressing a bias member intermediate the actuator body and a reservoir interface member which contact a flexible member partially defining the main interior volume. In some embodiments, the method may further comprise holding the actuator body in the second position by establishing an engagement with a retention feature defined in the reservoir assembly. In some embodiments, displacing the actuator body may comprise deforming the actuator body to transition it form a protruding state to a depressed state.

In accordance with an embodiment of the present disclosure, an apparatus for reconstituting a medical agent may comprise a diluent container spike. The apparatus may further comprise a medical agent container spike. The apparatus may further comprise at least one syringe port. The apparatus may further comprise a fluid bus linking the diluent container spike, medical agent spike, and each of the at least one syringe port, the fluid bus also including an outlet line. The apparatus may further comprise at least one valve associated with the fluid bus selectively gating fluid flow between each of the diluent container spike, the medical agent container spike, the outlet line, and each of the at least one syringe port.

In some embodiments, the at least one valve may include a stopcock. In some embodiments, each of the at least one valve may be a ball valve. In some embodiments, each of the at least one valve may be electromechanical. In some embodiments, the fluid bus and each of the at least one valve may be at least partially disposed within a housing. In some embodiments, the apparatus may further comprise a housing. The syringe port, diluent spike, and medical agent container spike each may be disposed within a respective dock defined in the housing. In some embodiments, the diluent spike may be on a first end of the fluid bus. A first syringe port of the at least one syringe port may be immediately downstream of the diluent spike. A second syringe port of the at least one syringe port may be immediately downstream of the first syringe port. The fluid bus may furcate downstream of the second syringe port into a branch leading to the medical agent container spike and the outlet line. In some embodiments, the at least one valve may include a first valve on the fluid bus intermediate the diluent spike and the first syringe port. The at least one valve may include a second valve on the fluid bus intermediate the first syringe port and the second syringe port. The at least one valve may include a third valve on a portion of the branch and a fourth valve on the outlet line. In some embodiments, each of the at least one valve may be a volcano valve having a manual actuator. There may be a displaceable diaphragm intermediate the manual actuator and a valve seat of each of the volcano valves.

In accordance with an embodiment of the present disclosure, an example shut-off for a mold for overmolding a component to a sharp bearing body from which at least one microneedle extends may comprise a shut-off body having a clamping face. The shut-off body may comprise at least one sharp receiving pocket defined in the clamping face. Each of the at least one sharp receiving pocket may have a set of sidewalls including a rounded sidewall segment, a ramped sidewall opposite the rounded side wall, and a set of lateral side walls connecting the ramped sidewall to the rounded sidewall segment. The rounded side wall segment and the lateral sidewalls may include a tapered region. The cross-sectional area of each of the at least one sharp receiving pocket may decrease in the tapered region as distance from the clamping face increases. The ramped sidewall may be sloped such that the sidewall increases in proximity to the rounded sidewall segment as distance from the clamping face increases.

In some embodiments, each of the at least one sharp receiving pocket may include a pit region. The pit region may be the portion of the sharp receiving pocket most distal the clamping face. In some embodiments, the pit region may extend from an end of the ramped sidewall most distal the clamping face in a direction substantially perpendicular to the clamping face. In some embodiments, the tapered region of the rounded sidewall and lateral sidewalls may be disposed intermediate a first region of each of the rounded sidewall and lateral sidewall and a second region of each of the rounded sidewall and lateral sidewall. In some embodiments, the maximum width of each of the at least one sharp receiving pocket may be at least double the maximum width of the at least one microneedle. In some embodiments, each of the at least one sharp receiving pocket may include a kerf receiving volume in a region of the pocket most proximal the clamping surface. In some embodiments, the depth each of the at least one sharp receiving pocket may be at least 800 microns. In some embodiments, the angle of the ramped surface may be substantially equal to the angle of the (111) crystallographic plane to the (100) plane of silicon.

In accordance with another embodiment of the present disclosure an example method of placing a sharp bearing from which at least one microneedle extends into a mold may comprise displacing the sharp bearing body to a first shut-off. The method may further comprise advancing each of the at least one microneedle into a respective sharp receiving pocket defined in the shut-off. The method may further comprise self-centering each of the at least one microneedle with the respective sharp receiving pocket. The method may further comprise advancing a set of kerf regions adjacent each of the at least one microneedle into the respective sharp receiving pocket. The method may further comprise seating a sharp bearing face of the sharp bearing body against a first shut-off clamping surface of the first shut-off. The method may further comprise displacing a second shut-off against a second face of the sharp bearing body, the second face being opposite the sharp bearing face. The method may further comprise applying a clamping force to the sharp bearing body via at least one of the first and second shut-offs. The clamping force may be applied in a direction perpendicular to the sharp bearing face of the sharp bearing body.

In some embodiments, self-centering each of the at least one microneedle into a respective sharp receiving pocket may comprise sliding a sloped face of each of the at least one microneedle along a ramped sidewall of the pocket. In some embodiments, self-centering each of the at least one microneedle into a respective sharp receiving pocket may comprise guiding each of the at least one microneedle with a taper sidewall region of the respective pocket which decreases the cross-sectional area of the respective pocket as distance from the first shut-off clamping face increases. In some embodiments, the method may further comprise displacing a tip of each of the at least one microneedle into a pit region of the respective pocket. In some embodiments, each of the at least one microneedle may be a silicon microneedle. In some embodiments, advancing each of the at least one microneedle into the respective sharp receiving pocket defined in the shut-off may comprise displacing a first microneedle into a respective first sharp receiving pocket and displacing a second microneedle in a respective second sharp receiving pocket. In some embodiments, the method may further comprise displacing a third microneedle into a third sharp receiving pocket.

In accordance with another embodiment of the present disclosure a microneedle array may comprise a sharp bearing body. The array may further comprise at least one microneedle projecting from a sharp bearing face of the sharp bearing body and monolithically formed therewith. Each of the at least one microneedle may include a rounded tip region and a trailing region. The rounded tip region may be devoid of straight spans and may include a rounded edge extending from the sharp bearing face to a tip of the microneedle. The rounded edge of the rounded tip region may extend to a pair of radiused tip region sidewalls on each side of a midplane of the microneedle. The trailing region may include a set of trailing region sidewalls extending from ends of the radiused tip region sideswalls. The trailing region sidewalls may be planar and oriented parallel to one another throughout their entirety. Each of the at least one microneedle may include a sloped face extending from the sharp bearing face at an end of the trailing region to the tip of the microneedle. Each of the at least one microneedle may further comprise a lumen extending therethrough. At least a majority of the lumen may be disposed in the rounded tip region of the microneedle. The lumen may form a passage through the entire microneedle array.

In some embodiments, the at least one microneedle may include a pair of microneedles. In some embodiments, the microneedle array may be formed of silicon. In some embodiments, the cross-sectional area of the sharp bearing body may increase as distance from the sharp bearing face increases. In some embodiments, the sidewalls of the sharp bearing body may include two sections of sidewalls substantially perpendicular to the sharp bearing face. The two sections of sidewalls may be separated by a step region substantially parallel to the sharp bearing face. In some embodiments, each of the at least one microneedle may have a height of at least 600 microns. In some embodiments, each of the at least one microneedle may have a height of at least 800 microns. In some embodiments, the rounded edge may be defined by a radius of 25-40 microns. In some embodiments, the radiused tip region sidewalls may be defined by a radius of 310-335 microns. In some embodiments, the lumen of each of the at least one microneedle may be symmetric about the midplane of the respective microneedle. In some embodiments, the lumen of each of the at least one microneedle may be spaced at a minimum distance of 25-30 microns from the rounded edge and radiused tip region sidewalls of the respective microneedle. In some embodiments, the lumen of each of the at least one microneedle may be a minimum of 65-80 microns from the rounded edge of the rounded tip region of the respective microneedle. In some embodiments, each of the at least one microneedle may be surrounded on all sides by an adjacent portion of the sharp bearing face. In some embodiments, the sharp bearing body may include a sidewall extending from the periphery of the sharp bearing face to a second face of the sharp bearing body opposite the sharp bearing face. The sidewall may have at least one step.

BRIEF DESCRIPTION OF THE DRAWINGS

These and other aspects will become more apparent from the following detailed description of the various embodiments of the present disclosure with reference to the drawings wherein:

FIG. 57A depicts a view of an example main body which may be included in a delivery device;

FIG. 57B depicts a side view of an example main body which may be included in a delivery device;

FIG. 58A depicts a top plan view of an example delivery device having a pair of petal members separated by a widened slit and an example reservoir assembly with a protruding body extending through the main body of the delivery device;

FIG. 58B depicts a bottom plan view of the example delivery device of FIG. 53A;

FIG. 58C depicts a perspective view of the example delivery device of FIG. 53A;

FIG. 59A depicts a bottom plan view of an example delivery device having a pair of petal members separated by a widened slit and an example reservoir assembly septum housing connected to a protruding by via tubing, the protruding body extending through the main body of the delivery device;

FIG. 59B depicts a top plan view of the example delivery device of FIG. 59A;

FIG. 59C depicts a perspective view of the example delivery device of FIG. 59A;

FIG. 60A depicts a perspective view of an example delivery device including a main body with a port through which a protruding body of an example reservoir assembly extends and a petal member with an aperture;

FIG. 60B depicts a detailed view of the indicated region of FIG. 60A;

FIG. 61A depicts a perspective view of an example delivery device including a main body with a port through which a protruding body of an example reservoir assembly extends and a petal member with an aperture flanked by reinforcing ribs;

FIG. 61B depicts a detailed view of the indicated region of FIG. 61A;

Figure 62:
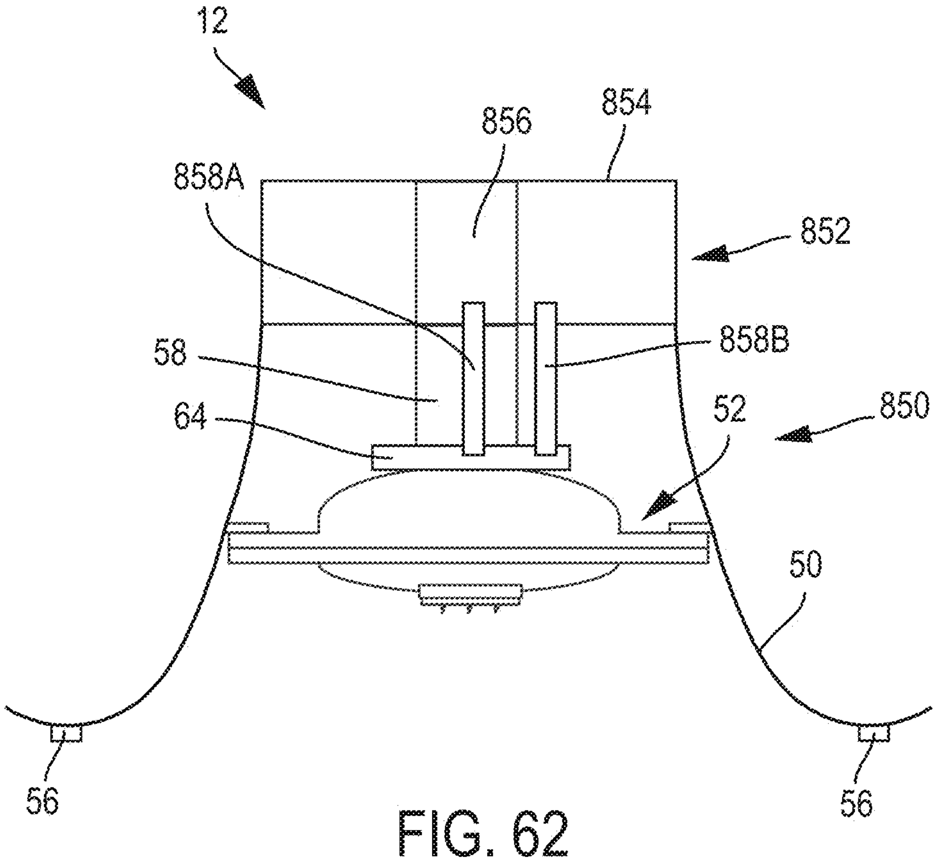
Figure 63A:
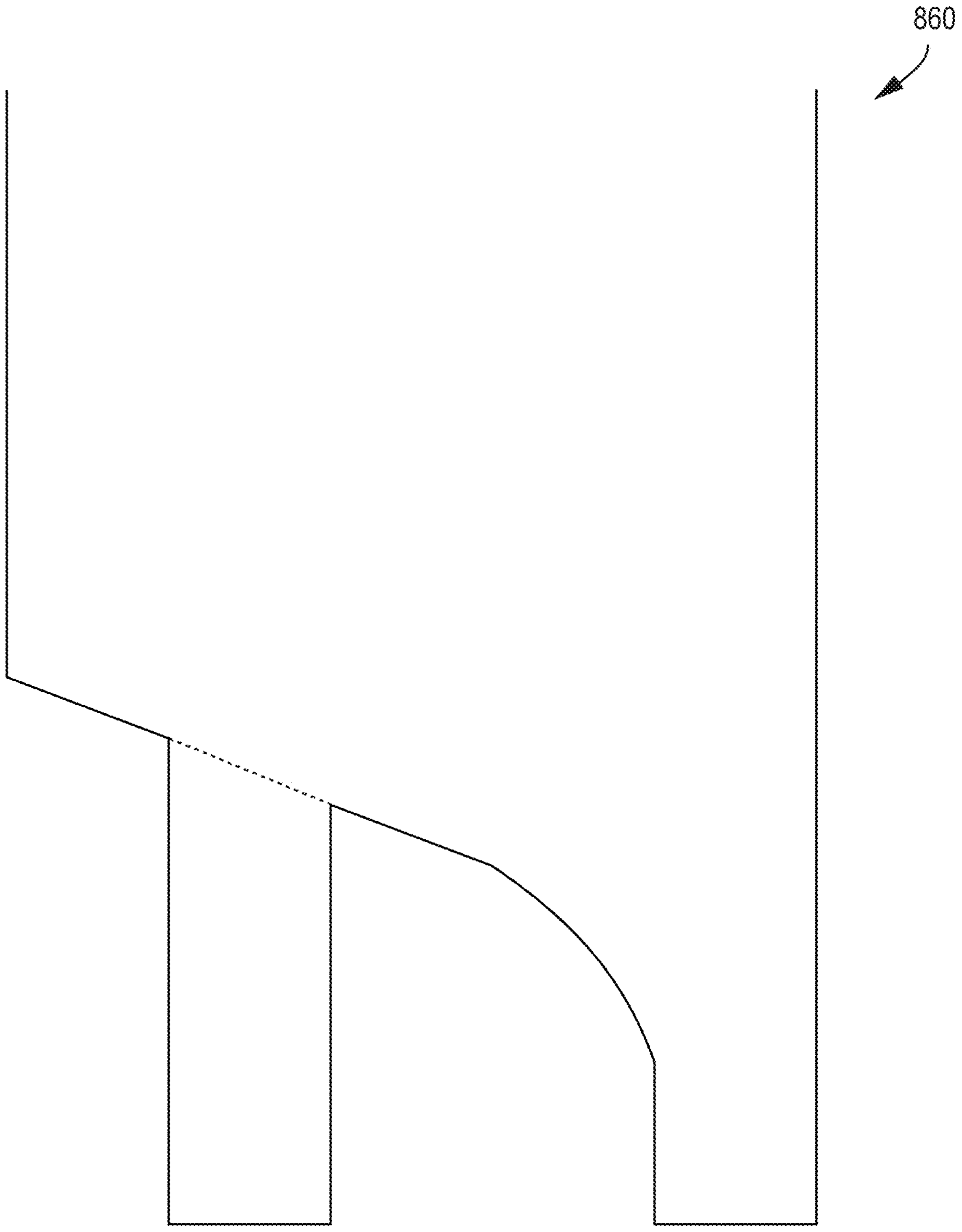
Figure 63B:
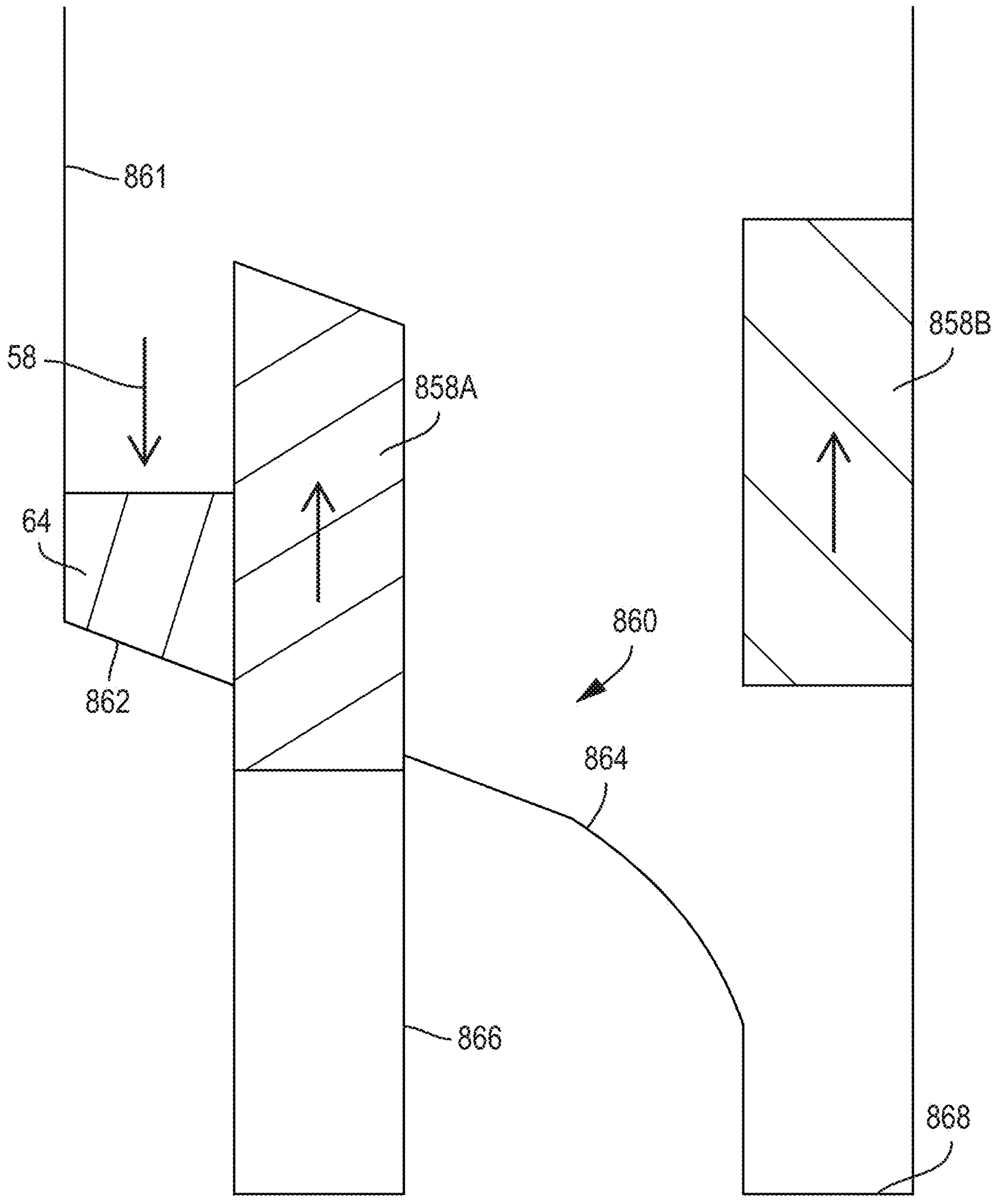
Figure 63C:
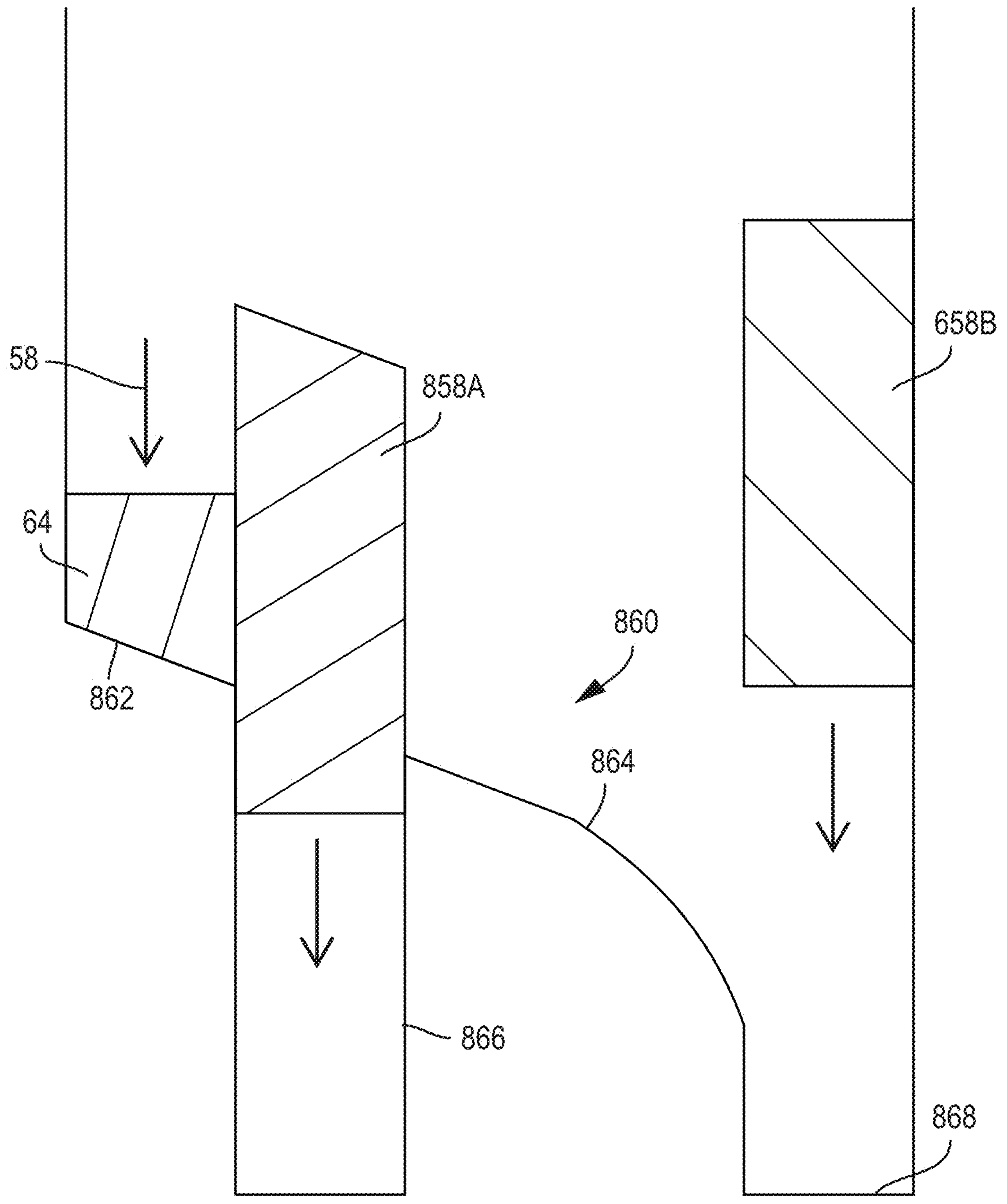
Figure 63D:
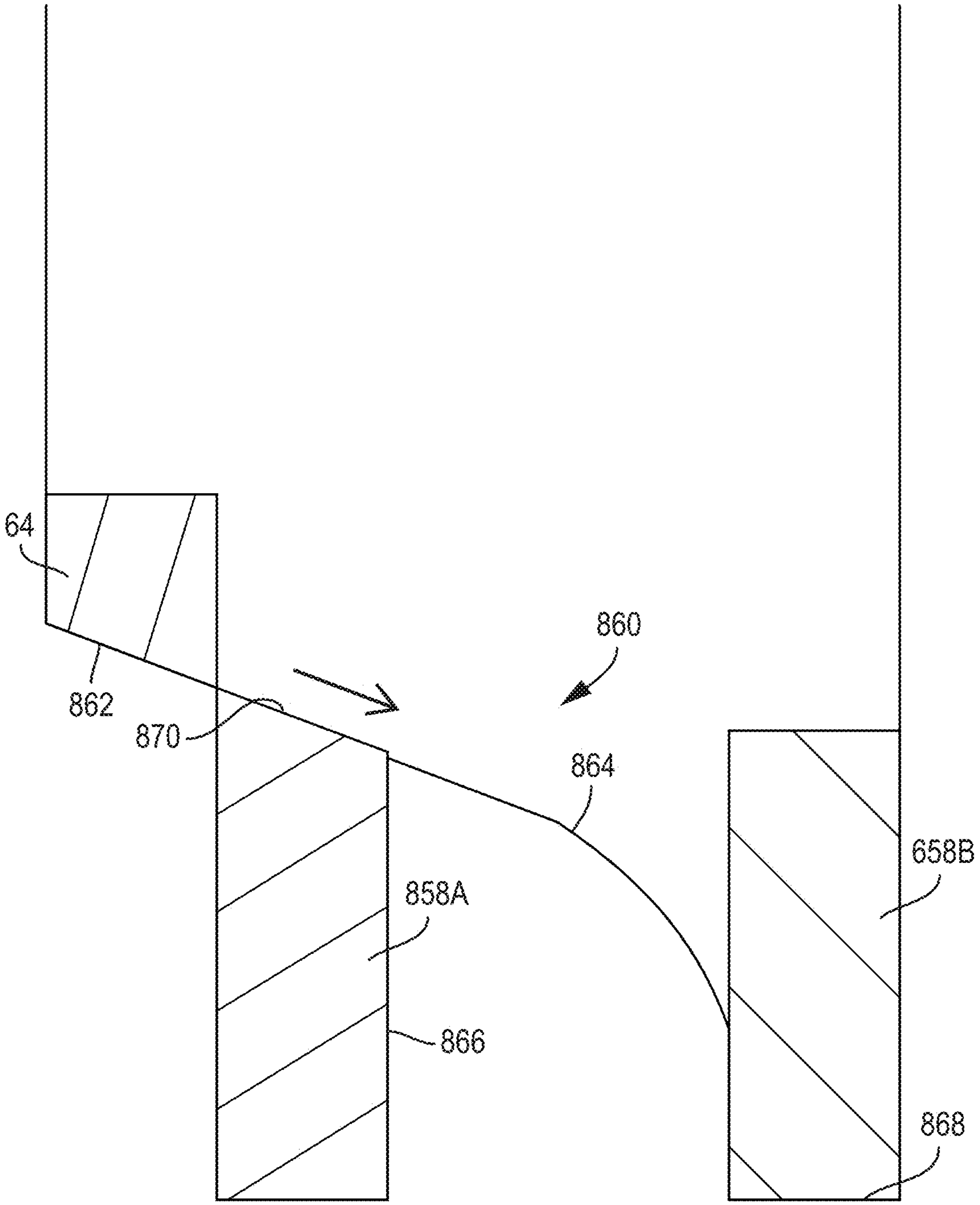
Figure 63E:
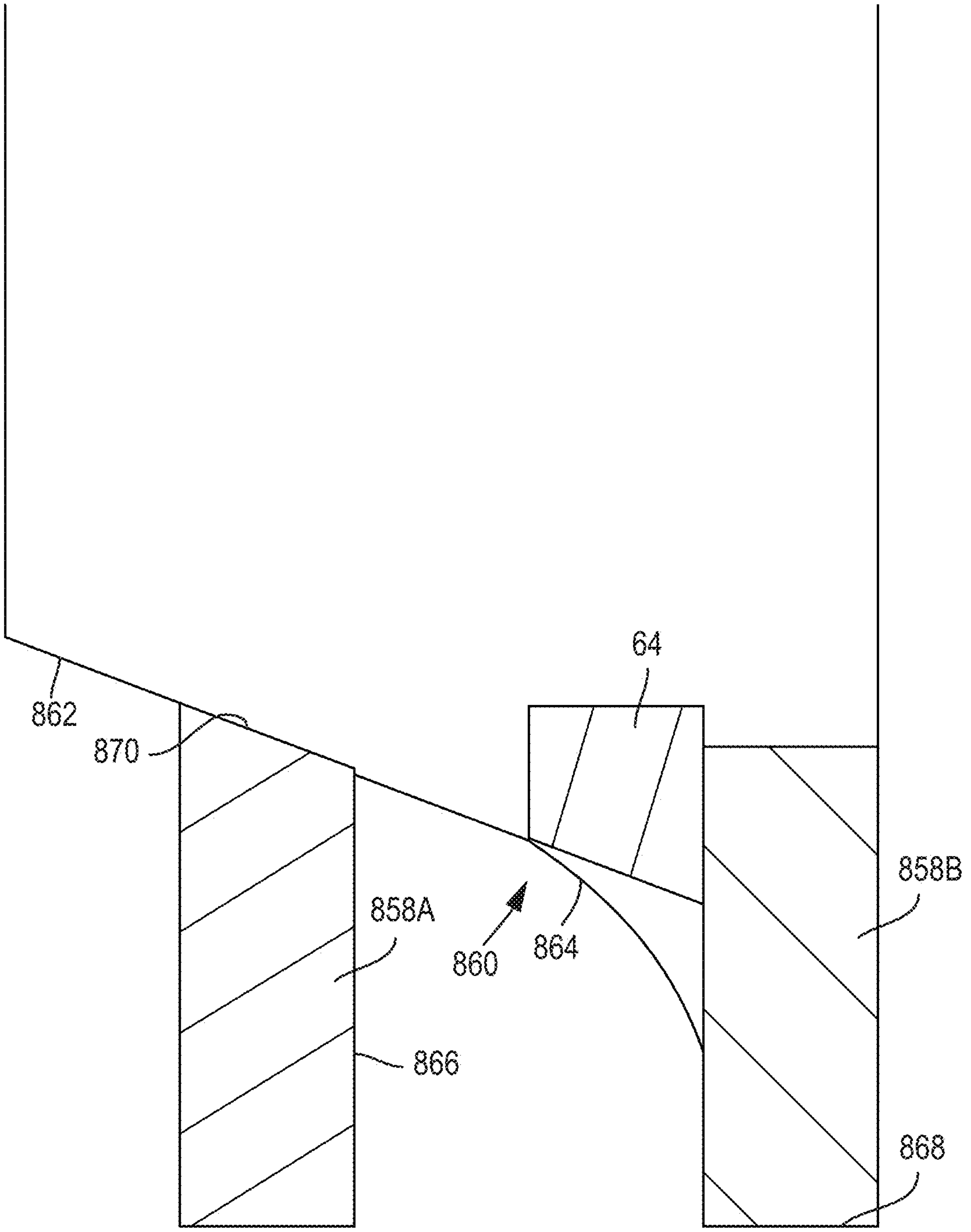
Figure 63F:
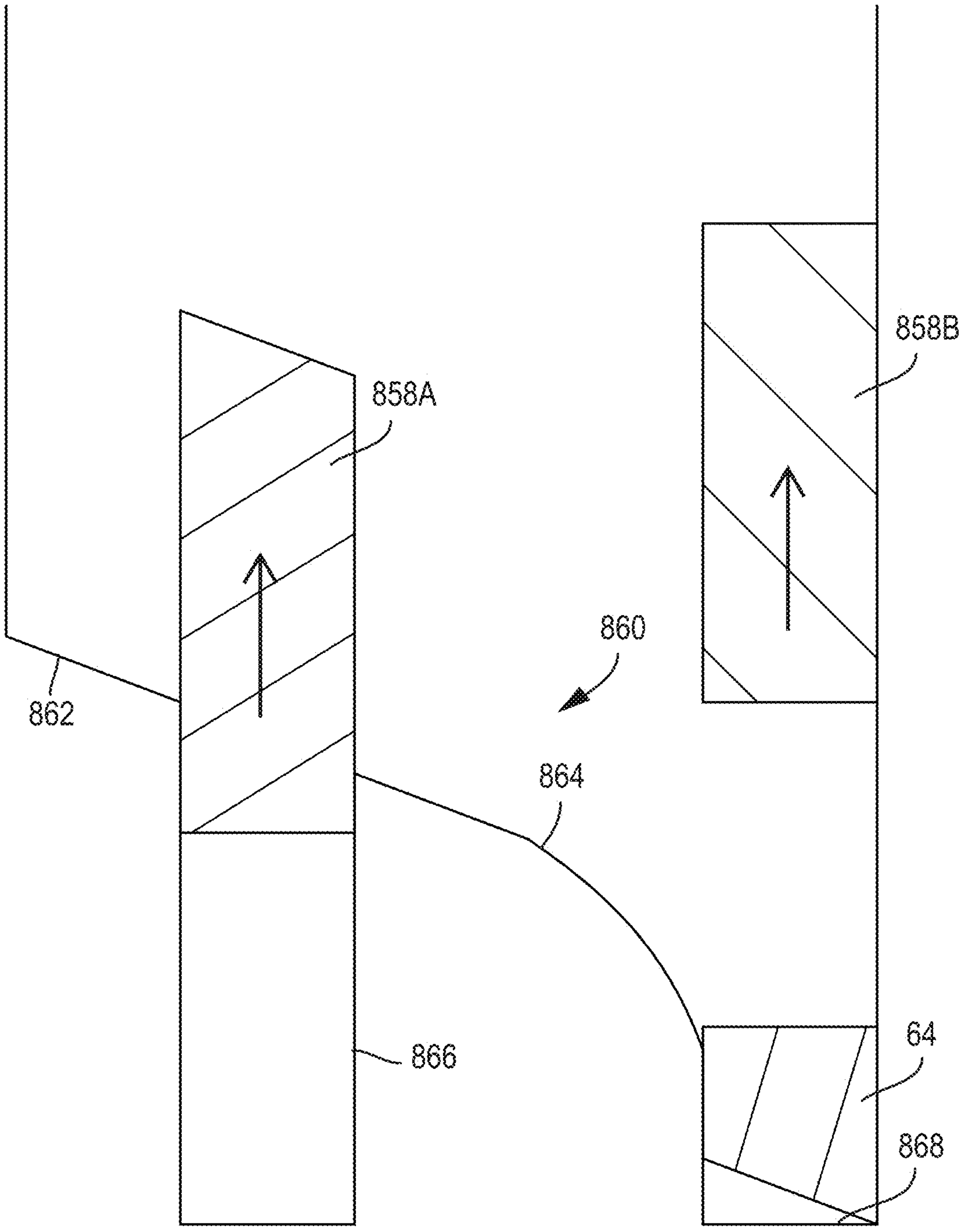
Figure 64A:
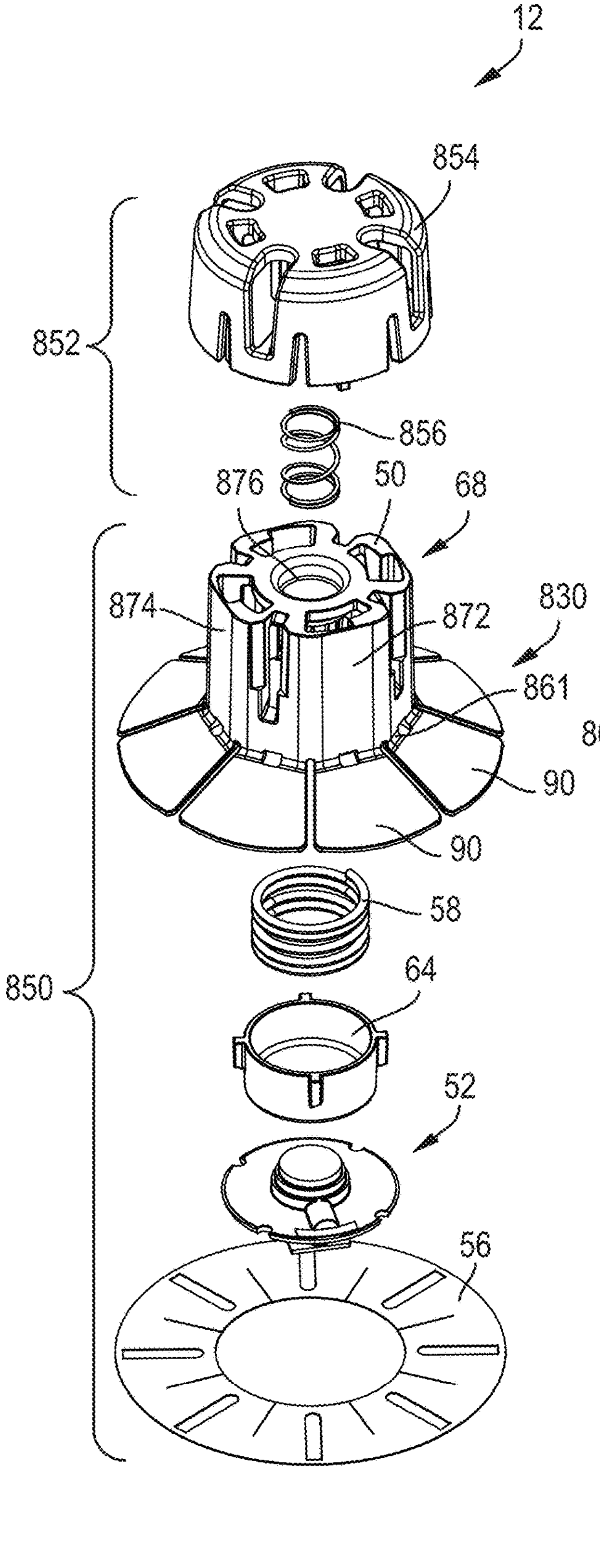
Figure 64B:
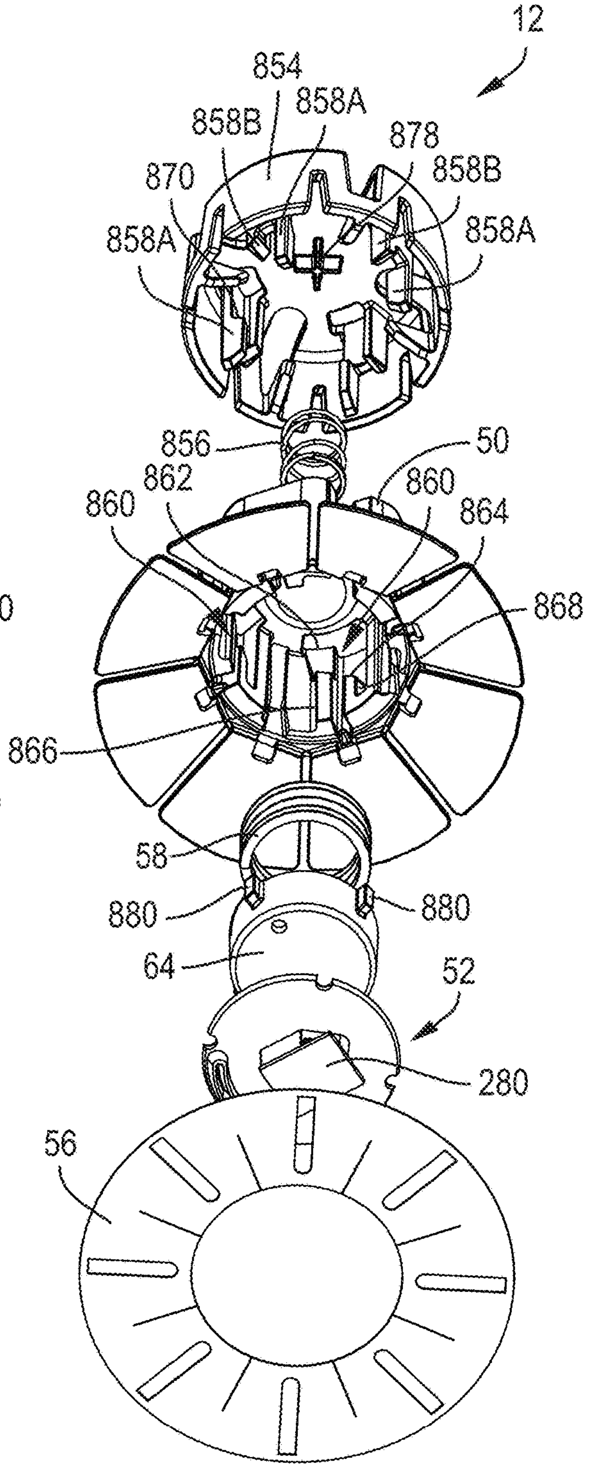
Figure 64C:
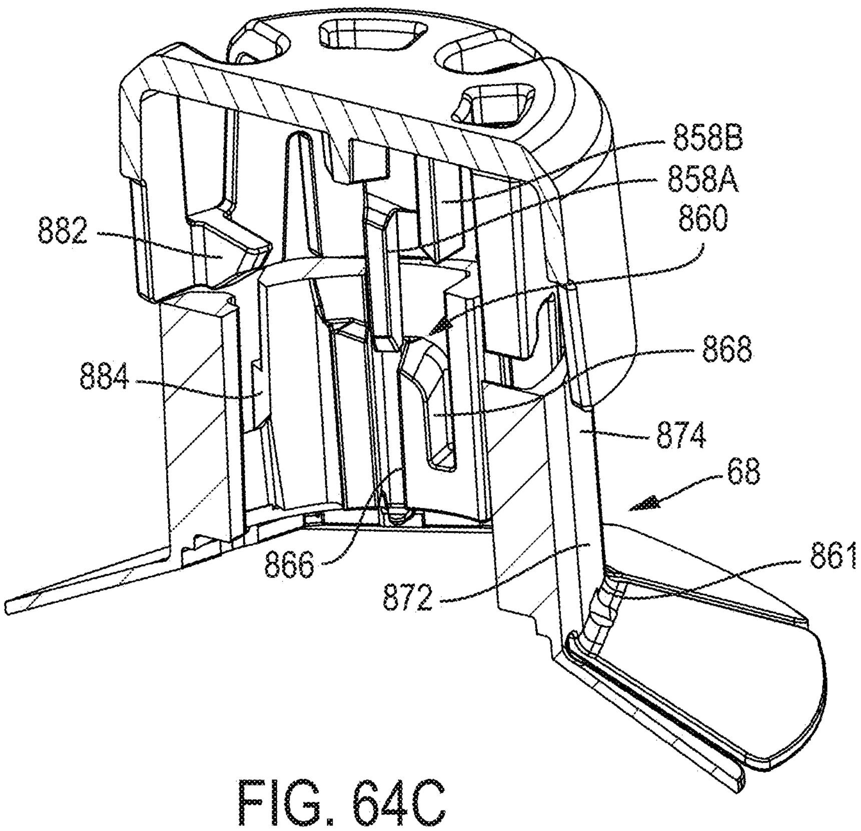
Figure 65A:
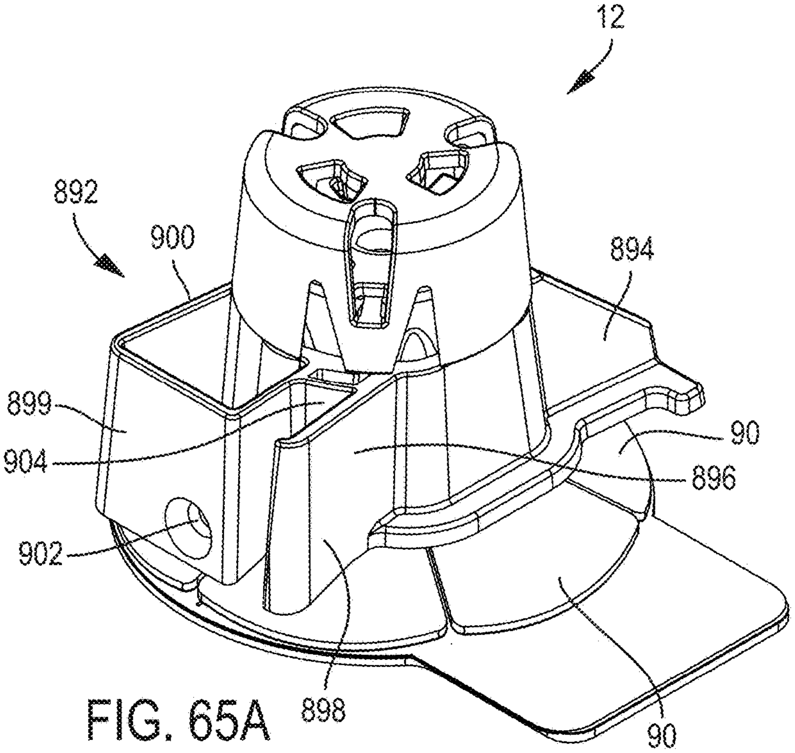
Figure 65B:
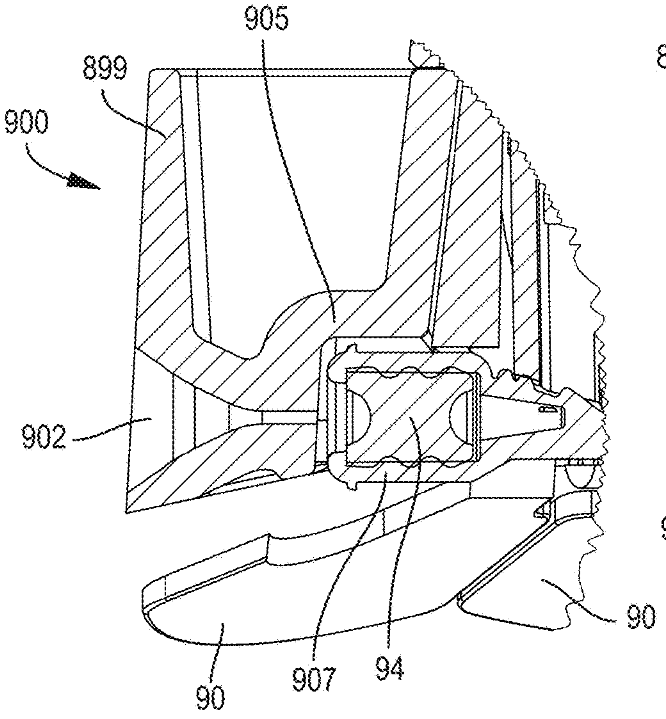
Figure 66:
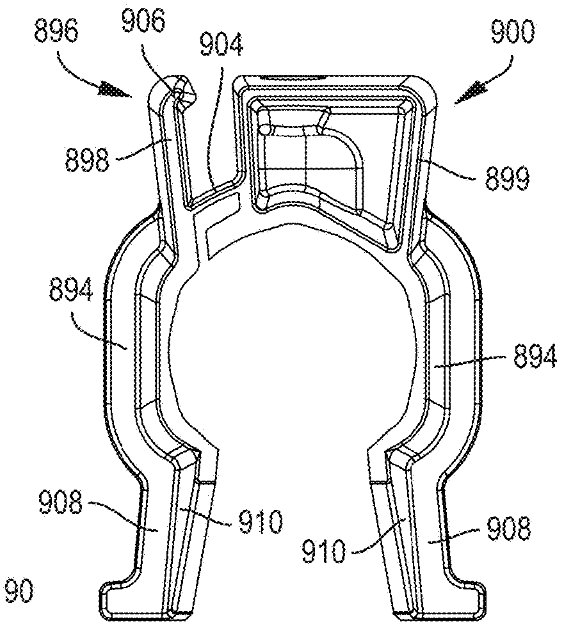
Figure 67:
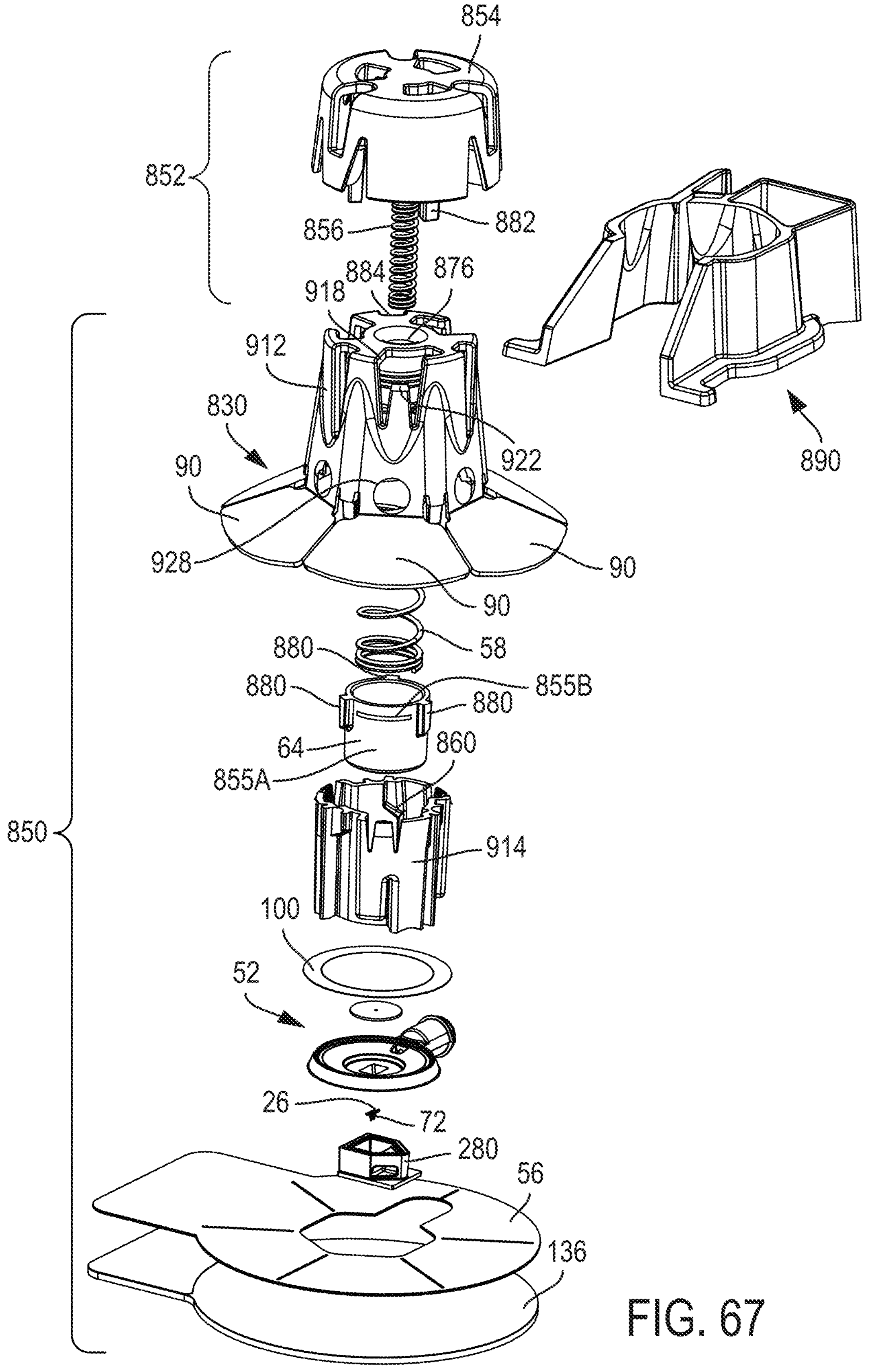
Figure 68:
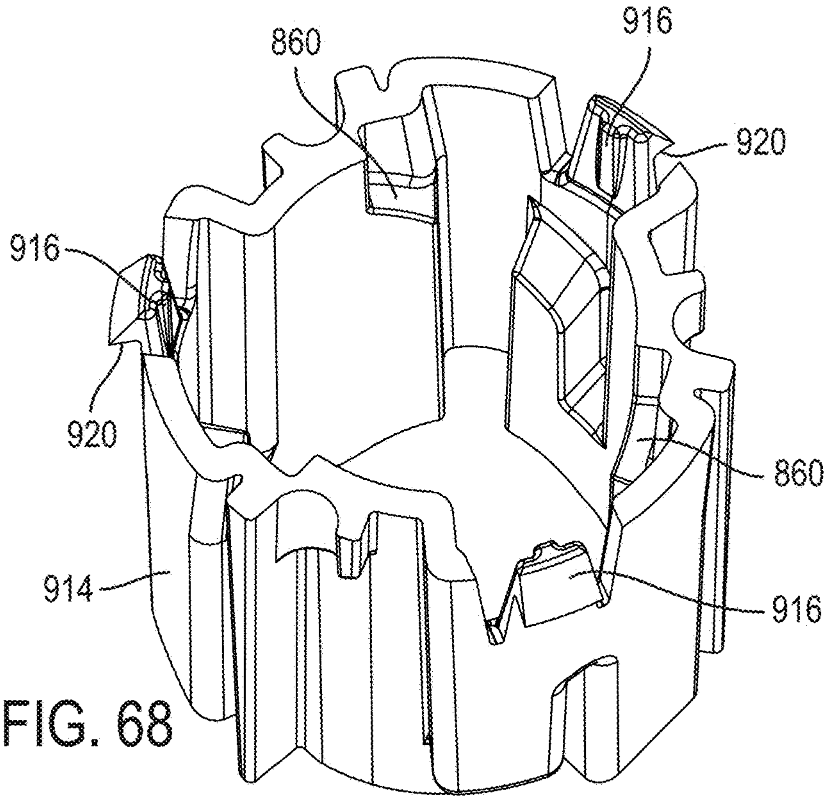
Figure 69:
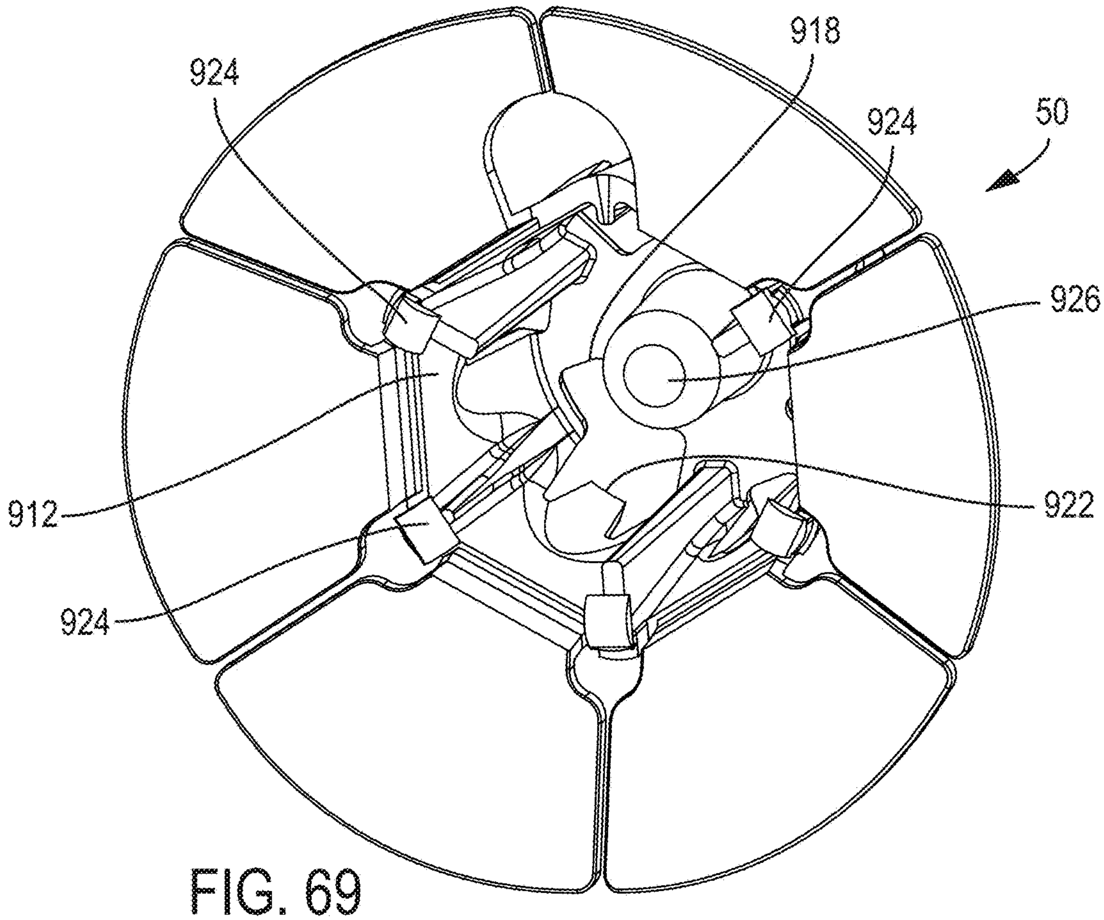
Figure 70:
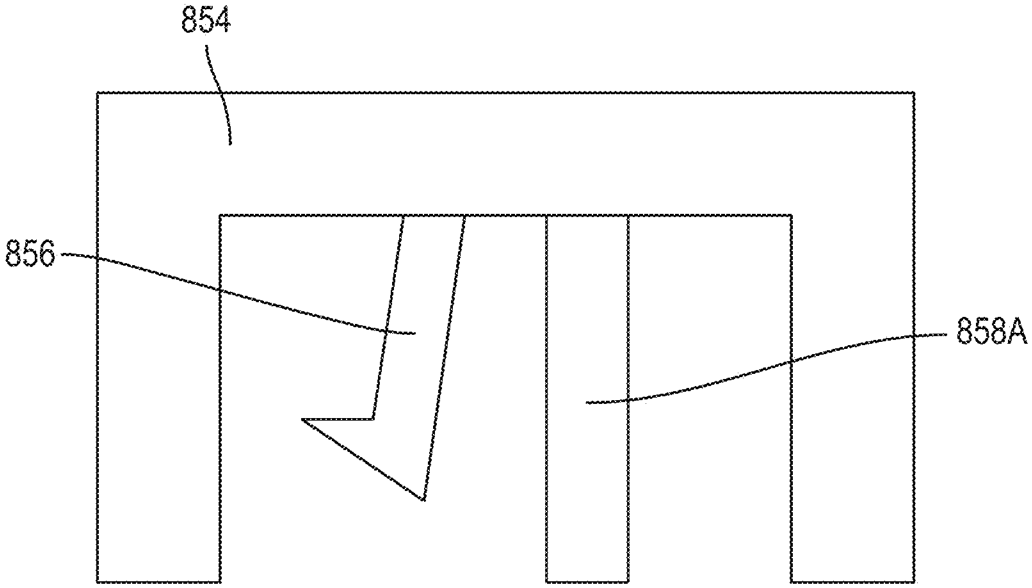
Figure 71A:
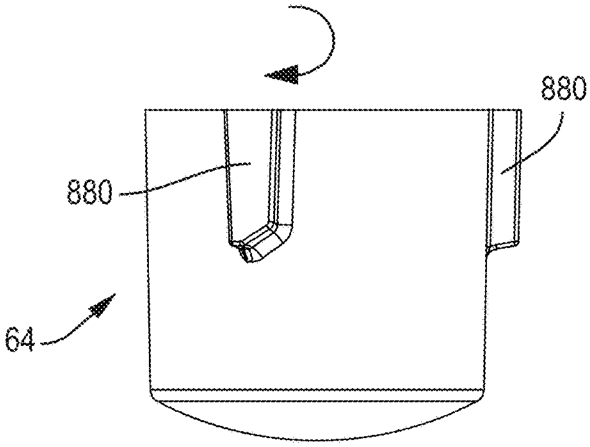
Figure 71B:
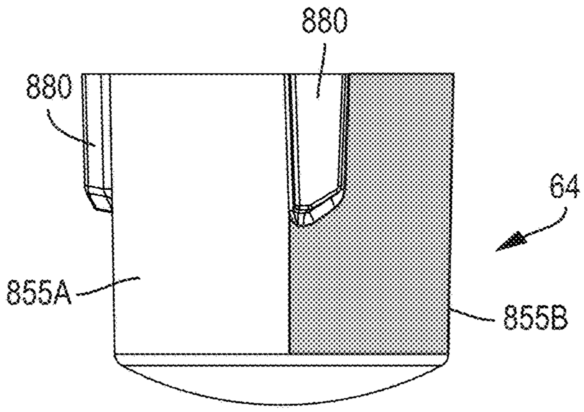

FIG. 62 depicts a block diagram of an example delivery device having a delivery unit and a trigger unit in accordance with various aspects and embodiments of the present disclosure;

FIG. 63A depicts an illustrative diagram of an example guide which may be including in a delivery unit of certain example delivery devices in accordance with various aspects and embodiments of the present disclosure;

FIG. 63B depicts and illustrative diagram of an portions of an example delivery device in an initial state in accordance with various aspects and embodiments of the present disclosure;

FIG. 63C depicts an illustrative diagram of portions of an example delivery device in a state in which pressure has been applied to a trigger body of the example delivery device in accordance with various aspects and embodiments of the present disclosure;

FIG. 63D depicts an illustrative diagram of an example delivery device transitioned into a trigger state in accordance with various aspects and embodiments of the present disclosure;

FIG. 63E depicts an illustrative diagram of an example delivery device at the end of a first stage of actuation of the delivery device in accordance with various aspects and embodiments of the present disclosure;

FIG. 63F depicts an illustrative diagram of an example delivery device at the end of a second stage of actuation of the delivery device in accordance with various aspects and embodiments of the present disclosure;

FIG. 64A depicts an exploded perspective view of an exemplary delivery device with a trigger unit and a delivery unit in accordance with various aspects and embodiments of the present disclosure;

FIG. 64B depicts another exploded perspective view of an exemplary delivery device with a trigger unit and a delivery unit in accordance with various aspects and embodiments of the present disclosure;

FIG. 64C depicts cross-sectioned view of a main body and trigger body of an example delivery device with a portion of a rigid guide body of the main body removed in accordance with various aspects and embodiments of the present disclosure;

FIG. 65A depicts a perspective view of an example delivery device with a lock installed thereon;

FIG. 65B depicts a cross-sectional view of a portion of an example delivery device and lock;

FIG. 66 depicts a top plan view of an example lock;

FIG. 67 depicts an exploded view of an example delivery device with a lock;

FIG. 68 depicts a perspective view of an exemplary guide insert;

FIG. 69 depicts a perspective view of an example main body of a delivery device;

FIG. 70 depicts a diagrammatic view of an example trigger body for a delivery device;

FIGS. 71A-71B depict views of an example reservoir interface member having regions of contrasting appearance.

Figure 72A:
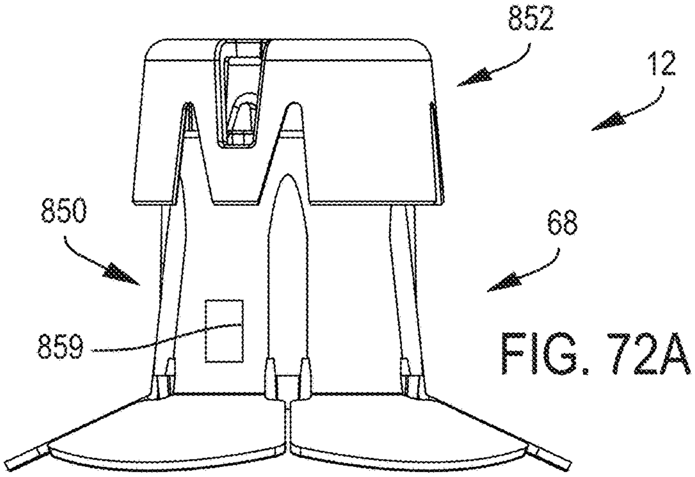
Figure 72B:
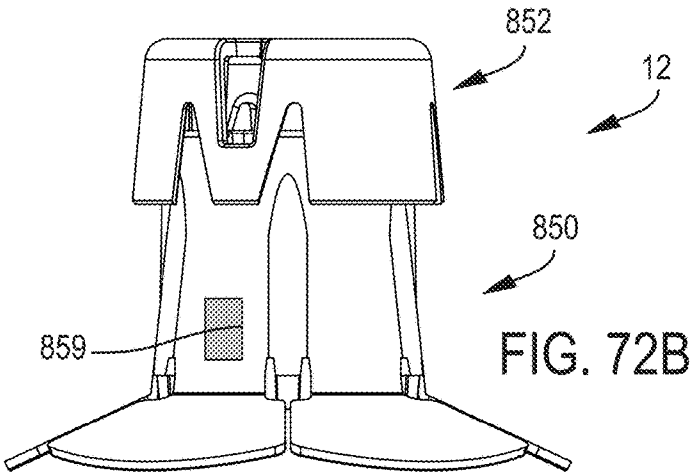
Figure 74A:
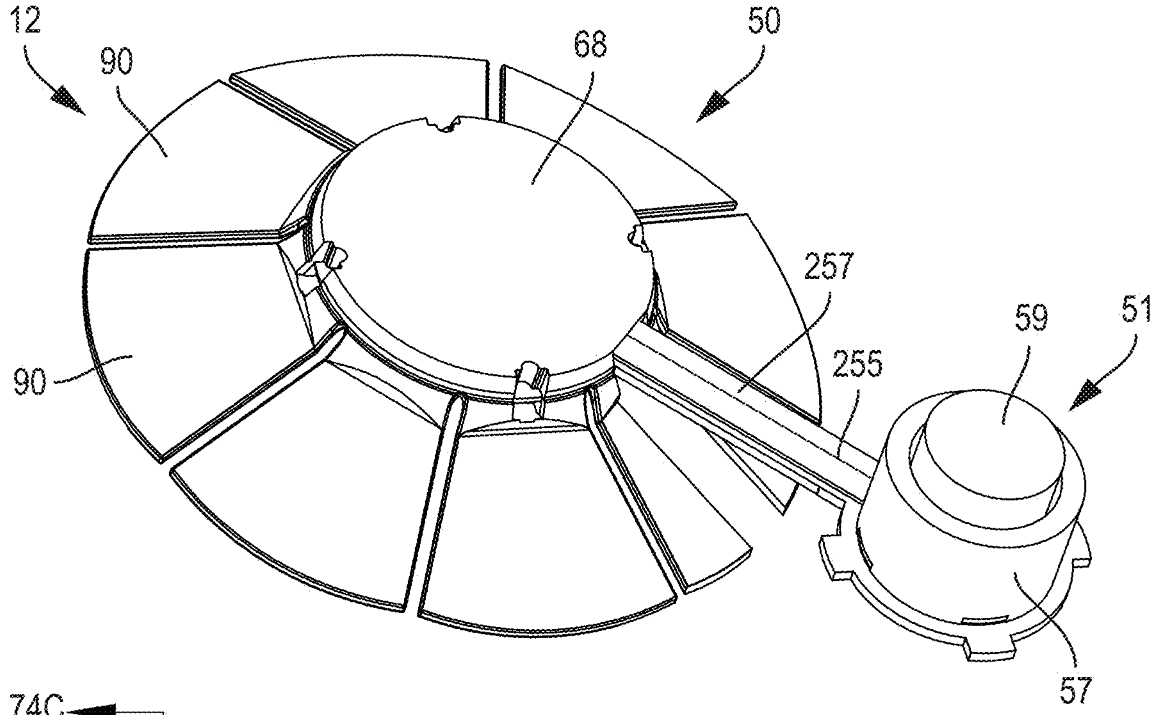
Figure 74B:
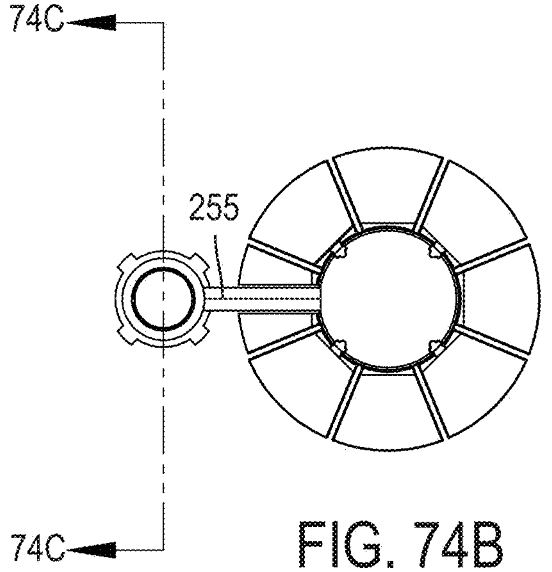
Figure 74C:
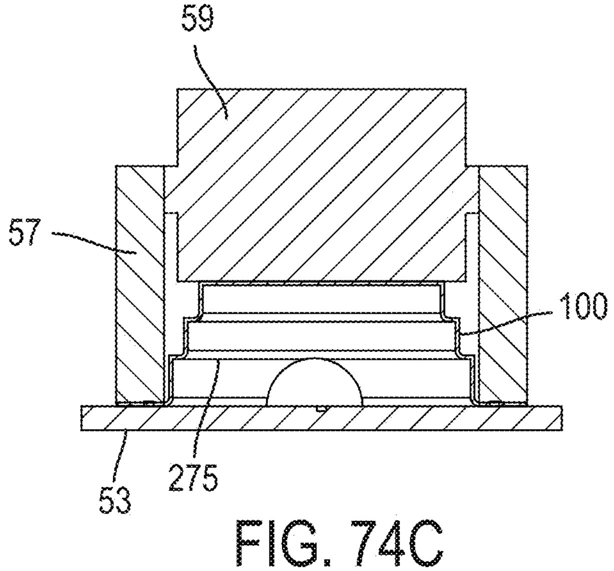
Figure 75:
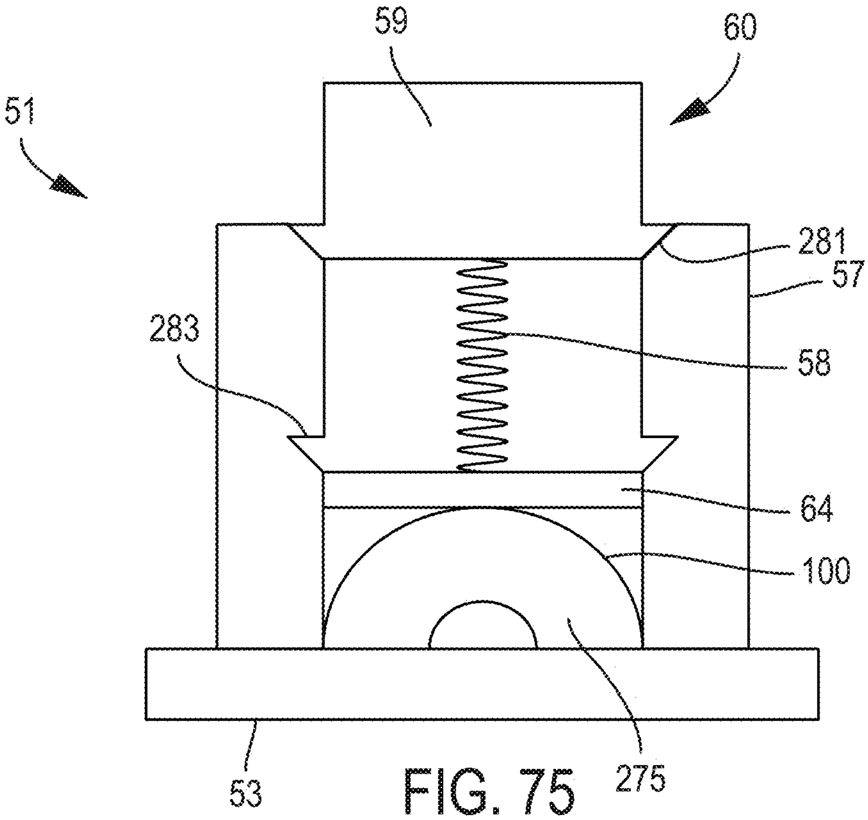
Figure 76:
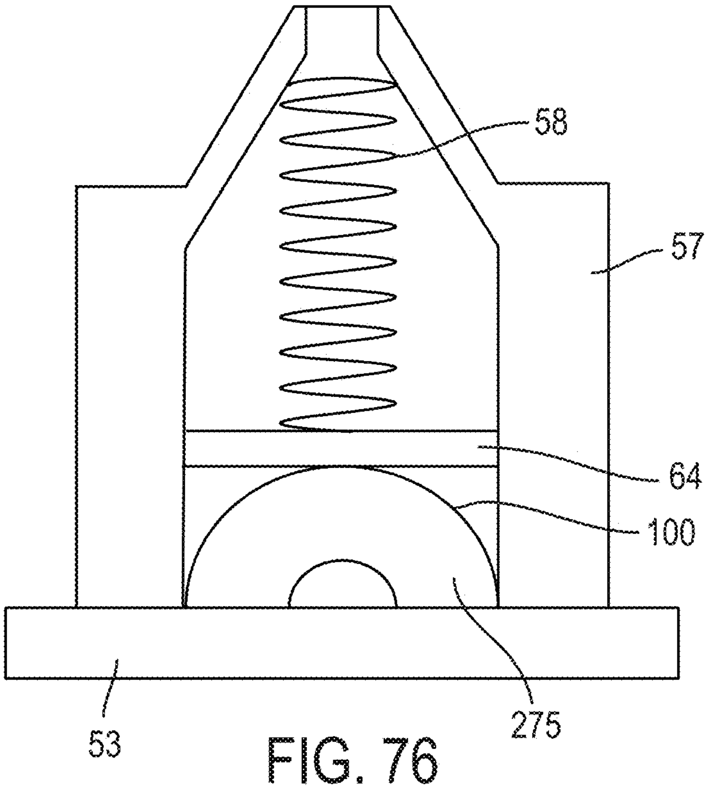
Figure 77:
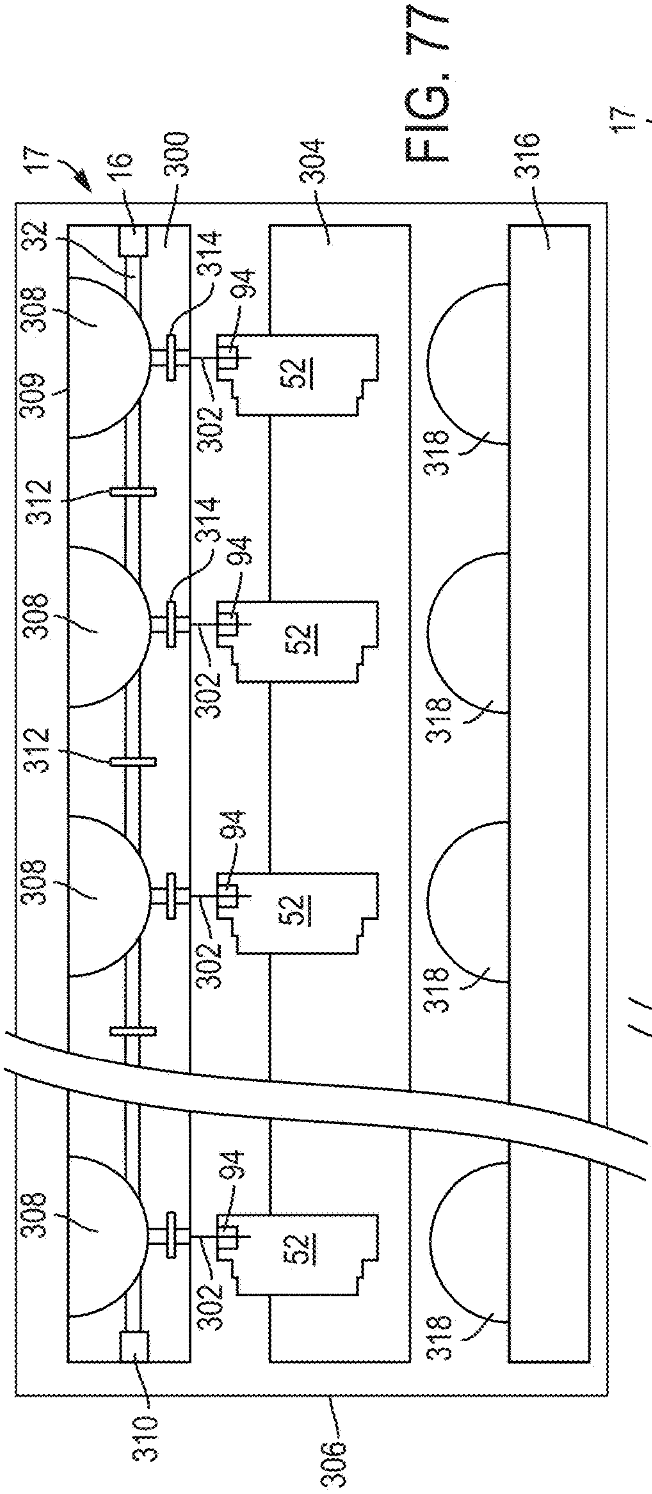
Figure 78:
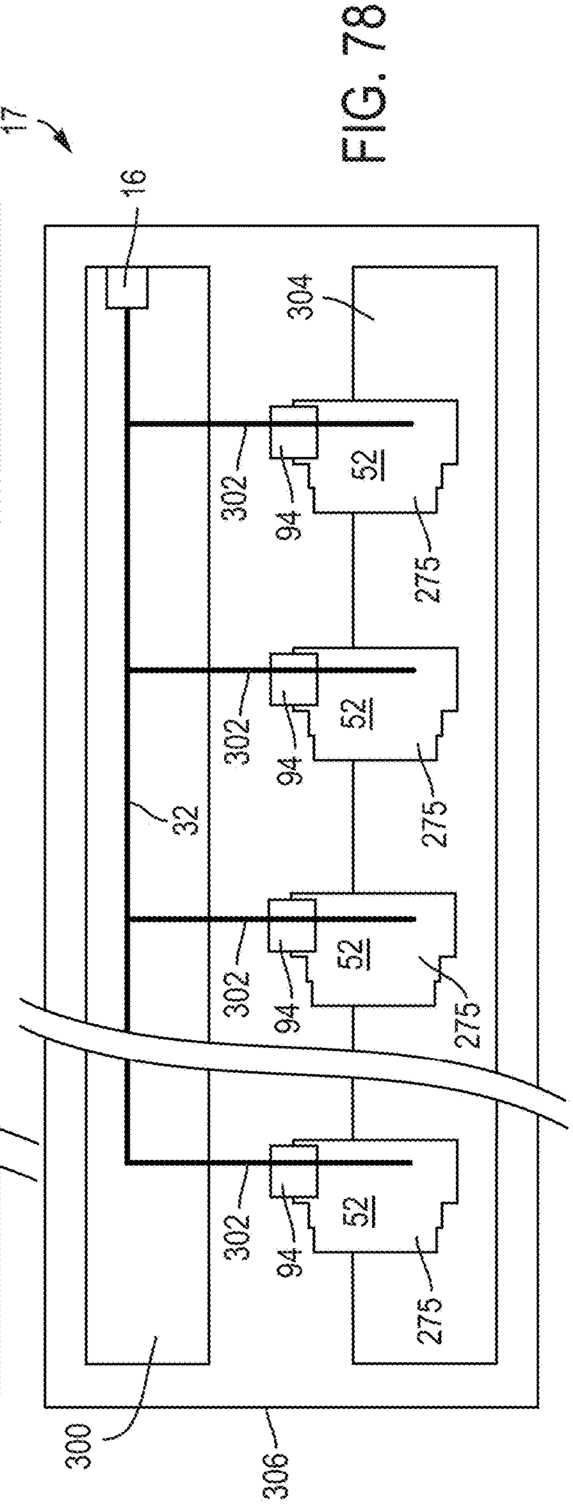
Figures 79, 80:
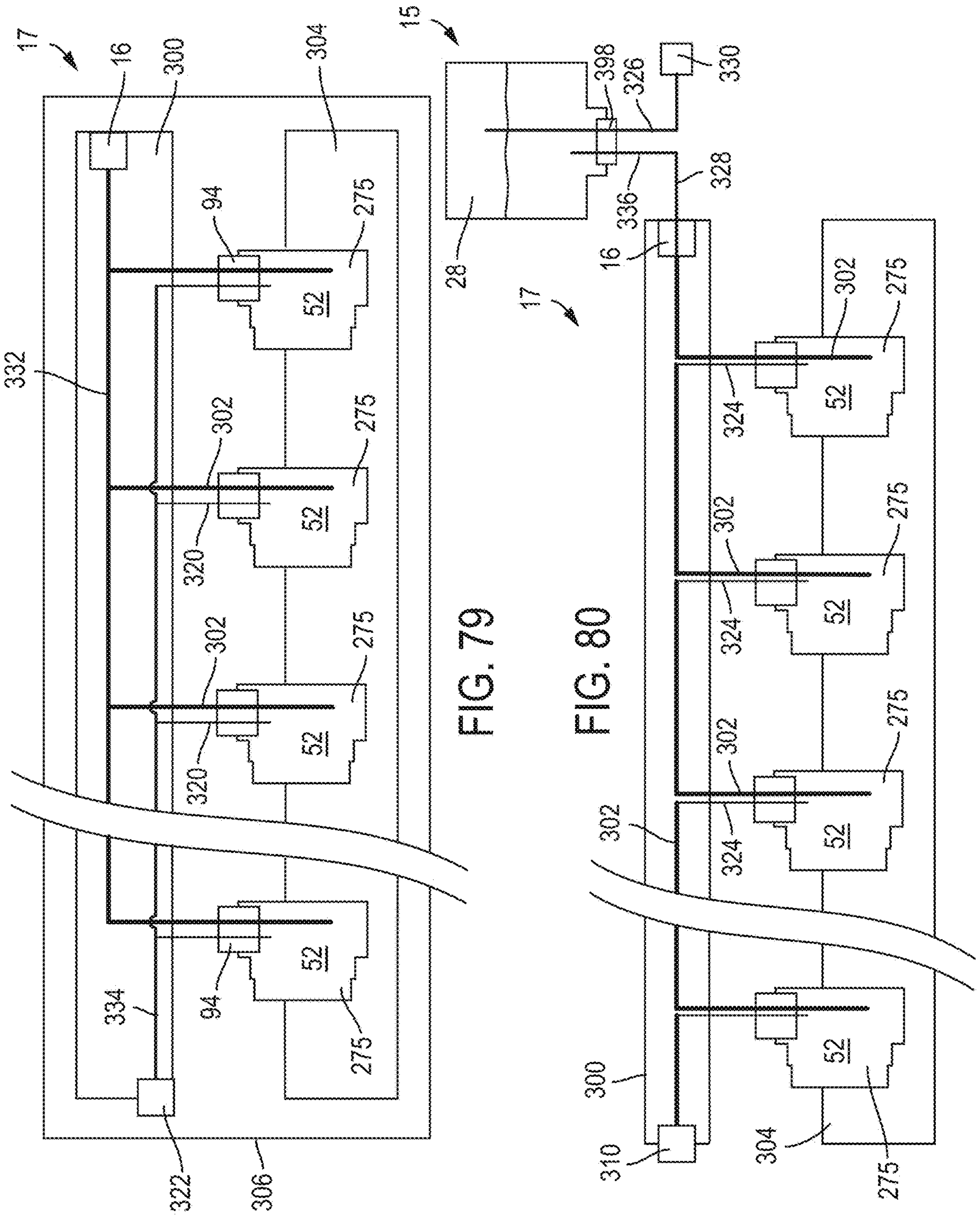
Figure 81A:
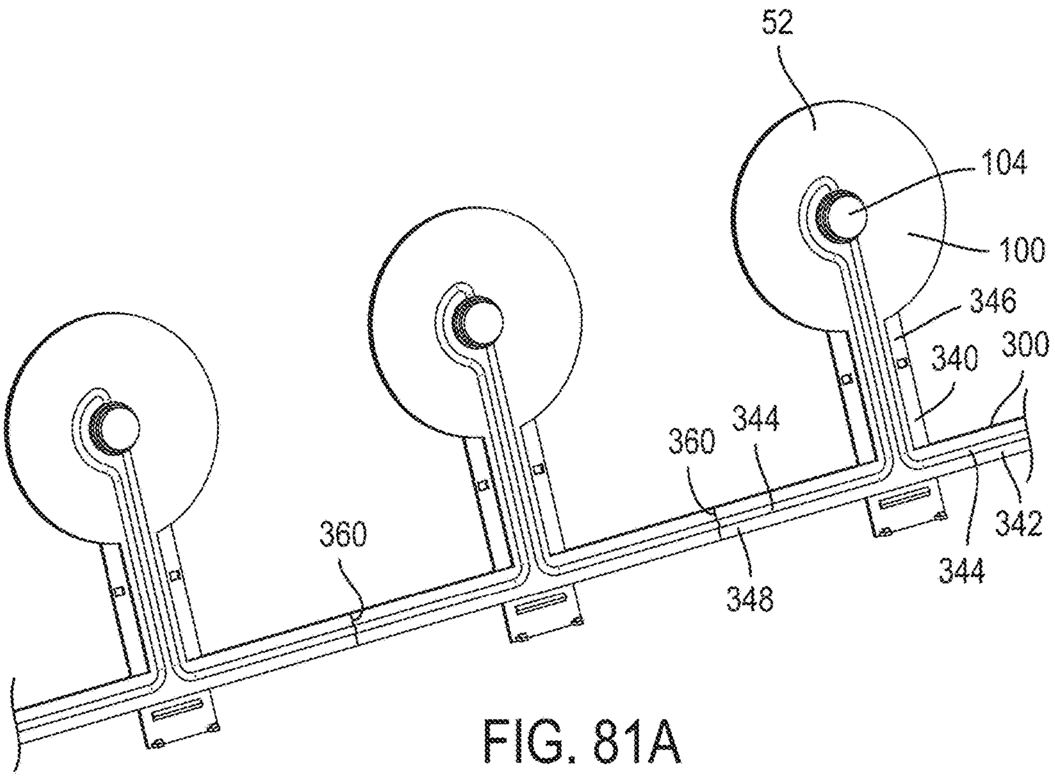
Figure 81B:
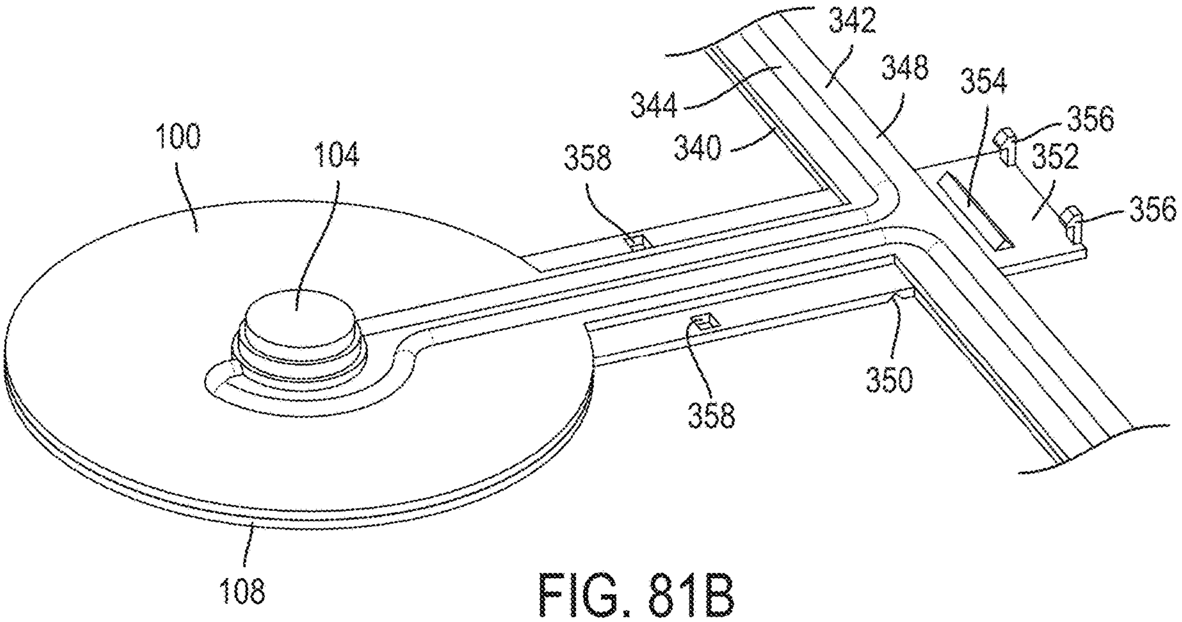
Figure 82:
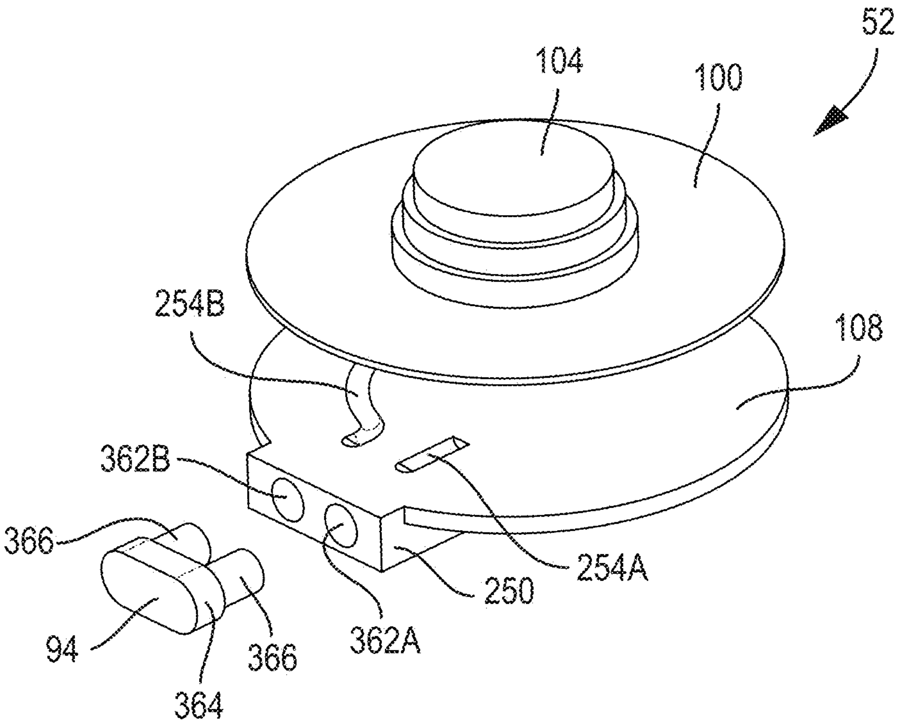
Figure 83:
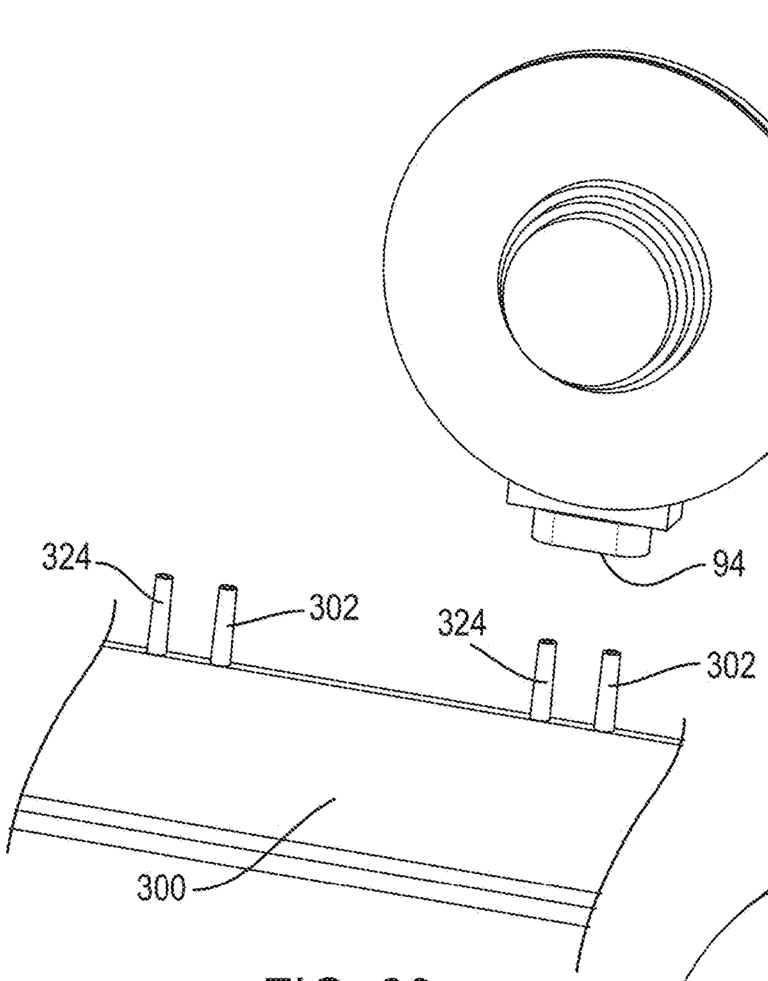
Figure 84:
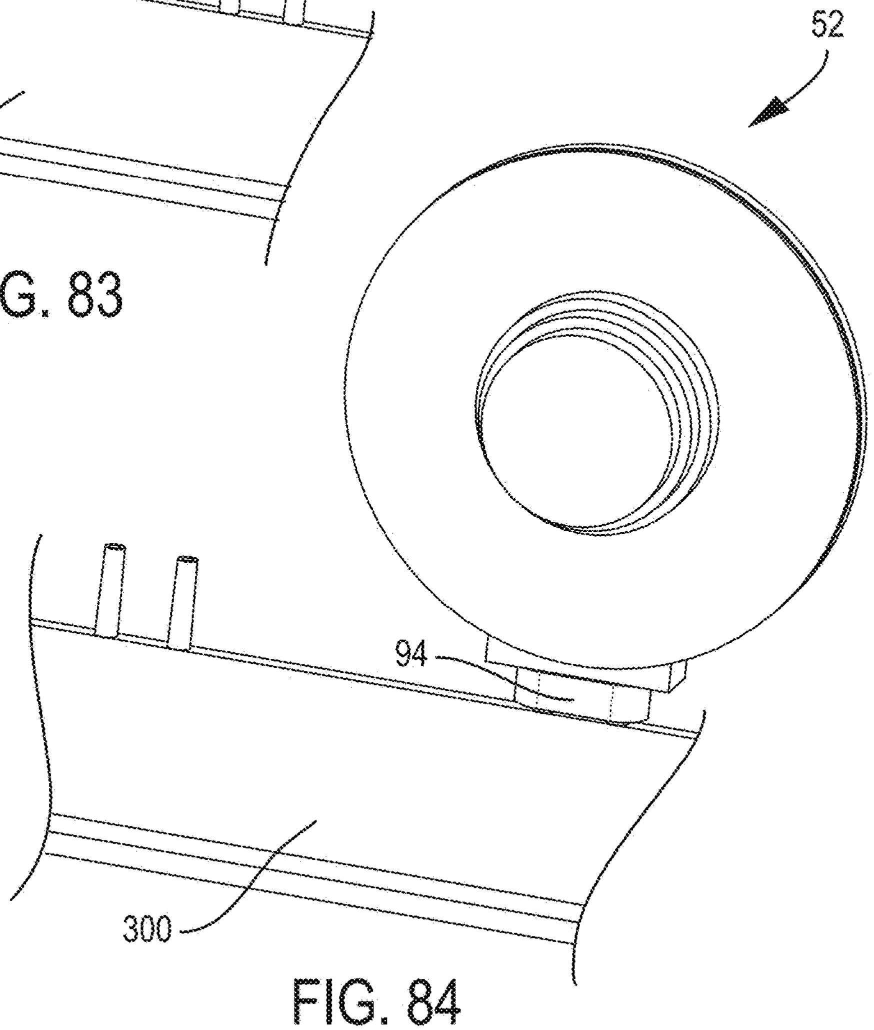
Figures 85, 86, 87, 88:
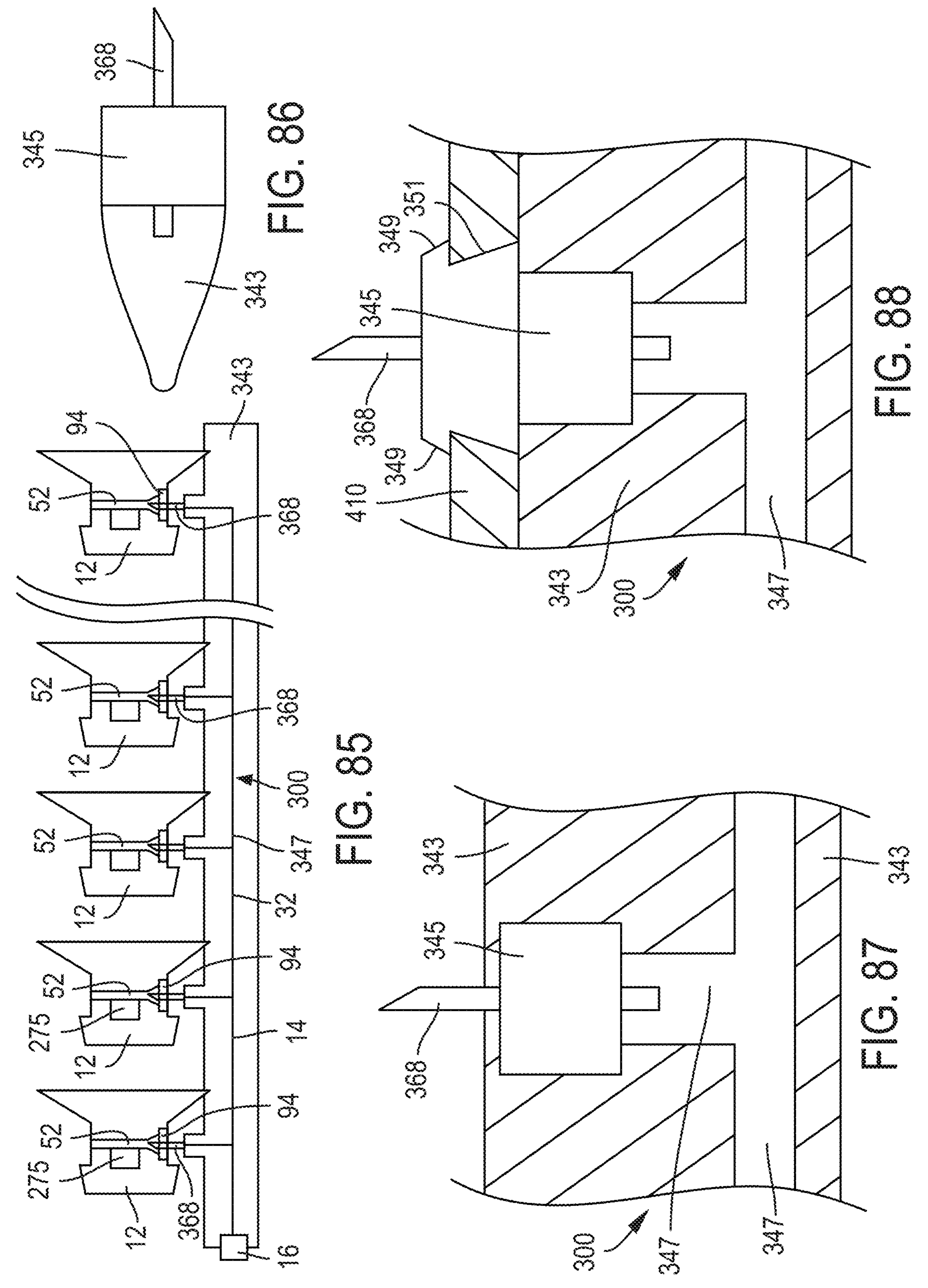
Figure 89:
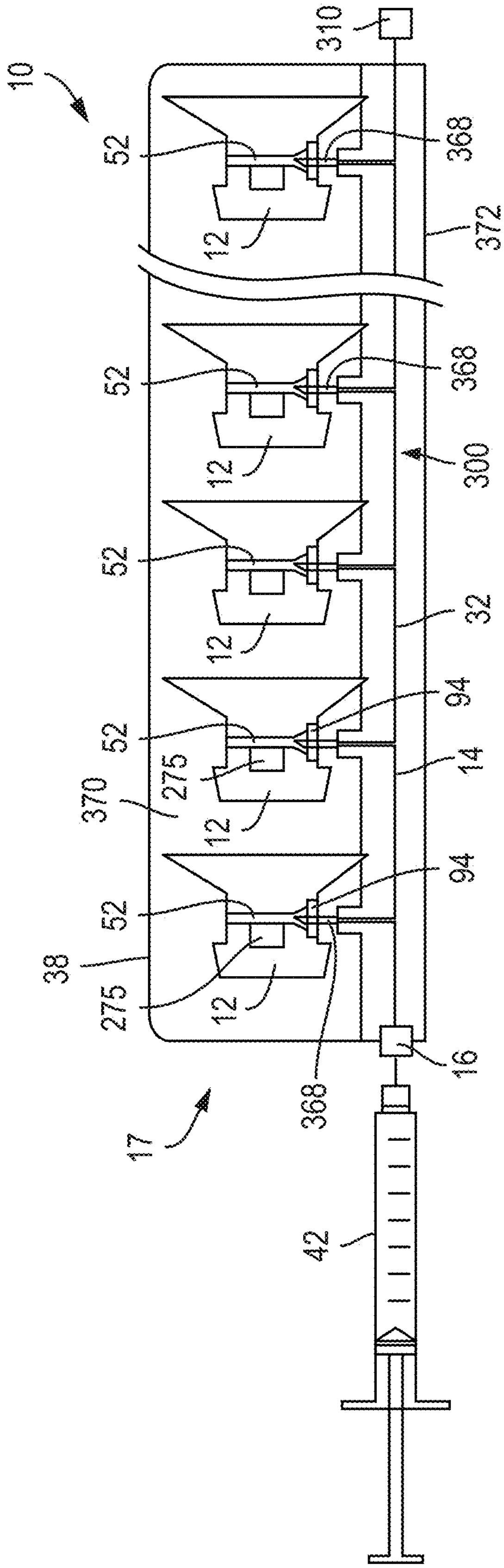
Figure 90:
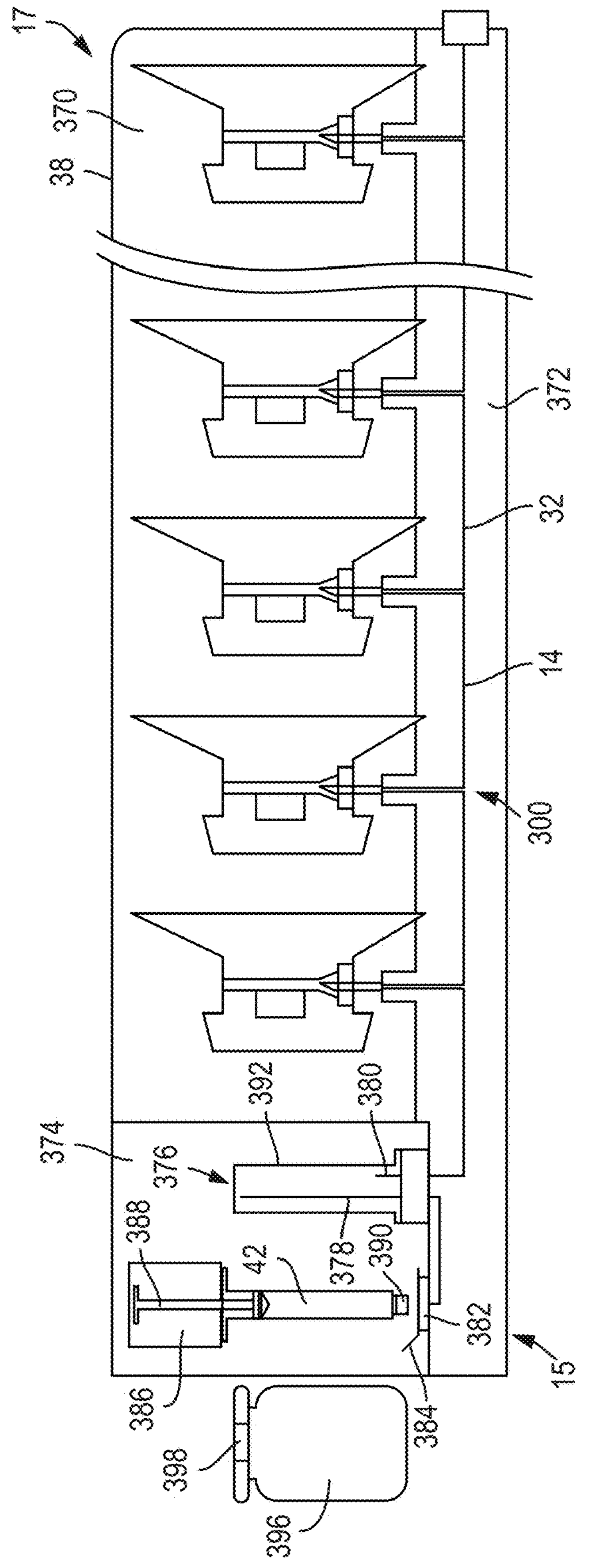
Figure 91:
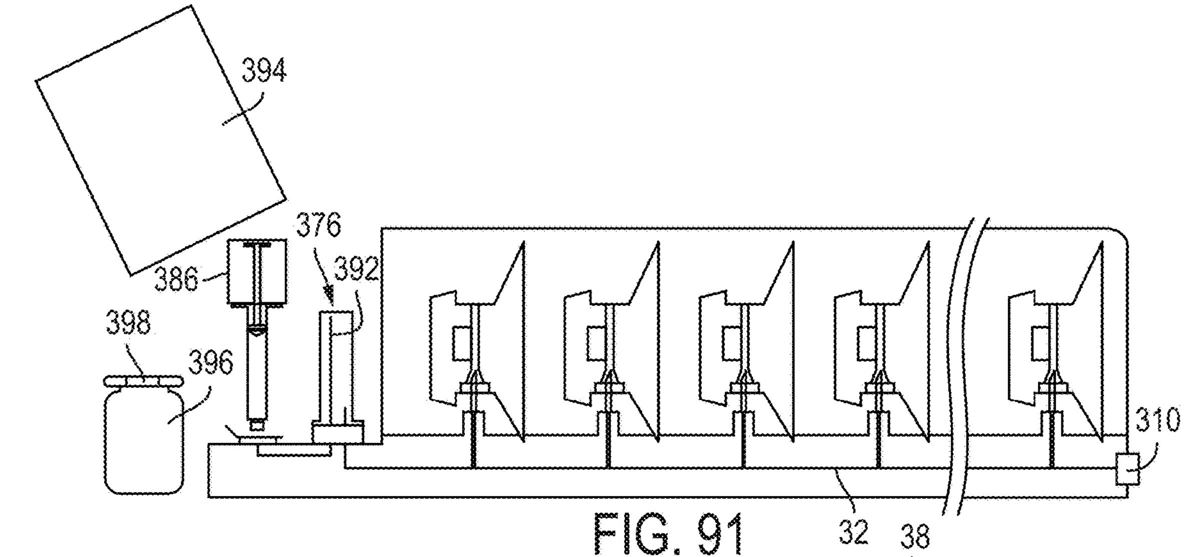
Figure 92:
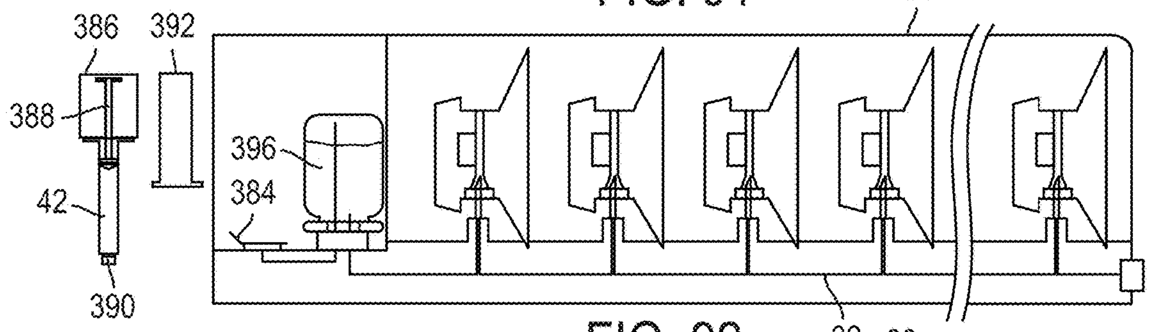
Figure 93:
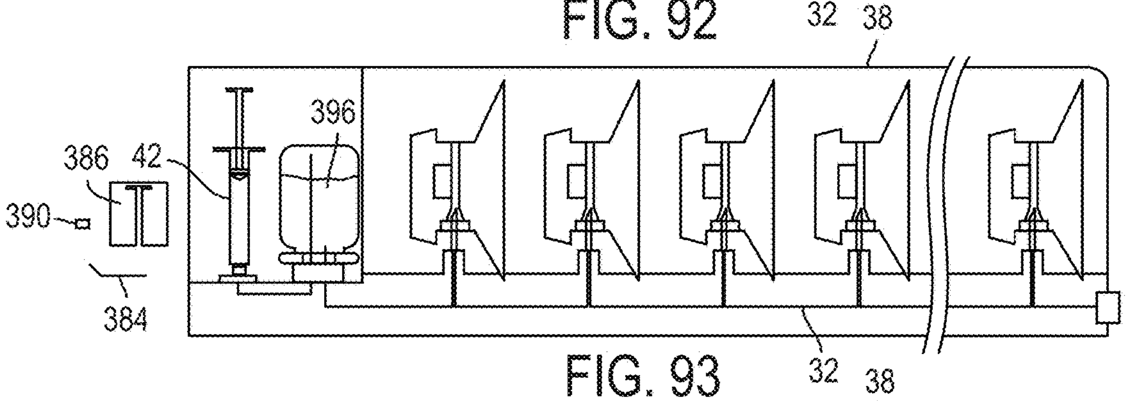
Figure 94:
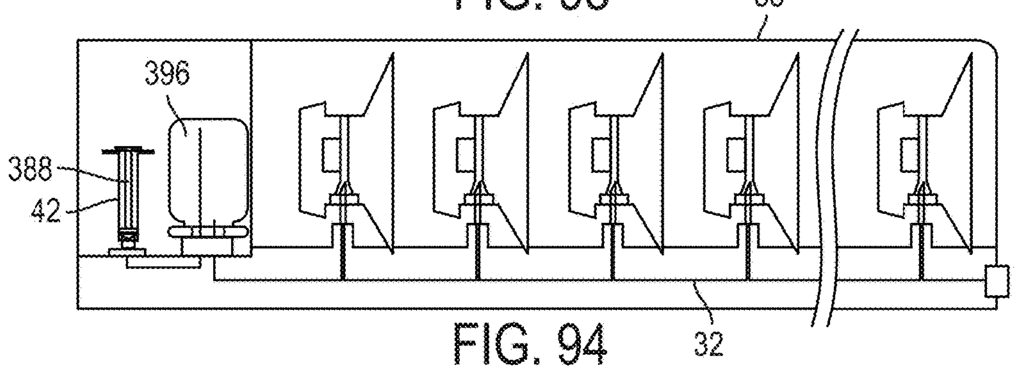
Figure 95:
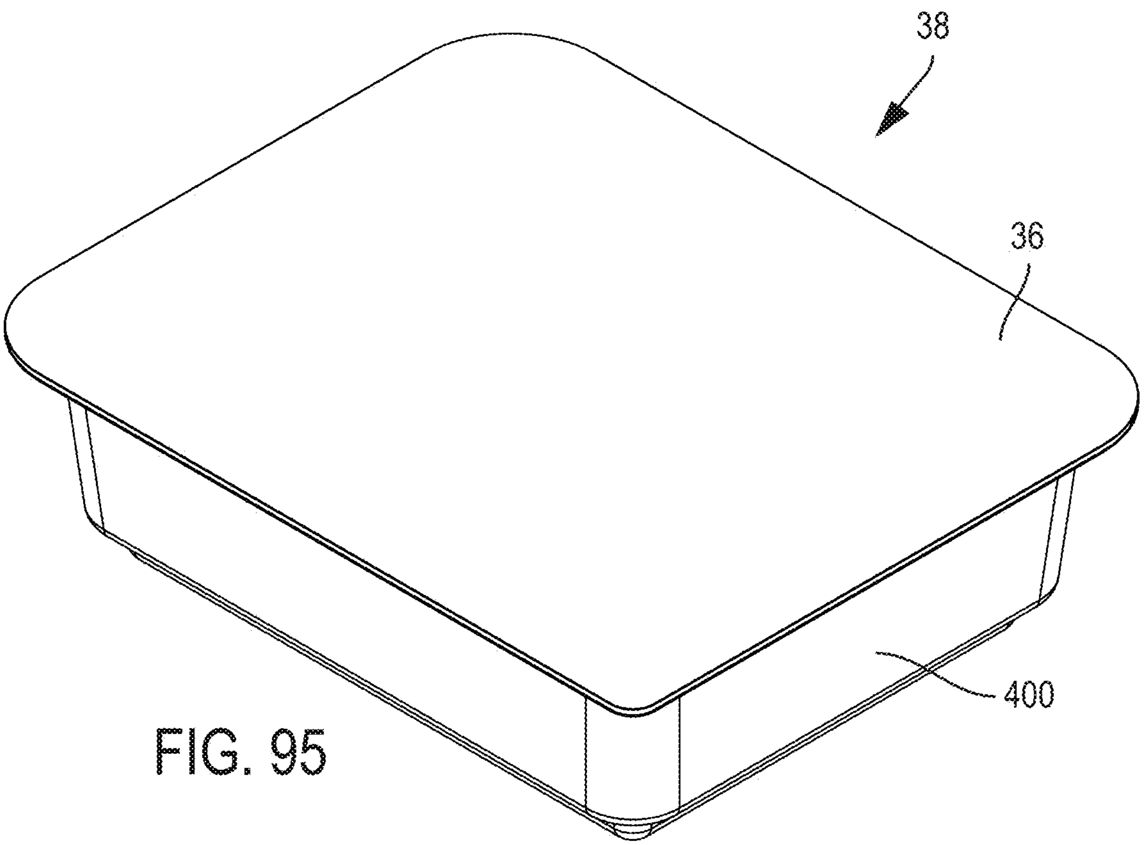
Figure 96:
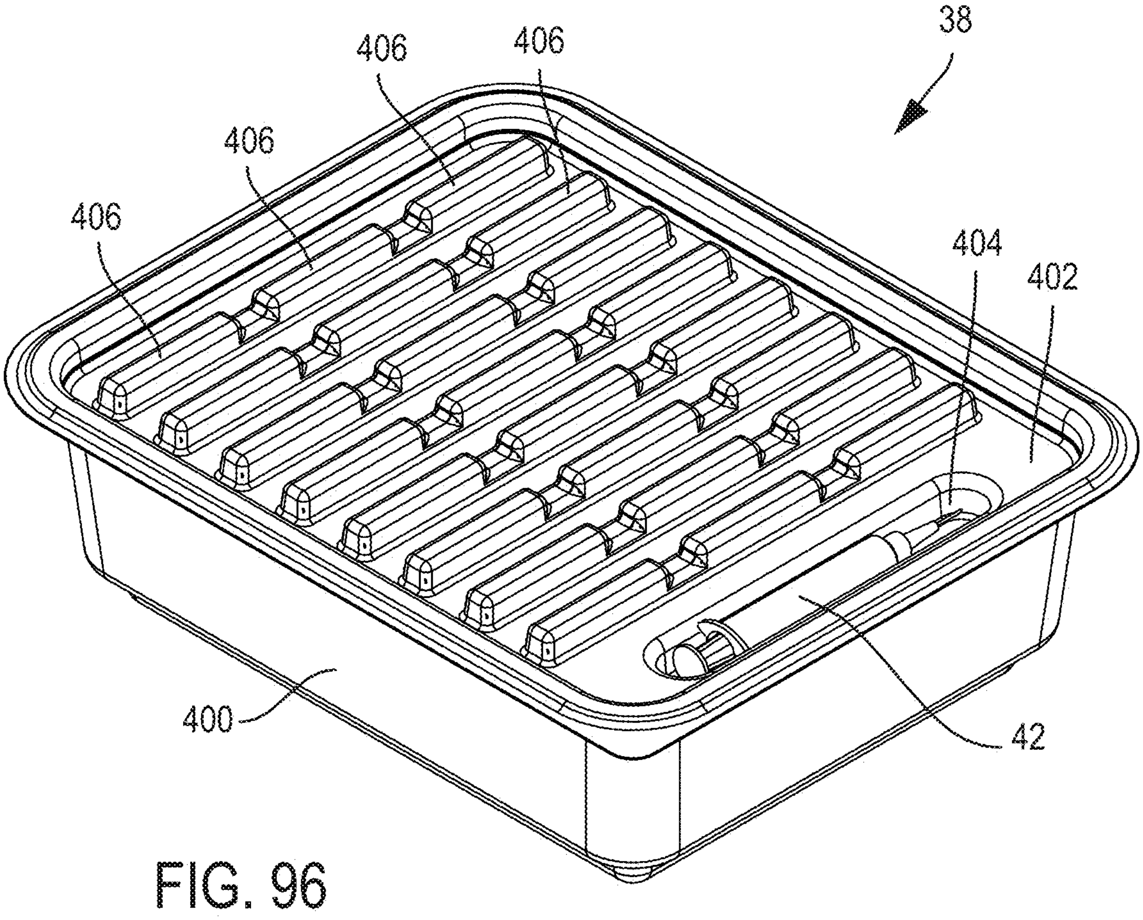
Figure 97:
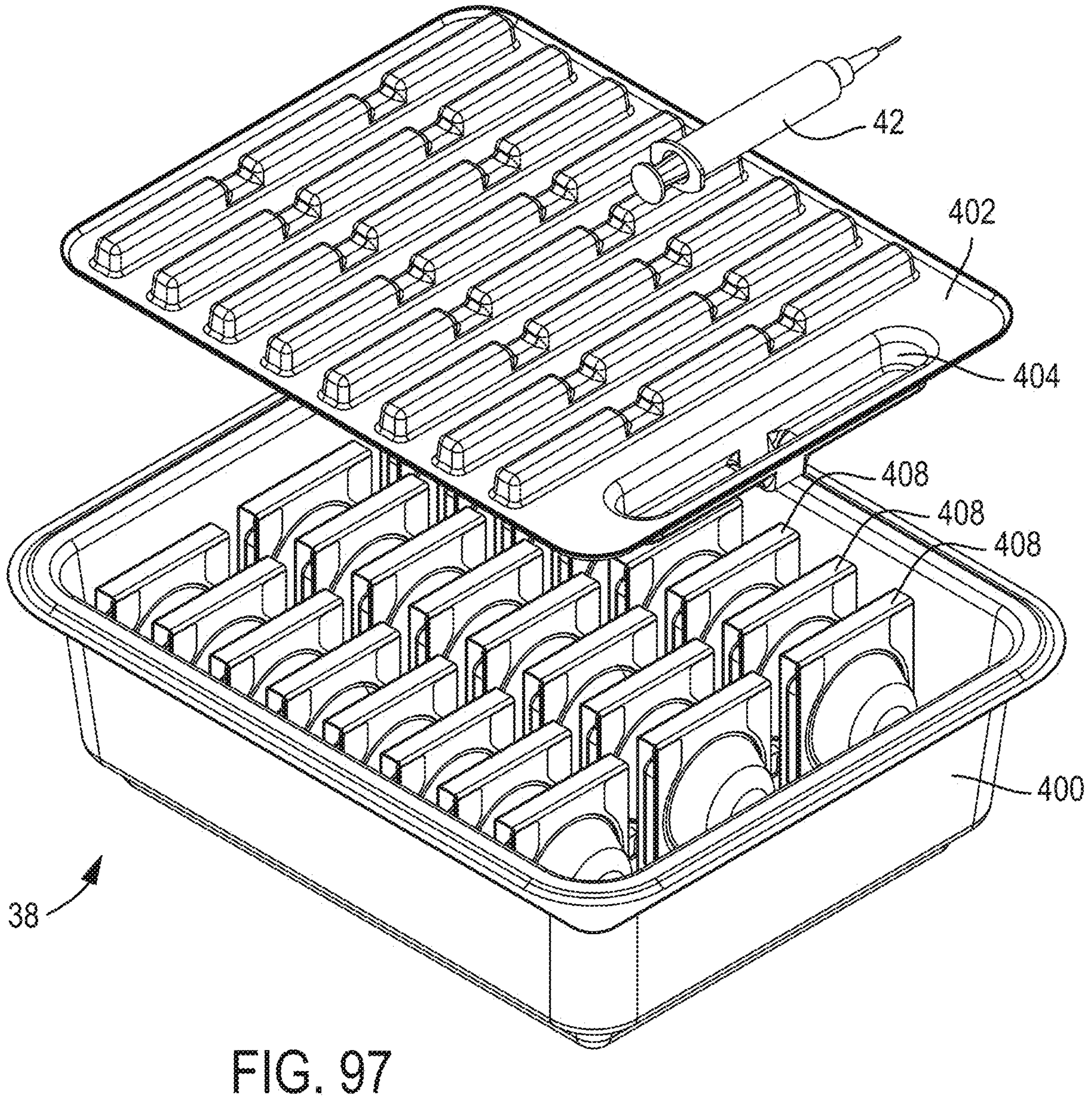
Figure 98:
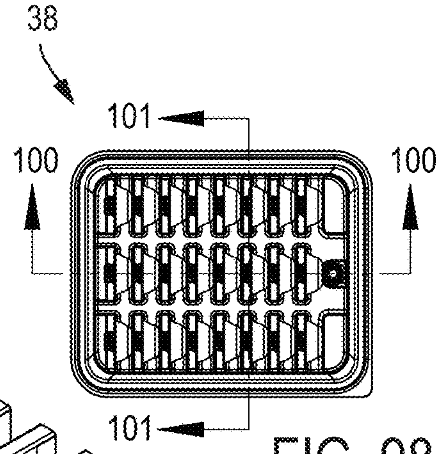
Figure 99:
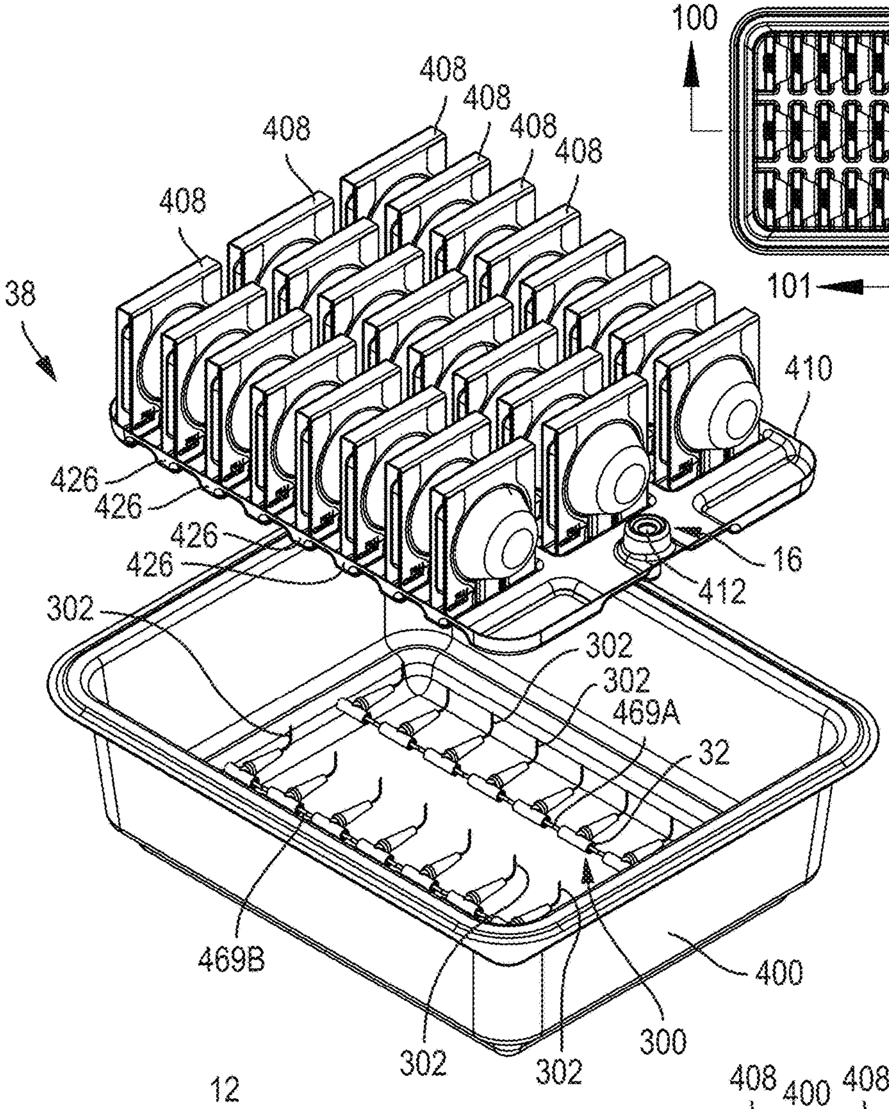
Figure 100:
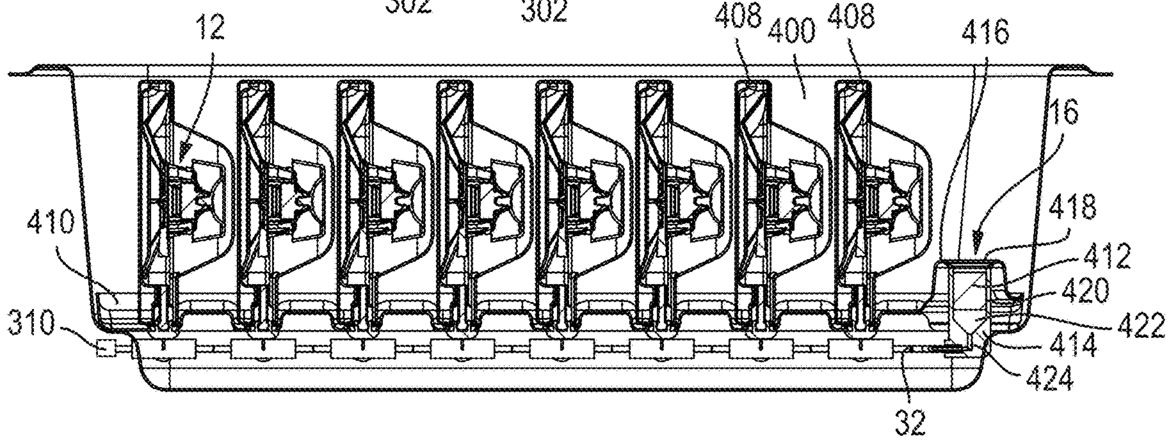
Figure 101:
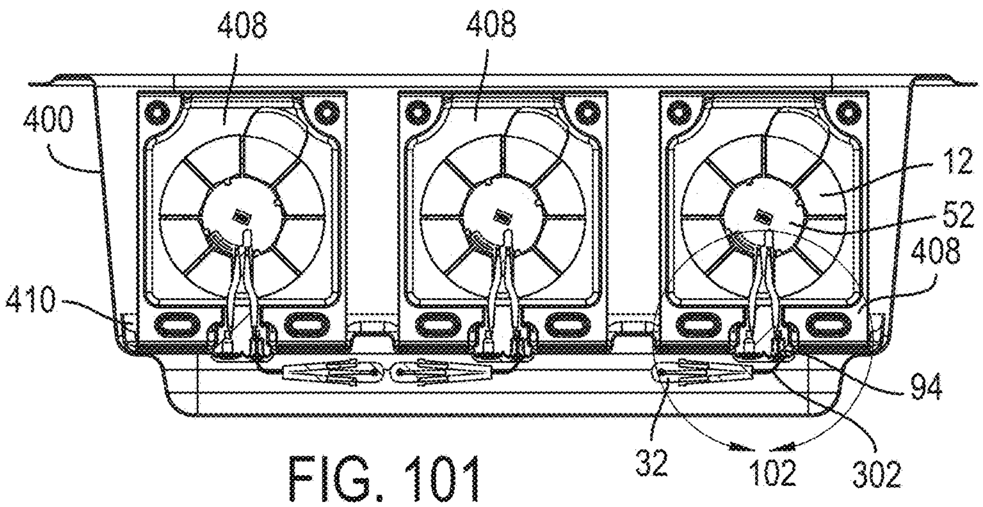
Figure 102:
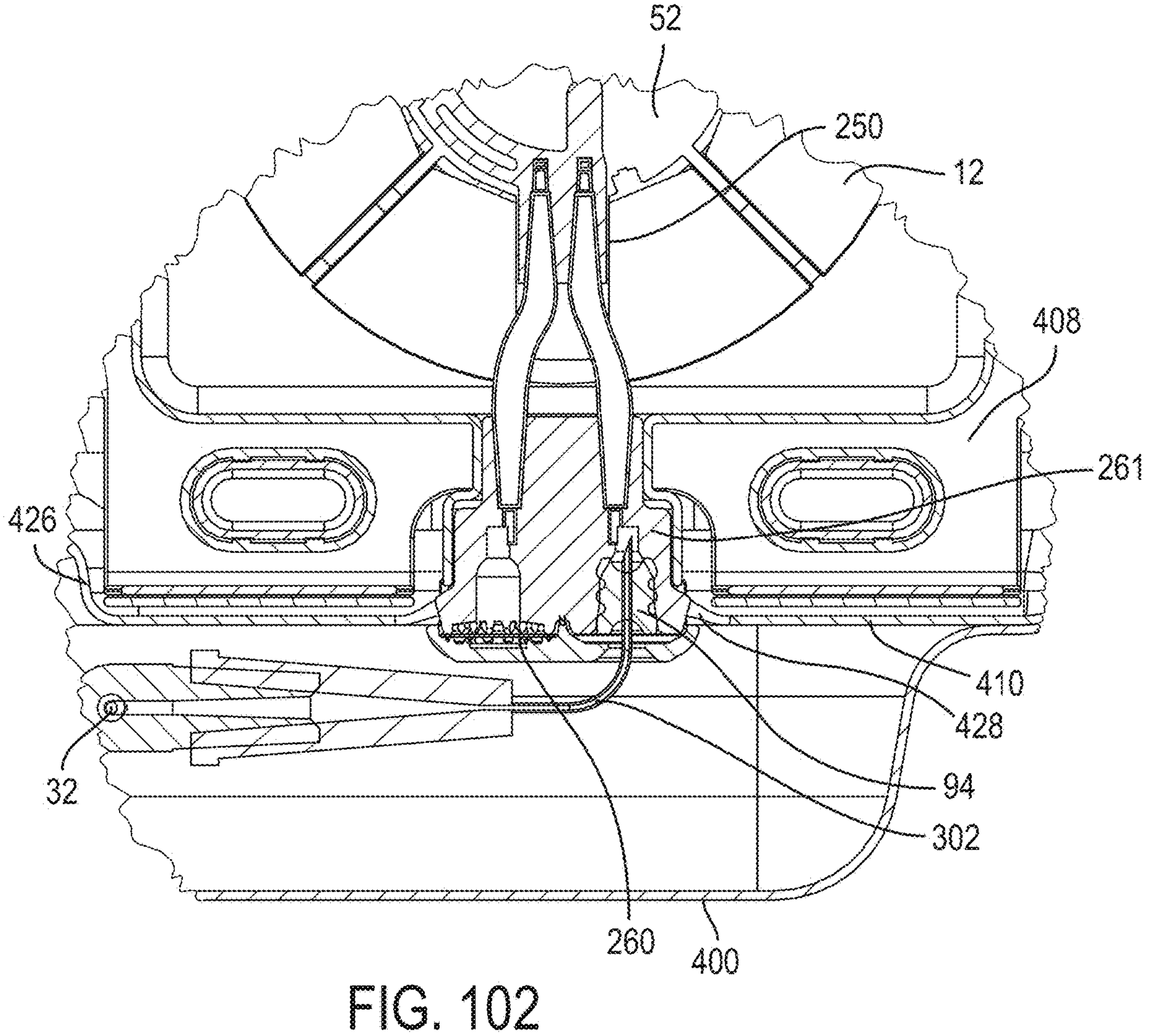
Figure 103:
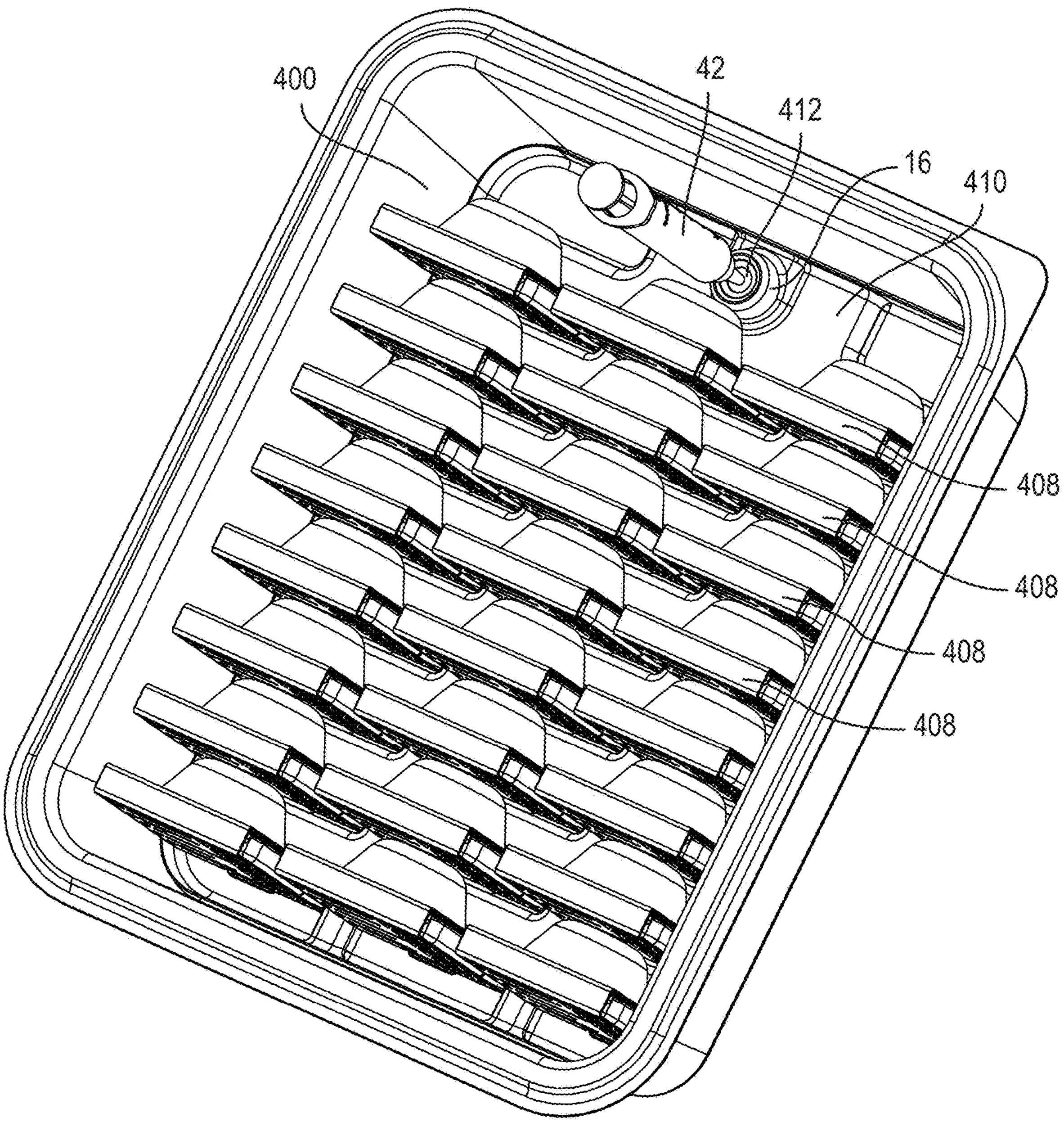
Figure 104:
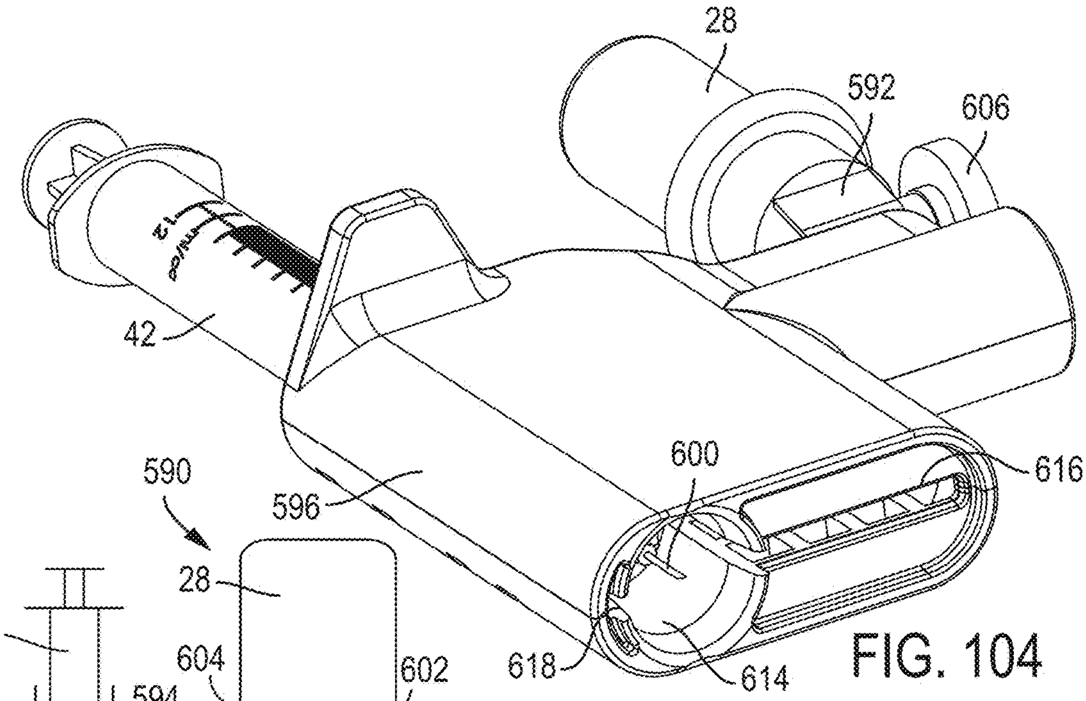
Figure 105:
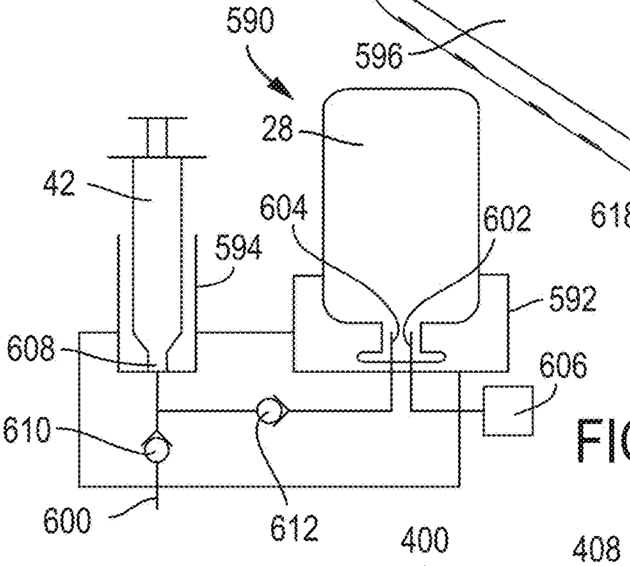
Figure 106A:
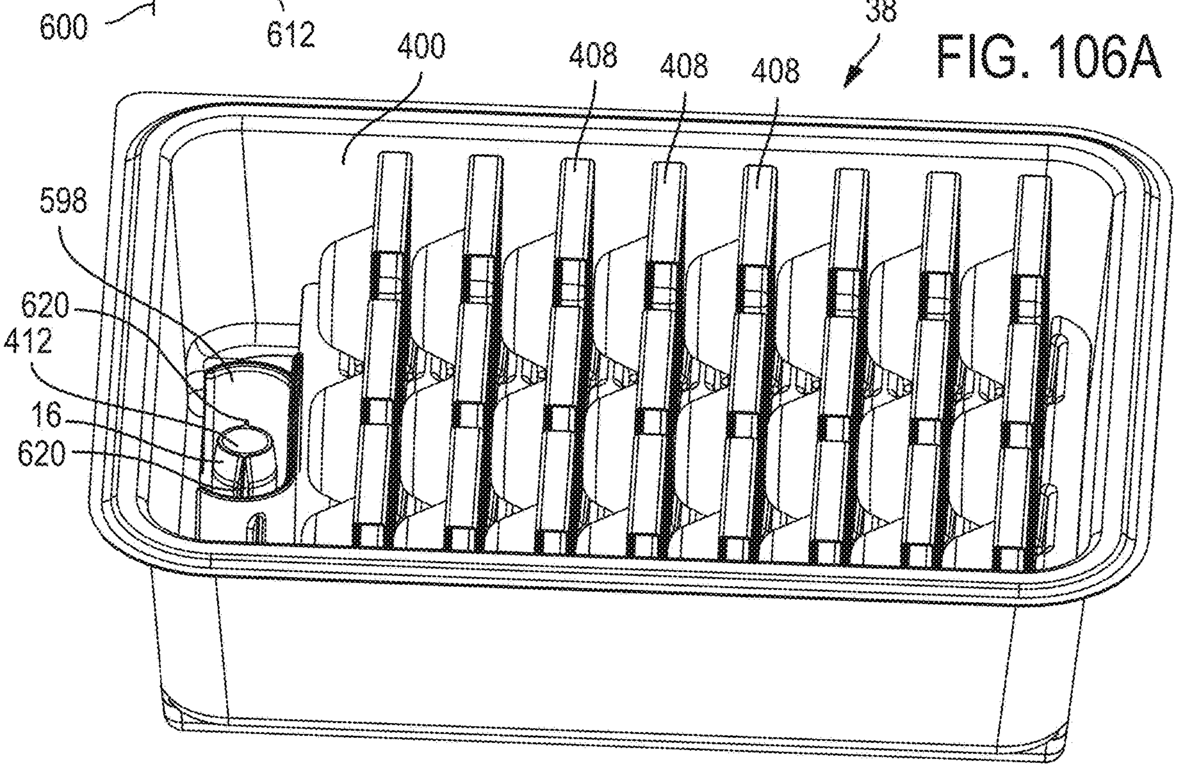
Figure 106B:
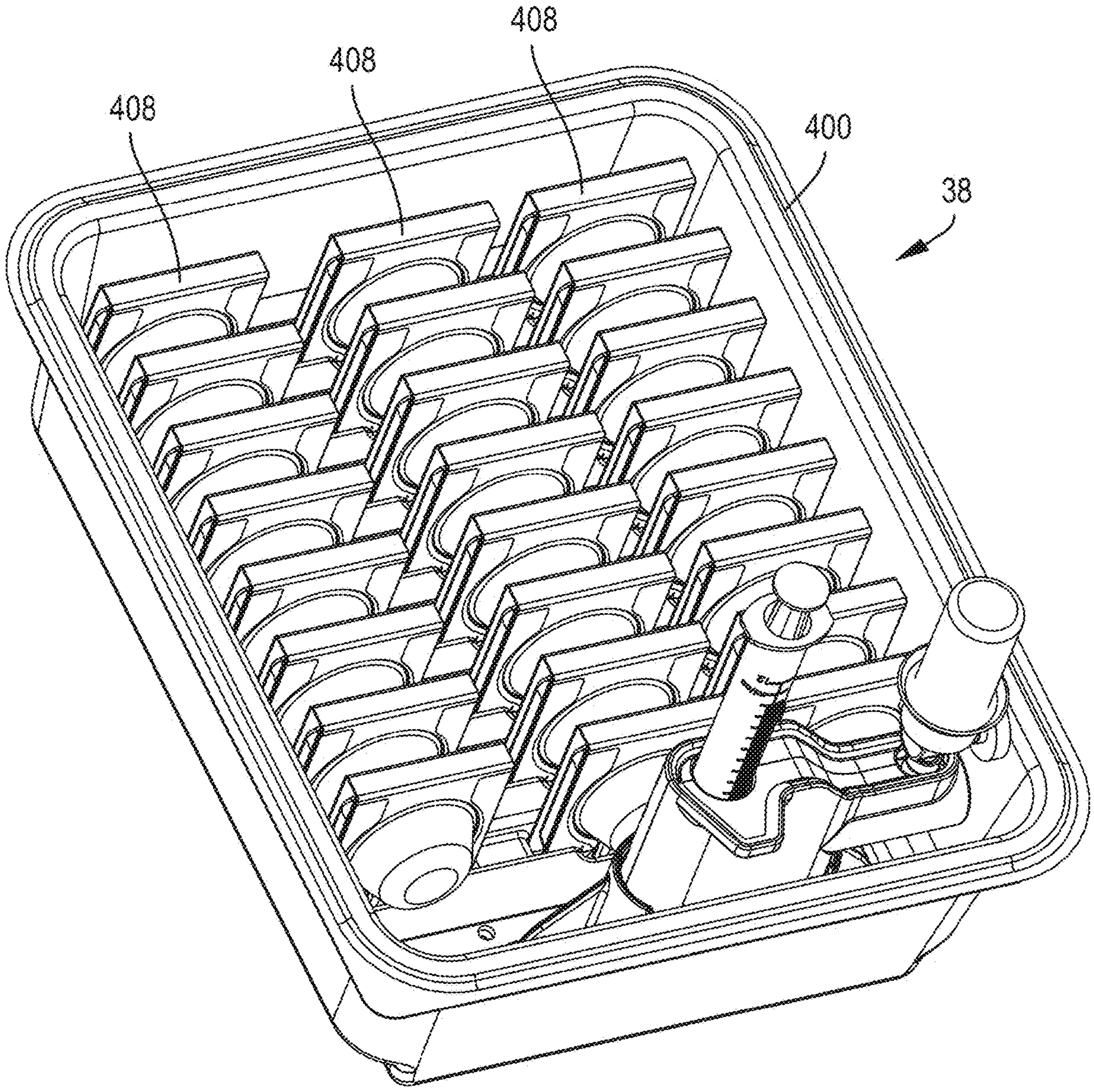
Figure 107:
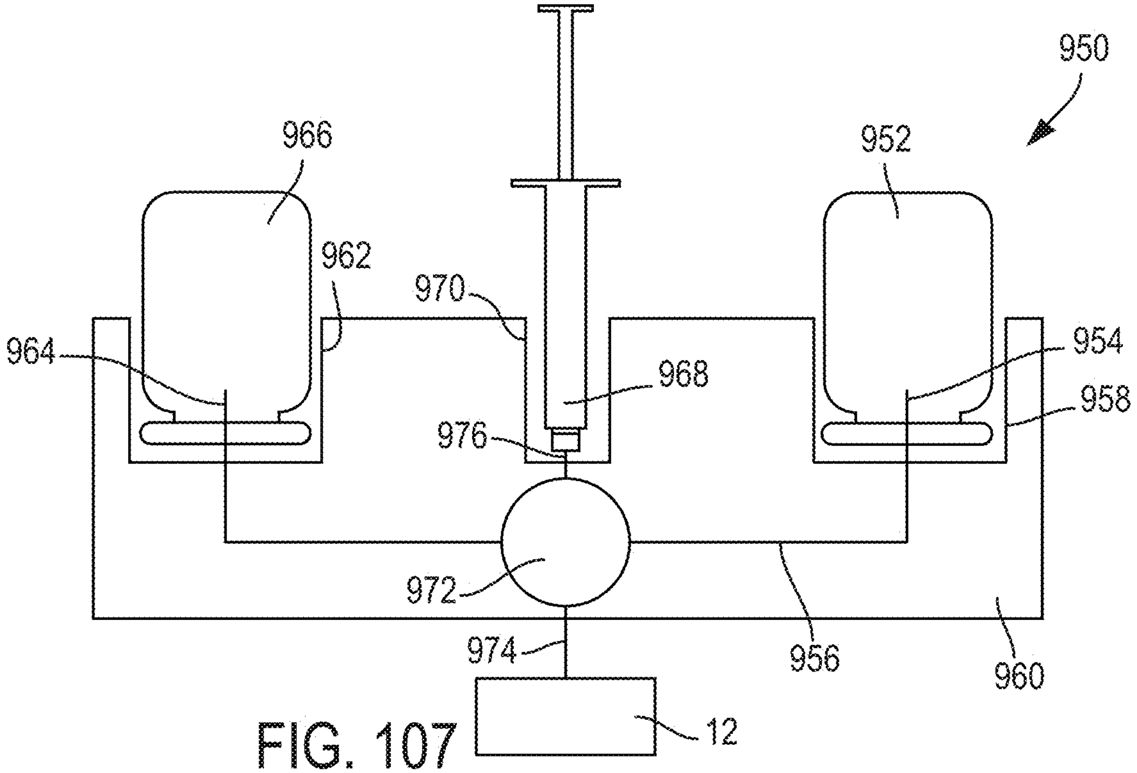
Figure 108:
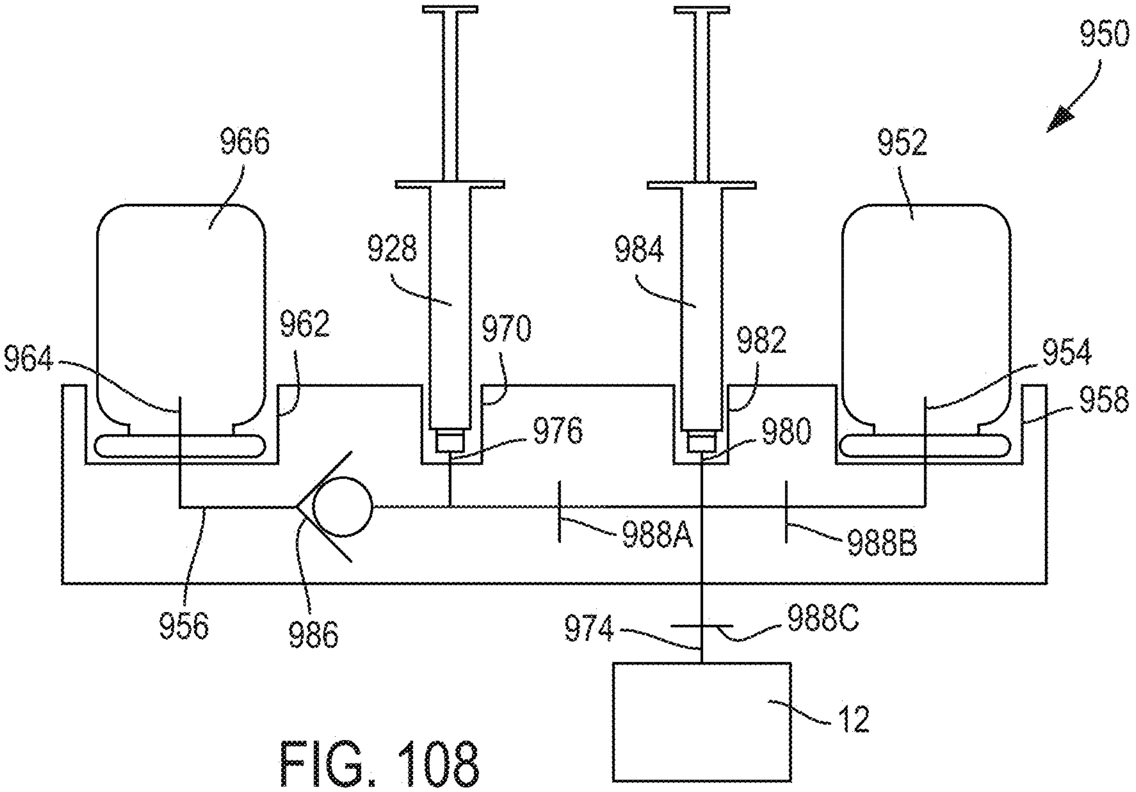
Figure 109:
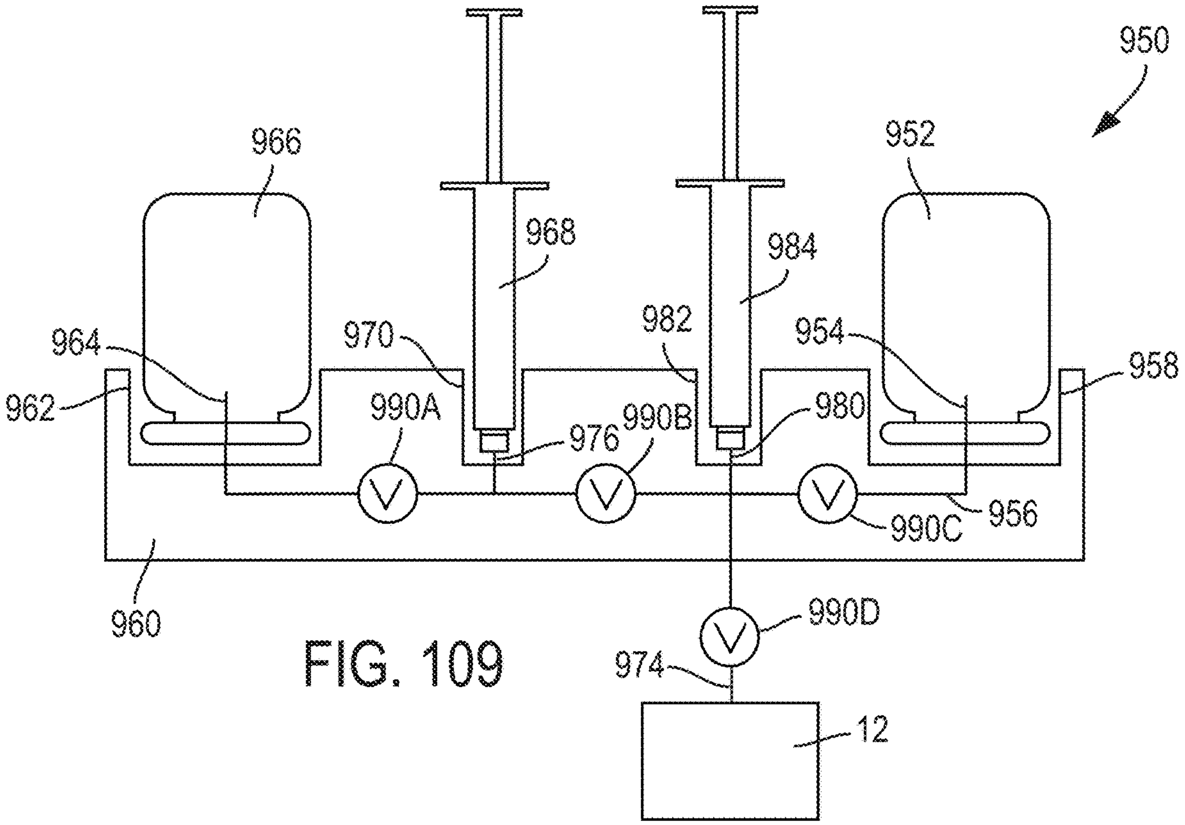
Figure 110:
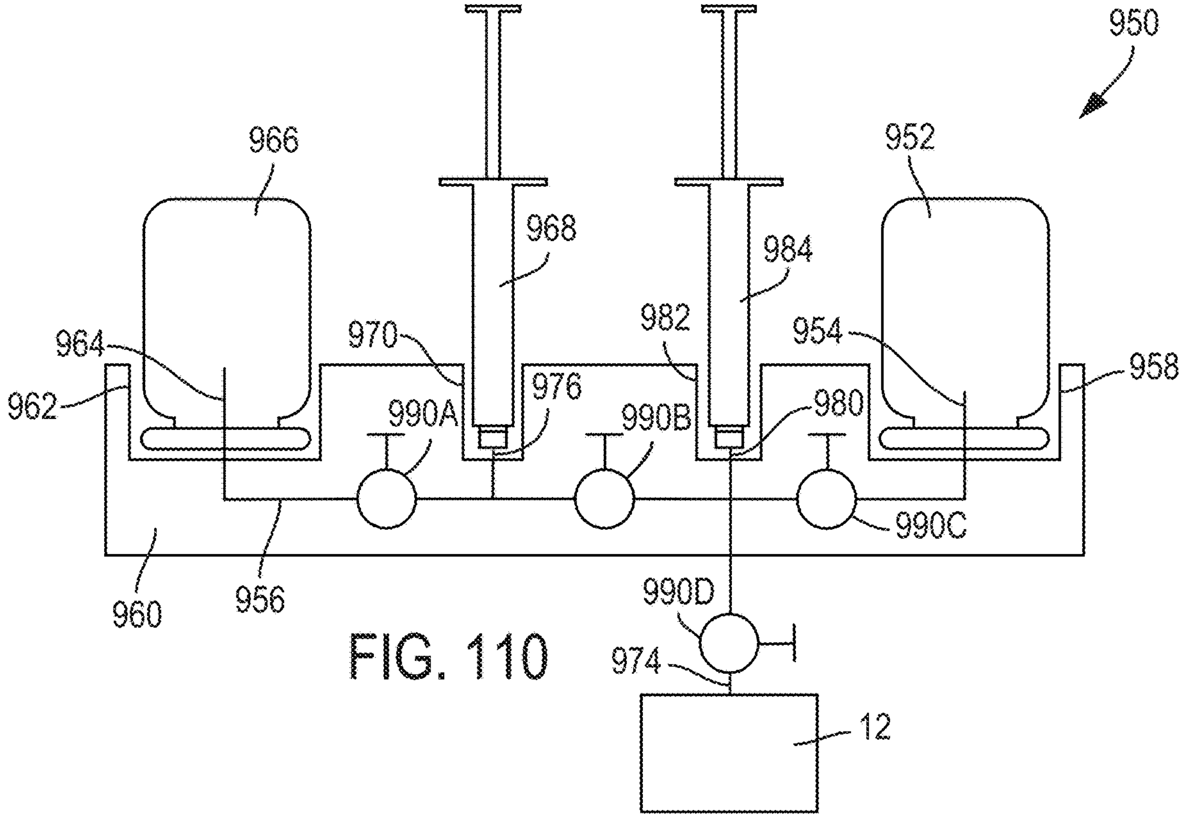
Figure 111A:
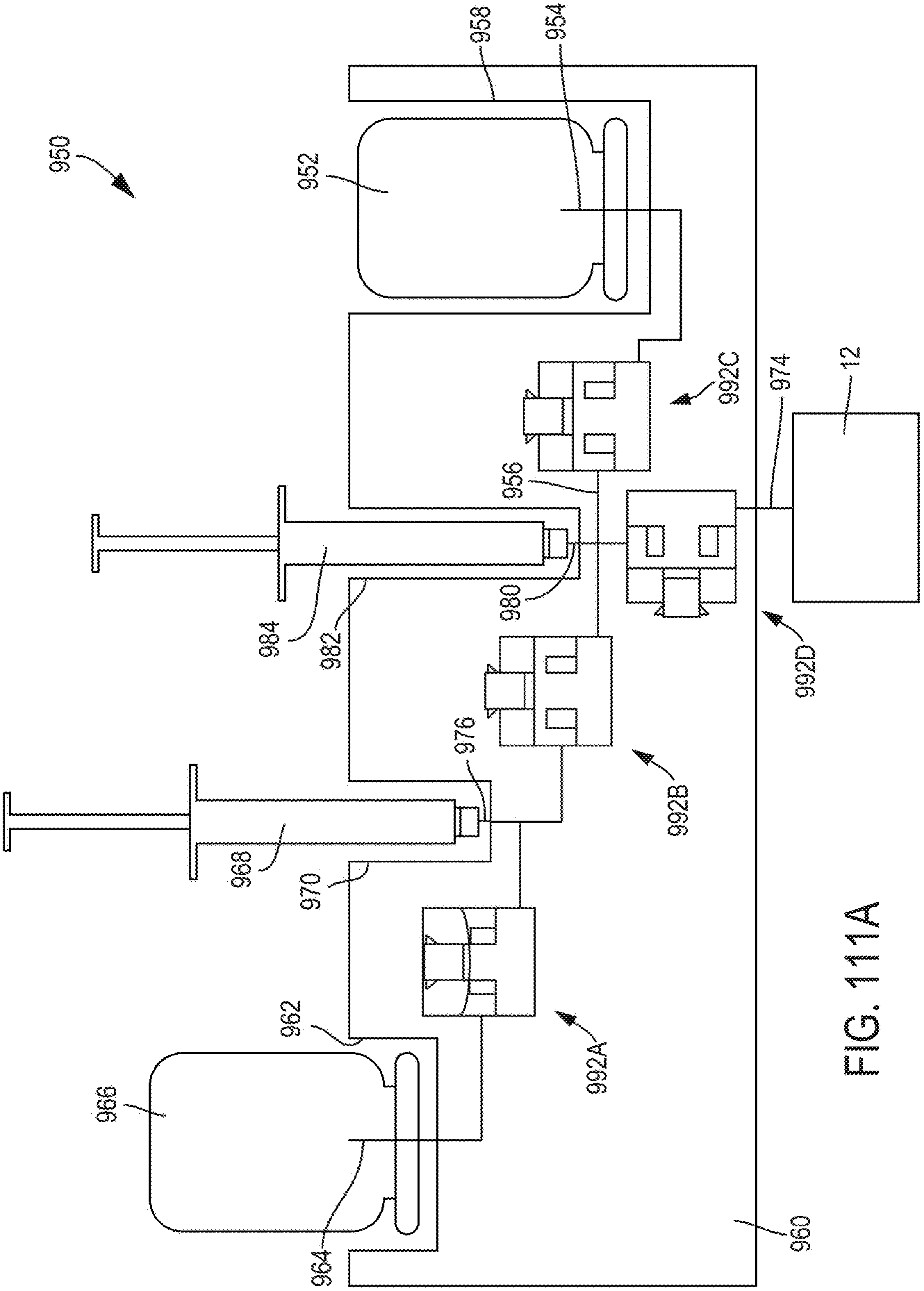
Figure 111B:
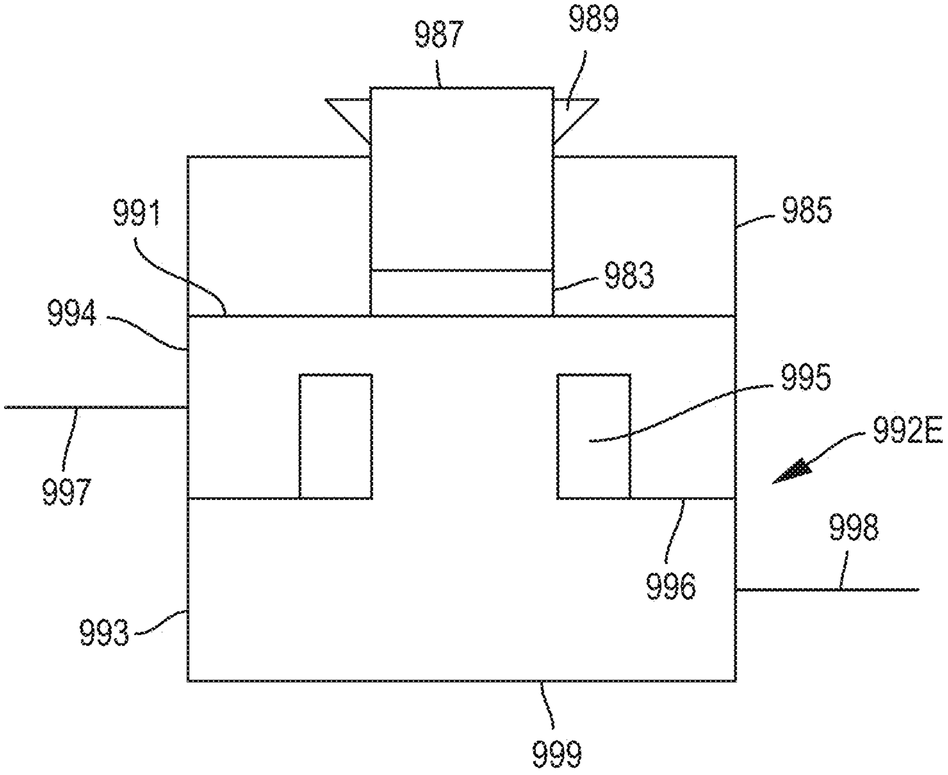
Figure 112:
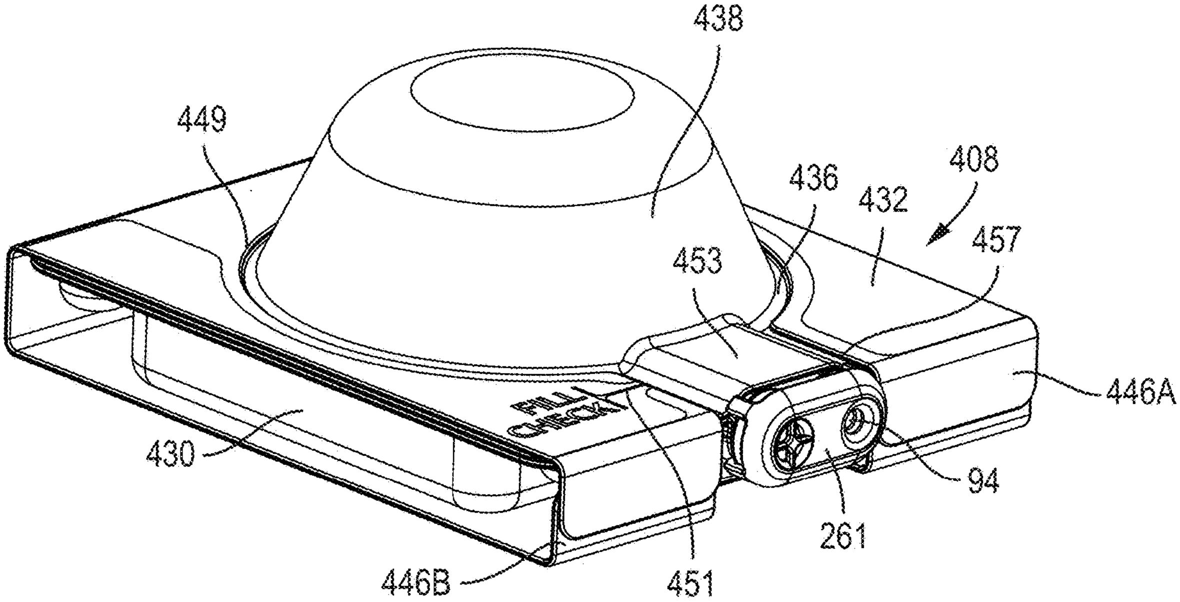
Figure 113:
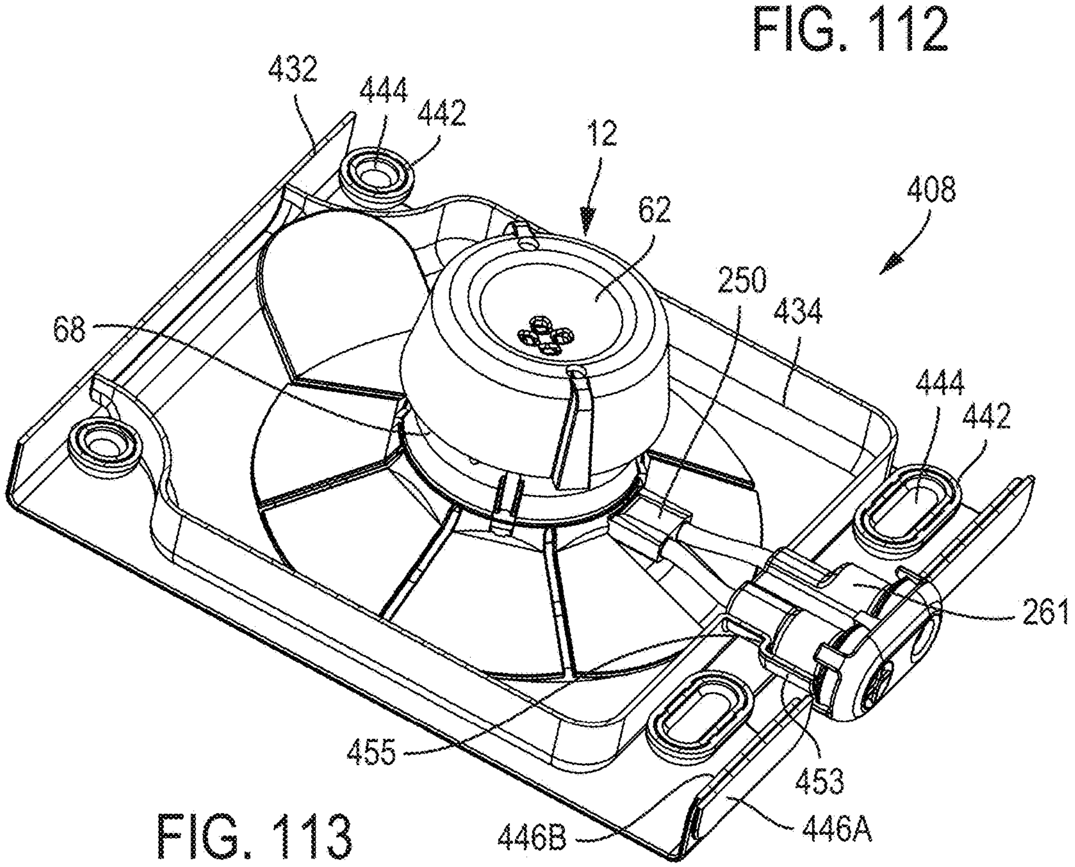
Figure 114:
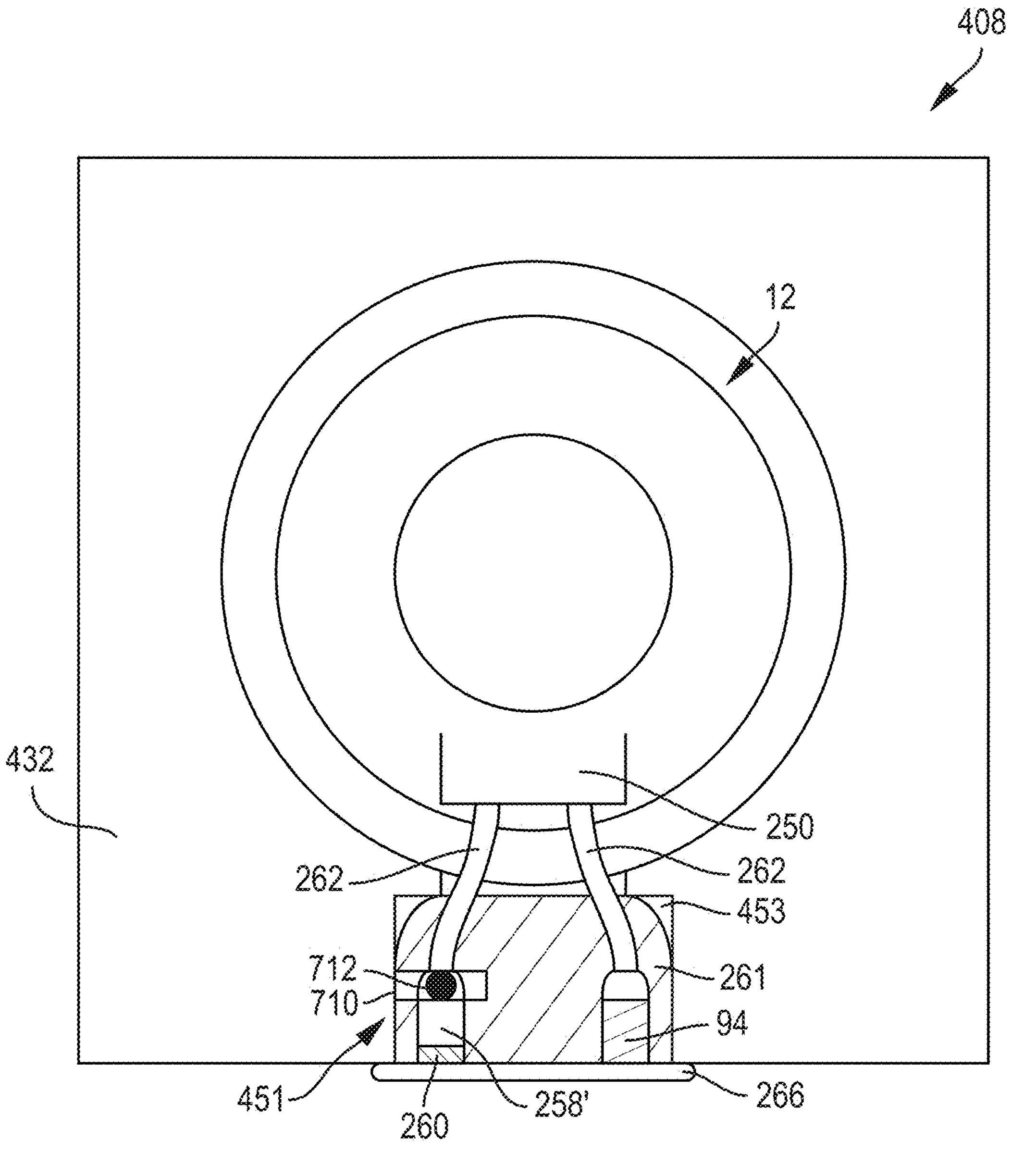

FIG. 72A depicts a view of an example delivery device having a window with which a first region of a reservoir interface member is aligned; and FIG. 72B depicts a view of an example delivery device having a window with which a second region of a reservoir interface member is aligned;

FIGS. 73A-73D depict representational block diagrams of an example delivery device having an outboard reservoir;

FIG. 74A depicts a perspective view of an example delivery device having an outboard reservoir;

FIG. 74B depicts a top plan view of an example delivery device having an outboard reservoir;

FIG. 74C depicts a cross-sectional view of an example outboard reservoir;

FIG. 75 depicts a representational block diagram of an example outboard reservoir; and FIG. 76 depicts a representational block diagram of an example outboard reservoir;

FIG. 77 depicts a block diagram of an example filling portion including a filling manifold with a number of fill chambers which may be included in various systems described herein;

FIG. 78 depicts a block diagram of another example filling portion which may be included in various systems described herein;

FIG. 79 depicts a block diagram of another example filling portion including a filling manifold with an agent carrying fluid bus and a venting bus which may be included in various system described herein;

FIG. 80 depicts a block diagram of another example filling portion with a filling manifold with an agent filling bus arranged for serial filling of delivery device devices or reservoir assemblies which may be included in various systems described herein;

FIG. 81A depicts a number of reservoir assemblies which are integrally formed with a filling bus;

FIG. 81B depicts a portion of the reservoir assemblies and filling bus of FIG. 81A;

FIG. 82 depicts an exploded view of a reservoir assembly including a protruding body arranged to receive a septum;

FIG. 83 depicts a filling manifold with sets of filling and series connecting spikes and a reservoir assembly of the type show in FIG. 82;

FIG. 84 depicts the reservoir assembly of FIG. 83 spiked onto a set of spikes on the manifold of FIG. 83;

FIG. 85 depicts a block diagram of an example filling manifold in fluid communication with the interior volume of reservoir assemblies of a number of delivery devices;

FIG. 86 depicts a view of an access sharp coupled to a piece of sheeting;

FIG. 87 depicts a view of a portion of an example filling manifold constructed of sheeting selectively bonded together to form flow paths and bonded to bodies on access sharps to couple the access sharps in fluid tight manner to the sheeting;

FIG. 88 depicts a view of an example filling manifold with an example access sharp with retention projections coupled into a locating tray which may be included in a container housing a number of reservoir assemblies or delivery devices;

FIG. 89 depicts a block diagram of an example system including a sealed container in which an isolated fill environment and a number of delivery devices are provided;

FIG. 90 depicts a block diagram of an example container having a first, second, and third compartment, the third compartment having an example spike assembly and pressure provisioning implement are enclosed;

FIG. 91 depicts a block diagram of the example container of FIG. 90 with the third compartment accessed;

FIG. 92 depicts a block diagram of the example container of FIG. 90 where a medicament container has been accessed via the spike assembly;

FIG. 93 depicts a block diagram of the example container of FIG. 90 where the pressure provisioning implement has been engaged with a pressure port of the third compartment;

FIG. 94 depicts a block diagram of the example container of FIG. 90 where the medicament container has been pressurized by the pressure provisioning implement and the contents of the medicament container have been dispensed into reservoir assemblies in the container;

FIG. 95 depicts a perspective view of an example container having a removable lid;

FIG. 96 depicts a perspective view of the example container of FIG. 95 with the lid removed;

FIG. 97 depicts a perspective, partially exploded view of FIG. 96 with an example cover tray and filling implement disassociated from the rest of the container;

FIG. 98 depicts a top plan view of the example container of FIG. 95 with the lid, cover tray, and filling implement removed;

FIG. 99 depicts a perspective, partially exploded view of the portion of the example container shown in FIG. 98;

FIG. 100 depicts a cross-sectional view taken at the indicated cut plane of FIG. 98;

FIG. 101 depicts a cross-sectional view taken at the indicated cut plane of FIG. 98;

FIG. 102 depicts a detailed view of the indicated region of FIG. 101;

FIG. 103 depicts a perspective view of a filling implement accessing a filling bus of an example container via a fluid introduction port of the container;

FIG. 104 depicts a perspective view of an example filling aid which may be included in certain example containers;

FIG. 105 depicts a fluid schematic for an example filling aid which may be utilized with certain example containers;

FIG. 106A depicts an example container with a cover tray and lid removed, the container including a guide for receiving a filling aid such as that shown in FIG. 104;

FIG. 106B depicts a perspective view of the example container of FIG. 106A with an example filling aid disposed within the guide, the filling aid having a syringe and a medicament reservoir docked thereto;

FIG. 107 depicts a schematic of an example medical agent reconstitution apparatus;

FIG. 108 depicts a schematic of another example medical agent reconstitution apparatus;

FIG. 109 depicts a schematic of another example medical agent reconstitution apparatus;

FIG. 110 depicts a schematic of another example medical agent reconstitution apparatus;

FIG. 111A depicts a schematic of another example medical agent reconstitution apparatus; and FIG. 111B depicts schematic view of an example volcano valve;

FIG. 112 depicts an example package in which a delivery device may be captured and placed within a container such as that depicted in FIG. 95 or FIG. 106A;

FIG. 113 depicts a partial cut away view of the example package of FIG. 112;

FIG. 114 depicts a representational diagram of an example package with a filling indicator.

Figure 115:
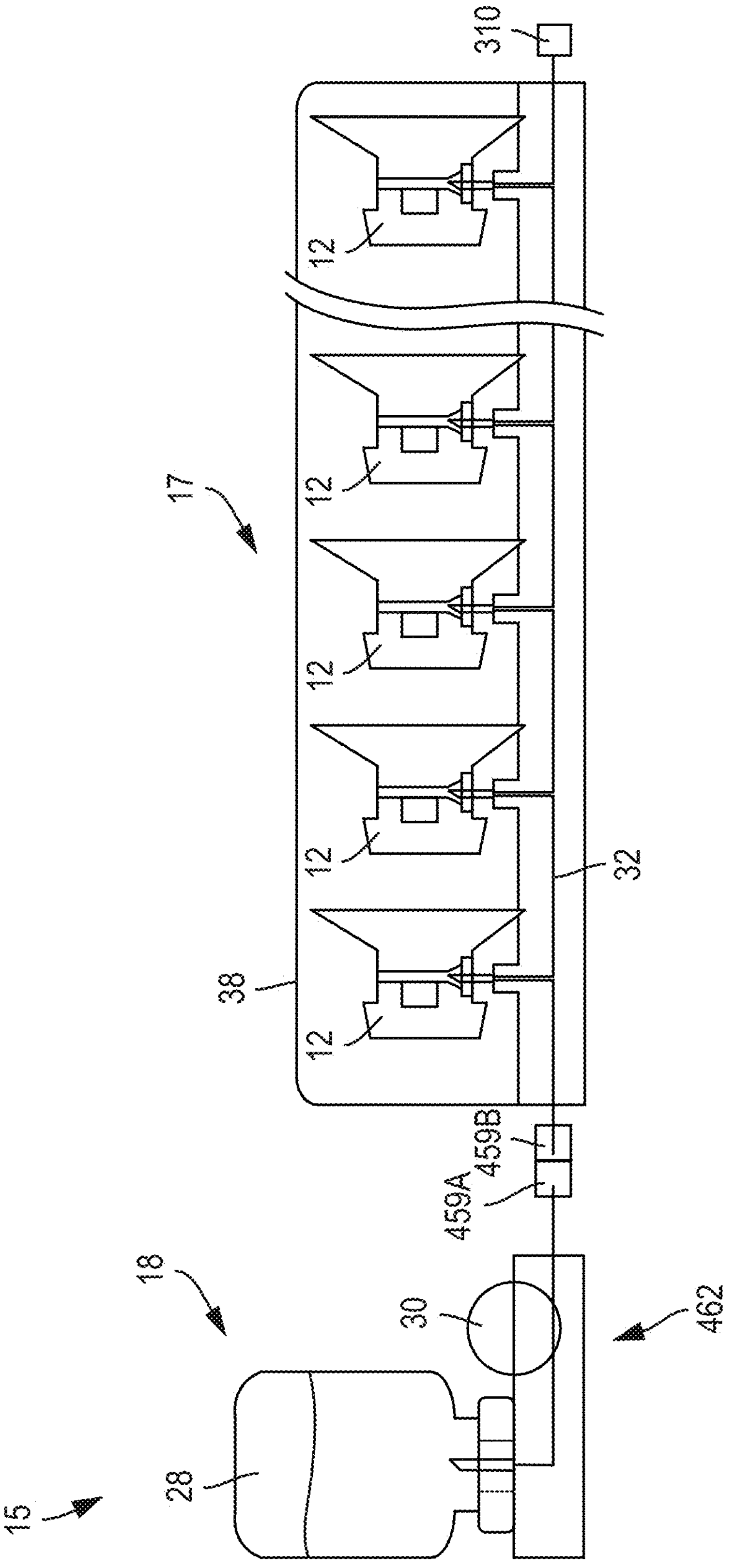
Figure 116:
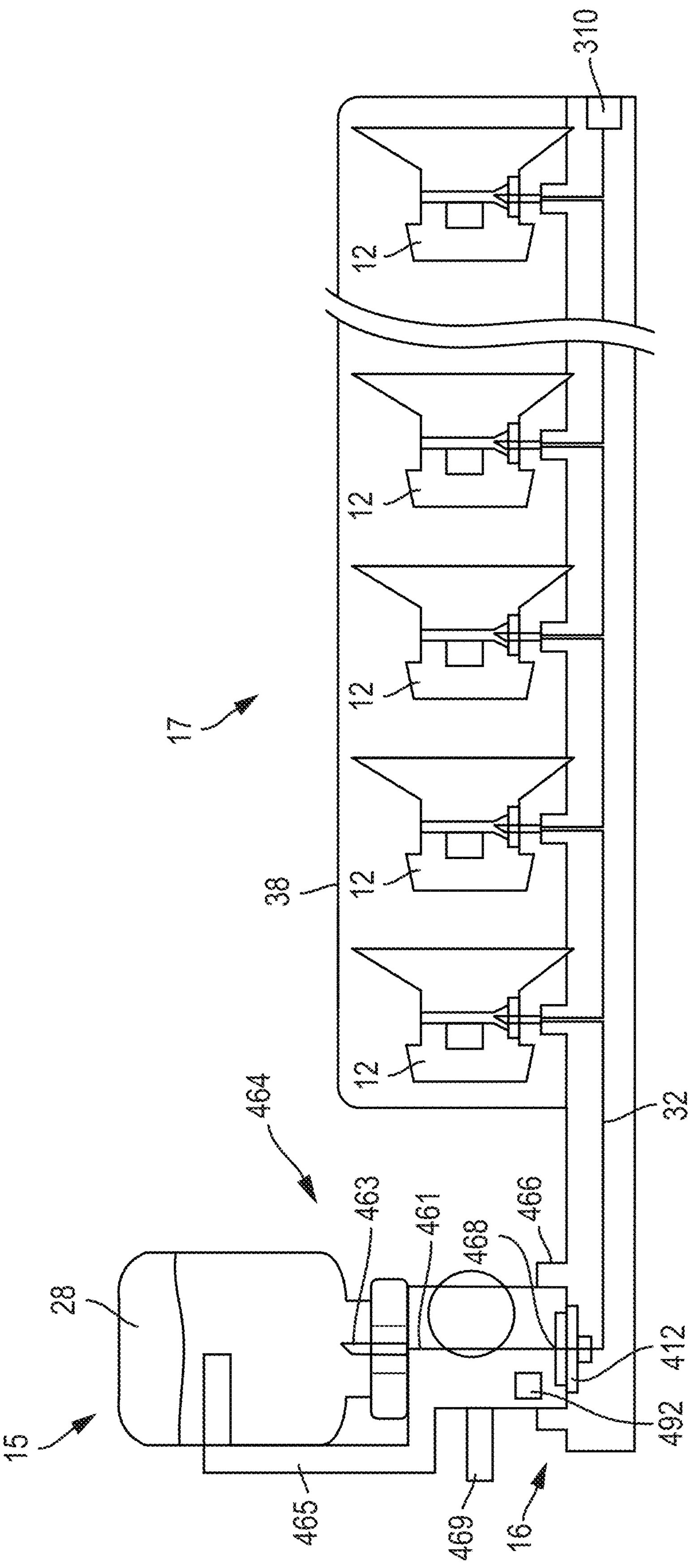
Figure 117:
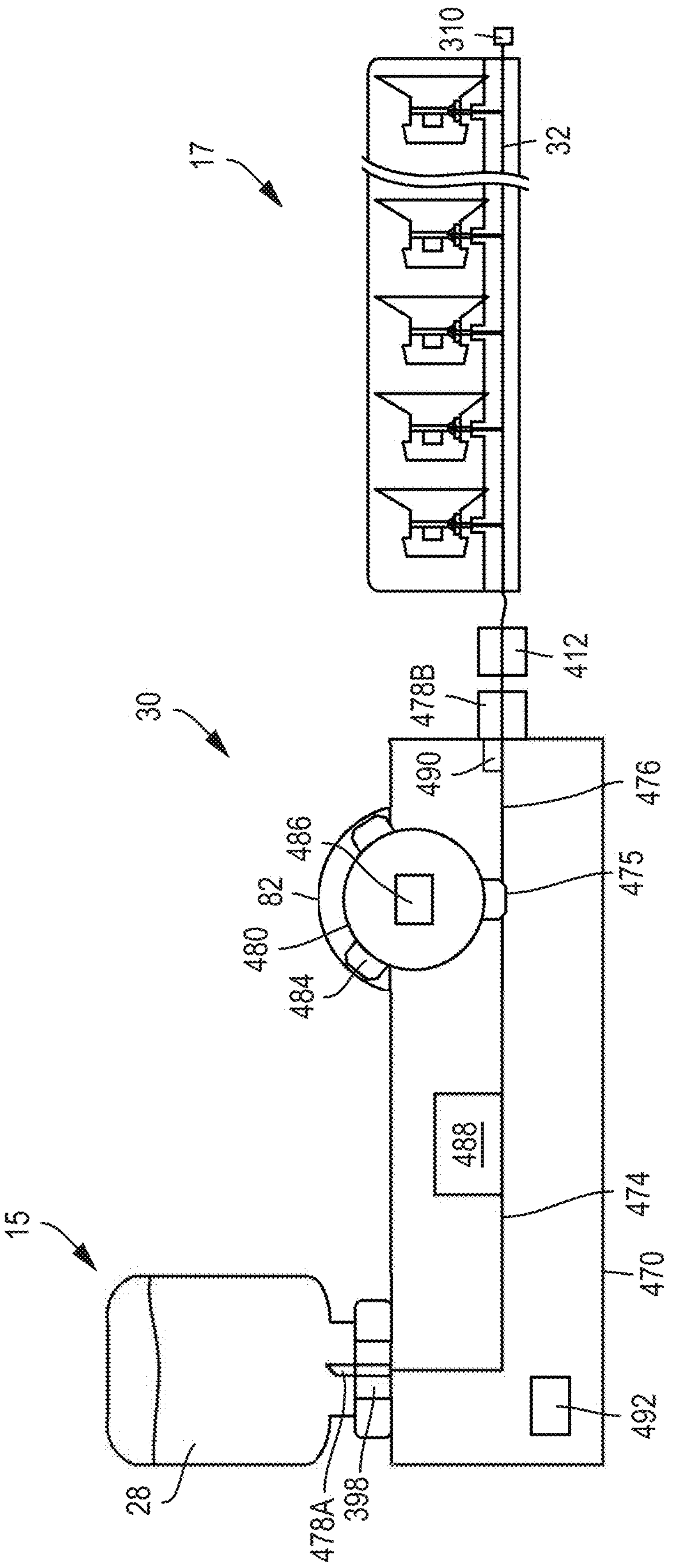
Figure 118:
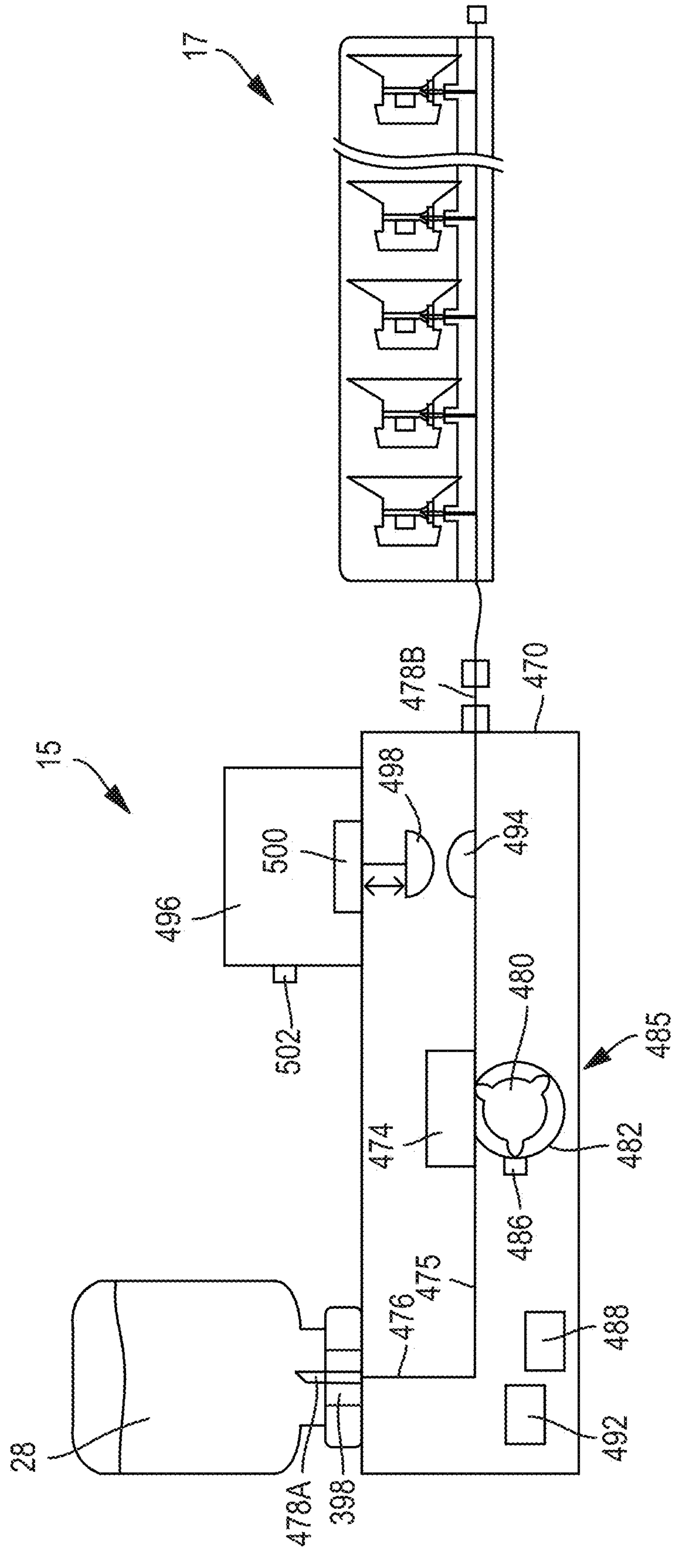
Figure 119:
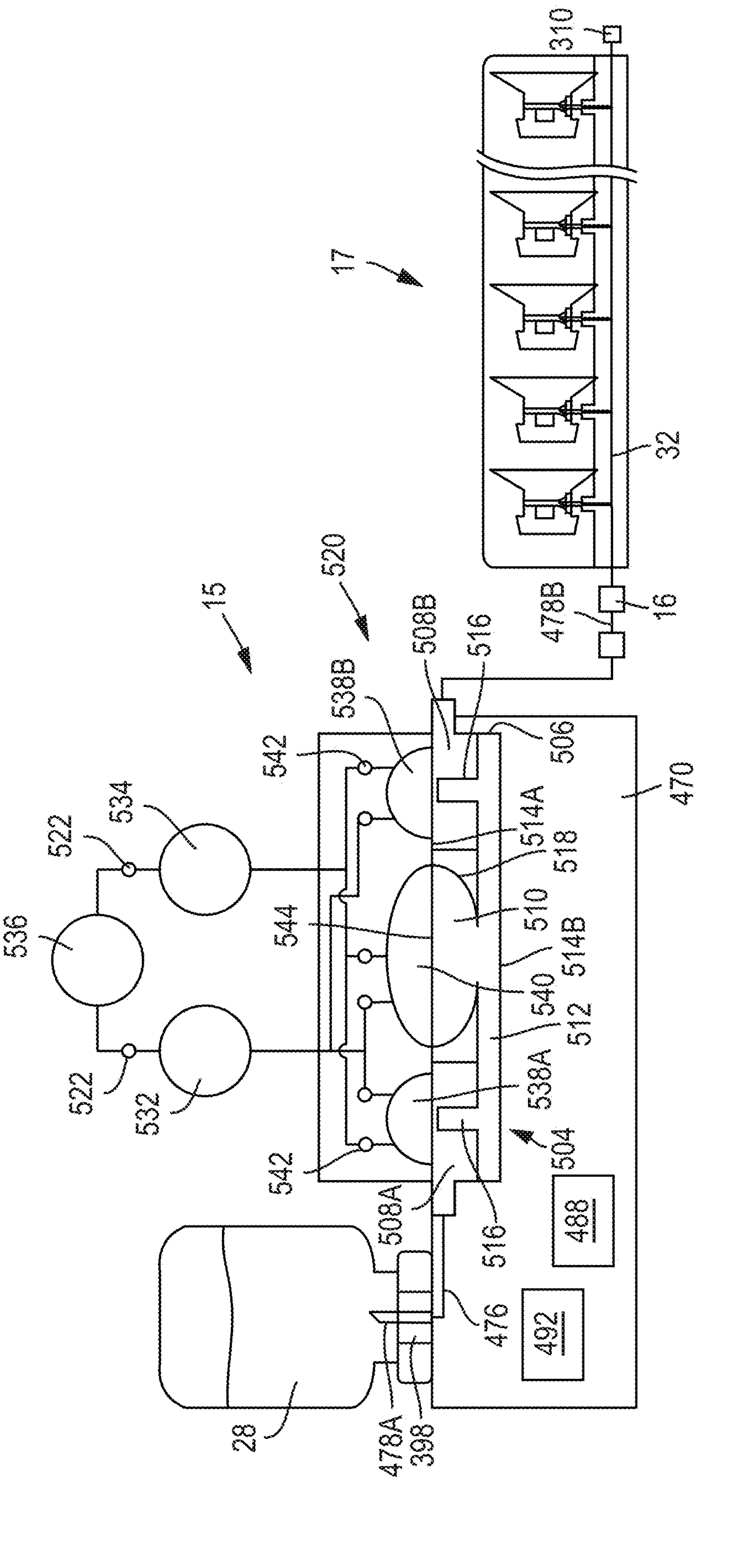
Figure 120:
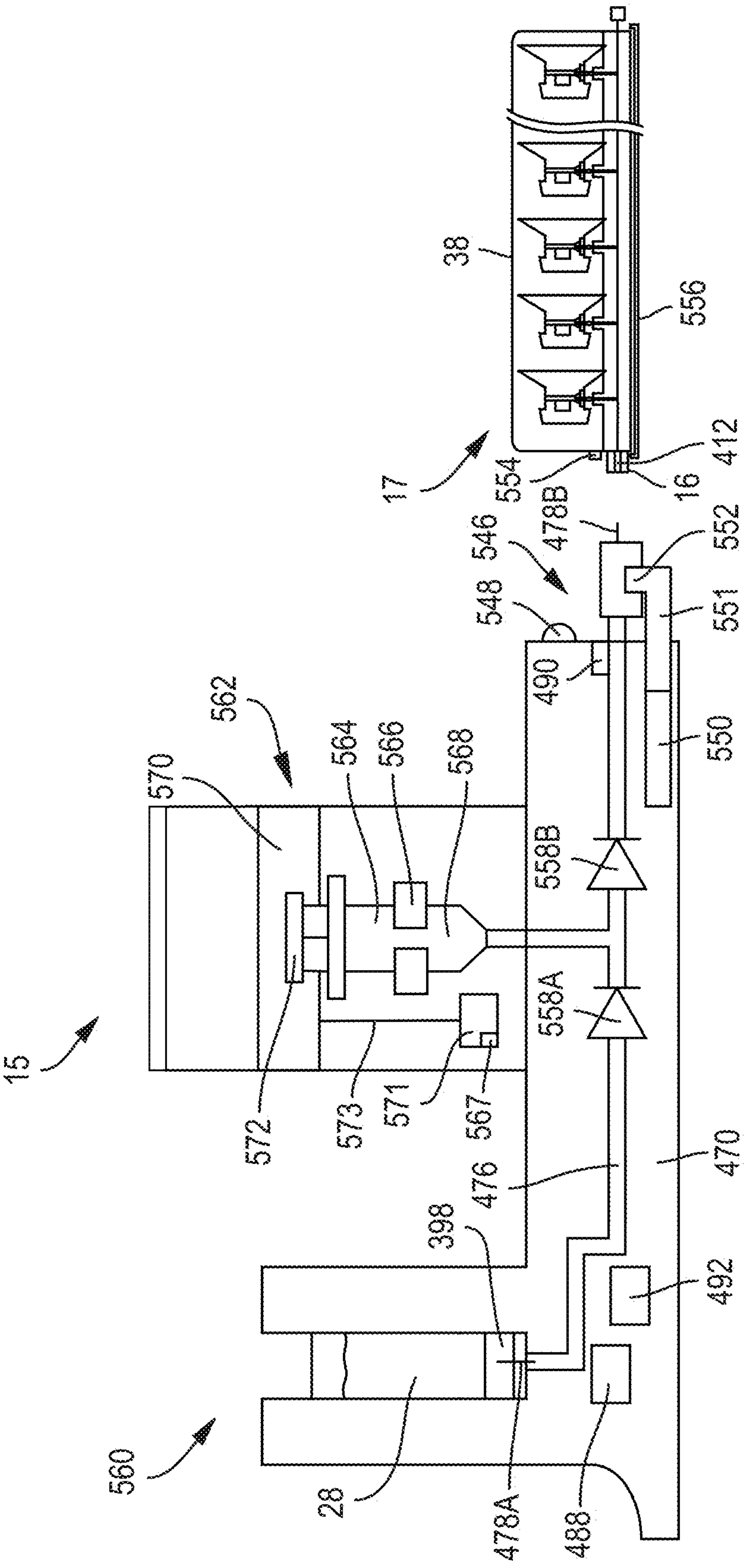
Figure 121:
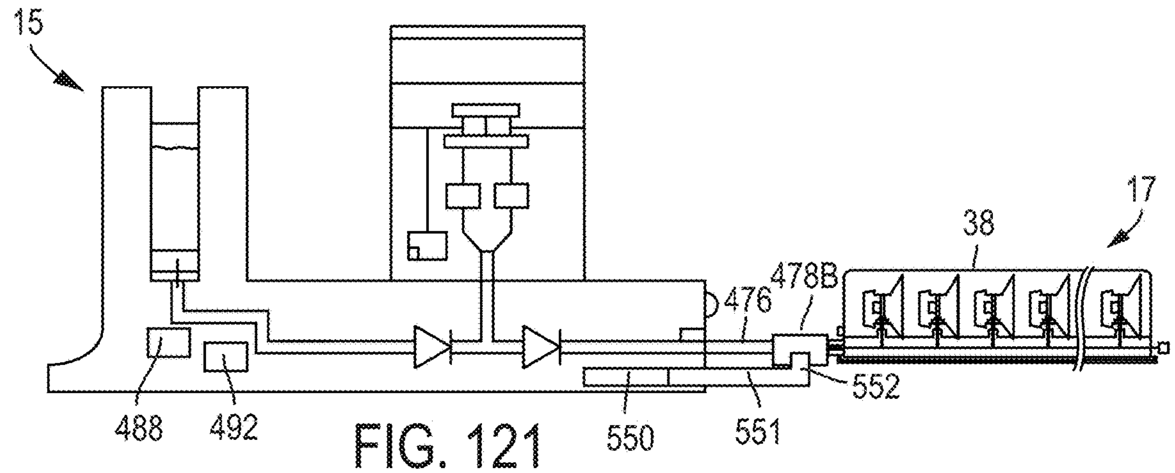
Figure 122:
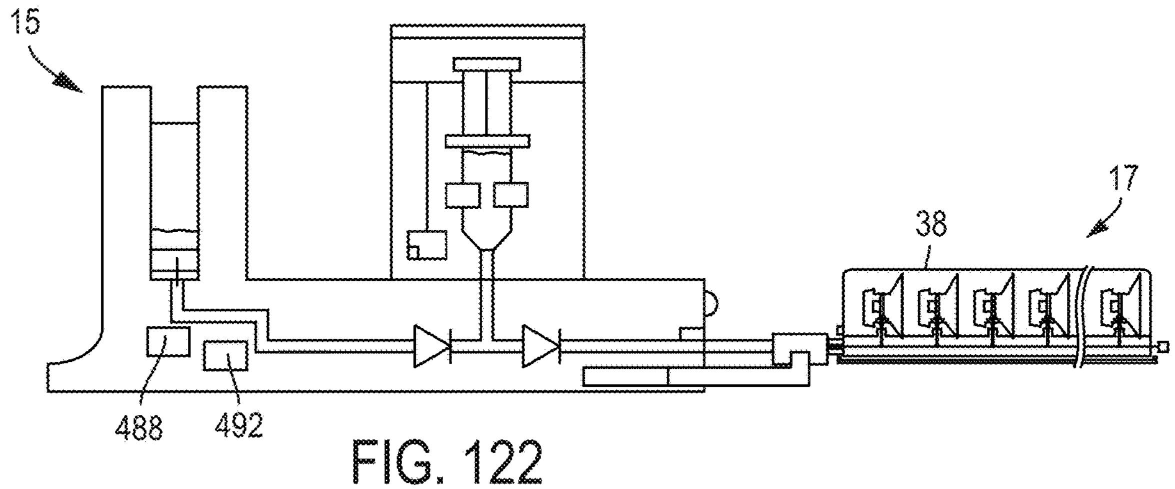
Figure 123:
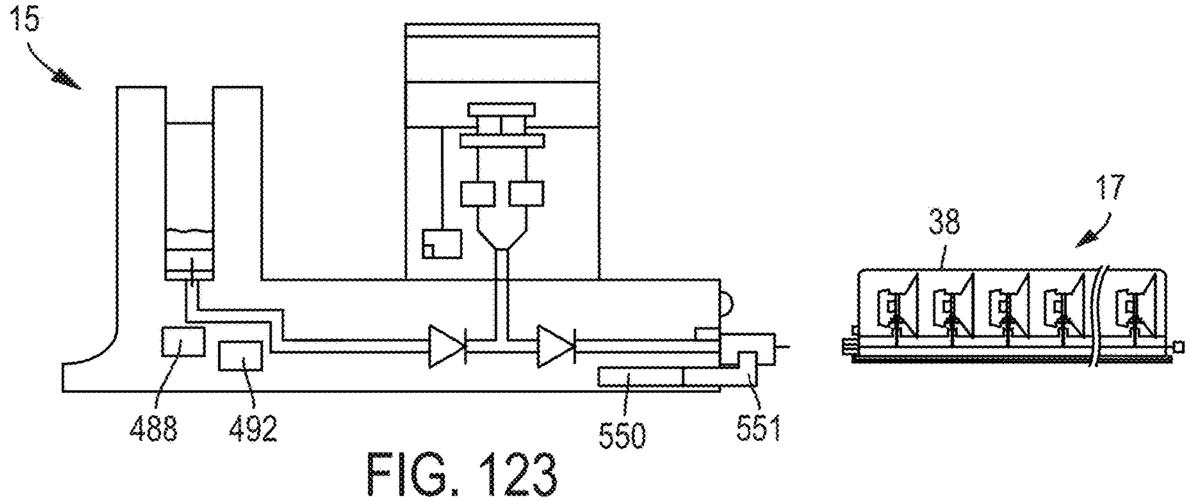
Figure 124:
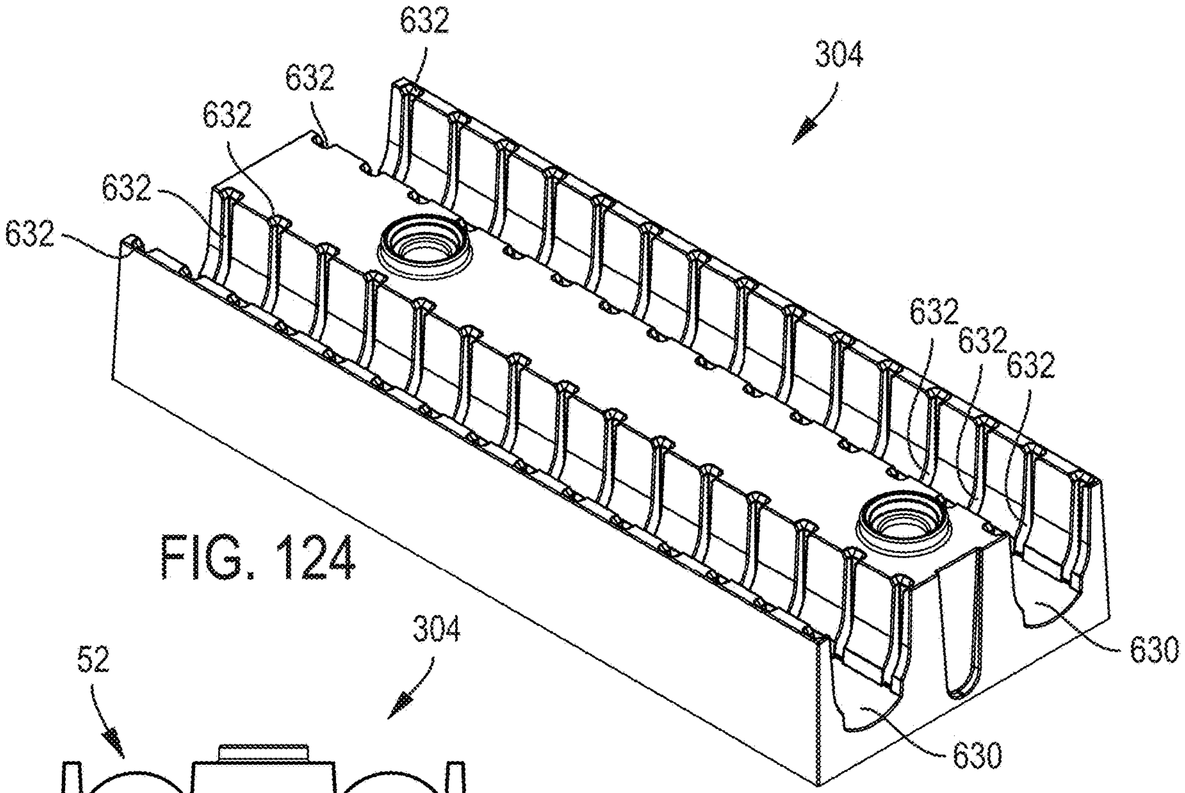
Figure 125:
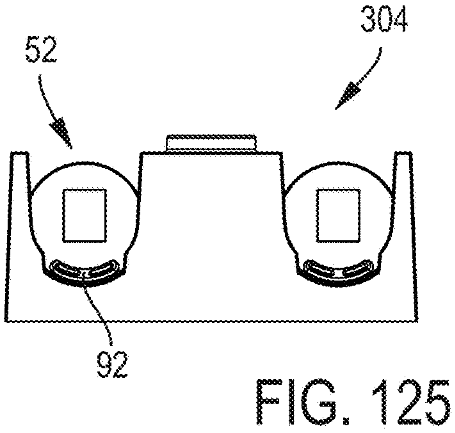
Figure 126:
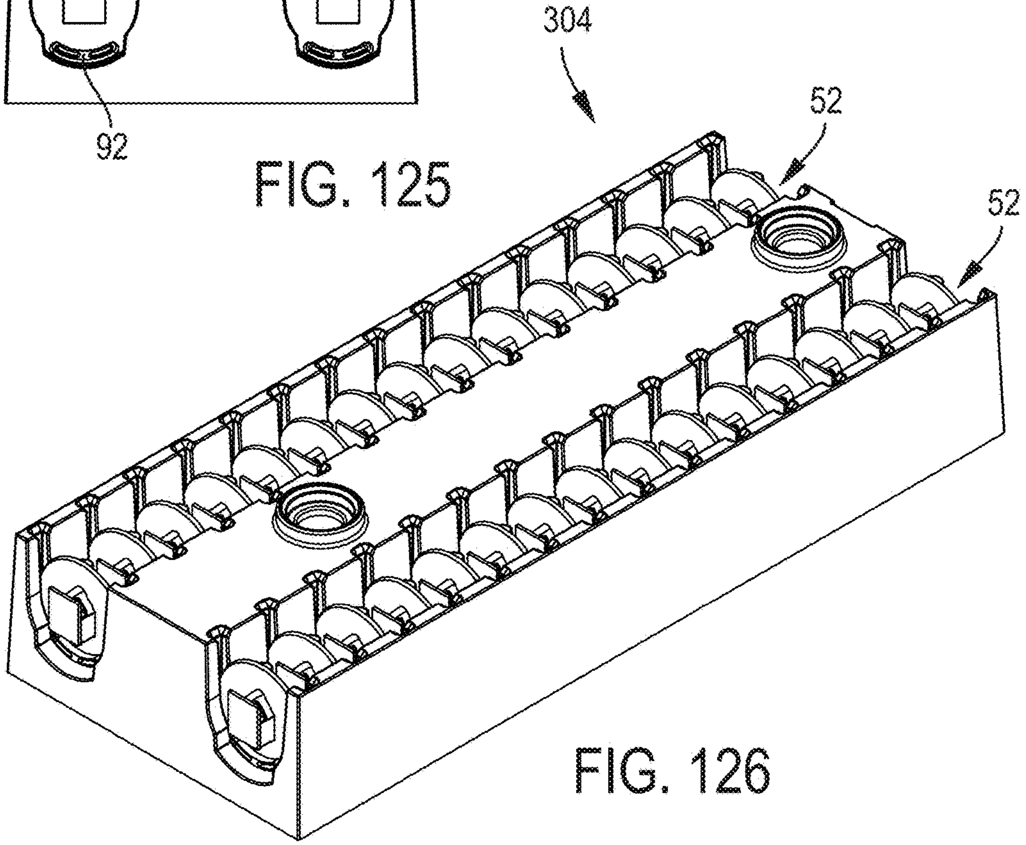
Figure 127:
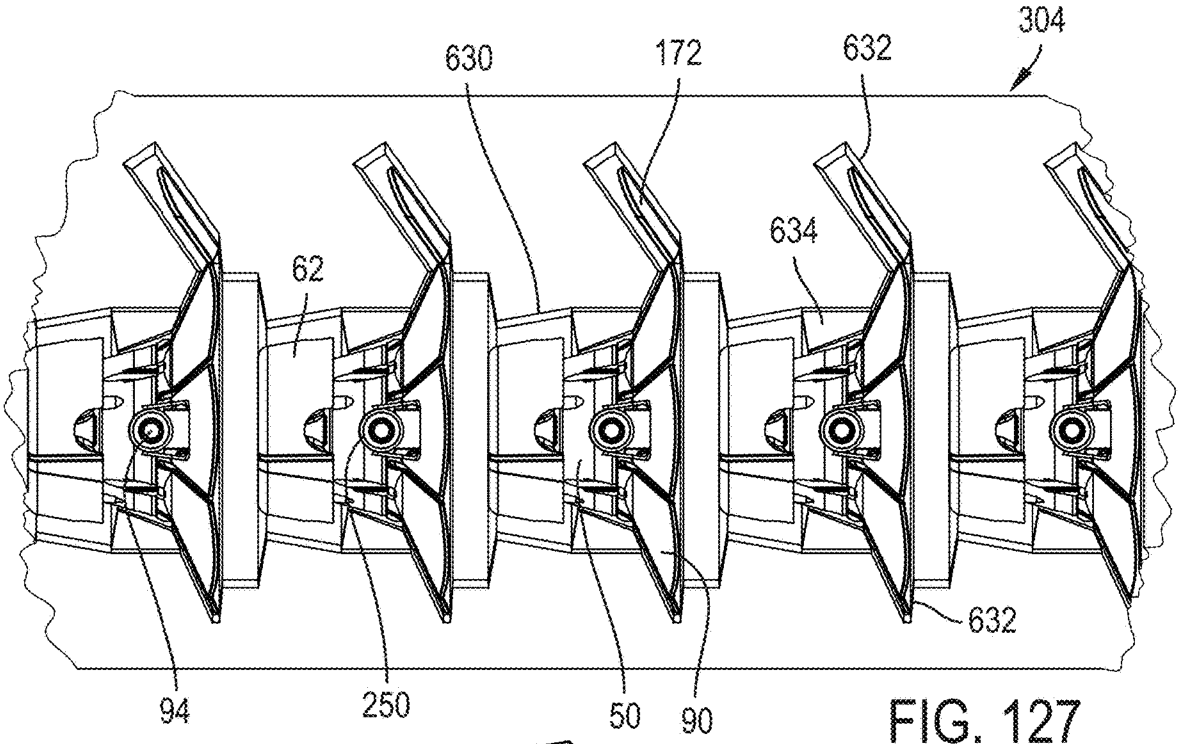
Figure 128:
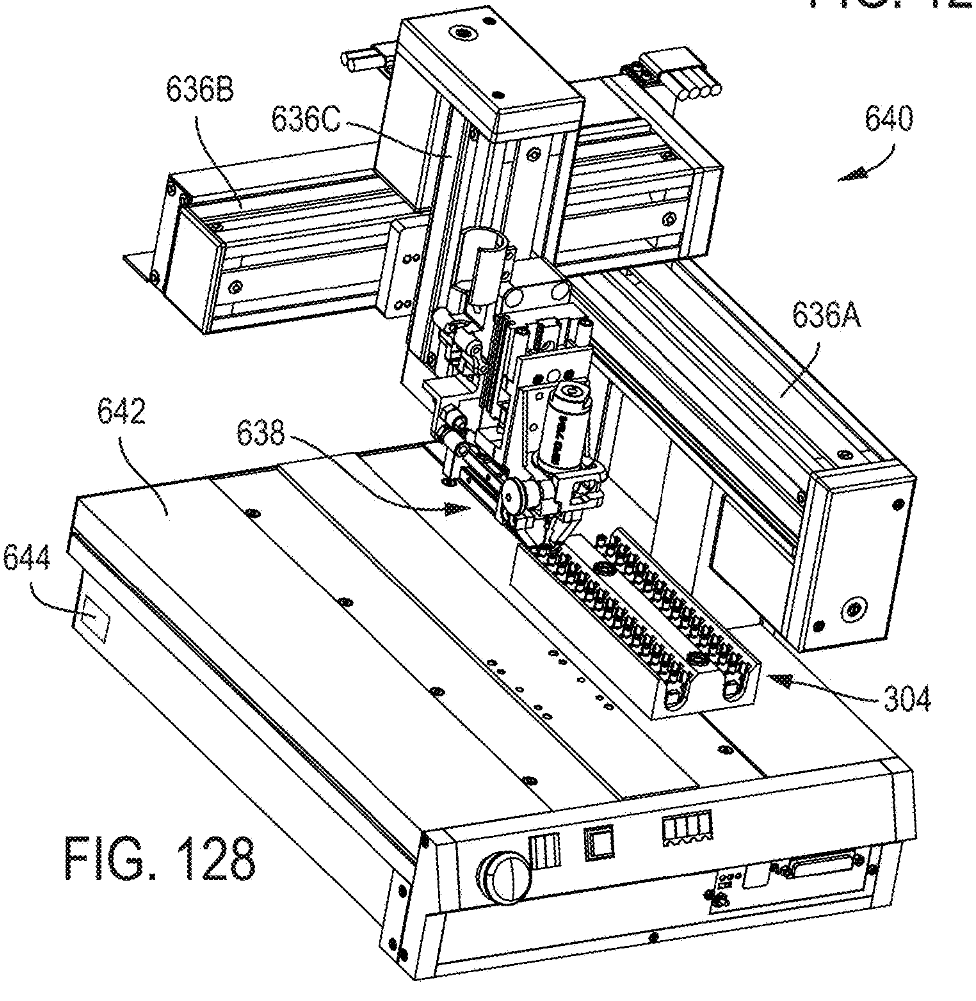
Figure 129:
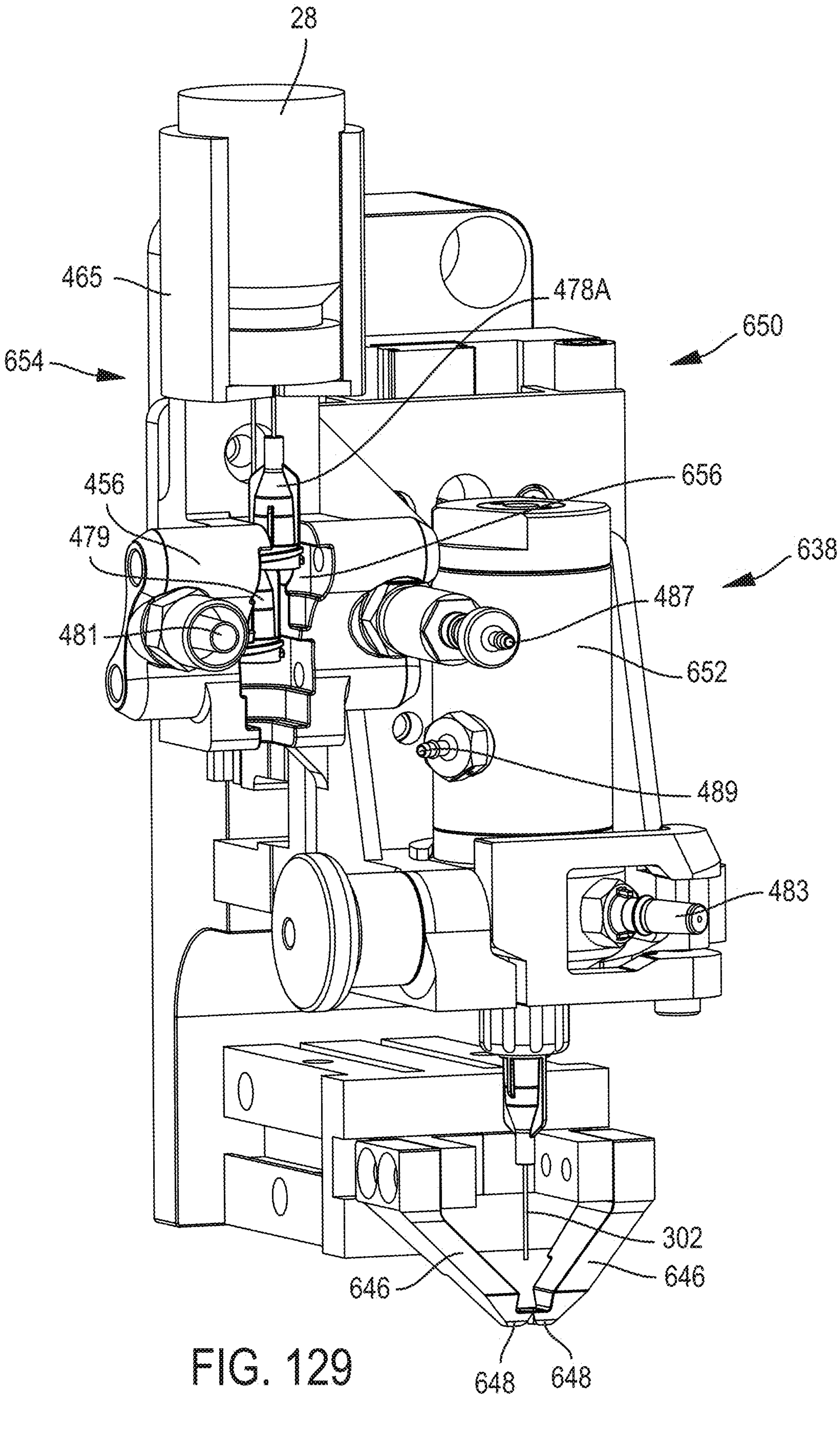

FIG. 115 depicts a block diagram of a system including a pumping portion and a filling portion;

FIG. 116 depicts a block diagram of a system including a pumping portion and a filling portion, the pumping portion being included in a handheld unit;

FIG. 117 depicts a block diagram of an example system including a pumping portion and a filling portion, the pumping portion including a peristaltic pump;

FIG. 118 depicts a block diagram of an example system including a pumping portion and a filling portion, the pumping portion including a diaphragm pump;

FIG. 119 depicts a block diagram of an example system including a pumping portion and a filling portion, the pumping portion including a pumping cassette and a pressure distribution assembly;

FIG. 120 depicts a block diagram of an example system including a pumping portion and a filling portion, the pumping portion including a syringe pump and a spiking assembly for automatically establishing fluid communication between the pumping and filling portions;

FIG. 121 depicts the example system of FIG. 120 with an outlet of a fluid handling set in the pumping portion actuated into fluid engagement with the filling portion;

FIG. 122 depicts the example system of FIG. 120 after the syringe pump has been powered to withdraw the plunger of a syringe of the fluid handling set installed on the syringe pump to fill agent into the syringe from a medicament reservoir docked on the pumping portion;

FIG. 123 depicts the example system of FIG. 120 after the syringe pump has been powered to drive agent out of the syringe and into reservoir assemblies in the filling portion and after the spike assembly has disconnected the filling and pumping portions of the example system;

FIG. 124 depicts an example cartridge which may be used to store and fill reservoir assemblies;

FIG. 125 depicts a side view of an example cartridge with a number of reservoir assemblies disposed in troughs in the cartridge;

FIG. 126 depicts a perspective view of an example cartridge with a number of reservoir assembly disposed in troughs of the cartridge;

FIG. 127 depicts a top plan view of a portion of a cartridge with a number of delivery devices disposed in cradle divots in the cartridge;

FIG. 128 depicts an example system for filling reservoir assemblies or delivery devices within a cartridge; and FIG. 129 depicts an example fill head which may be included in a system for filling reservoirs or delivery devices.

DETAILED DESCRIPTION

Figures 1A, 1B:
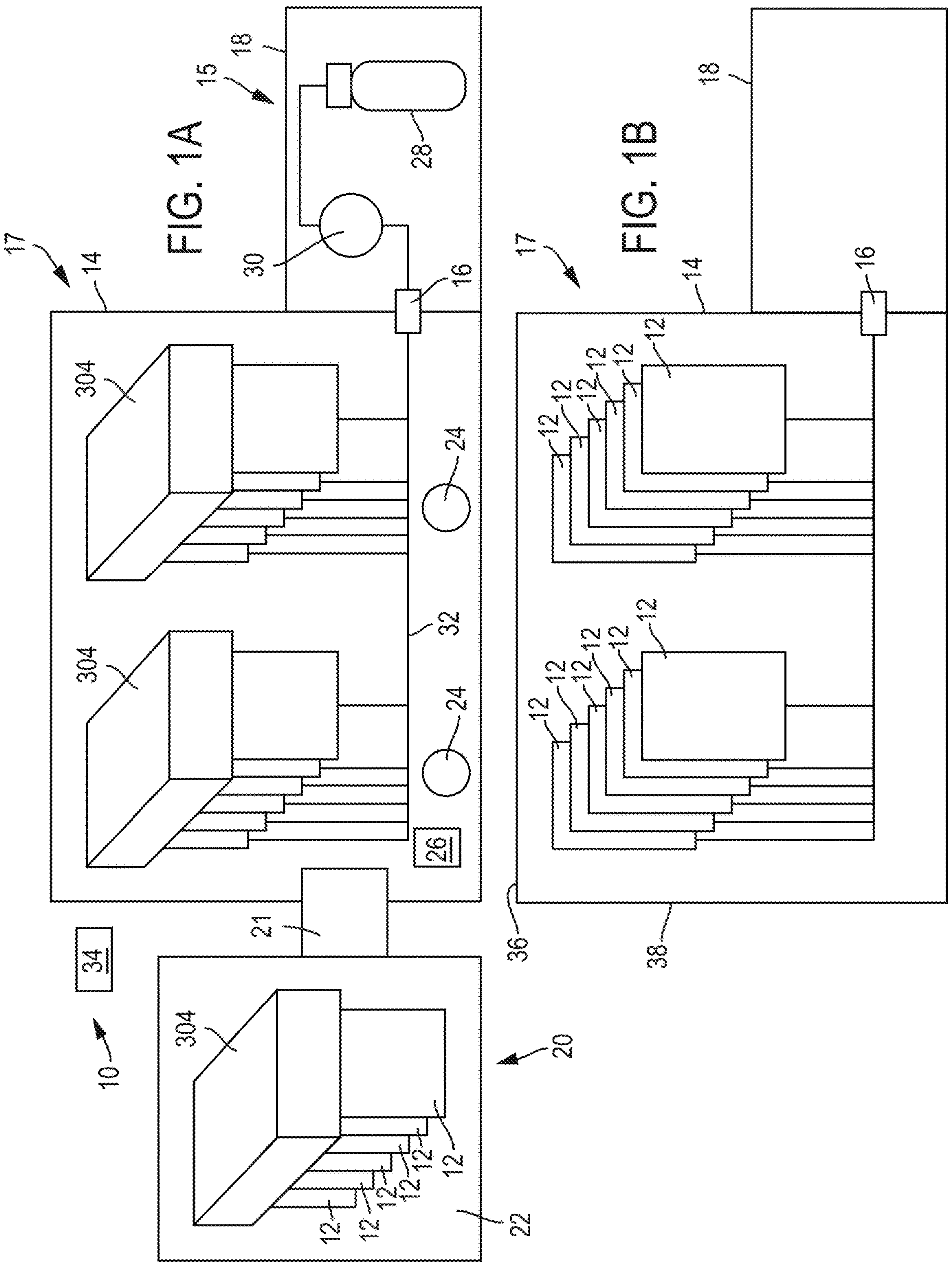
FIG. 1A depicts a block diagram of an example system for filling of delivery devices or reservoir assemblies.
FIG. 1B depicts a block diagram of another example system for filling of delivery devices or reservoir assemblies.
Figure 1C:
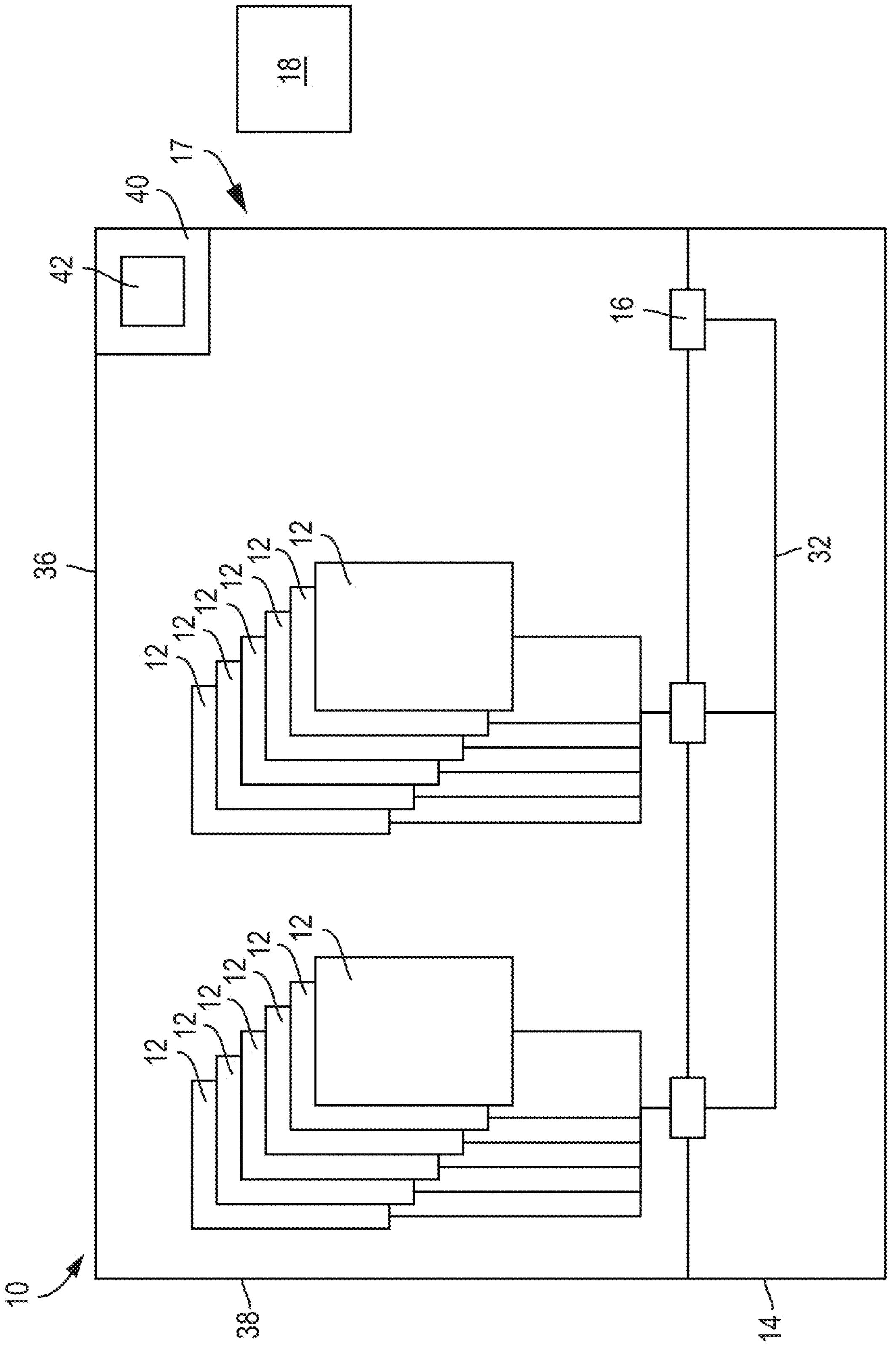
FIG. 1C depicts a block diagram of another example system for filling of delivery devices or reservoir assemblies.

Referring now to FIG. 1A-1C, a number of block diagrams of example systems 10 for filling of delivery devices 12 are depicted. Though any suitable delivery devices 12 such as those shown and described herein may be used, the delivery devices 12 may in certain embodiments, be delivery devices 12 which administer fluid to a shallow delivery destination. Any of the delivery devices or portions thereof disclosed in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023 which is hereby incorporated herein by reference in its entirety may also be used or modified for use with systems 10 described herein. Such a shallow delivery destination may be a destination between the stratum corneum and the subcutaneous tissue such as an intradermal destination. That said, delivery devices 12 which deliver to varied delivery destinations (e.g. subcutaneous, intramuscular, etc.) may be included in the systems 10 shown and described herein. Additionally, systems 10 may include or be used to fill a variety of delivery devices 12 which could target different delivery destinations.

The systems 10 may be particularly well suited for general purpose delivery devices 12 which may be filled with a variety of medicaments depending on the demands of a scenario at hand. For example, the systems 10 may be useful as a quick response tool for outbreaks of disease and could facilitate provisioning of delivery devices 12 filled with a vaccine or other countermeasure to an outbreak or potential outbreak. Any suitable vaccine could be used. For example, the vaccine may be but is not limited to, attenuated live vaccines, inactivated virus vaccines, acellular vaccines, cellular vaccines, toxoid vaccines, heterotypic or Jennerian vaccines, monovalent vaccines, polyvalent vaccines, nucleic acid vaccines (e.g. DNA, plasmid vaccine, mRNA), virus like particle vaccines, recombinant vector vaccines (e.g. replicating, non-replicating), dendritic cell vaccines, T-cell receptor peptide vaccines, chimeric vaccines, subunit vaccines, nanoparticle vaccines, recombinant protein vaccines, polysaccharide vaccines, and conjugate vaccines. It should be noted that these are not necessarily mutually exclusive. For instance, a vaccine could be a recombinant protein nanoparticle vaccine or some other combination of the above. Vaccine may also refer to a combination vaccine (e.g. DTaP, MMR, MMRV, etc.) or a vaccination agent which targets a single pathogen or multiple strains of a single pathogen.

Systems 10 shown and described herein may be particularly advantageous for countering pathogen outbreaks in communities which typically chose to forego vaccination or in communities which typically lack access to vaccination infrastructure. The systems 10 may also be well suited for use in outbreaks which may occur in relation to hostilities (e.g. deliberate pathogen release or instances of disease resulting from breakdown of existing medical infrastructure). Through use of such systems 10, many otherwise ready-for-use delivery devices 12 may be filled with a suitable agent and rapidly dispensed to individuals at need with minimal medical infrastructure at the point of filling. For certain agents and systems 10, only the agent (e.g. in a vial) and a syringe may be needed. Likewise, such systems 10 may be readily deployed in challenging terrain or locations due to the minimized infrastructure demands. Though examples herein are described in relation to humans, it shall be understood that the systems 10 described herein are not limited thereto. Such systems 10 may be useful in veterinary applications and would for instance help provide a flexible platform for expeditiously addressing outbreaks of disease in livestock populations.

Use of delivery devices 12 which administer fluid to a shallow delivery destination may be of particular attractiveness where systems 10 are used to facilitate vaccinations. Where the system 10 is part of a quick response toolkit for a pathogen outbreak, the amount of vaccine on hand may be limited (e.g. the pathogen is novel or an unexpected outbreak occurs). The population in need of vaccination may be larger than a local supply can satisfy.

In addition to being painless or substantially pain free, evidence suggests that shallow delivery of vaccines may provoke protective immune response with smaller amounts of vaccine antigen. As a result, dose sparing may be practiced allowing the same quantity of vaccine to be effective for immunizing a greater number of people. Alternatively or additionally, injection sparing may be possible. Shallow administration with delivery devices 12 such as those shown herein may allow for a single injection protocol where other routes of administration may require multiple injections over some period of time. Additionally, some studies have suggested that shallow administration may be particularly helpful in certain patient populations. For example, elderly populations may receive superior protection from vaccinations received intradermally than via other routes. That said, the Mantoux technique, which is typically used for intradermal administration, can pose reliability concerns and can be difficult to perform, especially without training. Pain associated with Mantoux injections may also make such injections undesired.

With systems 10 of the type shown and described herein, a local storage of vaccines may only be required to store a relatively small amount of vaccination agent for each pathogen of concern (e.g. 50-120 μl per individual). Thus, the same storage capacity could house sufficient vaccination agents for a wider variety of potential pathogens. Alternatively, the required storage volume at a point of need could be decreased. This could be of heightened importance where the local storage is at a remote location (e.g. a forward operating base or developing country with limited supporting infrastructure). As certain vaccination agents must be stored in cold chain conditions, limiting the burden relating to such storage may significantly defray costs and logistical concerns.

The example delivery devices 12 shown herein additionally are not limited to vaccine delivery devices. Such a delivery device 12 may fill a number of niches in the medical field. Other agents, for example, diagnostic or testing agents may be supplied via certain example delivery devices 12. For instance, allergens or potential allergens may be administered via the delivery device 12. Tuberculosis testing agents may be delivered via the delivery device 12. Such delivery devices 12 may also be used to deliver medication for endocrine disorders. For instance, insulin may be delivered with some exemplary delivery devices 12. Delivery devices 12 described and shown herein may also be well suited to deliver drugs for overdose intervention such as opioid antagonists (e.g. Naloxone).

Still referring to FIGS. 1A-1C, example systems 10 may have a filling portion 17 which may an include isolated fill environment 14. The isolated fill environment 14 may be a sterile environment or otherwise controlled environment. For example, the isolated fill environment 14 may conform to an ISO clean room standard. The isolated fill environment 14 may include a fluid introduction port 16. The fluid introduction port 16 may be placed into fluid communication with a medicament supply 18. The medicament supply 18 may be part of a pumping portion 15 of a system 10. Alternatively, a pumping portion 15 may be omitted and agent may be compelled manually from a medicament supply 18 (e.g. syringe or other delivery implement) into the filling portion 17 of the system 10.

Referring now to FIG. 1A, certain isolated fill environments 14 may optionally include a sterile rapid transfer port 20. In some embodiments, the rapid transfer port 20 may include an alpha flange portion 21 which is integrated into the wall of the isolated fill environment 14. The alpha flange portion 21 may dock with a beta container 22 (e.g. beta bag) which is filled with empty delivery devices 12. The beta container 22 may be sealed and terminally sterilized via gamma irradiation, ethylene oxide, or in any other suitable manner. The isolated fill environment 14 may include at least one glove port 24 through which a user may operate the rapid transfer port 20 and retrieve sterilized delivery devices 12 from the beta container 22.

The delivery devices 12 may preferably be provided in a cartridge 304. Where used, the cartridge 304 may house the delivery devices 12 in respective bays or receptacles (see, e.g., FIG. 99). Example cartridges 304 may also provide for a known spacing between delivery devices 12 to facilitate interface with automated filling equipment. In some instances, cartridges 304 may include locating projections or recesses which may interface with corresponding features in the isolated fill environment 14 to further assist in interfacing with automated filling equipment.

As discussed in greater detail elsewhere in the specification, in alternative examples of the systems 10 described herein, only a portion of the delivery devices 12 may be introduced to the isolated fill environment 14. For example a plurality of sterilized reservoir assemblies 52 (see, e.g., FIG. 30A) may be aseptically transferred into an isolated fill environment 14 and filled in the isolated fill environment 14. The reservoir assemblies 52 may be transferred out of the isolated fill environment 14 in a completely filled and sealed state. Subsequently, the reservoir assemblies 52 may be installed in respective delivery devices 12 in an ambient environment. This may be desirable as it may limit the amount of volume needed to ship the sterile components used by a system 10. It may also allow for a greater number of sterile components to be exposed to a sterilizing agent during a given sterilization procedure. It should be understood that where any embodiments herein is described as filling an assembled delivery device 12, it would be possible to alternatively fill a reservoir assembly 52 and vice versa. In certain examples, a reservoir assembly 52 or a delivery device 12 may be filled within a package 408 (see, e.g., FIG. 113). Packages 408 may, for instance, provide some protection against accidental transition of a delivery devices 12 into a delivery state and may be used where delivery devices 12 are transported after filling. Any systems 10 described herein may fill reservoir assemblies 52 or delivery devices 12 either in isolation or within a package 408.

In some examples, beta containers 22 may also be used to introduce components other than delivery devices 12 or reservoir assemblies 52 into an isolated fill environment 14. A sealing assembly 26 may, for instance be introduced to the isolated fill environment 14 via the rapid transfer port 20. The sealing assembly 26 may be a heat staking assembly with at least one heated body that may be used to close a fill access for each of the delivery devices 12. This may be done by pressing a flexible fluid path provided in a flexible portion of a reservoir assembly 52 into contact with a rigid portion of the reservoir assembly 52. The flexible portion may then be heat staked to the rigid portion to close the fluid path used as the fill access.

Still referring to FIG. 1A, once unfilled delivery devices 12 have been introduced to the isolated fill environment 14, fluid may be transferred from a pumping portion 15 of the system 10 to the filling portion 17 of the system 10. Agent may be supplied from a medicament supply 18 such as any of those shown or described herein. In the example shown in FIG. 1A, the medicament supply 18 includes a medicament container 28 (e.g. vaccine vial, or other multi-dose drug reservoir such as a bag, syringe, etc.). The medicament container 28 may be placed in fluid communication with a pump 30 which may compel fluid to be transferred from the medicament container 28, through the fluid introduction port 16 and into the isolated fill environment 14. The pump 30 may be any of a wide variety of pumps. For example, the pump may be a rotary peristaltic pump, peristaltic finger pump, syringe pump, diaphragm pump, pneumatically driven cassette based pumping system, etc.

Where a peristaltic based pumping system is used, the system may include any of those shown or described in U.S. Publication No. US 2023/0285662 A1, filed May 18, 2023, entitled "Medical Pump" which is incorporated herein by reference in its entirety. Where a syringe based pumping system is used, the system may include any of those shown or described in U.S. Pat. No. 10,391,241 B2, filed Feb. 20, 2015, Issued Aug. 27, 2019, and entitled "Syringe Pump Having a Pressure Sensor Assembly". Where a cassette based pumping system is used, the system may include any of the cassettes, pneumatic actuation assemblies, or other components shown or described in U.S. Publication No. US 2019/0316948 A1, filed Apr. 15, 2019, entitled "Medical Treatment System and Method Using a Plurality of Fluid Lines" or U.S. Pat. No. 5,350,357, filed Mar. 3, 1993, entitled "Peritoneal Dialysis Systems Employing a Liquid Distribution and Pumping Cassette That Emulates Gravity Flow" which are incorporated herein by reference in their entireties.

Delivery devices 12 may be filled in any suitable manner. Delivery devices 12 may be placed into fluid communication with a fluid delivery bus 32 (as shown) and fluid may be transferred into the delivery devices 12 through the fluid delivery bus 32 via the pump 30. This fluid communication may be established manually or in an automated fashion. In other examples, a sterile syringe may be introduced to the isolated fill environment 14 via the rapid transfer port 20 and fluid may be drawn into the syringe from a medicament container 28 via the fluid introduction port 16 (a pump 30 may be omitted in such examples). In other embodiments, an automated filling station may be provided within the isolated fill environment 14 and may dispense fluid into each delivery device 12. The automated filling station may be similar to the fill head 638 and filling gantry 640 shown in, for example, FIGS. 128-129. The automated filling station may be pre-sterilized and introduced to the isolated fill environment 14 via a rapid transfer port 20. In such examples, a cartridge 304 of delivery devices 12 may be docked in a known location and a controller 34 of the system 10 may orchestrate displacement of a gantry bearing a filling implement based on a coordinate system. The filling implement may be displaced to appropriate locations for each delivery device 12 and a predefined fluid volume may be dispensed into each delivery device 12. The controller 34 may be in data communication with a flow sensor and may halt delivery from the pumping portion 15 when the data signal from the flow sensor is indicative of a desired amount of fluid having been dispensed. Alternatively, the pump 30 may track delivery volumes and ensure a desired amount of fluid has been delivered to each delivery device 12. In some examples, a pressure transducer may be monitored by a controller and fluid transfer may be halted when the controller determines the data from the pressure transducer indicates a pressure spike has occurred. In some embodiments, an open loop may be utilized by the system 10. A time over which fluid is delivered in to each delivery device 12, for example, may be selected based on a pressure used to drive fluid into each delivery device 12.

Still referring to FIG. 1A, when delivery devices 12 have been filled and sealed (if not accessed via septum 94 see, e.g., FIG. 31), the delivery devices 12 may be transferred out of the isolated fill environment 14 via the rapid transfer port 20. For example, they may be placed back into the beta container 22 in which they were provided. The beta container 22 may then be disconnected and the delivery devices 12 may be provisioned as needed.

Referring now to FIG. 1B, in some system 10 embodiments, at least a portion of the sterilization package for the delivery devices 12 (or reservoir assemblies thereof) may also serve as the isolated fill environment 14. In such examples, isolated fill environment 14 may be provided within an overpack or container 38 having a removable panel 36. The removable panel 36 may be a peel-off lid (e.g. Tyvek material) in certain embodiments. The remaining exterior walls of the container 38 may be formed of a rigid plastic though a flexible bag type container could also be used in various embodiments. Each of the delivery devices 12 (or alternatively reservoir assemblies 52) may be installed into the sterilization package and into fluid communication with a fluid bus 32 included in the package. In certain examples, the fluid bus 32 may be in fluid communication with the fluid introduction port 16 and may include a number of delivery sharps 302 (see, e.g., FIG. 77). Each delivery device 12 may include a septum 94 (see, e.g., FIG. 31) which may be punctured by a respective delivery sharp 302. After fluid communication between the fluid bus 32 and a fluid holding interior volume of each respective delivery device 12 is established, the container 38 may be sealed and sterilized. A user may aseptically establish fluid communication with the fluid bus 32 through the sidewall of the container 38 via the fluid introduction port 16. Any medicament supply 18 or pumping portion 15 described herein may be used. Once the delivery devices 12 are filled, the sterile container 38 may be opened and the delivery devices 12 may be removed and distributed for use.

In some example systems 10, there may be a plurality of fluid buses 32. One fluid bus 32 may be in communication with the interior fluid holding volume of each delivery device 12 and provide a flow path from the fluid introduction port 16. Another of the fluid buses 32 may be a venting bus which includes a sterile filter (e.g. 0.2 μm filter). The venting bus 32 may also be in communication with each of the interior volumes of the delivery device 12 and may provide an exhaust path to the sterile filter for gas displaced from the delivery device 12 interior volumes as they are filled with agent. One such exemplary embodiment is further described in relation to FIG. 79. In alternative embodiments, the interior volumes of the delivery devices 12 may be supplied initially in a collapsed state. In such examples, the venting bus 32 may be omitted.

In other embodiments, and referring now primarily to FIG. 1C, the isolated filled environment 14 may be formed as a small portion of a larger container 38 in which the delivery devices 12 (or reservoir assemblies) may be shipped. For example, the isolated fill environment 14 may include only the fluid bus 32. As mentioned above, the fluid bus 32 may include a set of delivery sharps 302 (see, e.g., FIG. 102) which may puncture a septum 94 (see, e.g., FIG. 102) of each delivery device 12. This may place a fluid holding interior volume of each delivery device 12 into fluid communication with the fluid bus 32. The container 38 may then be sterilized. As shown, containers 38 may include a compartment 40 in which a filling implement 42 (e.g. syringe) is disposed. This filling implement 42 may be assembled into the container 38 before sterilization. As shown, the fluid introduction port 16 may be included within the interior volume of the container 38.

A user may open the container 38 by, for example, removing a peelable lid 36 and retrieve the filling implement 42. A volume of medicament may be withdrawn from a medicament supply 18 (e.g. vaccine vial) using the filling implement 42. The filling implement 42 may then access the fluid introduction port 16 to transfer fluid into the delivery devices 12 (or reservoir assemblies 52) via the fluid bus 32. The delivery devices 12 may then be removed from the container 38 and utilized as needed.

Figure 2A:
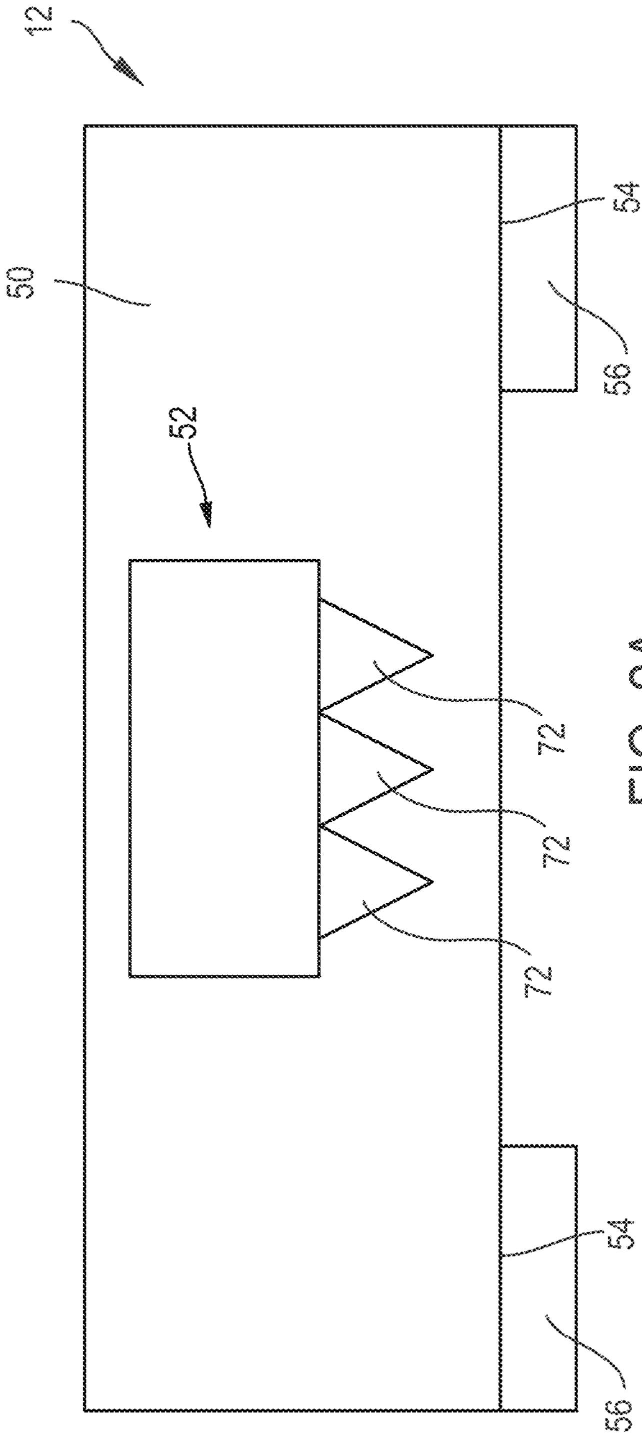
FIG. 2A is a block diagram of an example delivery device in a storage state.
Figure 2B:
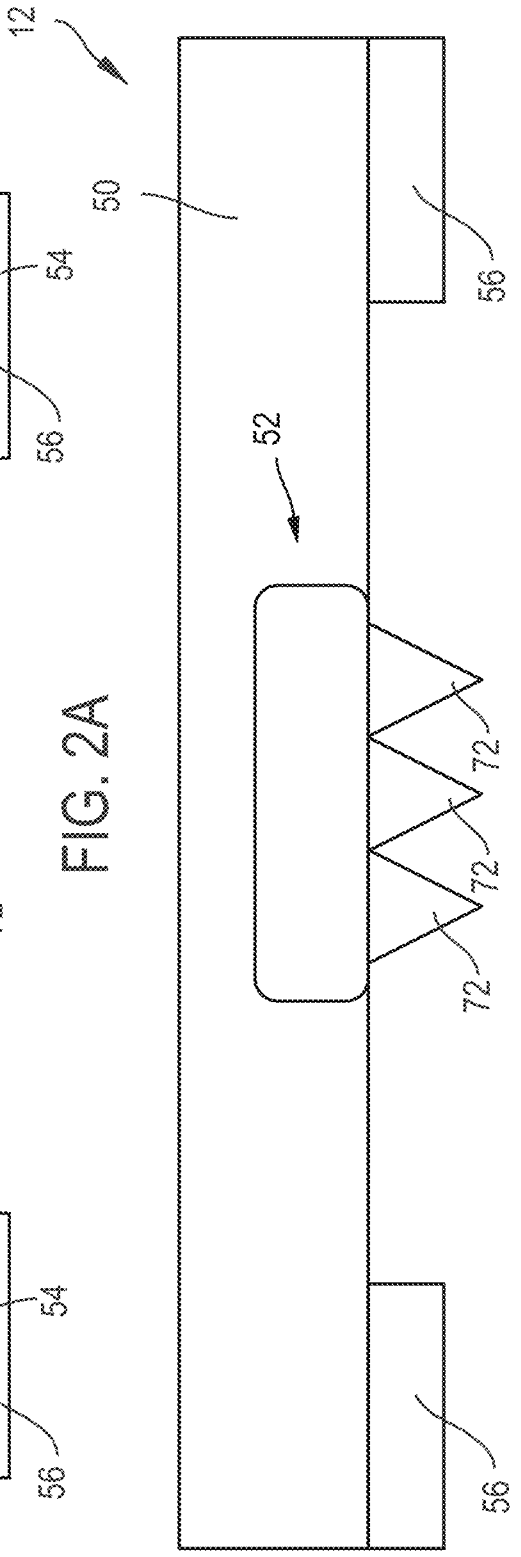
FIG. 2B is a block diagram of an example delivery device in a delivery state.

Referring now to FIGS. 2A-2B, an exemplary delivery device 12 is shown. Various delivery devices 12, may include a main body 50. The main body 50 may be a deformable body which may transition from a storage state (see FIG. 2A) to a delivery state (see FIG. 2B). In certain examples, this transition may be reversible, though in other embodiments the transition may result in a permanent change in the main body 50 and/or another part of the delivery device 12. For example, once transitioned to the delivery state, the main body 50 may plastically deform such that it is permanently distorted and may not be returned to the storage state. In other examples, a frangible included in the delivery device 12 may be broken upon transition of the main body 50 to the delivery state. Alternatively or additionally, a latch, lock, or other coupling may be engaged to hold the main body 50 in the delivery state or prevent the main body 50 from returning to the storage state. Destruction of a portion of the main body 50 or a portion of the delivery device 12 engaged to the main body 50 may be required to disengage such a coupling and this destruction may render the delivery device 12 inoperative. Where a permanent change is engendered upon transition to the delivery state, this permanent change may inhibit reuse as well as provide a user perceptible (e.g. visual) indication that the delivery device 12 has been used. An indication that the transition has occurred may also be generated by the delivery device 12. For instance, an audible or tactile indication may be generated upon engagement of a latch or breaking of a frangible.

In various examples, transition of the delivery device 12 from the storage state to the delivery state may be accomplished via bending, pivoting, or deformation of one or more regions of the main body 50. In certain examples, the main body 50 may include one or more hinges (e.g. living hinge to aid in lowering part count) at which the main body 50 may bend. In other embodiments, the main body 50 may be or include a bi-stable element which may have a first stable state which corresponds to the storage state and a second stable state which corresponds to the delivery state. The main body 50 may for example substantially or partially invert (e.g. convex to concave) in shape or have one or more invertible regions which at least partially invert when the delivery device 12 is transitioned from the storage state to the delivery state. In some embodiments, the main body 50 may include one or more regions which may invert while also including one or more regions which distort and at least partially restore as a result of the delivery device 12 being transitioned to a delivery state.

The transition may be affected via application of force throughout the entire transition. Alternatively, the transition may only require application of force throughout a portion of the transition. For example, in some embodiments a triggering force may be applied to initiate the transition and the transition may subsequently complete in the absence of any external application of force. For example, after application of the triggering force, the transition may be characterized by a snap-through buckling via which the main body 50 rapidly shifts into the delivery state.

The main body 50 may be at least partially covered with adhesive 56 over a first face 54 of the main body 50. The adhesive 56 may serve to couple the main body 50 to a skin surface at an infusion or injection site on a patient. Thus, the first face 54 may be a skin adjacent face or proximal (proximal and distal defined in relation to a patient) face of the main body 50. The main body 50 may be adhered to the skin when the main body 50 is in the storage state and then may be transitioned to the delivery state. As the transition occurs, at least two adhesive bearing portions (e.g. petal members 90 see FIG. 6) of the main body 50 may be displaced with respect to one another so as to stretch or spread a surface anchored to the main body 50 via the adhesive 56. As these portions may be adhered to the skin surface, the skin may be stretched as the adhesive bearing portions are displaced with respect to one another. This may be desirable as the skin may be rendered taught facilitating piercing of the skin by the delivery sharp(s) 72 as the main body 50 transitions to the delivery state. In certain examples, the adhesive bearing portions may be disposed, for example, in opposition to one another. The displacement of the two adhesive bearing portions may increase the distance between or spread apart the two adhesive bearing portions. In other embodiments, the distance between the two adhesive bearing portions may not increase or may even decrease while still causing stretching of the skin surface. This may for example occur if the transition causes a flat patch of skin to be pulled around a curve or contour of the main body 50 formed as the main body 50 distorts over the course of the transition. A displacement of adhesive bearing portions with respect to one another that results in stretching of the adhered skin (regardless of any positive or negative change in distance between the adhesive bearing portions) may be referred to as a spreading displacement. Two adhesive bearing portions which have been so displaced may be referred to as being spreadingly displaced.

Transition of the main body 50 to the delivery state may also result in a proximal displacement or lowering of the delivery sharp(s) 72 (e.g. microneedles) toward and into the skin. In embodiments where the delivery sharp(s) 72 are included as part of a reservoir assembly 52, the reservoir assembly 52 may also be proximally displaced. In some examples, the reservoir assembly 52 may be compressed between the skin surface and a section of the main body 50 when the main body 50 is transitioned from the storage state to the delivery state. Preferably, the delivery sharp(s) 72 may be inserted into the skin prior to the reservoir assembly 52 being substantially compressed. Compression of the reservoir assembly 52 may serve to drive fluid out of the reservoir assembly 52, through the delivery sharp(s) 72 and into the target delivery destination in the patient. In embodiments described herein, the delivery sharp(s) 72 may be covered prior to use. A fluid communication path from the reservoir assembly 52 out of the delivery sharp(s) 72 may not be available prior to use.

Figure 3:
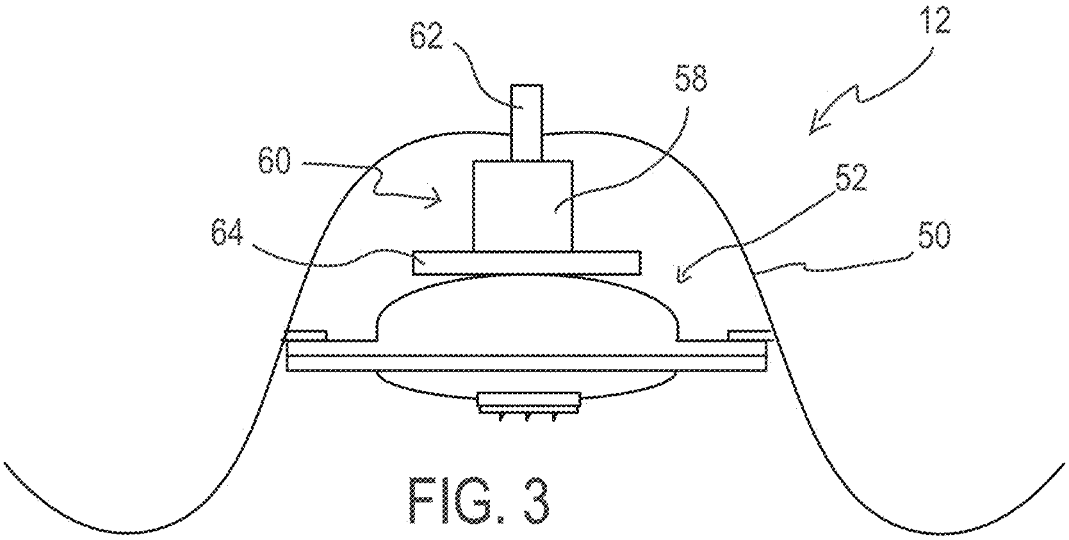
FIG. 3 depicts a representational illustration of an example delivery device including a dispensing assembly.

Referring now to FIG. 3, a block diagram of an exemplary delivery device 12 is depicted. As shown, the delivery device 12 may include a main body 50 and a reservoir assembly 52. The delivery device 12 may also include one or more bias member 58. The one or more bias member 58 may be included as part of a dispensing assembly 60 included in a delivery device 12. The dispensing assembly 60 may aid in applying pressure to the reservoir assembly 52 and aid in expelling fluid from the reservoir assembly 52 over the course of the injection. In some embodiments, the dispensing assembly 60 may include a depressor body 62 which may be coupled to or associated with the at least one bias member 58. The depressor body 62 may include or be coupled to (perhaps indirectly via the bias member 58) a reservoir interface member 64 which may also form part of a dispensing assembly 60 of a delivery device 12. In certain examples, a reservoir interface member 64 may be omitted and the bias member 58 may directly contact the reservoir assembly 52.

In some embodiments, the bias member 58 may be in an unstressed state when the associated delivery device 12 is in a storage state. User interaction with the delivery device 12 to transition the delivery device 12 to a delivery state may involve applying pressure to the depressor body 62 of the dispensing assembly 60. This may displace the depressor body 62 in the direction of the reservoir assembly 52. The depressor body 62 may include an engagement feature (e.g. catch or detent) which may engage with a retention feature of the delivery device 12 (e.g. one defined in the main body 50) to hold the depressor body 62 in the displaced position. Displacement of the depressor body 62 may in turn cause a bias to be stored in the bias member 58. With the delivery device 12 transitioned to the delivery state, the bias member 58 may restore to an unstressed state. As the bias member 58 restores, the reservoir interface member 64 of the dispensing assembly 60 may be urged against the reservoir assembly 52 to collapse the reservoir assembly 52 and drive fluid into a patient. Thus without, for example, sustained manual pressure against the delivery device 12, pressure may be applied to the reservoir 52 over a period of time sufficient to fully deliver contents of the reservoir assembly 52 (e.g. 5 minutes in certain embodiments).

In other embodiments, the bias member 58 may be in a stressed state when the associated delivery device 12 is in a storage state and may be coupled to or associated with the depressor body 62 of the dispensing assembly 60. The depressor body 62 may interface with a portion of the delivery device 12 (e.g. the main body 50) so as to resist displacement under the restoring force exerted by the bias member 58. This may prevent the bias member 58 from restoring from its stressed state. A catch or detent in the depressor body 62 may, for instance, be in engagement with the main body 50 when the delivery device 12 is in a storage state. User interaction with the delivery device 12 to transition the delivery device 12 to a delivery state may disengage the depressor body 62 such that the depressor body 62 is free to displace. Once the depressor body 62 is free to displace, the bias member 58 may restore to an unstressed or at least less stressed state and drive the reservoir interface member 64 of the dispensing assembly 60 against the reservoir assembly 52. Over a period of time, this may cause the reservoir assembly 52 to collapse such that fluid is driven out of the reservoir assembly 52 and into a patient.

Figure 4:
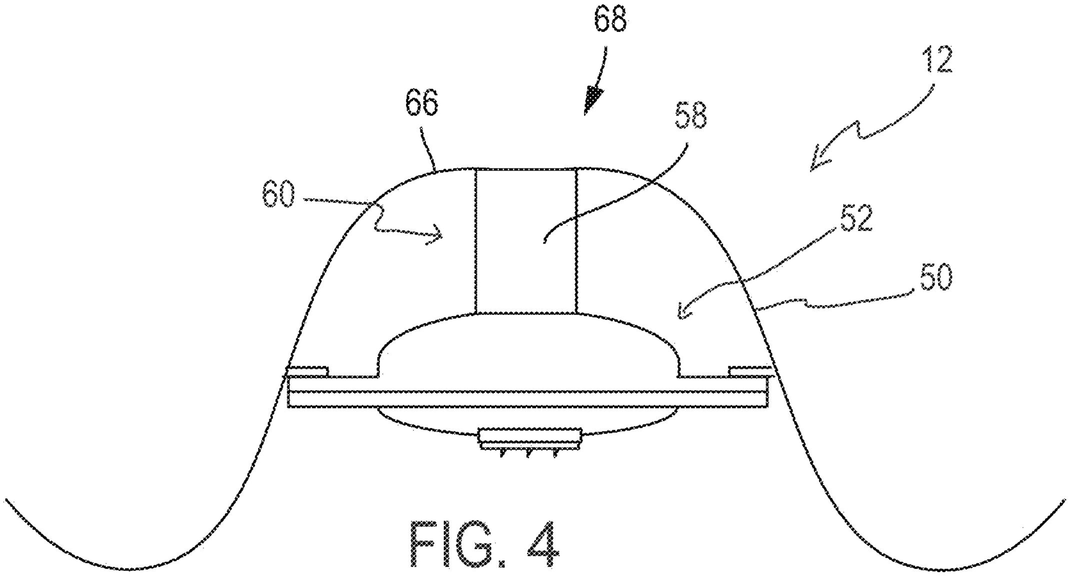
FIG. 4 depicts a representational illustration of an example delivery device including a bias member.

Referring now to FIG. 4, a block diagram of another exemplary delivery device 12 is depicted. As shown, the delivery device 12 may include a main body 50 and a reservoir assembly 52. The delivery device 12 may also include one or more bias member 58. The one or more bias member 58 may form the entire dispensing assembly 60. The one or more bias member 58 may directly contact the reservoir assembly 52 and may aid in applying pressure to the reservoir assembly 52 in order to deliver fluid out of the reservoir assembly 52. In certain examples, a reservoir interface member 64 (see, e.g., FIG. 3) may be included. Where included, the reservoir interface member 64 may (though need not necessarily be) be formed as a part of the at least one bias member 58 and may be integral therewith. The reservoir interface member 64 may directly contact the reservoir assembly 52. The at least one bias member 58 may be or include a spring, compression spring, conical spring, resilient foam, air bladder, rubber body, elastomeric body, any other suitable bias member, or some combination thereof.

Still referring to FIG. 4, the bias member 58 may be in an unstressed state when the associated delivery device 12 is in a storage state. No pressure may be applied to the reservoir assembly 52 in the storage state. In certain examples, the at least one bias member 58 (and optionally any reservoir interface member 64) may be entirely out of contact with the reservoir assembly 52 in the storage state (e.g. by 0.05-2 mm). Alternatively, the bias member 58 may contact, but not press against the reservoir assembly 52. When the delivery device 12 is used, the delivery device 12 may be transitioned to the delivery state as described elsewhere herein. As with various embodiments discussed herein, when transitioned to a delivery state, at least a portion of the delivery device 12 may at least partially invert. For example, at least the domed top surface 66 of the central region 68 may invert or partially invert. The distance between the reservoir assembly 52 and the inverted top surface 66 in the delivery state may be less than the distance between the reservoir assembly 52 and the top surface 66 in the storage state. This may in turn cause a bias to be stored in the bias member 58. The at least one bias member 58 may, in the example, be compressed when the top surface 66 is inverted. Additionally, where the at least one bias member 58 is spaced from the reservoir assembly 52 in the storage state, the at least one bias member 58 or reservoir interface member 64 (which may be a part of the bias member 58) may be displaced into contact with the reservoir assembly 52. The inverted top surface 66 may be sufficiently strong in the inverted state to withstand any force exerted by the at least one bias member 58. As the at least one bias member 58 restores, the at least one bias member (and/or reservoir interface member 64 if included) may press against the reservoir assembly 52 to collapse the reservoir assembly 52 and drive fluid into a patient. Thus without, for example, sustained manual pressure against the delivery device 12, pressure may be still applied to the reservoir assembly 52 over a period of time sufficient to fully deliver contents of the reservoir 12 (e.g. five minutes in certain embodiments).

Figure 5A:
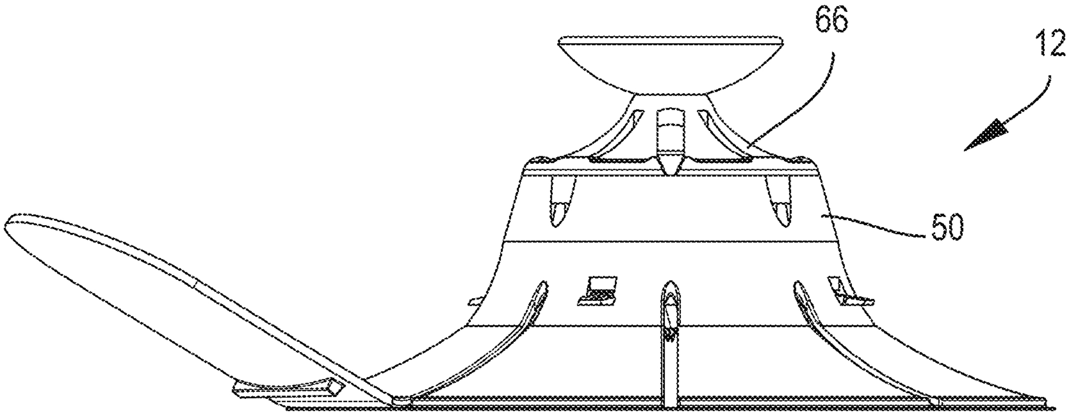
FIG. 5A depicts a side view of an example delivery device.
Figure 5B:
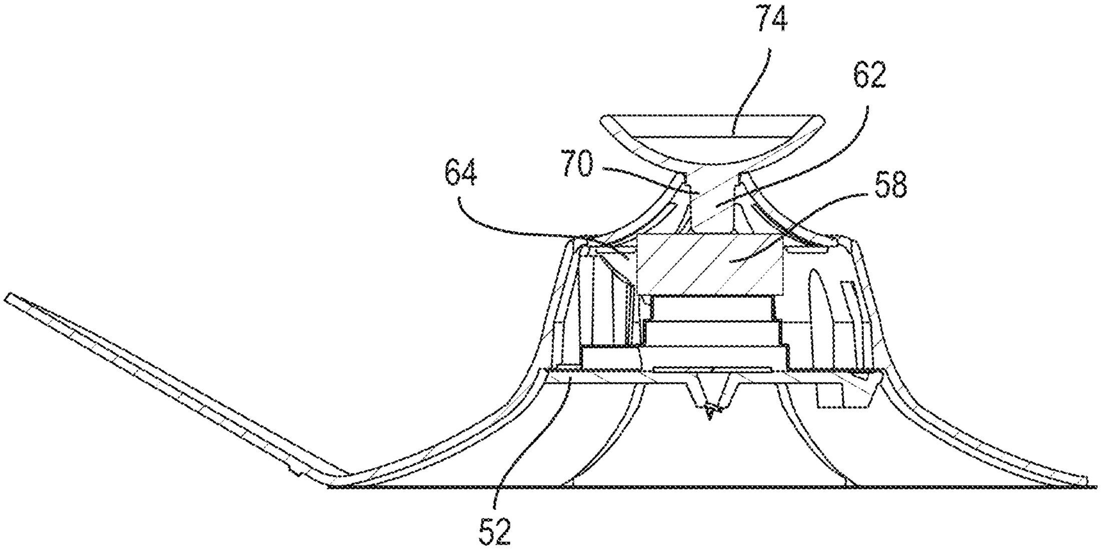
FIG. 5B depicts a cross-section view of an example delivery device.

Referring now to FIGS. 5A-5B, in certain examples, the bias member 58 may be a block of compressible material such as rubber or elastomer. The surface of the bias member 58 adjacent the reservoir assembly 52 may serve as the reservoir interface member 64 and may be substantially flat or planar in certain embodiments. Thus, various delivery devices 12 may include a reservoir interface member 64 which is compliant. The delivery device 12 depicted in FIGS. 5A-5B is shown in a storage state. As shown, the delivery device 12 may include a depressor body 62 which may be coupled to the top surface 66 of the main body 50. The top surface 66 of the main body 50 may have an infundibuliform or trumpet shape when in the storage state in certain examples. Such top surfaces 66 may be included in various other embodiments described herein. As shown, the depressor body 62 includes a post 70. The post 70 may extend through and be coupled to the top surface 66. The depressor body 62 may further include a dish body 74 coupled to the post 70. The dish body 74 may be disposed above the top surface 66 of the main body 50. The dish body 74 may provide an ergonomic location for a user to press against when transitioning the delivery device 12 to the delivery state. When the delivery device 12 is transitioned to the delivery state, top surface 66 may substantially invert and the bias member 58 may be compressed against the reservoir assembly 52. This may urge fluid to be dispensed from the reservoir assembly 52. In some embodiments, the bias member 58 may be coupled to an end of the post 70 opposite the dish body 74. For example, the bias member 58 may include a receiving recess 76 (see, e.g., FIG. 6) into which the end of the post 70 may be mated. Though a dish body 74 in the form of a concave dish is depicted, a dish like body need not be included in all embodiments. For example, the dish body 74 may be replaced by a relatively planar body or plate in certain embodiments.

Figure 6:
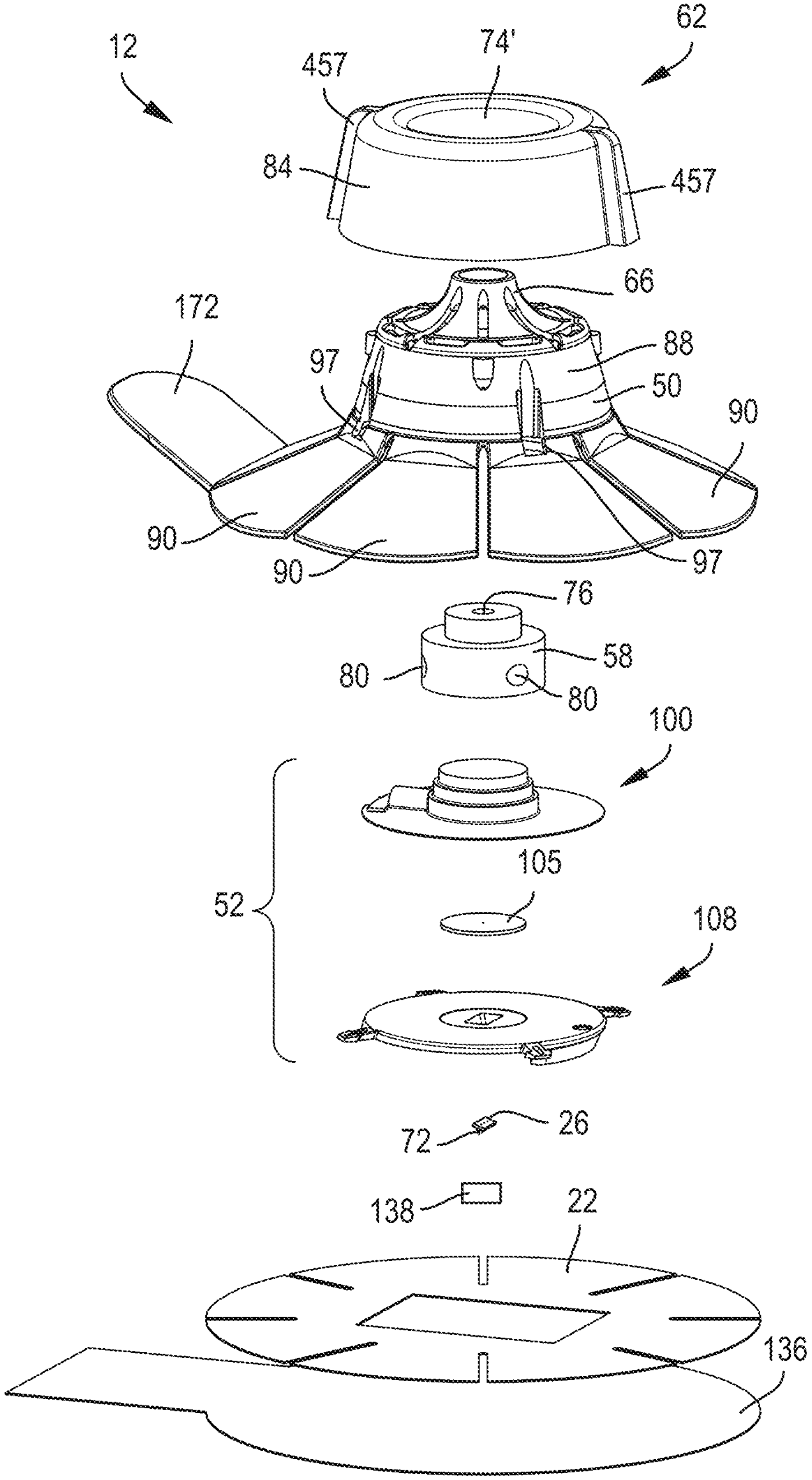
FIG. 6 depicts an exploded view of an example delivery device.

Referring now to FIG. 6, an exploded view of a delivery device 12 similar to that illustrated in FIG. 5B is depicted. As shown, some delivery devices 12 may include a bias member 58 which changes in width along its height dimension and is constructed of an elastomeric material such as a silicone material. For example, the bias member 58 may be tiered. In the example shown, the bias member 58 includes two tiers. Additionally, the bias member 58 may include one or more hollow region. In the example embodiment, the bias member 58 includes a plurality of passages 80 which extend through the bias member 58 to form hollow regions. The passages 80 may extend through at least one of the tiers and in the example embodiment, both are disposed in the first or base tier of the bias member 58. The passages 80 may be evenly spaced about the bias member 58 and are disposed such that the bias member 58 has a plane of symmetry in the example shown. As noted above, when the top surface 66 of the main body 50 is transitioned from its storage state position to the delivery state position, the bias member 58 may become compressed. Fluid may be driven out of the reservoir assembly 52 as the bias member 58 restores to a less compressed state. The passages 80 may make the initial application of force by the bias member 58 against the reservoir assembly 52 more gentle and less abrupt. This may make reservoirs assembly 52 more robust during use while still ensuring reservoirs assembly 52 are substantially emptied during delivery.

Figure 7A:
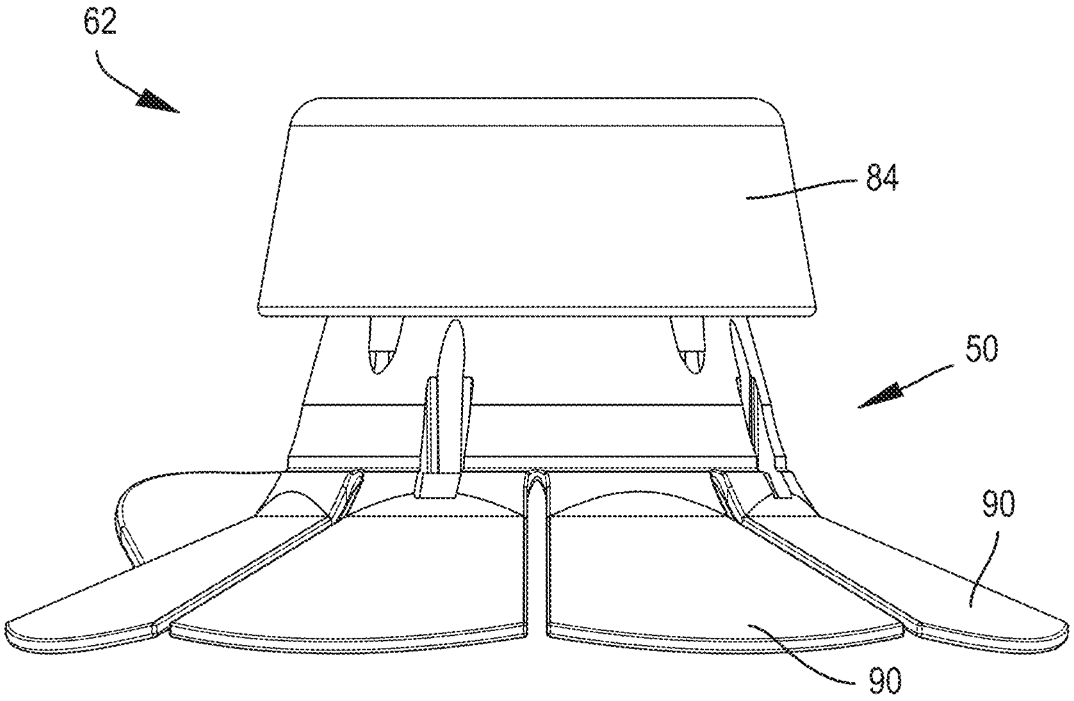
FIG. 7A-7B depict views of portions of an example delivery device respectively in a storage state and a delivery state.
Figure 7B:
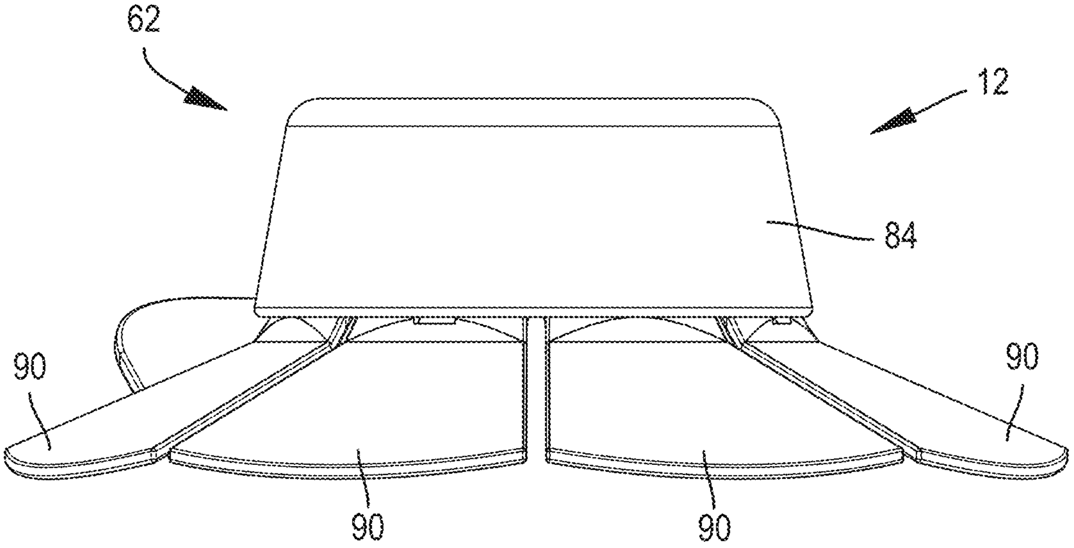
Figure 8:
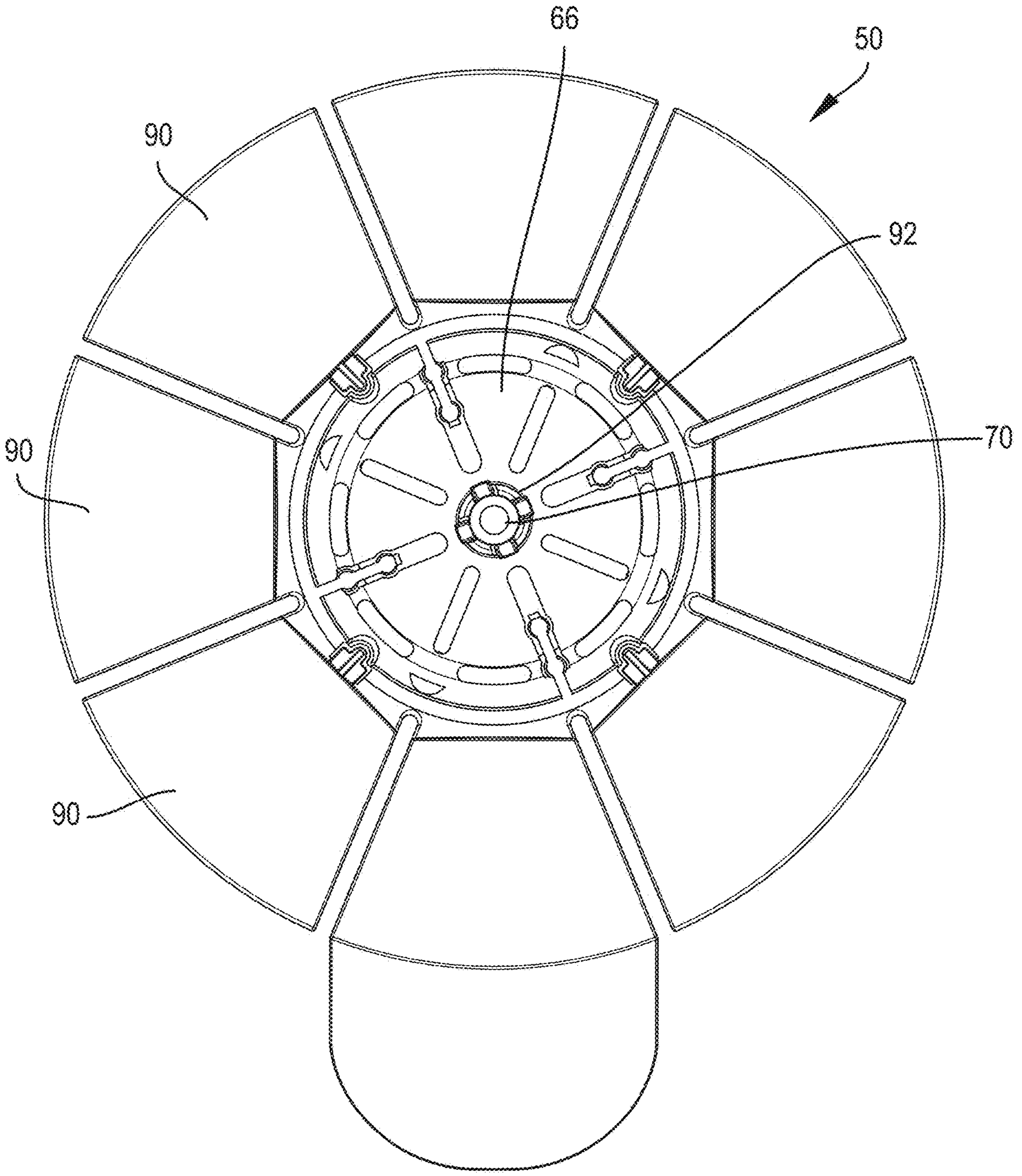
FIG. 8 depicts a bottom view of an example main body of a delivery device and a portion of a depressor body.

Referring now also to FIGS. 7A-8, various views of a main body 50 and a depressor body 62 are shown. The depressor body 62 of the delivery device 12 may include a dish region 82 from which a skirt 84 extends. The skirt 84 may include a set of ears 86 extending outwardly therefrom such as those shown in FIG. 6. Any ears 86 may be spaced at regular angular intervals. The dish region 74' may be shaped similar to dish bodies 74 described elsewhere herein. The skirt 84 may be sized to nest over a supporting structure 88 of the main body 50 when the delivery device 12 is transitioned from the storage state (FIG. 7A) to the delivery state (FIG. 7B). Thus, the supporting structure 88 may act as a guide which helps inhibit tilting of the depressor body 62 and assists in ensuring that the depressor body 62 displaces substantially along an axis as pressure is applied. When transitioned fully to the delivery state, the end of the skirt 84 opposite the dish region 74' may be near the petal members 90, but sufficiently spaced from the petals members 90 so as not to restrict movement of petal members 90. As described in greater detailed elsewhere herein, the end of the skirt opposite the dish region 74' may also include a number of indents to accommodate any protruding bodies 250 in which filters 260 or septa 94 are disposed. As shown best in FIG. 8, the depressor body may include a post 70. The post 70 may extend through a dogged aperture 92 in the central portion of the top surface 66 of the main body 50. As the depressor body 62 is pulled in a direction away from the main body 50, the dogs of the dogged aperture 92 may pivot and bite into the post 70 inhibiting the depressor body 62 from being disassociated from the rest of the delivery device 12. When the delivery device 12 is assembled, the post 70 may project into the receiving recess 76 in the bias member 58.

As mentioned above in relation to FIGS. 2A-2B, delivery devices 12 described herein may access and transfer fluid into a patient via at least one delivery sharp 72. Where a plurality of delivery sharps 72 are included they may be arranged in a one or two dimensional array and may extend from the reservoir assembly 52. Where multiple delivery sharps 72 are included, the delivery sharps 72 may be arranged in one or more rows and/or columns. Though three delivery sharps 72 arranged in a single row are depicted in certain example embodiments herein, the number and arrangement of delivery sharps 72 may differ in alternative embodiments. Any suitable number of rows and/or columns may be included in various examples. In various embodiments there may, for example, be a single row array of delivery sharps 72 including up to five delivery sharps 72. Preferably, the delivery sharps 72 may be arranged so as to prevent a bed of nails type scenario in which penetration of the skin via the delivery sharps 72 may be inhibited or inconsistent across users or delivery devices 12. This may occur when too many delivery sharps 72 are arranged in close proximity to one another. Thus, the array may be referred to as a spaced array of delivery sharps 72.

The delivery sharps 72 may be selected based on the desired target delivery destination in a patient. In certain embodiments, the target delivery destination may be a transcutaneous location. For example, the target delivery destination may be a subcutaneous delivery destination or an intramuscular delivery destination. For purpose of example, the delivery sharps 72 are depicted herein are shown as microneedles. Such delivery sharps 72 may be present in delivery devices 10 with shallow (e.g. above subcutaneous tissue) target delivery destinations. In alternative embodiments where, for instance, the target delivery destination is a subcutaneous or intramuscular location, conventional delivery sharps (e.g. 30-gauge needle) may be utilized in place of the delivery sharps 72 shown.

Figure 9:
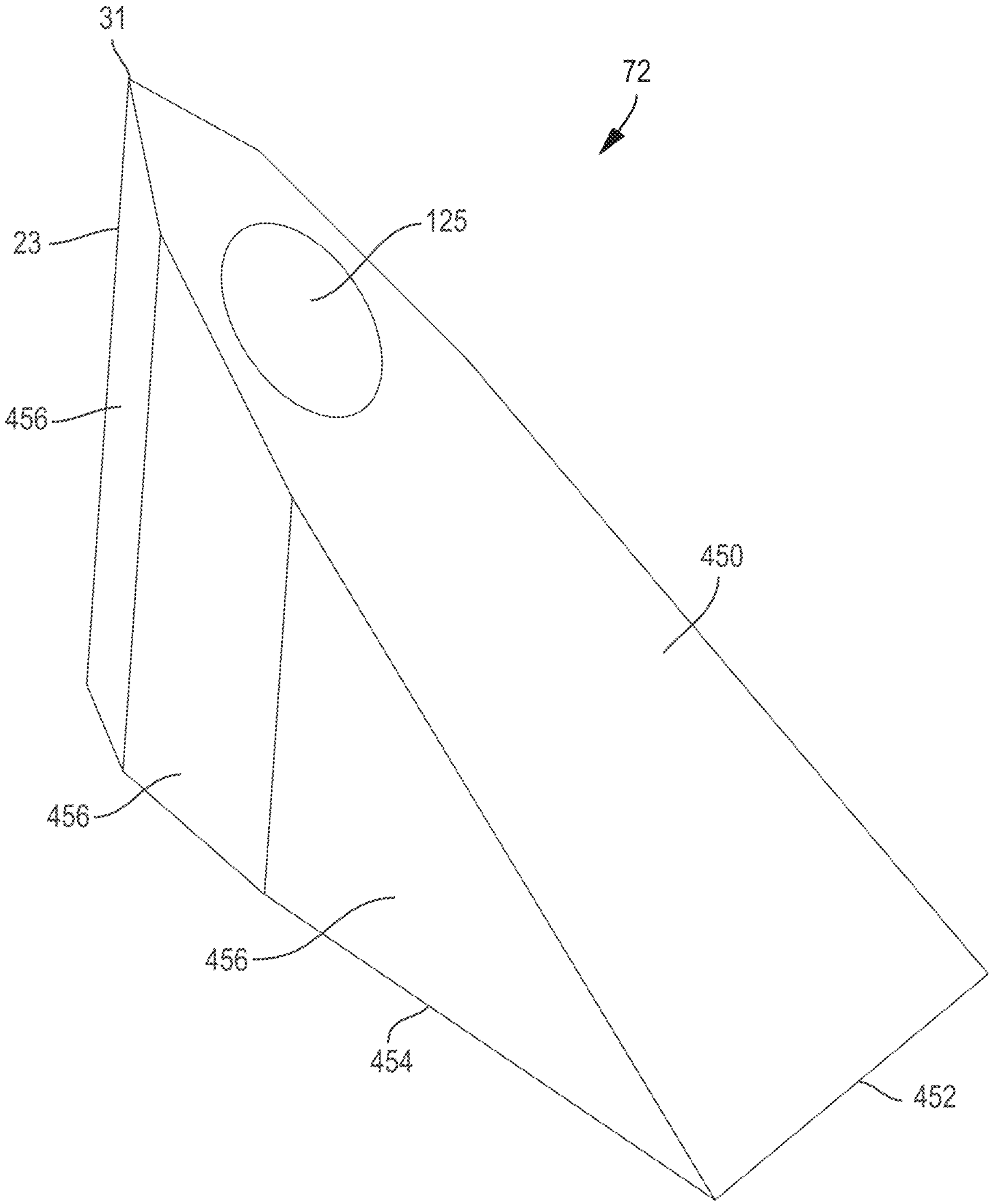
FIG. 9 depicts an exemplary microneedle.

Referring now also to FIG. 9, where microneedles are used, the microneedles described herein may, in certain embodiments, be MEMS produced, polyhedral (e.g. pyramidal), silicon crystal microneedles. These microneedles may be no greater than 1 mm in height, e.g. 0.6 mm or 0.8 mm. Longer (e.g. greater than 1 mm tall) or shorter microneedles may also be used. At least some edges of the microneedles may be rounded or filleted, though such microneedles may still be referred to herein as polyhedral. In some examples and as shown in FIG. 9, the microneedles described herein may be generally in the shape of a heptagonal prism (though pentagonal, nonagonal, and other polygonal prisms may also be used as the base shape) which has been diagonally sected to form a heptagonal ramp or pointed wedge. In such embodiments, the heptagonal prism may be sected by a plane extending from a vertex 31 of the top face of the prism through the most distal side 452 of the base 454. At least two sides of the base of the microneedle may be parallel. The side walls 456 may extend substantially perpendicularly from the base 454. The microneedle may be substantially symmetric about a line of symmetry extending from the vertex 31 to a point above the center of the most distal side 452. In other embodiments, the microneedles may be conically shaped. Any other suitable shape may be used. In the example, the vertex 31 is shown as a point which forms a tip of the microneedle. In other embodiments, this portion of a microneedle may be rounded (though may still be referred to herein as a vertex 31 and such microneedles may still be referred to as pointed). In such embodiments, the back facing edge 23 may be a round face or the back facing edge 23 and the adjacent side walls 456 may be replaced by a rounded face.

The points or tips of microneedles described herein may be solid and the flow lumens 125 through the microneedles may be offset from the points or tips (in FIG. 9 the vertex 31 forms the tip) of the microneedles. Hollow tipped microneedles in which the flow lumen 125 extends to the tip of the microneedle may also be utilized. In some embodiments, the microneedles may be NanoPass hollow microneedles available from NanoPass Technologies Ltd. of 3 Golda Meir, Nes Ziona, Israel. The microneedles may be etched with an appropriate etching technique or variety of different etching processes into a large wafer of silicon material. Arrays of microneedles may subsequently be singulated from the larger wafer. This may generate a number of microneedle type delivery sharps 72 which project from and are continuous with a sharp bearing body 26 (see, e.g., FIG. 11A).

Figure 10A:
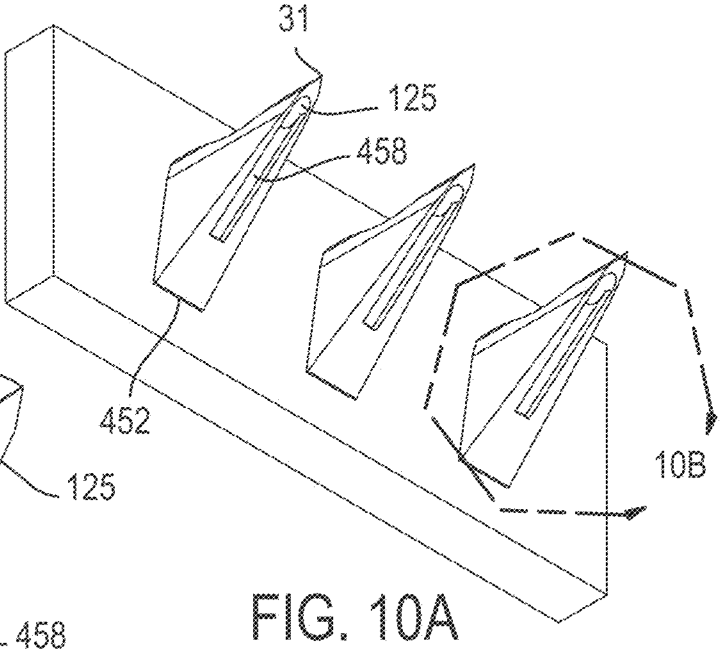
FIG. 10A depicts an example sharp bearing body incorporating microneedles.
Figure 10B:
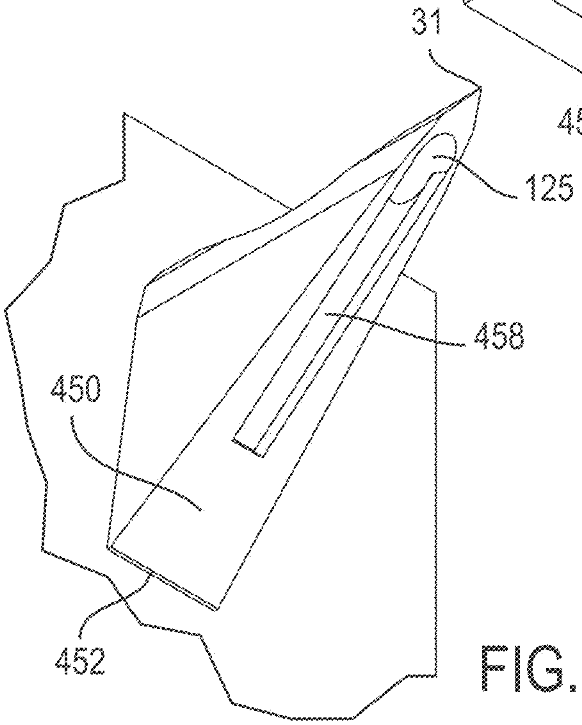
FIG. 10B depicts an example microneedle.

With reference to FIGS. 10A-10B, in some embodiments, microneedles may be constructed to include certain features that may help to reduce the pressure required to inject fluid, such as a medical agent, into the skin of a patient. In some examples, features common certain to insect stingers or biological venom administration structures may be incorporated. These features may include various recesses or depressions which are formed as part of each microneedle or at least one microneedle of a delivery device 12. These recesses or depressions may fluidly communicate with the flow lumen 125 of the respective microneedle. In some embodiments, different microneedles of a delivery device 12 may include different recesses or some microneedles may include a plurality of recesses which could be of different varieties (though need not be).

For example, as shown in FIGS. 10A-10B, a microneedle may include a channel or trough 458 on an exterior sloped face 450 leading from the flow lumen 125 toward the distal side 452. The channel 458 may allow medical agent to flow through it along the outer side of the microneedle to find a path of least resistance, or weakest link, into the skin. In the embodiments shown, medical agent may be routed by the channel 458 to flow along the outer side of the microneedle to a weak region in the skin in the event the outlet of the flow lumen 125 has been inserted to a greater depth than the depth of the weak region. The lamina lucida junction, an intradermal delivery destination, is a weak link in the skin structure, and is difficult to consistently inject directly into due to its relative thinness (it is typically on the order of 40 nm thick). A microneedle including a channel 458 may, for example, allow flow of medical agent to the lamina lucida junction when the lamina lucida junction has been passed by the outlet of the flow lumen 125. The channel 458 may facilitate distribution of the medical agent through a larger area of entry or injection. In some examples, incorporating a channel 458 into a microneedle may reduce the pressure required to inject a medical agent into the skin considerably.

An appropriate silicon etching technique (or mold in embodiments using polymeric microneedles) may be used to create steeper side walls of the channel 458. This may help inhibit the skin from bending into and occluding the channel 458. Etching techniques that could be used include, by way of non-limiting example, chemical etching techniques (e.g., acid). Suitable etching techniques may include ion based etching techniques (e.g. reactive ion etching). The etching process could be a wet etching process or a dry etching process. In some non-limiting embodiments, the channel 458 may be within a range of 50-60 microns wide from side to side. In some non-limiting embodiments, the flow lumen 125 may have a diameter of 50-60 microns. The channel 458 may have a width equal to the diameter or widest portion of the flow lumen 125 or the channel 458 may have a width which is less than or greater than the width of the flow lumen 125. In certain examples, the width of the channel 458 may be about 5-10 percent of the height of the microneedle.

To avoid leakage of the fluid from the channel 458, it may be desirable to ensure that the channel 458 terminates at least a certain distance beneath the surface of the skin yet also reaches the targeted skin layer (e.g., the lamina lucida junction) when the microneedle is inserted into the skin. In some embodiments the channel 458 extends from the flow lumen 125 to within at most 50 microns (e.g. 50-200 microns) of the base 454 of the microneedle. In some embodiments, the end of the channel 458 most proximal the base 454 of the microneedle may be at least below the stratum corneum (and perhaps one or more of the stratum lucidum, stratum granulosum, stratum spinosum, and stratum basale) when the microneedle is inserted into the skin. In some embodiments, the end of the channel 458 most proximal the base 454 may be disposed below the epidermis (e.g. in the basement membrane) or within the epidermis.

The channel 458 need not be straight or shaped in the manner shown in and described with reference to FIGS. 10A-10B. In some embodiments, the channel 458 may be a more meandering channel 458. A curved channel 458 could, for example, be used provided the dimensions of the microneedle are accommodated. Moreover, there need not be only one channel 458. More than one channel could be used provided the structural integrity of the microneedle is accommodated.

The depth of the channel 458 may be about 25 microns or more (e.g. 25-50 microns) in certain examples. The depth of the channel 458 may be or be less than 5 percent the height of the microneedle. While the depth of the channel 458 may be constant along the length of the channel 458, the depth of the channel 458 need not be constant along the length of the channel 458. Likewise, the width of the channel 458 need not be constant along the length of the channel 458 (see, e.g., FIG. 11B). The width of the channel 458 may be about 20-30 percent of the width of the distal side 452 of the microneedle at the narrowest point in the channel 458. In some embodiments, the width of the channel 458 may increase as distance to the distal side 452 decreases. In some embodiments, at its widest, the channel 458 may have a width which is 50% or more the width of the distal side 452.

Figure 11A:
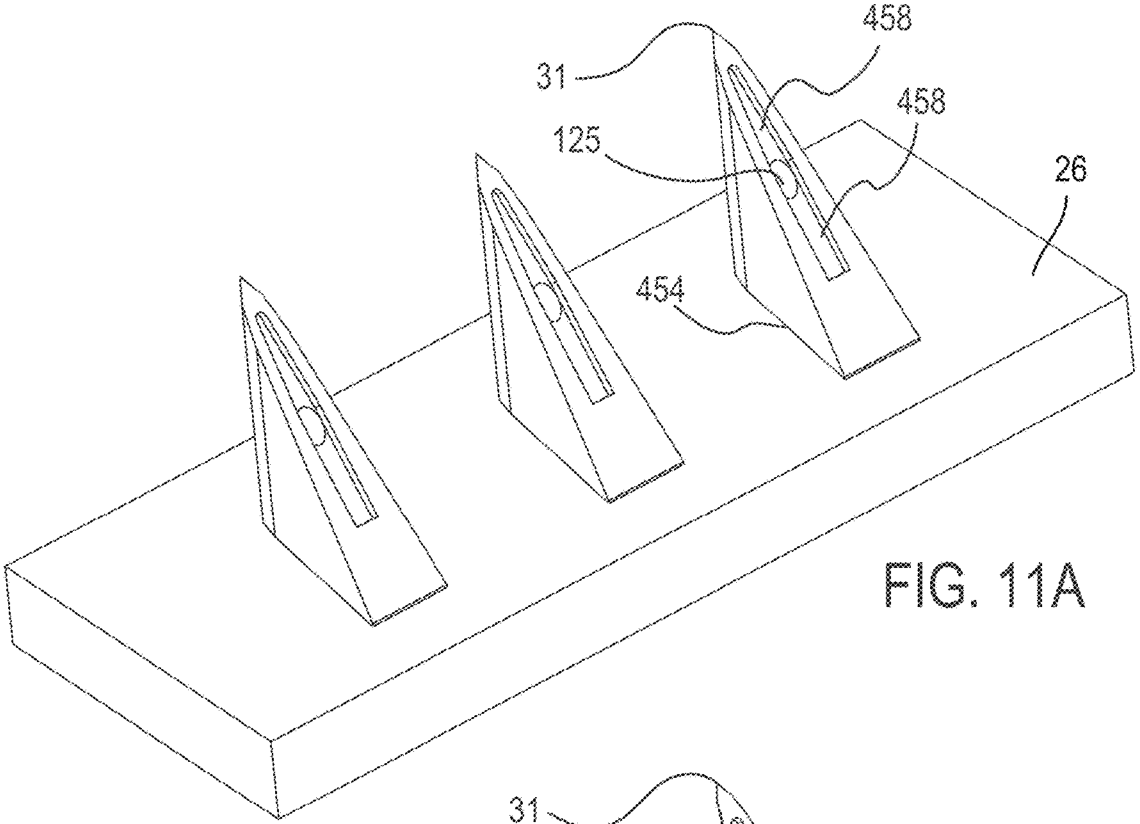
FIG. 11A depicts a perspective view of an example sharp bearing body including a set of exemplary microneedles.
Figure 11B:
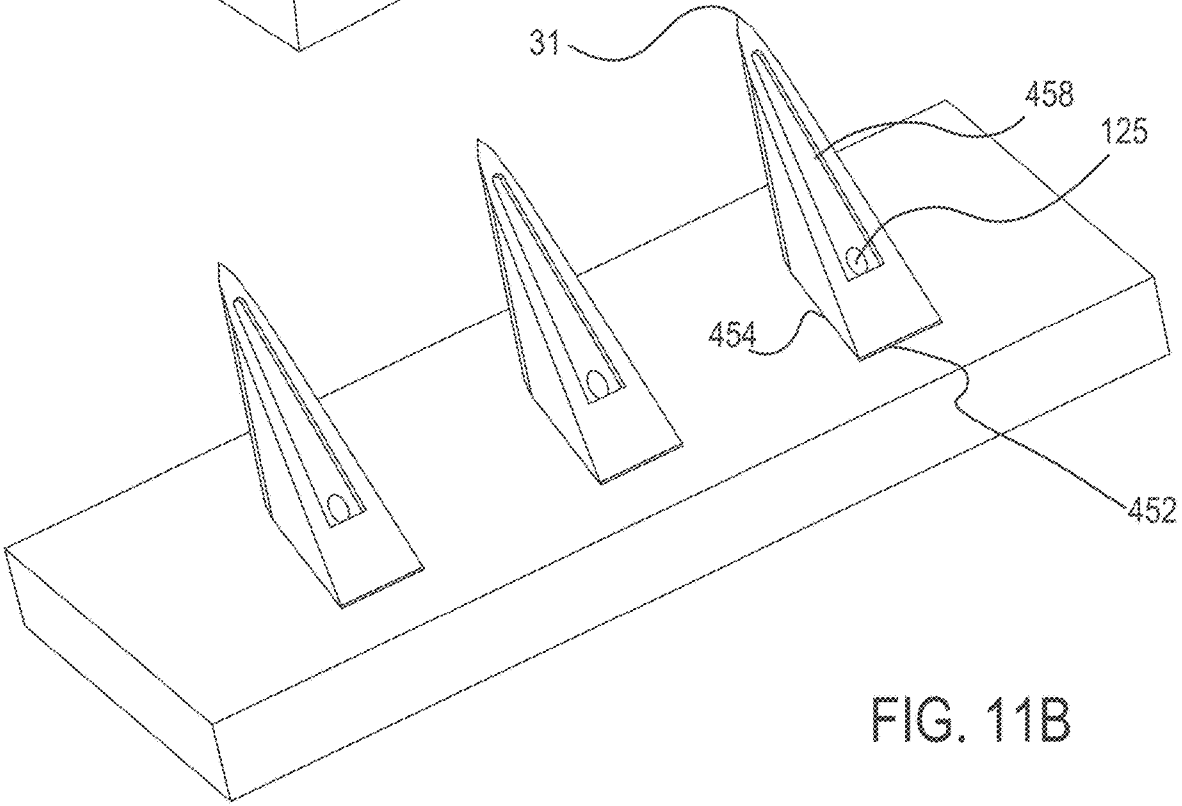
FIG. 11B depicts a perspective view of an example sharp bearing body including a set of exemplary microneedles.

Referring now also to FIG. 11A and FIG. 11B, in other examples, the channel 458 may extend from the location of the lumen 125 toward the tip or vertex 31 of the microneedle (see, e.g., FIG. 11B). Moreover, in some examples, the channel 458 may extend both toward the vertex 31 and toward the base 454 from the location of the lumen 125. That is, the channel 458 may include a portion on both sides of the lumen 125 (see, e.g., FIG. 11A). As shown, the lumen 125 may be located substantially centrally in the sloped face 450 of the microneedle. In such embodiments, a channel 458 may extend toward the distal side 452 of the base 454 and a channel 458 may extend toward the tip or vertex 31. In other embodiments, the lumen 125 may be positioned at (or near) an end of the channel 458 most proximal the base 454.

Figure 12A:
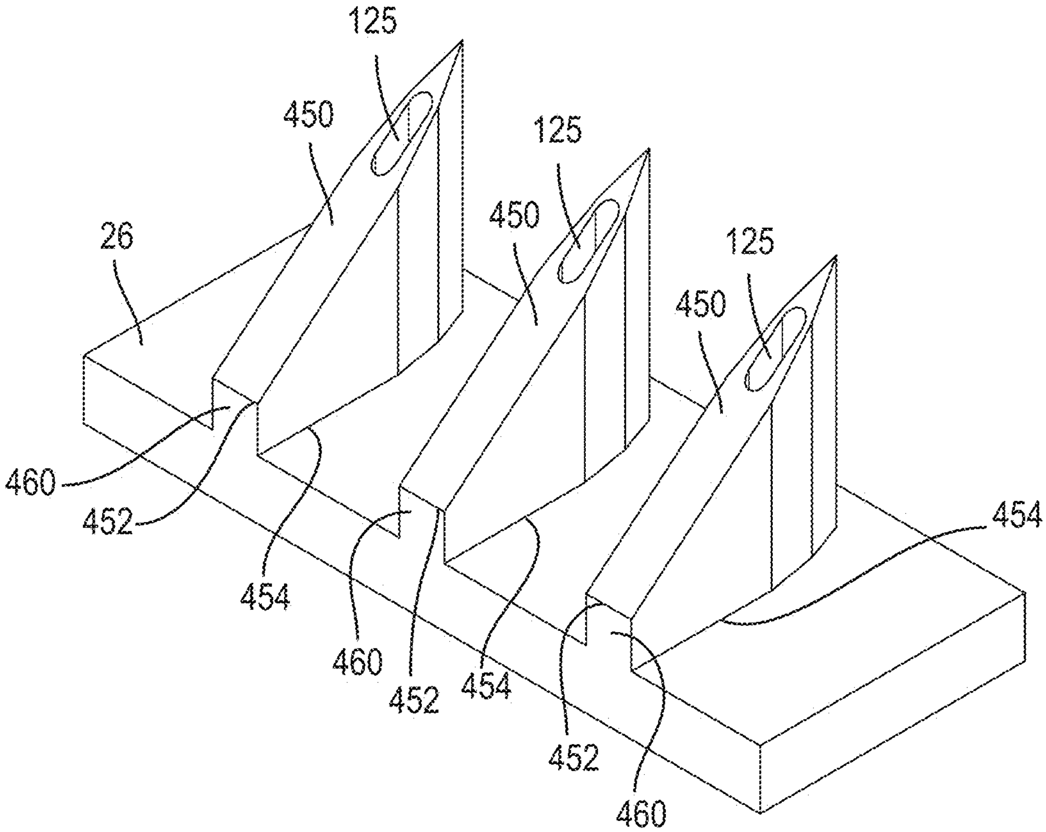
FIG. 12A depicts a perspective view of an example sharp bearing body include a set of exemplary microneedles.
Figure 12B:
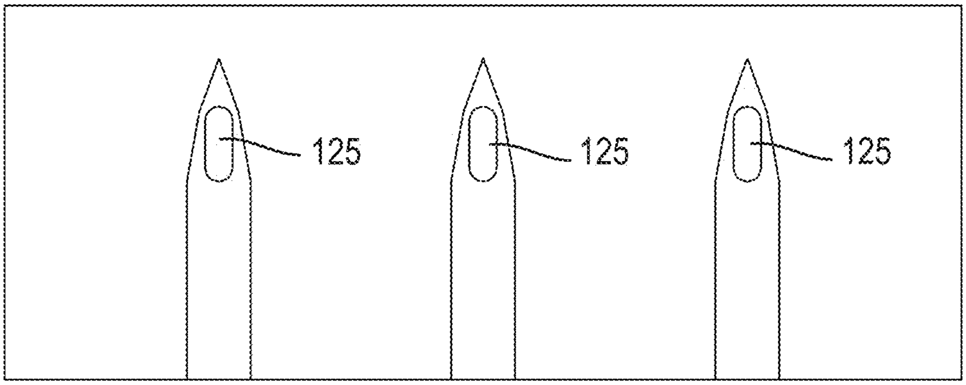
FIG. 12B depicts a top plan view of the example sharp bearing body shown in FIG. 12A.
Figure 13A:
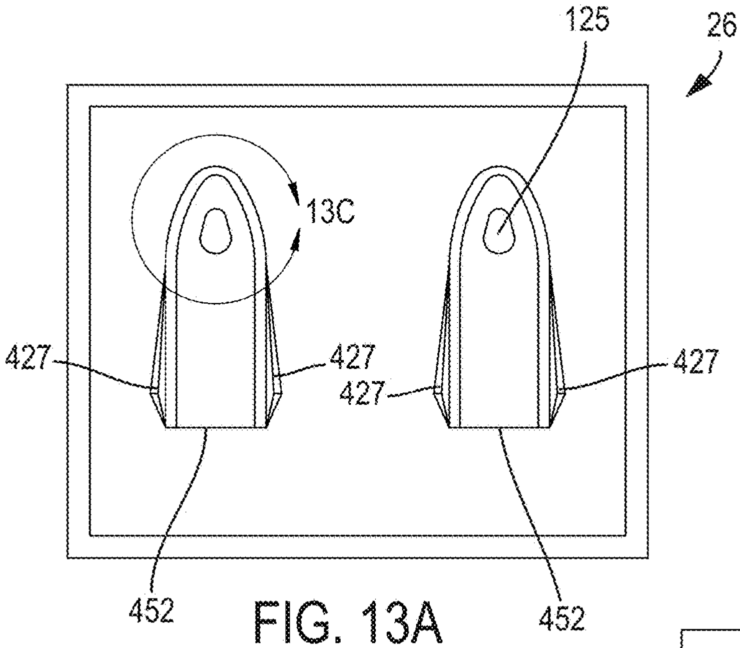
FIG. 13A depicts a top plane view of an example sharp bearing body.
Figure 13B:
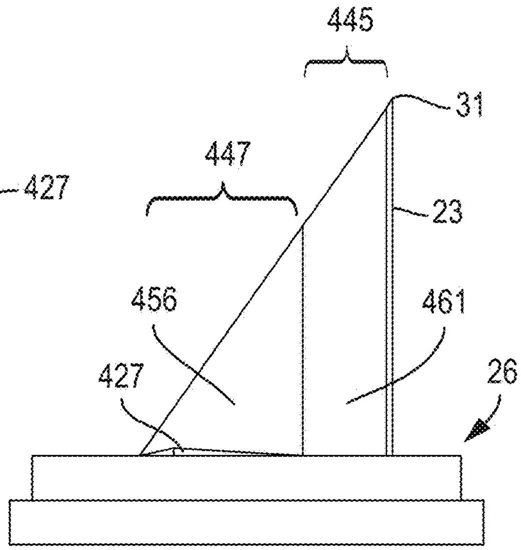
FIG. 13B depicts a side view of an example sharp bearing body.
Figure 13C:
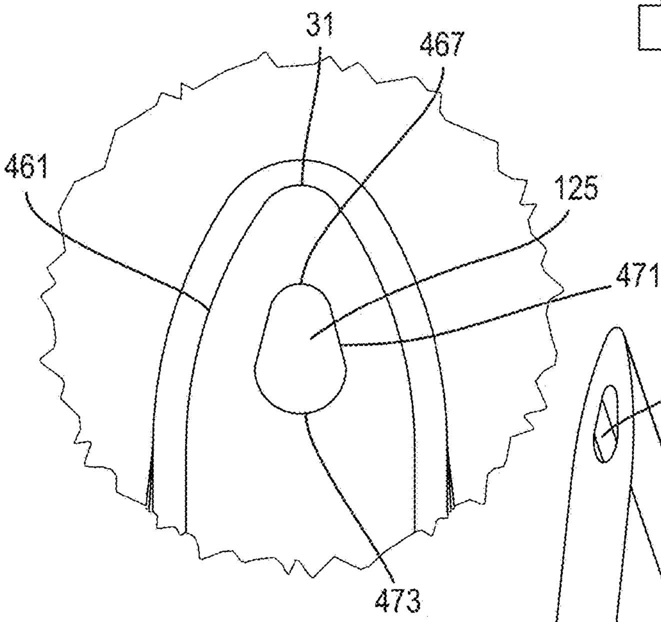
FIG. 13C depicts a detailed view of the indicated region of FIG. 13A.
Figure 13D:
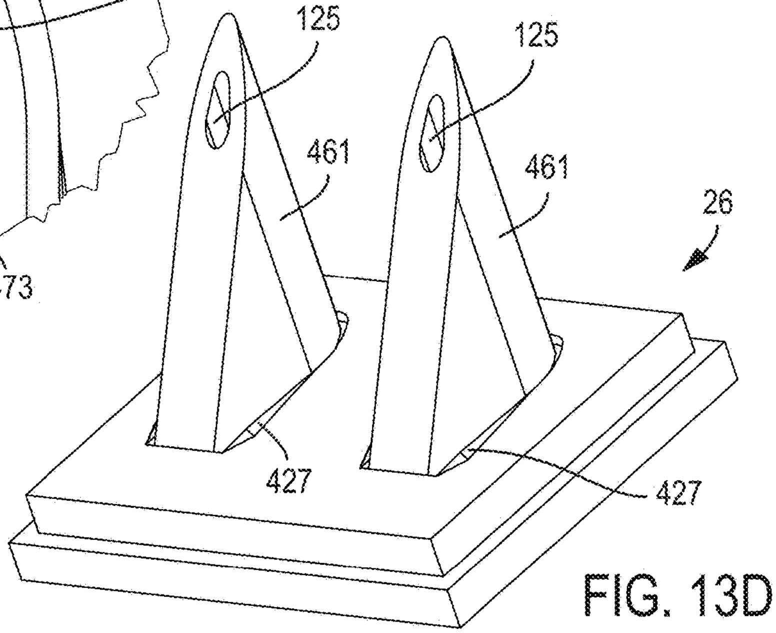
FIG. 13D depicts a perspective view of an example sharp bearing body.
Figure 14A:
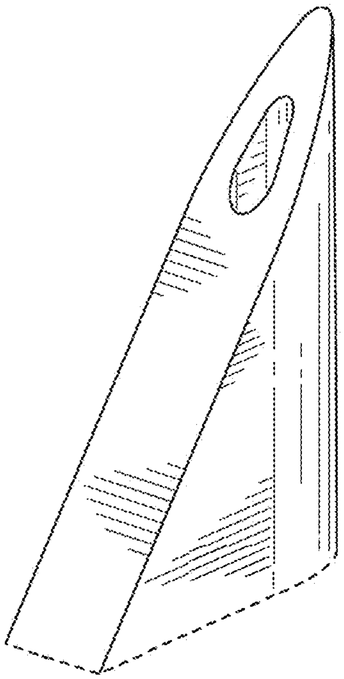
FIGS. 14A-14G depicts a series of views of an example microneedle.
Figure 14B:
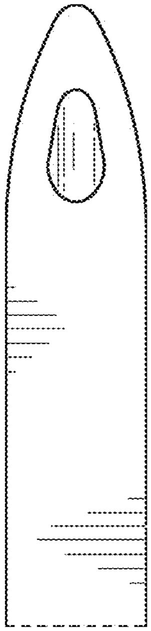
Figure 14C:
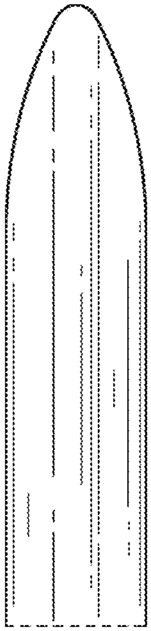
Figure 14D:
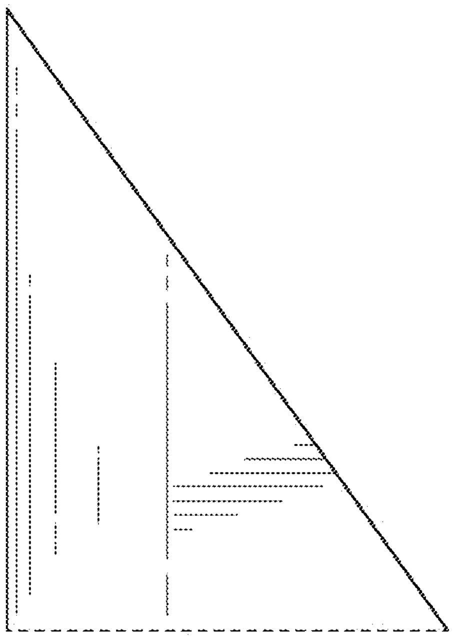
Figure 14E:
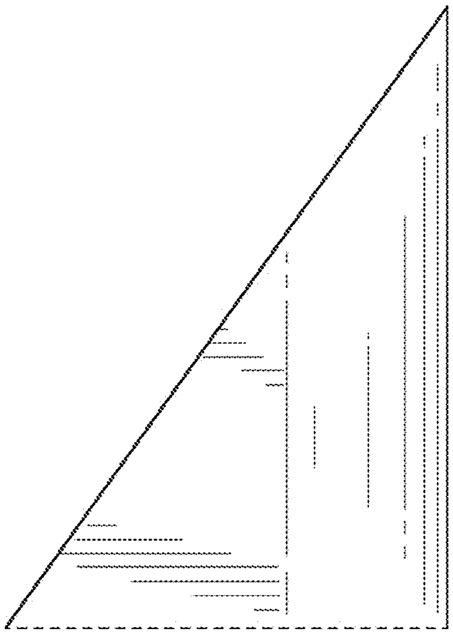
Figure 14F:
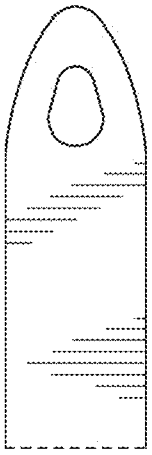
Figure 14G:
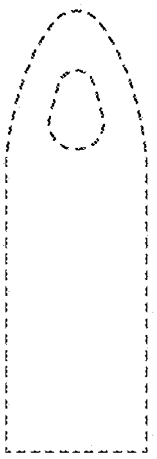

Referring now to FIGS. 12A-12B, views of a sharp bearing body 26 including a number of microneedles are shown. In certain embodiments, a channel 458 may not be included. Instead, a microneedle may include a flow lumen 125 with an elongate cross-section. Microneedles with channels 458 and elongate lumens 125 are also possible. When in place within the patient, an elongate lumen 125 may be in fluid communication with, for example, multiple layers of skin. Thus, a thin and/or weak layer of skin may be easier to target when the microneedle is advanced into a patient. Elongate lumens 125 may also help to lower pressure required to inject. Such elongate flow lumens 125 may have any suitable cross-section. In some embodiments, the cross-section may be oval or elliptical. Alternatively, a lumen 125 with an obround cross-section may be used as is shown in FIGS. 12A-12B. Polygonal cross-sectional shapes may also be used, such as though not limited to rectangular, trapezoidal, triangular, etc. In certain examples, the length (in the direction of elongation) of the cross-section of the lumen 125 may be up to 100-200 microns or greater (though could be less in certain examples). Where elongate lumens 125 are included, the end of the lumen 125 most proximal the distal side 452 may be spaced from the distal side 452 by at least a certain distance. The spacing may be such that, the end of the lumen 125 most proximal the distal side 452 may be at least below the stratum corneum (and perhaps one or more of the stratum lucidum, stratum granulosum, stratum spinosum, and stratum basale) when the microneedle is inserted into the skin. In some embodiments, it may be disposed below the epidermis (e.g. in the basement membrane) or within the epidermis.

Still referring to FIGS. 12A-12B in certain embodiments, the sloped face 450 of a microneedle may not extend to the base 454 of a microneedle. There may, for example, be a vertical face 460 extending from the base 454 to the distal side 452 of a microneedle. Where a vertical face 460 is included, the vertical face 460 may be aligned with a side (e.g. distal side 454) of a sharp bearing body 26 and may form an extension thereof. Including such vertical faces 460 may aid in reducing the size of a sharp bearing body 26 and may aid in ensuring consistent fluid delivery into a target destination for certain microneedles. Though shown in relation to FIGS. 12A-12B, any of the microneedles shown herein may be arranged with vertical faces 460.

Referring now to FIGS. 13A-13D, views of a sharp bearing body 26 including a pair of microneedles are depicted. Such sharp bearing bodies 26 may be preferable for certain fluid delivery applications such as those in which relatively slow delivery of fluid is acceptable or in scenarios where fluid is not delivered via a sustained, manually applied force. Such sharp bearing bodies 26 may also be particularly well suited where a user does not manually maintain the orientation of a delivery implement (e.g. syringe). By including only a pair of microneedles on a sharp bearing body 26, more sharp bearing bodies 26 may be created out the same wafer of silicon material even while increasing the height of the microneedles. This may also make such sharp bearing bodies 26 more cost efficient without adversely impacting delivery in devices where the orientation of the device is not manually maintained and relatively slow delivery is acceptable.

As shown, the sharp bearing body 26 is arranged such that the cross-sectional area of the sharp bearing body 26 increases as distance from the sharp bearing face of the sharp bearing body 26 increases. In the example, the sharp bearing body 26 has a stepped appearance, though any arrangement described in relation to FIGS. 18-22 may be used. Thought not shown, the example microneedles depicted in FIGS. 13A-13B could include a vertical face 460 as described in relation to FIGS. 12A-B and FIG. 22. Other features such as any channels 458 described herein may also be included.

As shown, each of the microneedles includes a tip region 445 and a trailing region 447 (isolated views of an example microneedle are shown in FIGS. 14A-14G). The tip region 445 includes a rounded vertex 31 and back facing edge 23. The vertex 31 and back facing edge may in certain examples have a radius of 40-25 microns (e.g. 34 microns). At least one additional radiused region 461 may connect the back facing edge 23 to the trailing region 447 on each side of the microneedle. In the example the at least one additional radiused region is a single constant radiused region on each side of the microneedle. In certain examples, the radius of this region may be 310-335 microns (e.g. 324 microns). Thus, the entire tip region 445 may be rounded with the sidewalls 456 in this region being devoid of straight spans or corners. This may generate a microneedle with a particularly robust tip region 445. The sidewalls 456 on each side of the microneedle in the trailing region 447 may be planar. In certain examples, the sidewall segments on each side of the microneedle may be oriented parallel to one another. In alternative examples, the sidewall segments in the trailing region 447 may be at a slight angle to one another (e.g. less than 25° to one another). Greater angles are also possible.

The lumen 125 for the microneedle may be disposed in the tip region 445 in a central position with respect to the sidewalls 456 on each side of the microneedle. The lumen 125 may be defined by a first radiused wall 467 most proximal the vertex 31 and back facing edge 23. The distance between the back facing edge 23 and the closest portion of the first radiused wall 467 may be 65-80 microns. The lumen 125 may also be defined by a second radiused wall 473 forming the portion of the lumen 125 most distal to the vertex 31 and back facing edge 23. The first radiused wall 467 may have a tighter radius than the second radiused wall 473. In some examples, the first radiused wall 467 may have a radius of 23.5-33.5 microns and the second radiused wall 473 may have a radius of 35-42.5 microns. Straight spans 471 may be present on each side of the lumen 125 to connect the ends of the first radiused wall 467 to respective ends of the radiused wall 473. The minimum distance between the sidewall of the microneedle and the closest wall of the lumen 125 may be 25-30 microns.

Figure 15A:
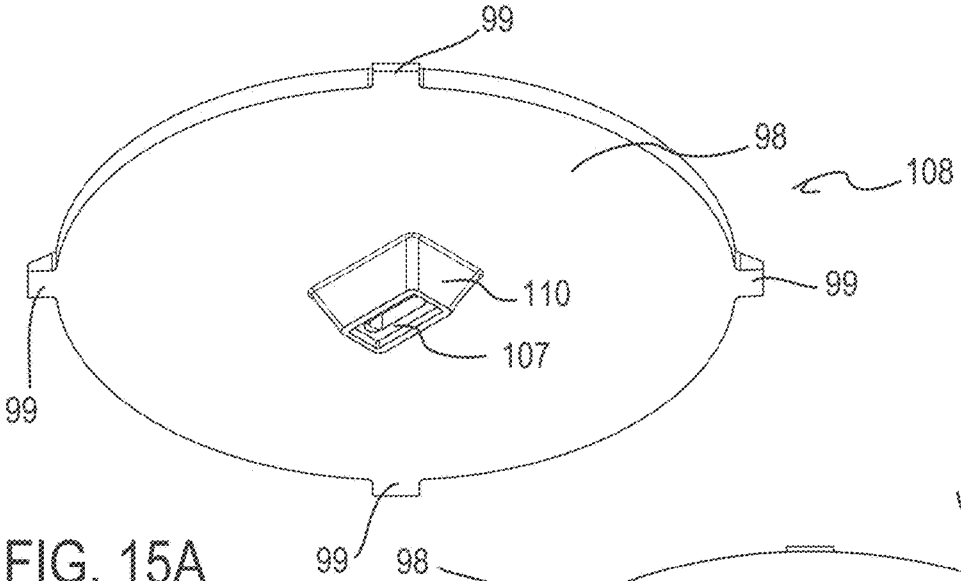
FIG. 15A depicts a perspective view of an example holder including a stage projection.
Figure 15B:
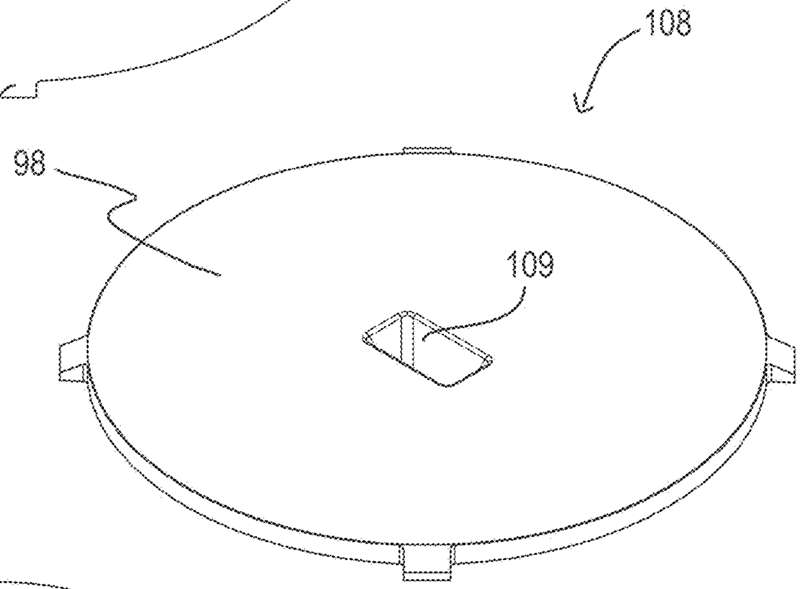
FIG. 15B depicts a perspective view of an example holder including a stage projection.
Figure 15C:
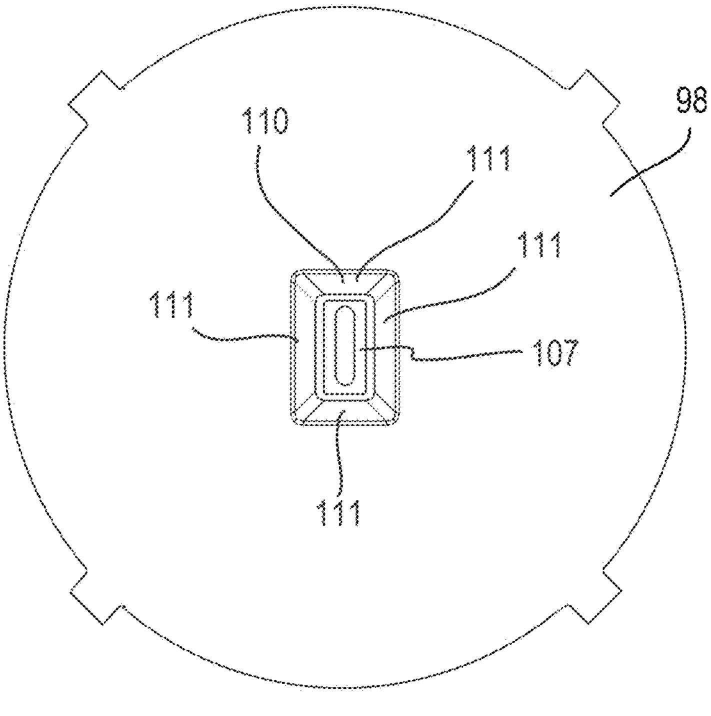
FIG. 15C depicts a bottom plan view of an example holder including a stage projection.

Referring now to FIGS. 15A-15C, delivery sharps 72 may be coupled to a reservoir assembly 52 (see, e.g., FIG. 37A) and be in fluid communication with an interior volume 275 of the reservoir assembly 52 in which agent may be stored. In certain examples, a sharp bearing body 26 including an array of microneedle type delivery sharps may be coupled to a rigid portion of a reservoir assembly 52 such as any of the holders 108 shown and described herein. The sharp bearing body 26 may be coupled to the holder 108 in any suitable fashion. For example, the sharp bearing body 26 may be coupled via adhesive. Alternatively, the sharp bearing body 26 and a holder 108 may be coupled together during an injection molding process. For example, the holder 108 may be injection molded around the sharp bearing body 26.

An exemplary holder 108 is depicted in FIGS. 15A-15C. A holder 108 may include a disk body 98. The disk body 98 may be substantially flat and may include a number of peripherally disposed tab projections 99. The tab projections 99 may be symmetrically disposed about the disk body 98 and may be spaced at regular angular intervals as shown in FIGS. 15A-15C. In alternative embodiments, the tab projections 99 may be asymmetrically disposed about the base or disposed at irregular angular intervals. The tab projections 99 may engage with receiving slits 97 (see, e.g., FIG. 6) disposed in a main body 50 of a delivery device 12. Thus, the tab projections 99 may be used to couple the holder 108 into place in a delivery device 12. Asymmetric or irregularly spaced tab projections 99 may allow for the holder 108 to be coupled to a main body 50 in a prescribed orientation which may be desirable in some examples.

Still referring primarily to FIGS. 15A-15C, a holder 108 may include at least one stage projection 110. Stage projections 110 may provide a well 109 on the distal side of the disk body 98. The stage projection 110 may extend proud of the proximal side of the disk body 98 by a height which may, in certain examples, be at least equal to the height of a microneedle (e.g. 600 microns) of the delivery device 12. The stage projection 110 may generally extend from the disk body 98 at a perpendicular angle. The side walls 111 of the stage projection 110 may be chamfered so as to extend in a non-perpendicular direction with respect to the proximal face of the disk body 98. The stage projection 110 may include a pocket 107. The pocket 107 may be sized to fit and accept a sharp bearing body 26 with delivery sharp(s) 72 thereon (e.g. any of those shown or described herein).

Figure 16A:
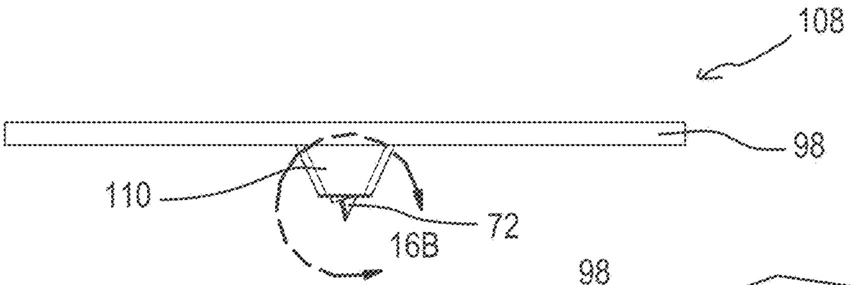
FIG. 16A depicts a side view of an example holder including a stage projection to which an example sharp bearing body is mounted
Figure 16B:
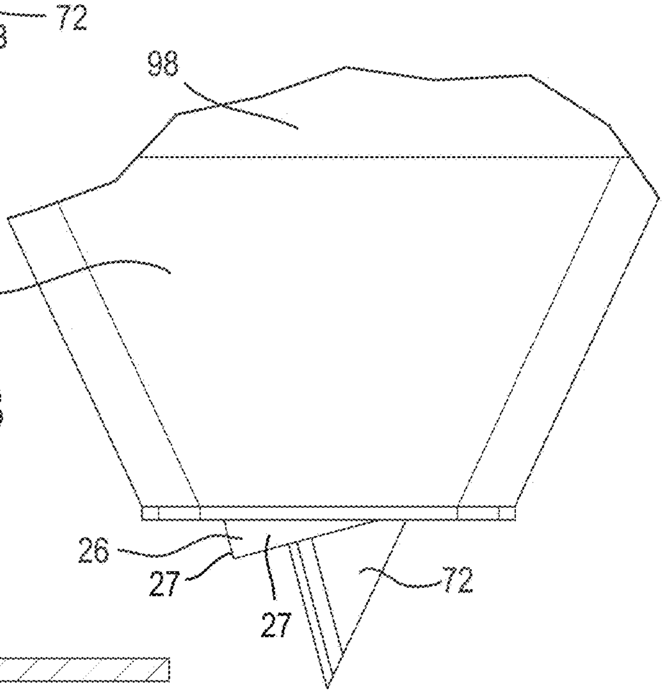
FIG. 16B depicts a detailed view of the indicated region of FIG. 16A.
Figure 16C:
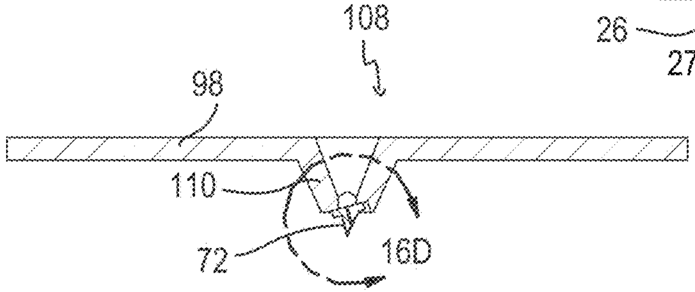
FIG. 16C depicts a cross-sectional view of an example holder including a stage projection to which an example sharp bearing body is mounted.
Figure 16D:
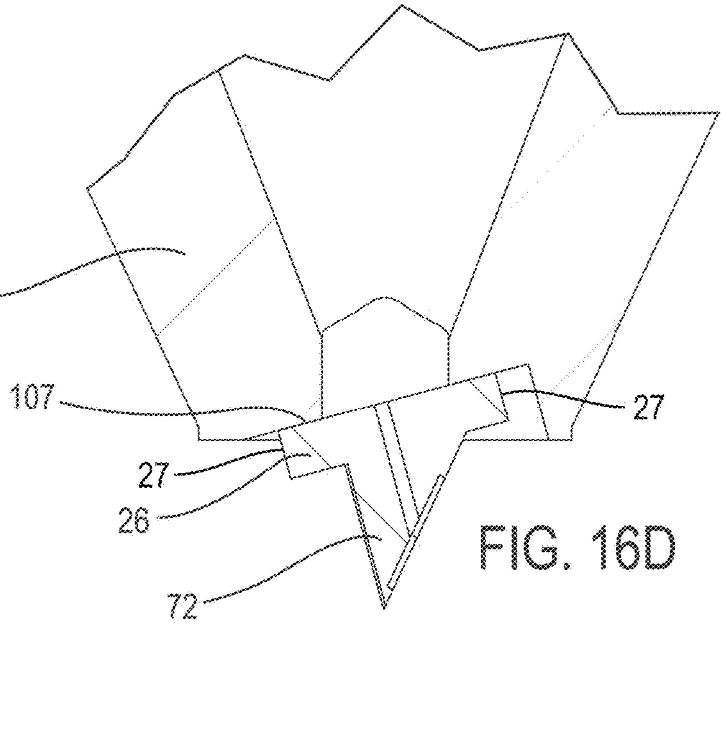
FIG. 16D depicts a detailed view of the indicated region of FIG. 16C.

Referring now to FIGS. 16A-16D, in some embodiments, the pocket 107 of the stage projection 110 may be in a non-parallel orientation with respect to the plane of the disk body 98. As best shown in FIG. 16D, when a sharp bearing body 26 is mounted to the pocket 107, the orientation of the pocket 107 may ensure that the delivery sharp(s) 72 (e.g. microneedles) extend at a prescribed angle with respect to the disk body 98. In the example embodiment, the pocket 107 may be oriented such that the delivery sharp(s) 72 extend at a 10-20° angle (e.g.) 15° with respect to a plane perpendicular to the disk body 98. In other embodiments, the pocket 107 may be oriented such that the delivery sharp(s) 72 project at a 45° or 60° angle or some angle therebetween. Any suitable angle may be used. In alternative embodiments, the entire stage projection 110 may project at the desired angle from the disk body 98. Thus, the delivery sharp(s) 72 may extend at that angle when coupled to the pocket 107.

Figure 17A:
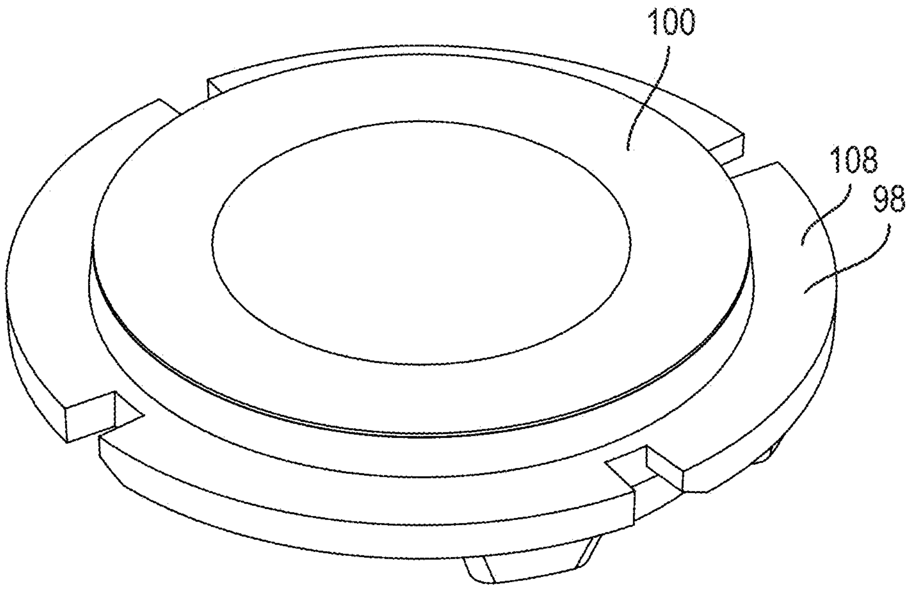
FIG. 17A depicts a perspective view of an example reservoir assembly.
Figure 17B:
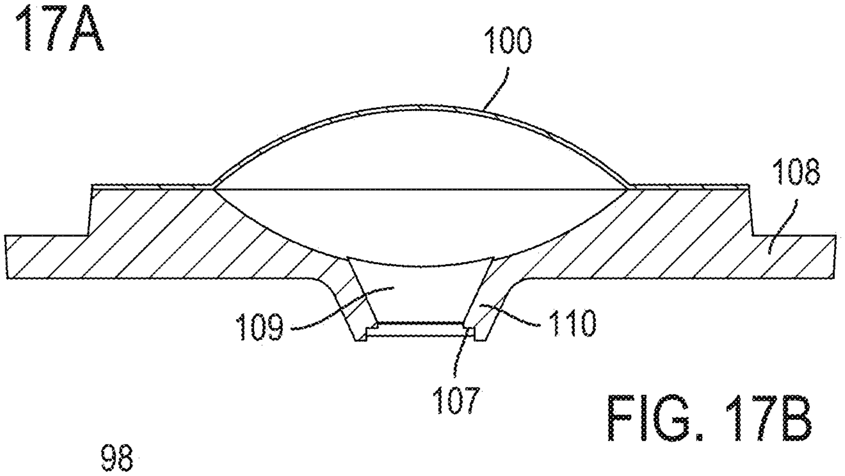
FIG. 17B depicts a perspective view of an example reservoir assembly.
Figure 17C:
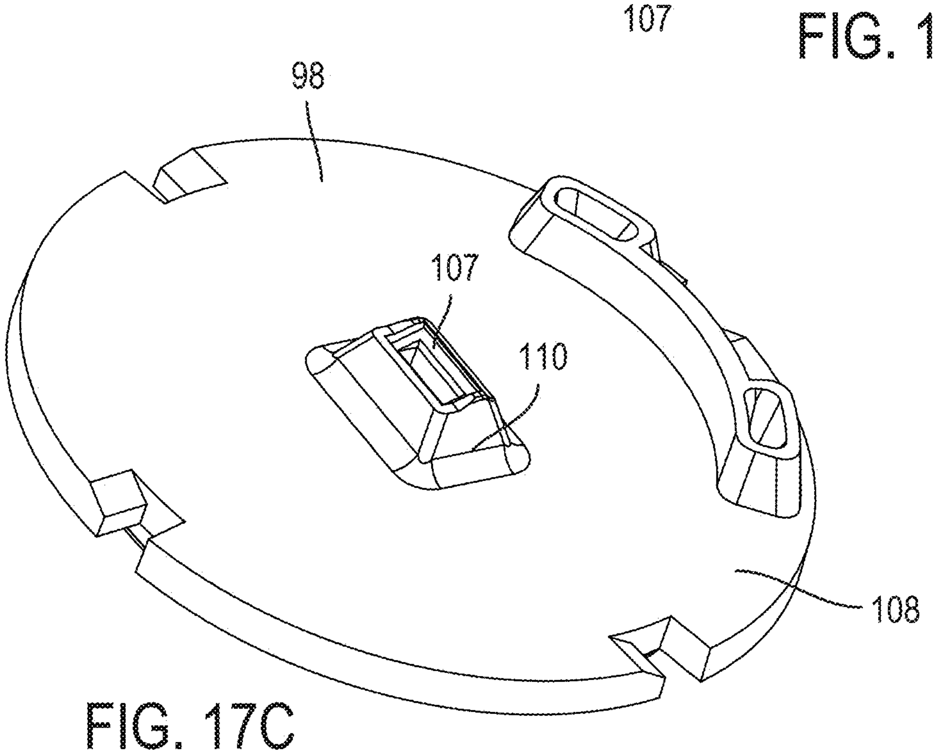
FIG. 17C depicts a perspective view of an example reservoir assembly.
Figure 18:
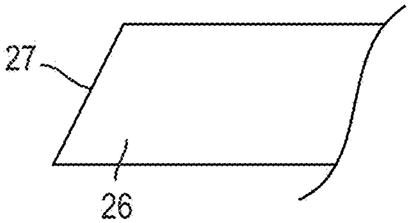
FIG. 18 depicts a view of a portion of an example sharp bearing body.
Figure 19:
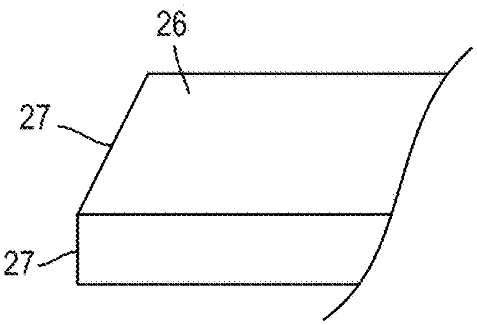
FIG. 19 depicts a view of a portion of another example sharp bearing body.
Figure 20:
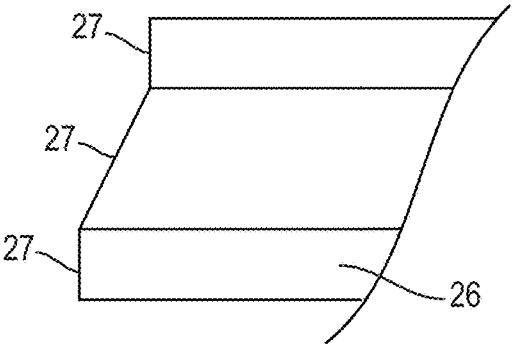
FIG. 20 depicts a view of a portion of another example sharp bearing body.

Another example holder 108 is depicted in FIGS. 17A-17C. As shown, the holder 108 may define a portion of a main interior volume 275 of the reservoir assembly 52. A remaining portion of the main interior volume 275 may be formed by a reservoir portion 100 which may be a flexible film in some examples. The reservoir portion 100 may be formed to have a rounded blister like shape when the reservoir assembly 52 is filled with agent. The reservoir portion 100 may be displaced against a similarly shaped depression in the holder 108 to deplete the main interior volume 275 of the reservoir assembly 52. Though not shown in FIGS. 17A-17C a sharp bearing body 26 may be coupled to the holder 108.

Sharp bearing bodies 26 may be coupled to any of the holders 108 described herein during a molding operation or via an adhesive. Where the sharp bearing body 26 is joined to any of the holders 108 described herein during molding, some material may be molded up the sidewalls 27 of the sharp bearing body 26 and over onto the face of the sharp bearing body 26 from which the delivery sharp(s) 72 project to capture the sharp bearing body 26. In alternative embodiments (and referring now to FIG. 18), the sidewalls 27 of the sharp bearing body 26 may be chamfered or at an angle which is not perpendicular to the face of the sharp bearing body 26 from which the delivery sharp(s) 72 extend. The footprint or cross-section of the sharp bearing body 26 may increase in area as distance from the sharp bearing face of the sharp bearing body 26 increases. Where the delivery sharp(s) 72 are silicon, a number of sets of delivery sharp(s) 72 may typically be formed on a large wafer and sharp bearing bodies 26 including the desired number of delivery sharp(s) 72 may be diced out of the wafer. To form the chamfered sidewalls 27, the dicing saw may have angled faces such that dicing process creates the desired chamfer or angle on the sidewalls 27. In certain embodiments, sidewalls 27 which are between 30-60° (e.g.) 45° may be used. Where chamfered sidewalls 27 are present, material may be molded up only a portion of the sidewall 27 to couple the sharp bearing body 26 to a holder 108. This may allow for a sharp bearing body 26 to be captured in a holder 108 (or any other molded component, e.g., a part of a delivery implement or an adapter for a syringe or other delivery implement which couples to that delivery implement via a luer lock or the like) without material being molded over onto the sharp bearing face of the sharp bearing body 26 (though this could optionally be done). Thus no molded material may act as a stand-off on the sharp bearing face blocking the full height of any delivery sharp(s) 72 from penetrating into the skin. Description in relation to a holder 108 may be generalized to other components and discussion of the holder 108 is merely exemplary.

In certain examples, and referring now to FIGS. 19-22, the peripheral region of a sharp bearing body 26 may be formed in a series of material removal operations. Where the sharp bearing body 26 is constructed of silicon, the sidewall 27 may be formed by dicing, etching, or some combination thereof. The sidewall 27 of the sharp bearing body 26 may include a number of regions which may be some combination of straight regions where the cross-sectional area of the sharp bearing body 26 is constant and chamfered or angled regions over which the cross-sectional area varies. In some embodiments, the sidewall 27 may be tiered and have a stepped appearance with one or more plateau regions. Such sidewalls 27 may make a sharp bearing body 26 amenable to being coupled into a component via molding without material being molded over onto the sharp bearing face. Such sidewalls 27 may also allow for more versatility in molding. For example, materials with a larger variety of shrinkage values after molding may be used to construct a holder 108 or other component (e.g. syringe adapter) to which a sharp bearing body 26 is to be coupled. Sharp bearing bodies 26 with such sidewalls 27 may be particularly robust against stress due to shrinkage loading during molding. Additionally, such sharp bearing bodies 26 may accommodate greater ejection loading when the molded component is ejected from the mold cavity. Sharp bearing bodies 26 with such sidewalls 27 may also facilitate creation of high quality, fluid tight interfaces between overmolded material and sharp bearing body 26 material. Such sidewalls 27 may increase the pressure at which an overmolded component such as a holder 108 or other component remains leak proof. Stepped sidewalls 27 may also help facilitate flow of injection molding material into cracks which may be formed in sharp bearing bodies 26 during handling by automation equipment and thus assisting in limiting rejection percentage.

In some examples, at least two sets of dicing cuts may be made to form the sidewalls 27 of the sharp bearing body 26. The sidewalls 27 may include a chamfered section extending from the sharp bearing face of the sharp bearing body 26 (see, e.g., FIG. 19). The chamfered section may be formed by a first set of cuts and may be oriented such that the cross-sectional area of the sharp bearing body 26 decreases as proximity to the sharp bearing face increases. The sidewalls 27 may also include a straight region where the cross-sectional area of the sharp bearing body 26 is substantially constant. The straight region of the sidewall 27 may be formed in a second set of dicing cuts and may define the remainder of the sidewall 27. In some embodiments, the sidewall 27 may include two straight regions and an intermediate chamfered region (see, e.g., FIG. 20). The straight regions of the sidewalls 27 may respectively be adjacent the sharp baring face and the opposing face of the sharp bearing body 26. A set of angled dicing cuts may be made to form the intermediate section and a second set of dicing cuts may be made to cut back a segment of the resulting chamfered face to form a straight region. The second straight region may be created with another set of dicing cuts. In alternative examples, at least one of the straight regions of the sidewall 27 may be a precision sidewall segment as described below.

Figure 21:
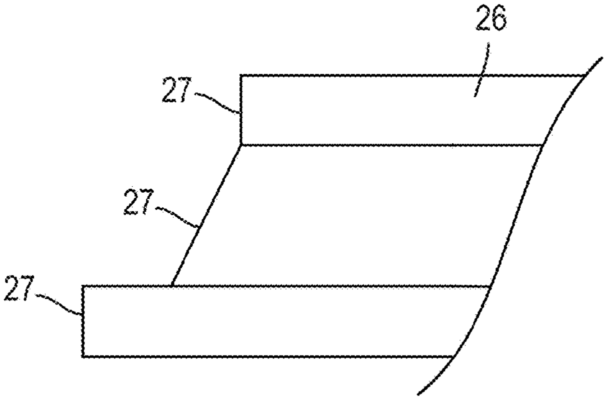
FIG. 21 depicts a view of a portion of another example sharp bearing body.
Figure 22:
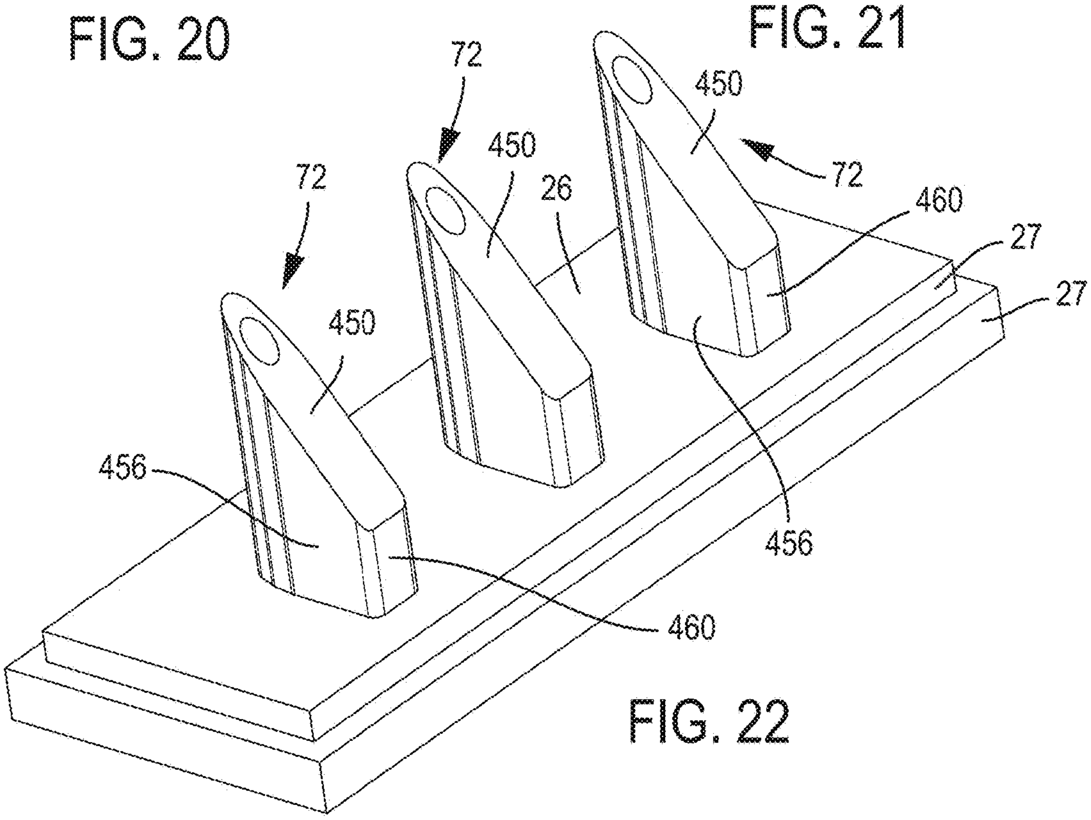
FIG. 22 depicts a perspective view of another example sharp bearing body having a plurality of example microneedles projecting therefrom.

In still other embodiments, and referring now to FIG. 22, the chamfer may be replaced by a stepwise change in cross-sectional area of the sharp bearing body 26. The stepwise change may be provided such that the footprint or cross-sectional area of the sharp bearing body 26 increases as distance from the sharp bearing face of increases. In some examples, the stepwise change in height may be created with a series of dicing cuts. One set of cuts may form a partial cut through the wafer material while another set of cuts may singulate each sharp bearing body 72 from the rest of the wafer. When forming the holder 108, material may be molded over the larger cross section portion of the sharp bearing body 26 and onto the step intermediate the large and small cross-sectional area portions of the sharp bearing body 26. Thus, the larger cross-sectional area region of the sharp bearing body 26 may be encased in the holder (or other component) material and a portion of the peripheral side wall most proximal the sharp bearing face of the sharp bearing body 26 may be only partially covered. Alternatively, the peripheral sidewall may be covered to a height even with the sharp bearing face. As shown in FIG. 21, in some examples there may be a small chamfer or radiused region where the step transitions to the sidewall 27 for the smaller cross-sectional area portion of the sharp bearing body 26. Such a step may be created by a dicing saw. Though described as a chamfer or radiused region any shape created by the dicing saw kerf may be present. The chamfer or radiused region may only be present for a fraction of the height of the smaller cross-sectional area region of the sharp bearing body 26 (e.g. less than 50% or less than 25%).

Referring primarily to FIG. 22, in various examples, the height of the large and small cross-sectional area portions of the sharp bearing body 26 may be substantially equal. The small cross-sectional area portion of the sharp bearing body 26 may be at least 50% of the height of the sharp bearing body 26. The width of the step between the large cross-sectional area portion of the sharp bearing body 26 and the small cross-sectional area portion of the sharp bearing body 26 may be less than the height of the small or large cross-sectional area portion of the sharp bearing body 26. In some embodiments, the width of the step may be no more than 50% of the height of the small cross-sectional area portion of the sharp bearing body 26. The width of the step may be greater than 50% of the height of the small cross-sectional area of the sharp bearing body 26 in other embodiments. In other examples, the width of the step may be at least 100% of the height of the small or large cross-sectional area portion of the sharp bearing body 26. The width of the step may be the same on each side of the sharp bearing body 26, though may differ in alternative examples. In some embodiments, the width of the step may be the same for each opposing side of the sharp bearing body 26.

Though sharp bearing bodies 26 described above may be particularly amenable to being attached to a holder 108 (or other component) via overmolding, sharp bearing bodies 26 may also be attached to a holder 108 (or other component) in other suitable manners. For example, sharp bearing bodies 26 described herein may be coupled to a holder 108 (or other component) via swaging (e.g. heat swaging or laser swaging operation).

Figure 23A:
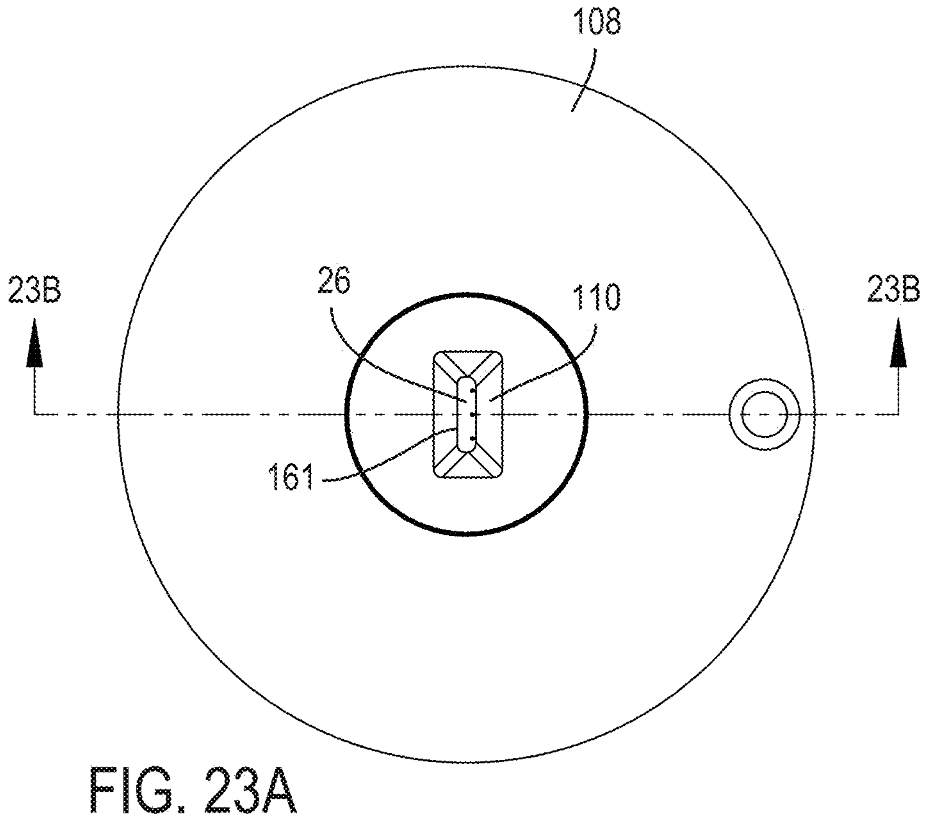
FIG. 23A depicts a view of a backside of a sharp bearing body overmolded into a molded component.
Figure 23B:
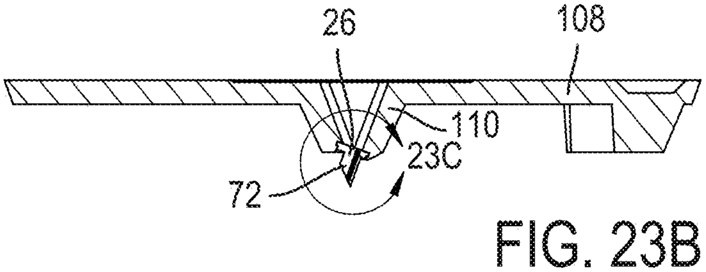
FIG. 23B depicts a cross-sectional view taken at the indicated cut plane of FIG. 23A.
Figure 23C:
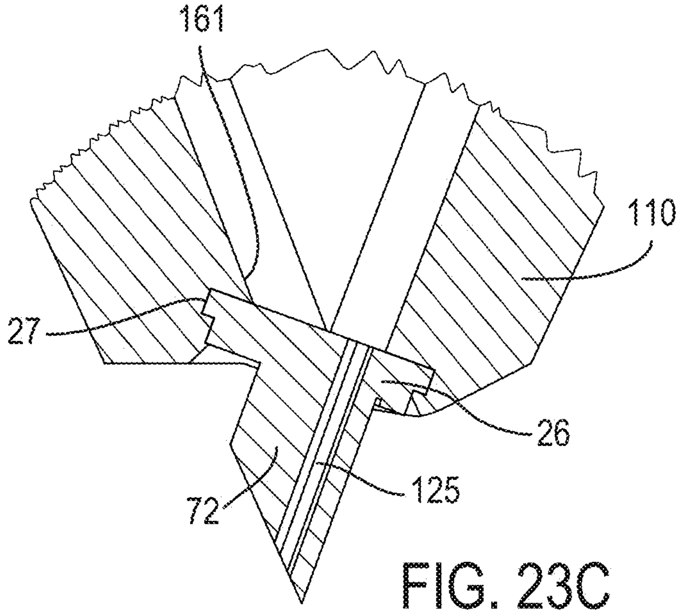
FIG. 23C depicts a detailed view of the indicated region of FIG. 23B.

Referring now to FIG. 23A-23C, a view of a backside and two cross-sectional views of a sharp bearing body 26 coupled to a holder 108 via injection molding are respectively depicted. While material may be molded over a chamfered or stepped portion (or both) of the sidewall 27 of a sharp bearing body 26, it may also be desirable that material is also molded over a portion of the rear face of sharp bearing body 26. As shown, in some examples, material may be permitted to flow at least over the peripheral edges of the rear face of the sharp bearing body 26 to create a frame 161 over the rear face. In some embodiments, material for the frame 161 may be allowed to flow over other regions of the rear face (and perhaps a majority of the rear face), but be blocked from reaching the lumens 125 of the sharp bearing body 26. This may be accomplished by including a shutoff in the mold for the holder 108 (or other component) which obstructs flow of material over portions of the rear face which are desired to be bare. Including some compliance (see, e.g., compliant member 665 of FIG. 24) in the portion of the mold including the shutoff may be desirable as it may aid in maintaining the integrity of the sharp bearing body 26 during the molding operation. By embedding a section of the sidewall 27 and portion of the rear face of the sharp bearing body 26 in the molded material, a sharp bearing body 26 may be robustly retained in a holder 108 or other component. Additionally, the interface between the sharp bearing body 26 and the holder 108 or other component may be leak resistant up to relatively high pressures.

Where sharp bearing bodies 26 are singulated from a wafer in a series of material removal operations, the manner in which the material is removed may be leveraged to assist in placement of the sharp bearing body 26 into a mold cavity. It may be desirable to have features on the sidewalls 27 which are positionally defined with a high degree of precision (+/−1-3 microns). These features may be referred to as precision sidewall segments. Such segments may allow for automation equipment to place a sharp bearing body 26 substantially blindly into a target destination in a mold cavity. This may be particularly important where the vision system's field of view is obstructed by the sharp bearing body 26 and/or end effector holding the sharp bearing body 26 when the sharp bearing body 26 is placed. The precision sidewall 27 segments may allow the sharp bearing body 26 to be in a highly know position relative to the automation equipment. Inclusion of precision sidewall segments may decrease time required to place the sharp bearing body 26 in a mold cavity. In such examples a portion of the sidewall 27 of a sharp bearing body 26 defining a substantially constant cross-section portion of the sharp bearing body 26 may be formed via an etching process. For example, a highly anisotropic etch such as a deep reactive ion etch may be utilized to form a portion of the sidewall 27 for the sharp bearing body 26. A second portion or portion(s) of the sidewall 27 may be formed in a set of dicing cuts which may be used to singulate the sharp bearing body 26 from the wafer. In some examples precision sidewall 27 segments may form the bounds of a constant cross-sectional area portion of the sharp bearing body 26 on two opposing sides of the sharp bearing body 26. The remainder of the sidewalls 27 may be formed via dicing. Additionally, etched side wall 27 portions may allow for sidewalls 27 which are defined (at least in part) by non-straight line segments. In some examples, only a small portion of the sidewall 27 may be etched. For example, for each sharp bearing body 26 which is to be individualized from a larger wafer, at least one passage may be etched through (or at least partially through) the wafer material in a precise position. The position chosen for the hole may ensure that a portion of the hole forms a section of the sidewall 27 of the sharp bearing body 26 when the sharp bearing body 26 is diced from the wafer. There may for example be sidewall 27 portions defined by remnants of holes on at least two opposing sides of a sharp bearing body 26. Two such precision sidewall 27 segments defined by hole remnants may be included on each of the opposing sides in certain non-limiting examples. Thus, the small divot or notch (e.g. a semi-circle or half-moon shape) in the sidewall 27 may act as a precision sidewall 27 segment which may assist in automated placement of the sharp bearing body 26 into other equipment (e.g. molds).

As mentioned above in relation to FIGS. 12A-12B, certain delivery sharps 72 may be formed with vertical faces 460. In some embodiments, and still referring primarily to FIG. 22, vertical faces 460 of any delivery sharp(s) 72 included on a sharp bearing body 26 may be disposed inboard of the periphery of the sharp bearing body 26. Thus, the footprint of each delivery sharp 72 may be surrounded on all sides by a portion of the sharp bearing face of the sharp bearing body 26. By positioning the delivery sharps(s) 72 inboard of the periphery of a sharp bearing body 26, coupling of the sharp bearing body 26 to a holder 108 during an injection molding operation may be facilitated. This may allow for an edge surface (e.g. chamfered or stepped) to be included such that the sharp bearing body 26 may be robustly coupled to a holder 108 without molding material onto the sharp bearing face of the sharp bearing body 26. Additionally, it avoids having vertical faces 460 of the delivery sharp(s) 72 which are continuous with the outermost portion of the sidewall 27 that may present sealing issues when a sharp bearing body 26 is coupled to a holder 108 via injection molding. Additionally, it may allow for a shut-off 664B to contact the sharp bearing face of the sharp bearing body 26 around all sides of the delivery sharps 72. Where the delivery sharp(s) 72 are one or more microneedles formed of silicon, sharp bearing bodies 26 with arrays of microneedles may generally be diced out of a wafer including a relatively large number of microneedle arrays. When the microneedles are formed, the microneedles may be formed such that their sloped faces 450 extend all the way to sharp bearing face of the sharp bearing body 26. The angle of the sloped face 450 may be defined by a crystallographic plane (e.g. 1 1 1) of the wafer. A dicing saw may be used to both separate individual sharp bearing bodies 26 from the larger wafer and to remove a portion of the microneedle to form the vertical face 460 at the desired position. The dicing saw may be moved at high speed over the sharp bearing face and across the portion of the microneedles to be removed. A portion of the sharp bearing face may be removed as this occurs such that the sharp bearing face in this region may be recessed after the vertical faces 460 for the microneedles are formed. This may allow a sharp bearing body 26 with silicon microneedles to maintain a small footprint even with tall microneedles despite the sloped face 450 having an angle defined by the crystallographic plane of the wafer. Additionally, this may facilitate use of sidewalls 27 described above which may make a sharp bearing body 26 highly amenable to being coupled to a holder 108 (or other component such an adapter which is part of or couples to a delivery implement) via injection molding.

Still referring to FIG. 22 the sidewalls 456 of the delivery sharp(s) 72 on a sharp bearing body 26 may be angled or rounded such that the width of the delivery sharp(s) 72 decreases adjacent the vertical face 460. The etch used to define the outline of the delivery sharp(s) 72 may be made such that the width of the delivery sharp(s) 72 decreases as proximity to the sacrificial portion of the delivery sharp(s)

72. In some embodiments, the decrease in width may continue into sacrificial portion or the portion of the delivery sharp(s) 72 to be removed. When the vertical face 460 is formed, this may allow the transition from the sidewalls 27 to the vertical face 460 to be less sharp and thus more robust.

Though sharp bearing bodies 26 may be coupled to other components via adhesives, this can be a time consuming process which is poorly suited to high volume manufacturing. Molding arrays of microneedles into other components allows for efficient high volume mass manufacture of microneedle based fluid delivery platforms. Overmolding of material onto arrays of microneedles to form larger components is a particular challenge in the implementation of microneedles in fluid delivery devices. A fluid tight seal between the sharp bearing body 26 and overmolded material needs to be reliably formed without compromising the integrity of the sharp bearing body 26. Silicon wafer material, from which certain delivery sharps 72 and sharp bearing bodies 26 may be formed is brittle and can break fairly easily. This material is subjected to a number of stresses (ejection loading, thermal expansion and contraction of materials, etc.) during an overmolding process. Moreover, slight misalignment can result in chips, cracks, or other undesired marring of sharp bearing bodies 26 or delivery sharps 72. Additionally, the distance from the sharp bearing face to the opposing face of various sharp bearing bodies 26 may typically be about 200 μm. Thus, the available space for formation of an interface between the overmolded component and the sharp bearing body 26 which is fluid tight up to high pressures (e.g. at least 90 p.s.i.) is relatively small. Additionally, depending on the design of the overmolded component, such pressures may elastically distort the overmolded material in the vicinity of the sharp bearing body 26 presenting further sealing challenges. Moreover, a strong bond between an initial part and the second material used in the overmolding procedure is typically considered critical. Sharp bearing bodies 26 may typically be formed of a material that is dissimilar to material used to form the overmold. Silicon wafer material, for example, will not melt during the overmolding procedure and will not chemically bond with the overmolded material.

Components may be overmolded to sharp bearing bodies 26 as described below in relation to FIGS. 24-29. Though the below description is provided in the context of a holder 108 for a delivery device 12, it should be appreciated that the description is generalizable for use with components other than holders 108. For example, adapters for delivery implements such as syringes may be formed similarly to as described herein. Additionally, infusion sets for prolonged delivery of agent to a shallow delivery destination (similar to subcutaneous insulin infusion sets for instance) or subcomponents thereof may be formed as described across FIGS. 24-29. Such components may, for example, include any of those shown and described in U.S. Publication No. US20230277759A1, filed Mar. 3, 2023, and entitled "Systems, Methods, and Apparatuses for Medical Agent Administration", which is hereby incorporated by reference in its entirety. Any other drug delivery hardware which interfaces with patient anatomy via one or more microneedle may be formed similarly to as described herein.

As mentioned in relation to FIGS. 16A-16D, it may be desirable that the delivery sharps 72 of a component be coupled into that component in a tilted orientation. The sharp bearing body 26 and delivery sharps 72 may be tilted about a tilt axis that extends perpendicular to an axis of the component into which they are molded. For example the delivery sharps 72 may be tilted 15-25° from the orientation in which they would extend parallel to an axial dimension of the component. Though it adds complexity to the mold 660 (multiple shut off planes, part ejection systems not perpendicular to part geometry, etc.), it may be desirable to overmold the material with a mold 660 incorporating a stepped parting line.

Figure 24:
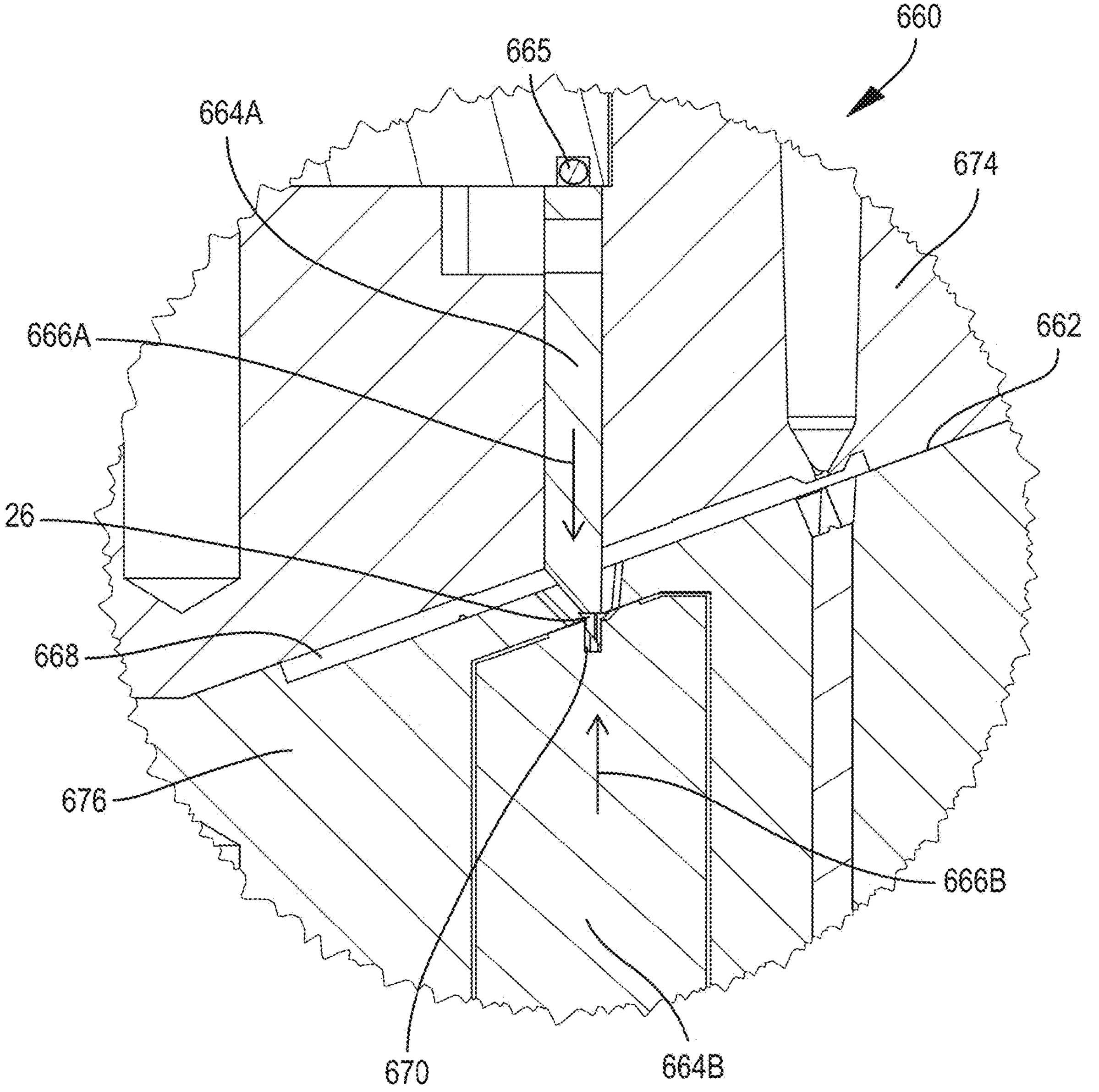
FIG. 24 depicts a cross-sectional view of an example mold which may be used to overmold a component onto a sharp bearing body.
Figure 25:
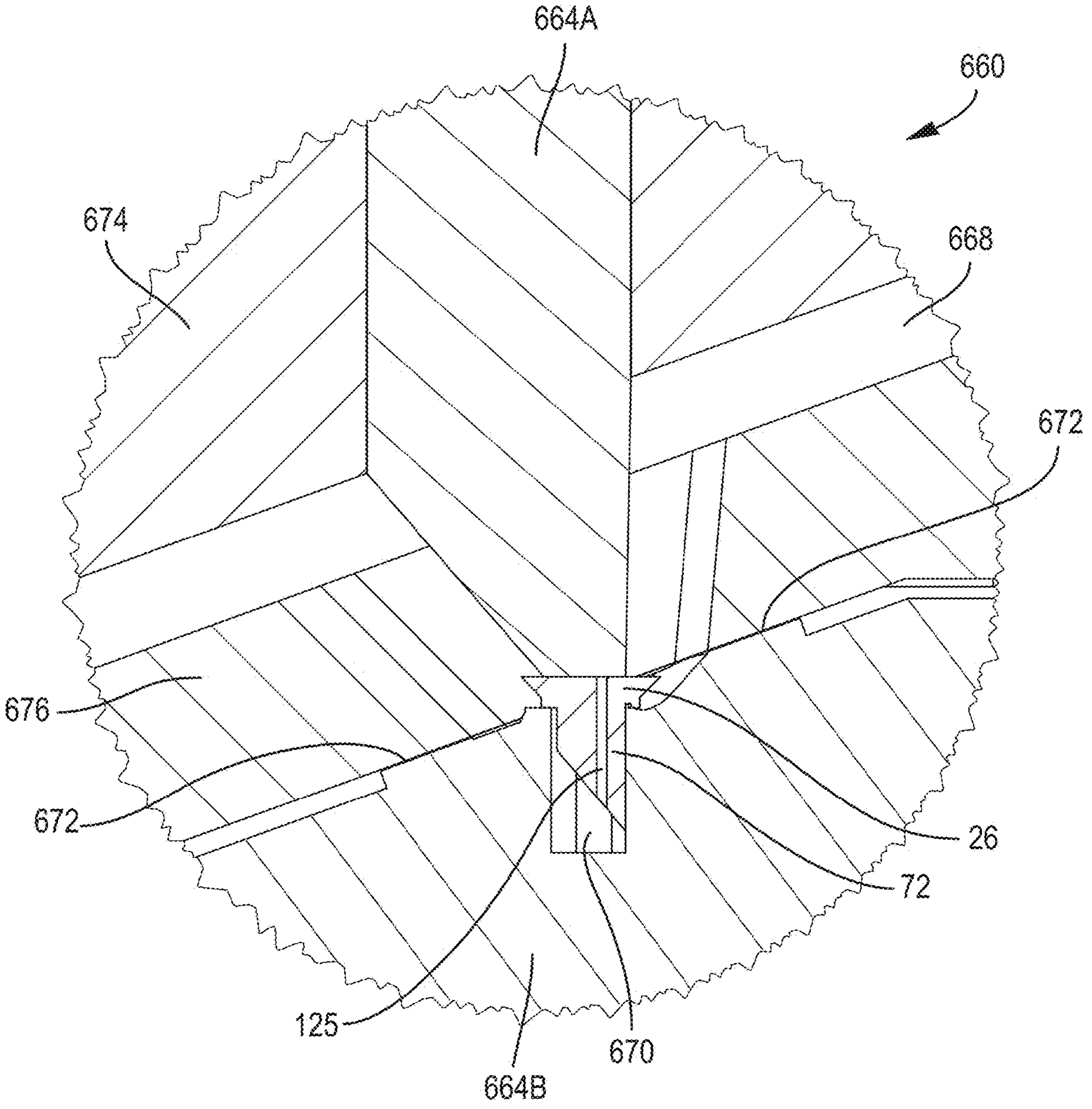
FIG. 25 depicts another cross-sectional view of an example mold which may be used to overmold a component onto a sharp bearing body.

Referring now to FIGS. 24-25, the parting plane 662 for the mold 660 may be oriented such that the sharp bearing body 26 may be deposited into the mold 660 in an orientation in which the force of gravity is normal to the sharp bearing face of the sharp bearing body 26. This may assist in retaining the sharp bearing body 26 in a stable resting orientation within the mold 660 prior to clamping.

Still referring to FIGS. 24-25, preferably, the shut-offs 664A, B may clamp against two parallel surfaces of the sharp bearing body 26. In the example, the shut-offs 664A, B clamp against the sharp bearing and opposing face of the sharp bearing body 26. Thus, the shut-offs 664A, B may block material from being molded over the sharp bearing face or into openings to the lumens 125 on the opposing face. The clamping force (indicated by arrows 666A, B) applied to the shut-offs 664A, B may be kept normal to the sharp bearing face and opposing face of the sharp bearing body 26 by incorporating a stepped parting line. This will help to ensure that the shut-offs 664 A, B do not deflect or have a tendency to misalign on the sharp bearing body 26 once pressure is applied to clamp the sharp bearing body 26 between the shut-offs 664A, B. This may facilitate repeatable and reliable seal creation around the periphery of the sharp bearing body 26 when material is injected into the mold cavity 668. Additionally, it may assist in maintaining the integrity of the sharp bearing body 26 and delivery sharps 72. For example, the shut-off 664B which clamps against the sharp bearing face of the sharp bearing body 26 will include at least one pocket 670 for the delivery sharps 72 on the sharp bearing body 26. The sharp pocket(s) 670 entirely surround the delivery sharps 72. With deflection or misalignment, the walls sharp pocket 670 on the shut-off 664B may contact and damage the delivery sharps 72. The stepped parting line may also help to constrain the nature of any misalignment of the sharp bearing body 26 within the mold 660 such that any misalignment from the ideal position may be kept substantially within a plane. That is, any misalignment may tend to be in a fore/aft, left/right, or rotational yaw type manner. As a result, despite any potential misalignment, the surfaces of the sharp bearing body 26 against which the shut-offs 664A, B press may still be substantially within the plane in which they are anticipated to be. Thus, any misalignment may be kept substantially in directions where the greatest degree of forgiveness is present. This may help inhibit damage to the sharp bearing body 26 and delivery sharps 72 which could be incurred in the event that pitch or roll type misalignment was present during clamping.

Still referring to FIGS. 24-25, as mentioned above creation of a good seal between the overmolded component and the sidewalls 27 of the sharp bearing body 26 is challenging. This seal is formed over a very small region and is required to be fluid tight even when exposed to high pressure (e.g. 90 p.s.i. or greater). The mold 660 may be constructed such that vents 672 in the mold cavity 668 are included adjacent the interface to be formed between the sharp bearing body 26 and the material filled into the mold 660. Instead of incorporating the shut-off 664B as a monolithic part of the "B" block 676 of the mold 660, the shut-off 664B shown in the example embodiment is part of an insert which is deposited in the "B" block 676 of the mold 660. By including the shut-off 664B as a separate component, an interface between the shut-off 664B insert and the surrounding "B" block 676 material is created. This interface may be leveraged to create a number of appropriately sized venting pathways directly abreast the interface between the sharp bearing body 26 sidewalls 27 and the component to be overmolded. This ensures that the mold breathes particularly well in this region and that material fills at this interface in a predictable, consistent, and repeatable manner without any dieseling.

Figure 26A:
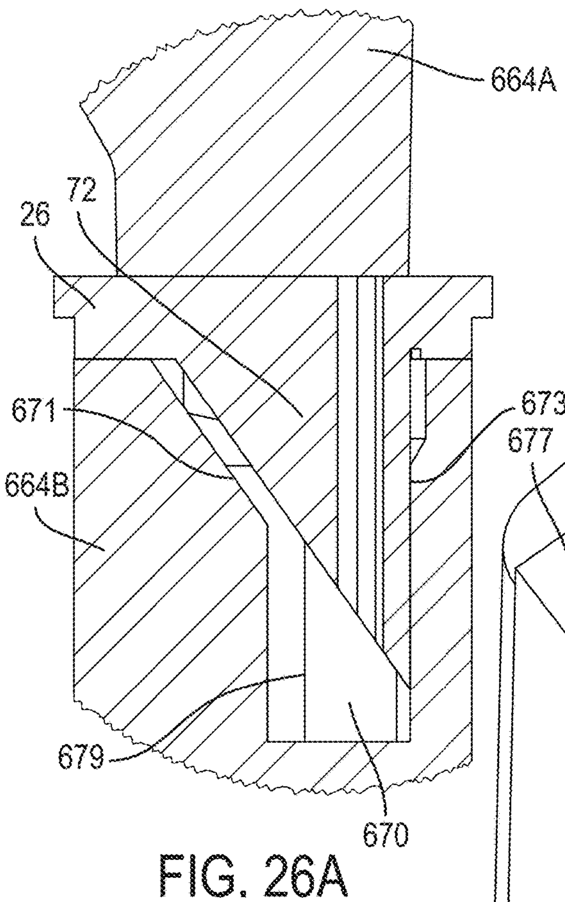
FIG. 26A depicts a cross-sectional view of an example sharp bearing body and set of shut-offs.
Figure 26B:
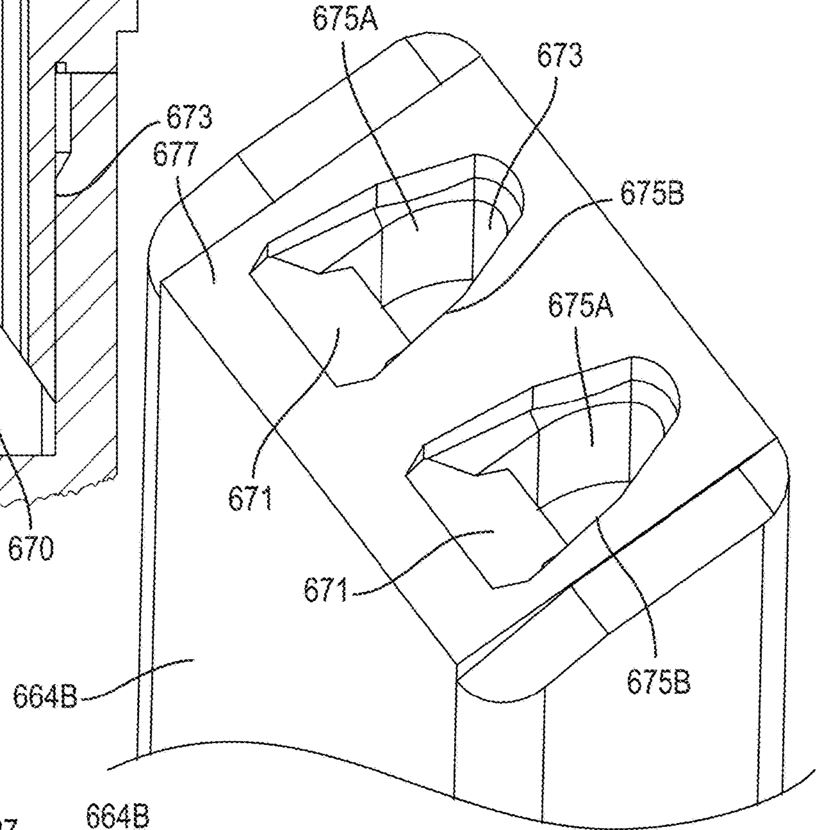
FIG. 26B depicts a perspective view of an example mold shut-off.
Figure 26C:
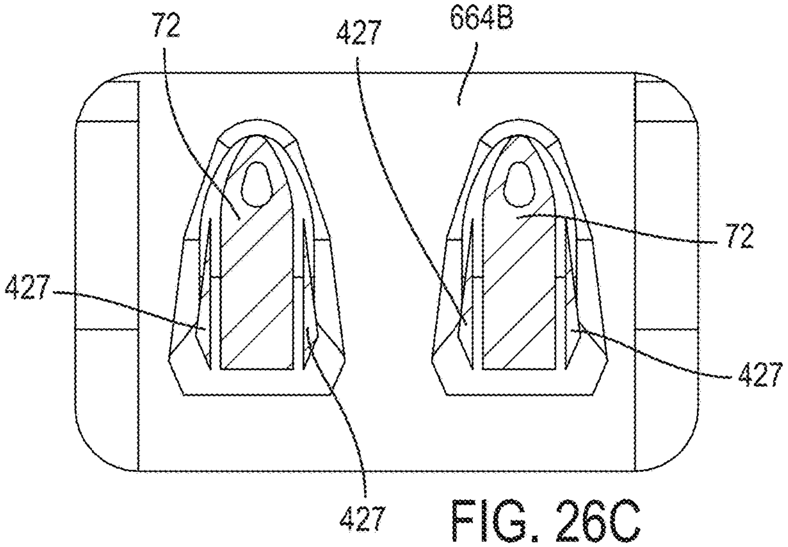
FIG. 26C depicts cross-sectional view depicting a set of microneedles positioned in pockets of an example shut-off.

Referring now to FIGS. 26A-26C a number of view of example shut-offs 664A-B are depicted. The shut-offs 664A-B may clamp against a sharp bearing body 26 during an injection molding operation where a component is overmolded to the sharp bearing body 26. The shut-offs 664A-B may ensure that a robust fluid tight seal (e.g. up to at least 90 psi) is formed by the overmolded material. At the same time, the shut-offs 664A-B may be arranged to help assist in ensuring a highly reliable positioning of the sharp bearing body 26 while mitigating any potential for damage to the delivery sharps 72 or sharp bearing body 26.

As shown, shut-off 664A clamp may clamp against a central region of the rear face of the sharp bearing body 26. The exterior surface walls of the shut-off 664A in the vicinity of the sharp bearing body 26 may be smooth and devoid of steps. The exterior walls may also extend in a direction substantially perpendicular to the clamped rear face of the sharp bearing body 26. This may help to ensure good flow of material to the regions immediately adjacent the sharp bearing body 26. In turn, this may ensure that a reliable seal is formed by the material overmolded onto the sharp bearing body 26.

Shut-off 664B may include a pocket 670 for each delivery sharp 72 present on the sharp bearing body 26. In the example embodiment, two pockets 670 are depicted, however, additional pockets 670 of the same type may be included in shut-offs 664B for sharp bearing bodies 26 with a greater number of delivery sharps 72. The pockets 670 may be constructed to encourage a highly repeatable and reliable sharp bearing body 26 position within a mold 660. The pockets 670 may also bestow this reliable positioning while mitigating potential to damage the delivery sharp 72 or sharp bearing body 26 as the sharp bearing body 26 is installed in a mold 660.

As best shown in FIG. 26B, the pockets 670 each include a ramped sidewall 671. Opposite the ramped sidewall 671 the pockets 670 include a rounded sidewall section 673. Lateral sidewalls 675A, B connecting the rounded sidewall section 673 to the ramped sidewall 671 may also be present. The width of the pocket 670 may generally increase as distance from the rounded sidewall section 673 increases. The rounded sidewall section 673 and lateral sidewalls 675A, B may taper such that the cross-sectional area of the pocket 670 decreases as distance from the clamping face 677 of the shut-off 664B increases. The slope of the taper on the lateral sidewalls 675A, B may be gentlest at the end regions of the lateral sidewalls 675A, B most proximal the ramped sidewall 671. The width of the pocket 670 may be greatest where the distal side 452 of the base 454 of the delivery sharp 72 is positioned. The tapered region of the rounded sidewall 673 and lateral sidewalls 675A, B may be intermediate two straight wall segments which extend substantially perpendicular to the clamping face 677 of the shut-off 664A, B.

As the sharp bearing body 26 is installed in the mold 660, the delivery sharps 72 may be placed into the pockets 670 of the shut-off 664B. The pockets 670 may guide the delivery sharps 72 into position within their respective pockets 670. The taper on the sidewalls 673, 675A, B may serve to gently funnel the delivery sharps 72 such that they self-center within the pockets 670. Additionally, the sloped face 450 of the delivery sharp 72 may slide along the ramped sidewall 671 of the respective pocket 670. This may tend to bring the back facing edge 23 of the delivery sharp 72 into contact with the rounded sidewall section 673 as shown best in FIG. 26A. The pockets 670 may also include a pit region 679. The pit region 679 may be sized to accept the tip 31 of the delivery sharp 72 when the delivery sharp 72 is introduced into the pocket 670 over any of a range of positions. Thus, the tip 31 of the delivery sharp 72 may generally be out of contact with the pocket 670 in the event of minor misalignment and may only contact the pocket 670 as the delivery sharp 72 self-aligns with further advancement into the pocket 670. Thus, the deliver sharp 72 may be substantially protected against damage when the sharp bearing body 26 is located on the shut-off 664B.

Referring primarily to FIG. 26C, a cross-sectional view of a pair of delivery sharps 72 in pockets 670 of an example shut-off 664B is depicted. The cross-section is taken at the plane of the sharp bearing face of a sharp bearing body 26 to illustrate the position of the delivery sharps 72 within the respective pockets 670. As shown, each delivery sharp 72 has associated kerf regions 427 (see also FIGS. 13A-13D) which are artefacts of the etching process used to form silicon delivery sharps 72. It is desirable to carefully accommodate the kerf regions 427 in any shut-off 664B. The kerf regions 427 are relatively delicate and prone to chipping. Particulate formation in the mold 660 may be undesired for a number of reasons. For example, silicon is quite hard and silicon particulate may negatively impact mold 660 longevity. Additionally, particulate trapped between the shut-offs 664A, B and the sharp bearing body 26 may damage the sharp bearing body 26 when clamping force is applied. Silicon particulate may also become entrapped in the overmold material. This may further complicate the challenge of repeatably and reliably generating a fluid tight high pressure seal at the interface of the sharp bearing body 26 and the overmolded material.

Still referring to FIG. 26C, the width of the open ends of the pockets 670 directly lateral to where the distal side 452 of the base 454 of the delivery sharp 72 is received may be selected to be about double (e.g. 85-115%) the width of the distal side 452 of the delivery sharp 72. This may help to ensure that the kerf regions 427 are accommodated within the pocket 670 for an associated delivery sharp 72. The tapered region of the lateral sidewalls 675A, B may begin at a depth greater than the maximum height of the kerf regions 427. Thus, the cross-sectional area of the pocket 670 may be at its greatest throughout the volume of the pocket 670 where the kerf regions 427 may be positioned. As mentioned above, the pockets 670 may substantially self-center respective delivery sharps 72 as a sharp bearing body 26 is installed in the shut-off 664B. The self-centering of the respective delivery sharp 72 may be substantially complete before the kerf regions 427 are advanced into the volume of the pocket 670 helping to ensure the kerf regions 427 maximum clearance from the walls of the pocket 670. By self-centering the respective delivery sharps 72 prior to the kerf regions 427 advancing into the pocket 670 the cross-sectional area at the open end of the pockets 670 may be kept relatively small. This may help to maximize the amount of the sharp bearing body 26 available for use as a shut-off surface.

Figure 27:
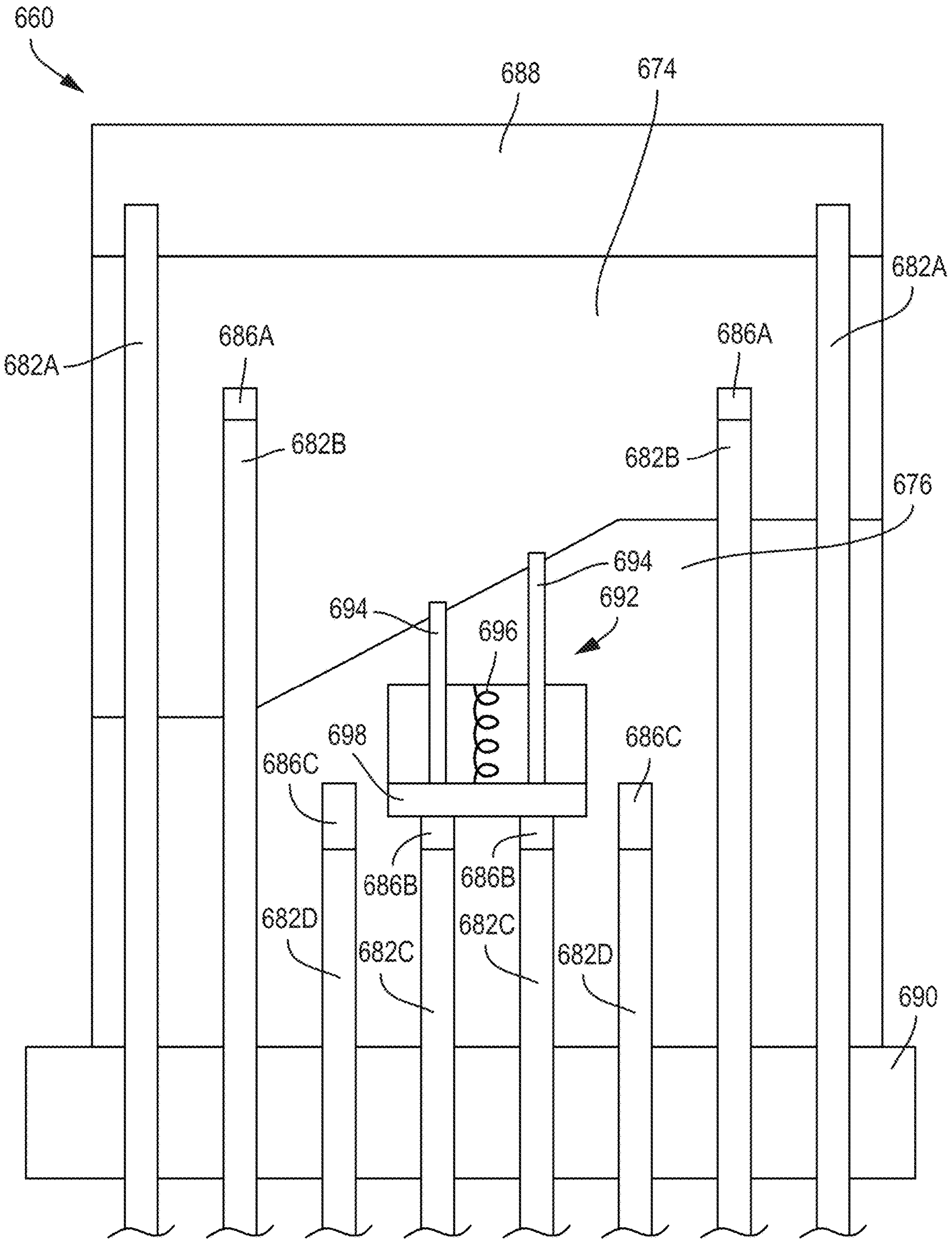
FIG. 27 depicts a block diagram depicting various portions of an example mold and a number of ejector pins.

Referring now to FIG. 27, an example block diagram 680 of a mold 660 is depicted. The example mold 660 includes a multi-stage ejection arrangement with a variety of ejector pins 682A-D disposed within guide pockets 684 defined in the mold 660. The hydraulics of the molding machine may be used to drive the ejector pins 682A-D to remove components of the mold 660 and the molded assembly in a controlled and repeatable sequence. The terminal ends of the ejector pins 682A-D are spaced varying travel distances 686A-C from the ends of their respective guide pockets 684.

The ejector pins 682A for a runner plate 688 of the mold 660 are arranged with the shortest travel distance. The ejector pins 682B for the "A" block 674 of the mold are positioned with a first intermediate travel distance 686A. The ejector pins 682C for the sharp bearing body 26 and overmolded part are positioned with a second intermediate travel distance 686B greater than the first intermediate travel distance 686A. The ejector pins 682D which disassociate the "B" block 676 from the mold base 690 have a longest travel distance 686C.

As the hydraulics displace the ejector pins 682A-D, all of the ejector pins 682A-D may move in tandem with one another. The runner plate 688 of the mold 660 is initially ejected from the mold 660. The ejector pins 682A for runner plate 688 may have no travel distance (as shown) to cover and may be in contact with the ends of their respective guide pockets 684 when in their initial position. As the runner plate 688 is ejected, the molded component may be automatically de-gated. The ejector pins 682B for the "A" block 674 of the mold 660 may then contact the ends of their respective guide pockets 684. Further displacement of the ejector pins 682B may disassociate the "A" block 674 from the mold 660. Subsequently, the ejector pins 682C for the sharp bearing body 26 and the molded component contact the bottoms of their respective guide pockets 684 driving the overmolded assembly out of the mold 660. The ejector pins 682C for the overmolded assembly may act on a knockout subassembly 692 within the mold 660. This subassembly 692 may include a set of part side ejector pins 694 on a sled 698 which are driven by the hydraulic side ejector pins 682C. The subassembly 692 is biased (e.g. via one or more compression spring 696) to a home position. After ejection, the bias drives the subassembly 692 back to the home position within the "B" block 676. A final ejection step drives the "B" block 676 of the mold 660 off of the mold base 690 as the ejector pins 682D contact the ends of their respective guide pockets 684.

In an alternative ejection arrangement, the travel distances 686A, 686B may be the same. Thus, the ejector pins 682B for the "A" block 674 of the mold 660 and those acting on the knockout subassembly 692 may begin to displace their respective portions of the mold 660 at the same time. The knockout subassembly 692 thus chases the "A" block 674 of the mold 660 in lock step as the "A" block 674 of the mold 660 is separated from the "B" block 676. The overmolded assembly would then stick on the "A" block 676 of the mold 660 when the knockout subassembly 692 is driven back to its home position. A vacuum grabber (or other suitable picking end-effector) could be used to remove the overmolded assembly. The overmolded assembly could be separated from the "A" block 674 in any other suitable manner. The delivery sharps 72 on the sharp bearing body 26 will be displaced out of the sharp pocket(s) 670 of the shut-off 664B insert in the "B" block 676 in a highly controlled manner along a direction parallel to the axes of the ejector pins 682A-D. This limits opportunity for the delivery sharps 72 on the sharp bearing body 26 come into contact with the pocket(s) 670 in the shut-off 664B and may help to inhibit damage to the delivery sharps 72 during the molding process.

Figure 28:
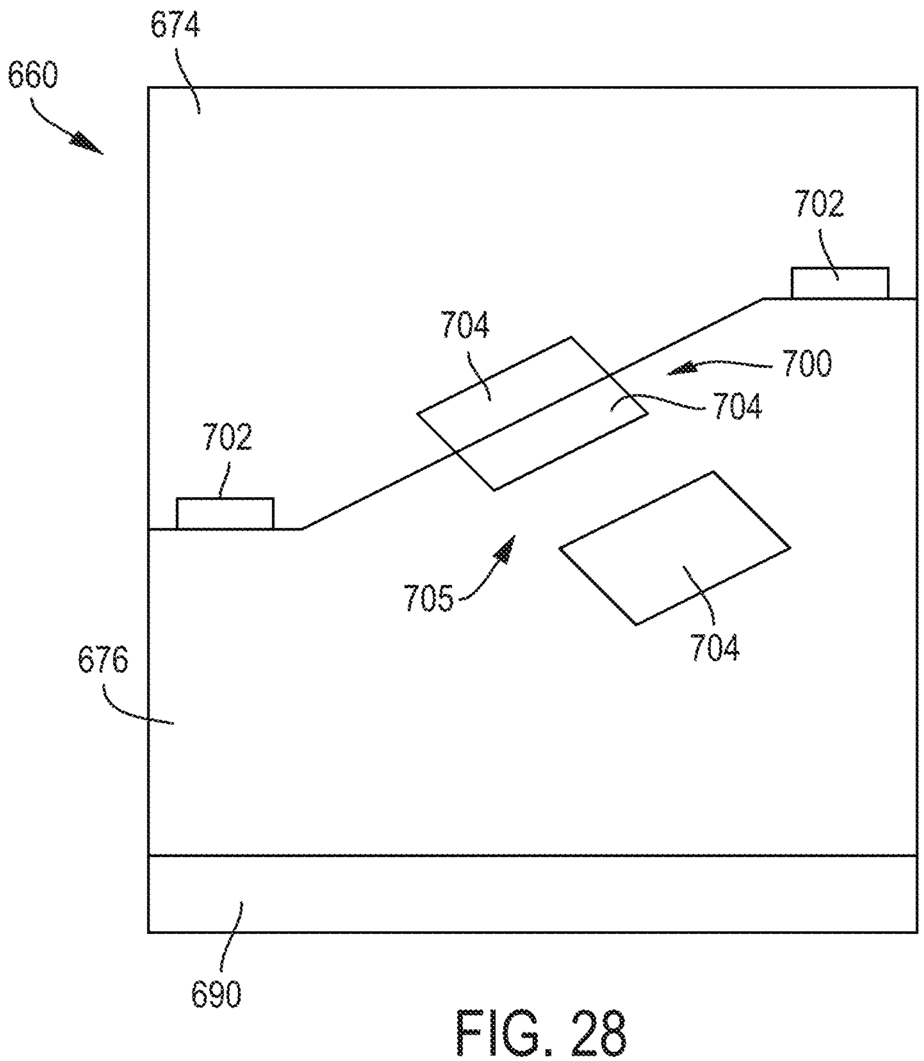
FIG. 28 depicts a block diagram of an example mold.

Referring now also to FIG. 28, the molds 660 described herein may include a resting clamping assembly 700 which may provide a resting clamping force that holds the "A" block 674 and "B" block 676 firmly against one another. A resting clamping force may assist in keeping the sharp bearing body 26 and delivery sharps 72 firmly in place when mold 660 is initially closed before the injection molding machine hydraulics are pressing on clamping platens of the machine. In the example shown in FIG. 28, the resting clamping assembly 700 include a set of rare earth magnets 704 disposed in the "A" block 674 of the mold 660 and the "B" block 676 of the mold 660. When the mold 660 is initially closed, the attraction between the magnets 704 may clamp the sharp bearing body 26 in place. Elastomer cushions 702 may be built into the parting line. These elastomer cushions 702 add some compliance which mitigates potential shock on the sharp bearing body 26 when the magnets 704 drive the "A" block 674 and "B" block 676 of the mold 660 together. Though magnets 704 are used, this clamping may be accomplished in any other suitable manner.

The mold 660 may also include a retainer assembly 705 that maintains the "B" block 676 of the mold 660 against the mold base 690 for at least a portion of the ejection sequence. For example the retainer assembly 705 may hold the "B" block 676 of the mold 660 in place as the "A" block 674 of the mold 660 is ejected. Thus the "B" block 676 will be held in a tightly controlled position as relative displacement of the "A" block 674 occurs. This may help to prevent movement of the delivery sharps 72 within the sharp pocket(s) 670 of the shut-off 664B minimizing potential for the delivery sharps 72 to be compromised. In the example embodiment, the retainer assembly 705 is provided by the magnets 704 in the "B" block 676. As shown, a greater number of magnets 704 are installed in the "B" block 676 than the "A" 674. In the example embodiment, the "B" block 676 includes double the number of magnets 704 than the "A" block 674. This ensures that the "B" block 676 is attracted to the mold base 690 strongly enough to be retained against the mold base 690 as the "A" block 674 is ejected.

Figure 29:
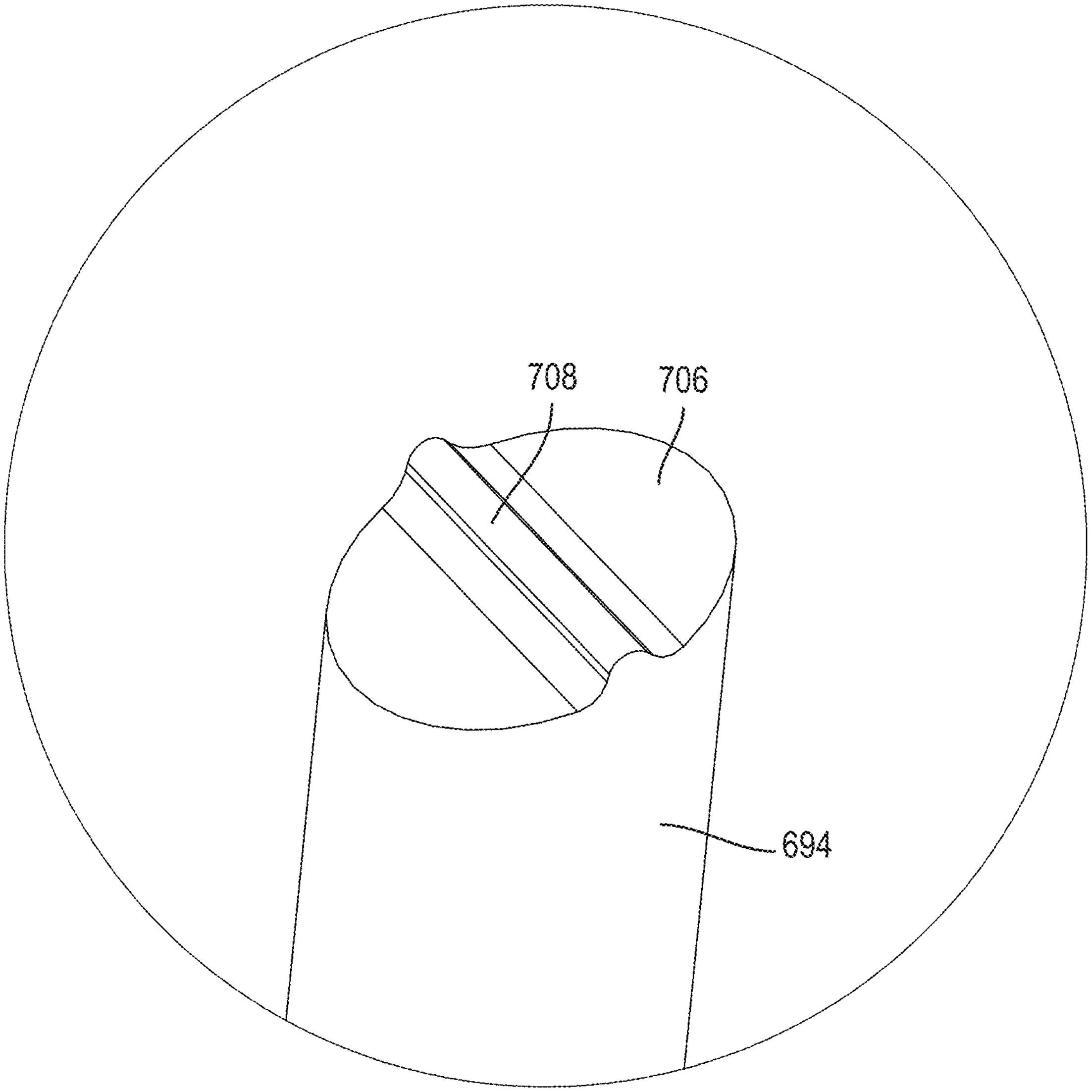
FIG. 29 depicts a view of a portion of an example ejector pin with a cleat.

Referring now to FIG. 29 a detailed view of a terminal end 706 of a part side ejector pin 694 of a knockout subassembly 692 which may be included in a mold 660 is depicted. Due to the stepped parting line incorporated into the mold 660, the overmolded component needs to be ejected on a wedge. With a flat terminal end 706, some of the linear ejection force will be translated into lateral deflection force. This may lead to an overmolded component not ejecting cleanly or may place side loads on the part side ejection pins 694 which may damage the part side ejection pins 694. As shown, the terminal end of part side ejector pins 694 may be arranged such that the molded component and the part side ejector pins 694 have interlocking features. As shown, a cleat 708 may be placed in the terminal end 706 of each part side ejector pin 694. Thus, as material is injected into the mold 660, the material may be overmolded onto the cleats 708 and the terminal ends of the part side ejector pins 694 may be embedded into the molded component. The overmolded material will buttress the part side ejector pins 694 against any side loading ensuring that the molded assembly ejects cleanly.

As shown, the cleats 708 may be included as raised ridges which span across the terminal end 706 of each part side ejector pin 694. The ridges may run in a direction perpendicular to the lateral deflection force which would be experienced by each of the part side ejector pins 694. Additionally, the ridges forming the cleats 708 may be rounded. Thus, the cleats 708 may easily (e.g. automatically) release from the molded assembly as the ejection sequence transpires. Though shown as a ridge, other generously drafted raised features may be included in alternative embodiments. The part side ejector pins 694 could alternatively include a recessed feature or features which would interlock with material of the molded component. It may, however, be preferred that raised features be used in order to avoid creating protrusions on the patient contacting side of the overmolded component.

Referring now to FIGS. 30A-48, reservoir assemblies 52 may include a septum 94 which may be penetrated by a dispensing sharp 302 in order to fill the reservoir assembly 52. Septa 94 may self-seal upon removal of the dispensing sharp 302 so as to establish a fluid tight barrier between the ambient environment and the interior fluid holding volume of the reservoir assembly 52. Septa 94 may be installed within a bay 202 or aperture 130 within a rigid portion (e.g., holder 108) of a reservoir assembly 52 during manufacture. Additionally holders 108 described herein which are devoid of bays 202, apertures 130, and septa 94 may be modified to include such components and features. Any of the arrangements described below may for example be used.

When a septum 94 is installed in a reservoir assembly 52, the axial dimension of a septum 94 may be disposed in any number of suitable orientations relative to the rigid portion of a reservoir assembly 52. In some embodiments, the axial dimension of a septum 94 may be disposed such that it is non-parallel to a surface of the rigid portion of the reservoir assembly 52. In certain of such examples, the axial dimension of a septum 94 may be substantially parallel to an axial dimension of the rigid portion of the reservoir assembly 52. Such septa 94 may be described herein as axially oriented septa 94. In alternative embodiments, the axial dimension of a septum 94 may extend in a direction outward from the periphery of the reservoir assembly 52. For example, the axial dimension of the septum 94 may be aligned with a radial dimension of the rigid portion. Such septa 94 may be described herein as radially oriented septa 94. In still other embodiments, the axial dimension of a septum 94 may be parallel to or fall within a plane of the rigid body of the septum 94 while not being aligned with the radial dimension. Such septa 94 may be described herein as secant or tangentially oriented septa 94. In other examples, the axial dimension of the septum 94 may extend outwardly from the periphery of the reservoir assembly 52 but be tilted relative to the radial dimension of the reservoir assembly 52. Thus, the axial dimension of the septum 94 may be neither parallel nor perpendicular to the axial dimension of the reservoir assembly 52.

Where reservoir assemblies 52 include septa 94, the septa 94 may be disposed to have an externally accessible face or the host reservoir assembly 52 may include an access port 200 through which the septum 94 may be pierced via a dispensing sharp 302. The access port 200 need not be aligned with the axial dimension of the septum 94. For example, an axially oriented septum 94 may be associated with an access port 200 that defines a sharp access pathway 218 running skew or non-parallel to the axial dimension of the septum 94. Regardless of the septum 94 orientation, a sharp access path 218 may be non-parallel (e.g. perpendicular or some other angle) to the plane of the rigid portion, parallel to the axial dimension of the rigid portion, radially oriented with respect to the rigid portion, or may have a secant/tangential orientation to the rigid portion. When pierced, the tip 116 of the dispensing sharp 302 may be advanced to a space in communication with the main interior volume 275 of the reservoir assembly 52 such that fluid may be transferred to the reservoir assembly 52 to fill the reservoir assembly 52.

Figure 30A:
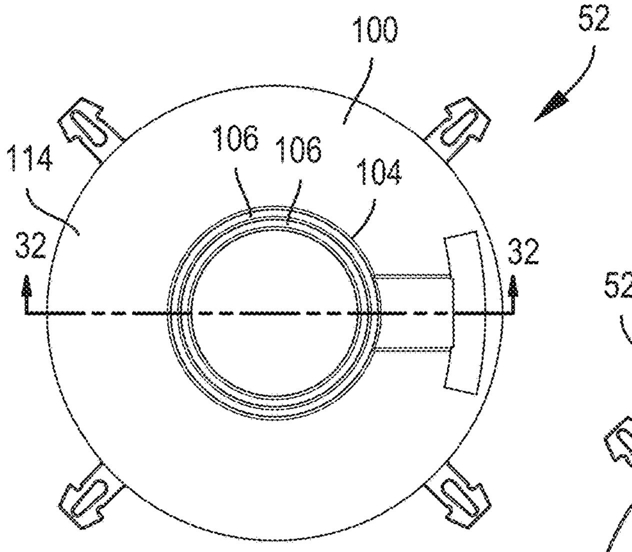
FIG. 30A depicts a top plan view of an example reservoir assembly.
Figure 30B:
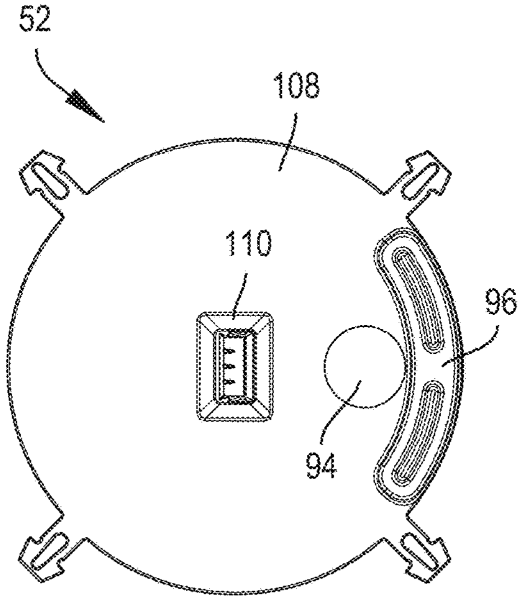
FIG. 30B depicts a bottom plan view of an example reservoir assembly.

Referring now to FIGS. 30A-30B, a top plan and bottom plan view of an example reservoir assembly 52 are depicted. The example reservoir assembly 52 may, for example, be included in various delivery devices 12 such as any of the exemplary delivery device 12 embodiments described herein. As shown, various example reservoirs assemblies 52 may include at least one septum 94. A septum 94 may be disposed in an off-center location in the reservoir assembly 52 adjacent a rocker member 96 (see, e.g., FIGS. 49A-49B) in certain examples. When the reservoir assembly 52 is assembled, the septum 94 may have a first portion which may be in fluid communication with the main interior volume 275 of the reservoir assembly 52. The septum 94 may also include an externally accessible portion. In some embodiments, the reservoir assembly 52 may include a flow channel which is in fluid communication with the main fluid holding volume of the reservoir assembly 52, but is sealed from the exterior environment by the septum 94. The flow channel may extend from a space adjacent the first portion of the septum 94 to the main fluid containing volume of the reservoir assembly 52. The flow channel may be defined by a portion of a disk body 98 of the reservoir assembly 52 and a reservoir portion 100 of the reservoir assembly 52. The reservoir assembly 52 may be filled through the septum 94 (e.g. via a dispensing sharp 302) and fluid may flow through the flow channel (if included) to the main interior cavity of the reservoir assembly 52.

Figure 32:
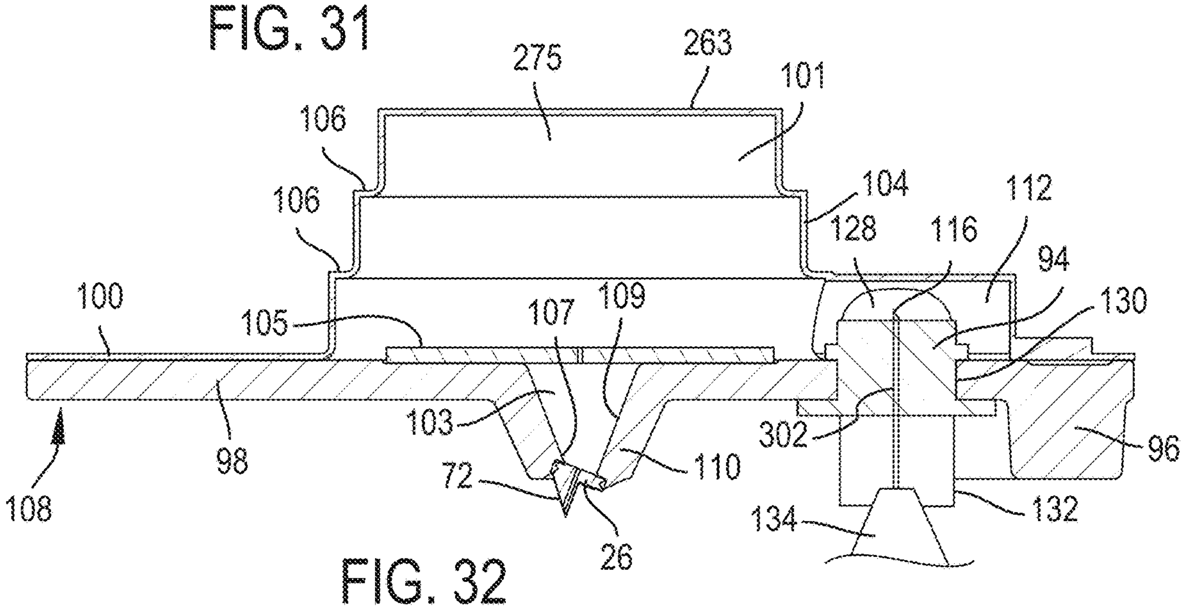
FIG. 32 depicts a cross-sectional view of an example reservoir assembly including a septum.

Referring now also to FIG. 32, the example reservoir assembly 52 includes a reservoir portion 100 with a wall 104 arranged to facilitate collapse of the fluid holding volume of the reservoir assembly 52 when pressure is exerted on the wall 104. The wall 104 in the example embodiment includes a number of step regions 106. Thus, the wall 104 may have a tiered appearance. The main interior volume 275 of the example reservoir assembly 52 is a step pyramid or ziggurat shaped volume defined by the wall 104 in the example depicted. As shown, the reservoir assembly 52 is in a filled state. The holder 108 or rigid portion of the reservoir assembly 52 includes a stage projection 110 and a rocker member 96 (see, e.g., FIGS. 49A-49B).

In the example shown, a side channel 112 of the reservoir portion 100 has been sealed closed by heat staking the reservoir portion 100 material to the holder 108. The portion of the side channel 112 at the periphery of the flange 114 is sealed against the holder 108 leaving the remaining portion of the side channel 112 open. In alternative embodiments, the reservoir portion 100 may not include a side channel 112. The entire peripheral region of the flange 114 may be coupled to the disk body 98 during manufacture. In certain example embodiments, the wall 104 forming the cavity in the reservoir portion 100 may include an offshoot or a node which extends away from the main portion of the cavity.

Figure 31:
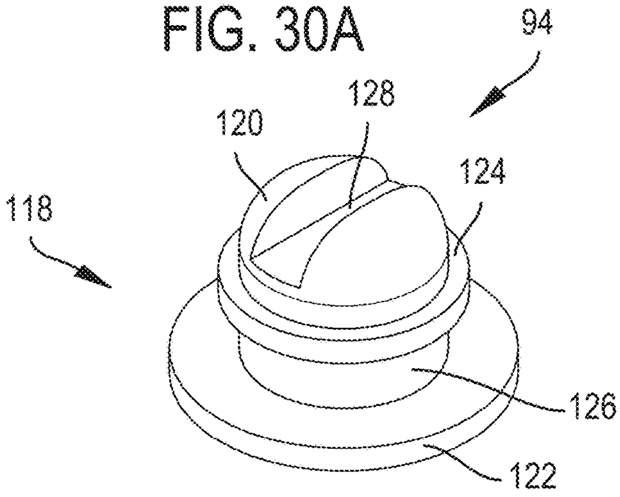
FIG. 31 depicts a perspective view of an example septum.

Referring now primarily to FIGS. 31-32, when desired, example reservoir assemblies 52 may be filled by establishing fluid communication between an interior fluid holding volume 275 of the reservoir assembly 52 and a filling implement 42 (see, e.g., FIG. 97). In various examples, a filling implement 42 (see, e.g., FIG. 97) such as a syringe may be used and may include a dispensing sharp 302. The dispensing sharp 302 may be advanced through the septum 94 and fluid may be transferred from the filling implement 42 into the main interior volume 275 of the reservoir assembly 52 via the dispensing sharp 302. Any adhesive member 56 on the delivery device 12 may include an open region to allow access to the septum 94 via the dispensing sharp 302 (or the adhesive member 56 may be coupled to the delivery device 12 after filling). Once a desired volume of fluid has been transferred into the reservoir assembly 52, the dispensing sharp 302 may be withdrawn from the septum 94. The septum 94 may be constructed of a self-sealing material such that when the dispensing sharp 302 is withdrawn, the septum 94 provides a robust seal between the main interior volume 275 of the reservoir assembly 52 and the external environment. In some examples, prior to transferring fluid into the reservoir assembly 52, a vacuum may be pulled on the reservoir assembly 52 via the filling implement 42 (e.g. by withdrawing the plunger of a syringe). The dispensing sharp 302 may be removed from the septum 94 and any gas sucked out of the reservoir assembly 52 may be expelled from the filling implement 42. This may help to ensure a minimal volume of gas is present in the reservoir assembly 52 prior to filling.

Reservoir assemblies 52 including a septum 94 such as that shown in FIGS. 30A-30B (or any other such reservoir assemblies 52 described herein) may be shipped in an unfilled state. Though reservoir assemblies 52 (either alone or installed in a delivery device 12) may be filled individually via a syringe or the like in a system 10 such as that described in relation to FIG. 1A, reservoir assemblies 52 may also be provided in communication with a fluid bus 32. For example, the reservoir assemblies 52 may be distributed for filling with their septa 94 in a pierced state in systems 10 described above in relation to FIGS. 1B-1C.

The reservoir assemblies 52 may be filled at a pharmacy, hospital, physician's office, vaccination site, forward operating base, front line position, field hospital, or other patient care setting. Alternatively, reservoir assemblies 52 may be filled at a local distribution center from which they may be subsequently disseminated to the surrounding population. The reservoir assemblies 52 may be filled temporally proximate use of a delivery device 12. Thus, agent may only be contained in the delivery device 12 for a short period of time (e.g. minutes to weeks). This may allow for reservoir assemblies 52 or delivery devices 12 to be shipped without need for cold chain distribution networks. Additionally, this may help limit need for prolonged agent compatibility testing and facilitate a more nimble response to public health crises. It may also facilitate the use or a wider variety or materials for the construction of agent contacting portions of a delivery device 12.

In certain examples, the reservoir assemblies 52 may include a guard which helps to inhibit contact of the reservoir portion 100 with the tip 116 of a dispensing sharp 302. The guard may help keep the reservoir portion 100 in spaced relation to the dispensing sharp 302 during filling of the reservoir assembly 52. The guard may, for example, block a portion of the reservoir portion 100 from displacing into a sharp receiving region of the reservoir assembly 100 where the tip 116 of a dispensing sharp 302 may be disposed during filling.

Referring primarily to FIG. 31, an example embodiment of a septum 94 is depicted. As shown, the septum 94 includes a plug portion 118 and a standoff 120 which may act as a guard. The plug portion 118 may include a first end 122 and a second end 124. The first and second ends 122, 124 may be connected by a stem body 126. The stem body 126 may be narrower (e.g. have a smaller diameter) than either of the first and second ends 122, 124. The first end 122 may be wider (e.g. larger diameter) than the second end 124. The standoff 120 may project from the second end 124. In the example shown, the standoff 120 is shaped substantially as a hemisphere and includes a recessed channel 128. The recessed channel 128 may extend across the width of the standoff 120 forming a canyon type feature in the standoff 120.

Referring primarily to FIG. 32, as shown, the holder 108 may include an aperture 130 which extends through the disk body 98 of the holder 108. The septum 94 may be a fluid tight plug for this aperture 130 when the reservoir assembly 52 is assembled. For example, the septum 94 may be installed in the reservoir assembly 52 by advancing the standoff 120 and second end 124 through the aperture 130. The standoff 120 may have a shape (e.g. a spherical segment) which helps guide the septum 94 into the aperture 130. When installed, the stem body 126 may be disposed within the bore of the aperture 130. The first end 122 may be disposed against the face of the holder 108 from which the stage projection 110 extends. The second end 124 may be disposed within the side channel 112 (or in an offshoot or node projecting from the main cavity of the main interior volume 275 of the reservoir assembly 52). Thus the plug portion 118 may establish a fluid tight seal between the exterior environment and the main interior volume 275 of the reservoir assembly 52. The stem body 126 of the septum 94 may have a width (e.g. diameter) which is slightly larger than that of the aperture 130 such that the stem body 126 is under compression when the septum 94 is installed within the reservoir assembly 52.

When installed within the reservoir assembly 52, the section of the reservoir portion 100 in which the side channel 112 (or offshoot or node from the main cavity of the reservoir assembly 52) is formed may be inhibited from displacing into the recessed channel 128 by the remainder of the standoff 120. The portions of the standoff 120 adjacent the recessed channel 128 may hold the reservoir portion 100 above the recessed channel 128. Thus, the recessed channel 128 may form a sharp receiving volume within the reservoir assembly 52. The tip 116 of a dispensing sharp 302 may be advanced into the recessed channel 128 while being kept spaced away from the material forming the reservoir portion 100.

In certain embodiments, an adapter 132 may be utilized with any suitable filling implement 42 to ensure that the dispensing sharp 302 is prevented from advancing into the septum 94 beyond a certain distance. The adapter 132 may, for example, couple to a filling implement 42 or hub 134 to which the dispensing sharp 302 is attached. The adapter 132 may extend along a portion of the dispensing sharp 302 shortening the exposed length of the dispensing sharp 302. The adapter 132 may contact or bottom out against the reservoir assembly 52 as the dispensing sharp 302 is introduced into the septum 94 and inhibit further displacement of the dispensing sharp 302 into the septum 94. The adapter 132 may ensure that the tip 116 of the dispensing sharp 302 is limited from displacing out of the recessed channel 128. In alternative embodiments, an adapter 132 may be omitted. The dispensing sharp 302 may have an exposed length (e.g. extending from a hub 134 which is shorter than a height of the septum 94, but longer than a distance between the first end 122 of the septum 94 and the most proximate point of the recessed channel 128. Thus, when inserted, the tip 116 of the dispensing sharp 302 may be disposed within the recessed channel 128.

The interior volume of the reservoir assembly 52 is partitioned into a first portion 101 and a second portion 103. Any other reservoir assemblies 52 described herein may be partitioned in like manner. The first portion 101 and the second portion 103 may be in fluid communication with one another via a flow restrictor 105. The flow restrictor 105 may be disposed between a portion of the interior volume of the reservoir assembly 52 proximal to the delivery sharps 72 and a portion more distal to the delivery sharps 72. The flow restrictor 105 may be an orifice plate with one or more orifice extending therethrough in certain embodiments. In some embodiments a flow restrictor 105 with a 15-25 micron orifice may be included. In other embodiments, an orifice may be up to 100 microns in diameter (e.g. 70-80 microns or 75 microns). In some embodiments, the orifice may have diameter greater than 100 microns. The orifice size may be selected based on considerations such as the viscosity and/or surface tension of the agent(s) filled into the reservoir assembly 52, the desired speed of injection and how quickly it is desired to ramp up injection pressure. The orifice may be a funnel type shape and may taper toward a smallest cross-sectional area as distance toward one of the first or second portions 101, 103 decreases. An orifice plate may be an injection molded component though could be formed in any other suitable manner.

Still referring to FIG. 32, the first portion 101 of the reservoir assembly 52 may include a majority of the interior volume 275 of the reservoir assembly 52. The second portion 103 may be disposed proximal to the delivery sharp(s) 72 relative to the first portion 101. Thus, the flow restrictor 105 may separate a large first portion 101 from a smaller second portion 103 which is most proximal the delivery sharp(s) 72. The first portion 101 may have a volume substantially equal to the fill volume of the reservoir assembly 52 in certain examples. The flow restrictor 105 may be disposed upstream of at least the pocket 107 into which a sharp bearing body 26 may be coupled. As shown in the example, the flow restrictor 105 may separate a well 109 in the holder 108 from the remainder of the interior volume 275 of the reservoir assembly 52. In such embodiments, the flow restrictor 105 may be coupled to the distal face of the disk body 98 over the well 109. In some examples, a small depression may be included in the face of the disk body 98 to help locate the flow restrictor 105. A set of ridges 102 (see, e.g., FIG. 38A) may also be included in certain examples to assist in locating the flow restrictor 105 during assembly. The flow restrictor 105 may be coupled to the disk body 98 via heat stake, sonic weld, solvent bonding, or in any other suitable manner.

In certain examples, the first and second portion 101, 103 of a partitioned reservoir assembly 52 may be filled with different fluids. For example, the first portion 101 may be filled with an agent desired to be delivered (drug, vaccine, medical agent, etc.). The portion proximal the delivery sharp(s) 72 may be filled with a gas (e.g. sterile or cleanroom air from the manufacturing environment, inert gas, etc.). The orifice may be sized such that the properties of the agent (e.g. surface tension, viscosity) prevent the agent from passing to the second portion 103 without addition of pressure on the reservoir assembly 52. Thus, despite the first and second portions 101, 103 being in fluid communication, the second portion 103 may remain unwetted by any agent filled into the reservoir assembly 52 during manufacture until use. When the delivery device 12 is used, there may be a latency period during which fluid is forced into the second portion 103 from the first portion 101. Pressure in the second portion 103 may then ramp up until a pressure at which the patient's anatomy begins to accept the delivery. The pressure may remain relatively steady (or at least not spike considerably) once delivery begins.

When a delivery device 12 including a partitioned reservoir assembly 52 is transitioned to a delivery state, at least one bias member 58 (e.g. a conical spring, foam body, rubber body, elastomeric body, see, e.g., FIG. 6) may cause pressure to be exerted against the first portion 101 of the reservoir assembly 52. Depending on the embodiment, the at least one bias member 58 may directly contact the reservoir assembly 52 or pressure may be exerted through a reservoir interface member 64 or other components of a dispensing assembly 60. The flow restrictor 105 may cause the pressure of fluid in the second portion 103 of the reservoir assembly 52 to slowly ramp up to a pressure at which injection into a patient begins. Thereafter, the flow restrictor 105 may limit build-up of pressure in the second portion 103 as the injection progresses. Thus the injection will tend to occur at or near the lowest pressure at which the patient will accept the delivery.

Referring now to FIGS. 33A-33E, various views of another example reservoir assembly 52 including a septum 94 are depicted. The example septum 94 is axially oriented and the sharp access pathway 218 is also axially oriented. As shown best in FIG. 33C, the rigid portion of the example reservoir assembly 52 (in this embodiment the holder 108) includes a bay 202. A flow channel 204 extends through a wall of the bay 202 to a face of the holder 108 against which the collapsible reservoir portion 100 is coupled. When the septum 94 is installed in the bay 202, the septum 94 may be spaced from a receiving volume 206 (best shown in FIG. 33D) in the bay 202 with which the flow channel 204 communicates. The septum 94 may be retained in the bay 202 by a swaging operation which displaces material of the holder 108 from its orientation after molding to a position in which it overhangs a portion of the septum 94. A peripheral wall 212 of the bay 202 may be heat swaged over the septum 94 for example. This swaged portion of the peripheral wall 212 may define the sharp access pathway 218 for the reservoir assembly 52. An overhanging swage also inhibits removal of the septum 94 by a user.

When the reservoir portion 100 is coupled to the holder 108 it may be heat staked in place. The reservoir portion 100 may include a main interior volume 275 which is tiered as described in relation to FIGS. 30A-30B. The example reservoir portion 100 also includes a set of flow passages 208 and a bay receptacle 210. These features may be thermoformed into the reservoir portion 100. The bay receptacle 210 may be placed over the bay 202 and heat staked to a peripheral wall of the bay 202 (which may be swaged over the septum 94). Thus there may be a fluidically sealed volume 214 upstream of the septum 94.

When heat staked to the holder 108, the reservoir portion 100 may not be coupled to an area adjacent the periphery of at least a portion of the bay 202. Thus a flow path 216 may be created around the bay 202. The main interior volume 275 of the reservoir assembly 52 may be in communication with the receiving volume 206 in the bay 202 via the flow channel 204 and flow path 216. The flow passages 208 formed in the reservoir portion 100 may extend from the main interior volume 275 to the flow path 216 around the periphery of the bay 202. Thus, the flow passages 208 may further facilitate transfer of fluid from the receiving volume 206 to the main interior volume 275. In alternative embodiments, the holder 108 may include flow recesses 254A, B (see, e.g. FIG. 43B) which together with the reservoir portion 100 form sealed fluid pathways to the main interior volume 275.

Figure 33A:
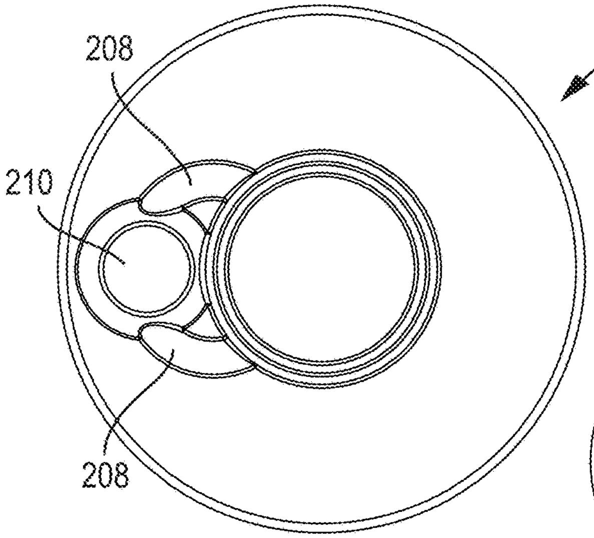
FIG. 33A depicts a top plan view of an example reservoir assembly with a septum.
Figure 33B:
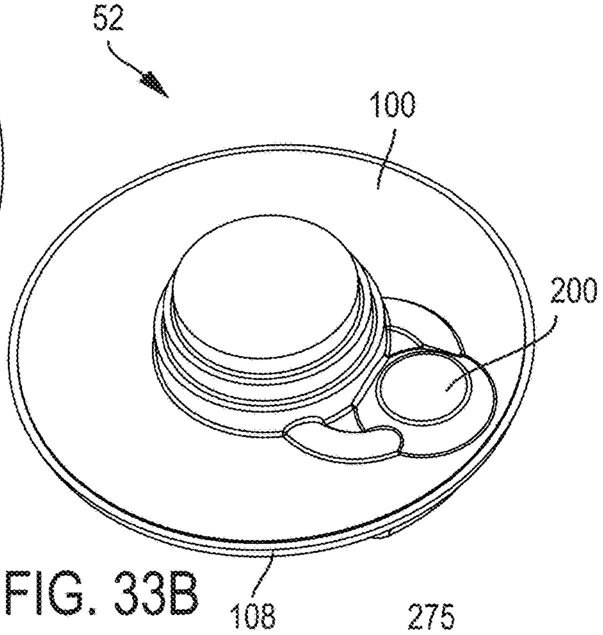
FIG. 33B depicts a perspective view of an example reservoir assembly with a septum.
Figure 33C:
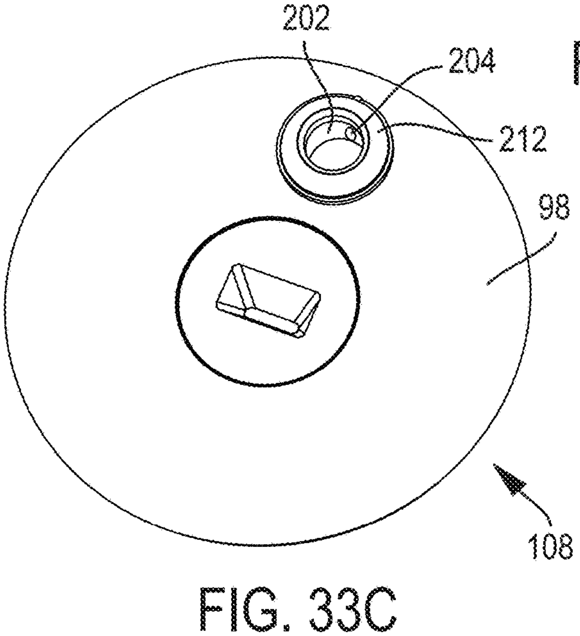
FIG. 33C depicts a perspective view of an example rigid reservoir portion for a reservoir assembly including a bay in which a septum may be installed.
Figure 33E:
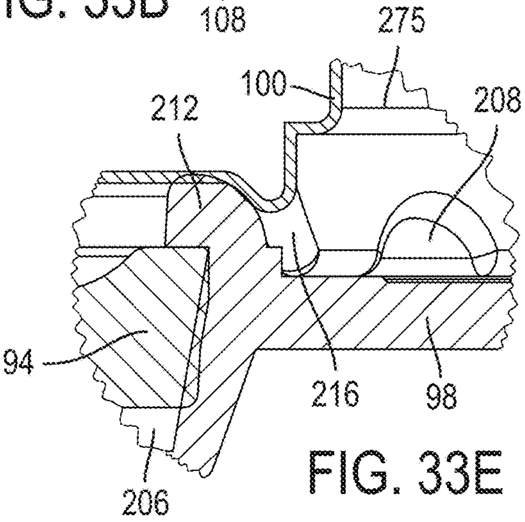
FIG. 33E depicts a detailed view of the indicated region of FIG. 33D.
Figure 33D:
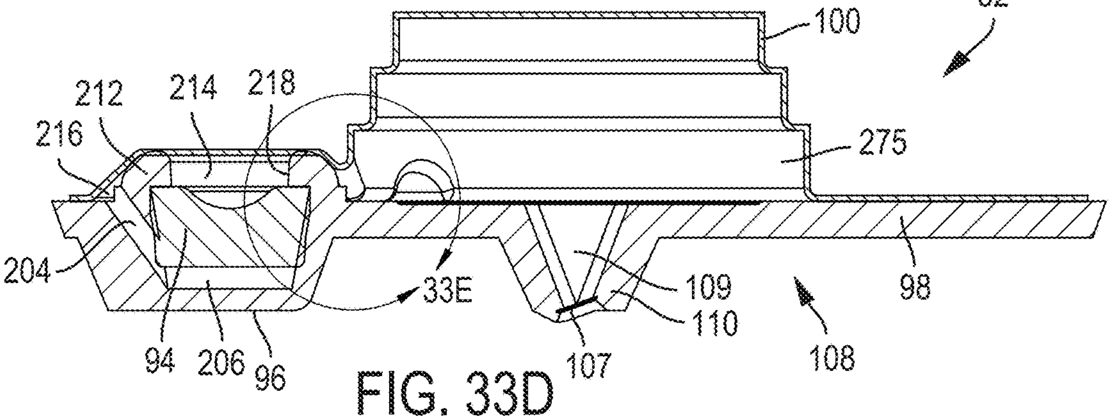
FIG. 33D depicts a cross-sectional view of an example reservoir assembly including a septum.
Figure 34A:
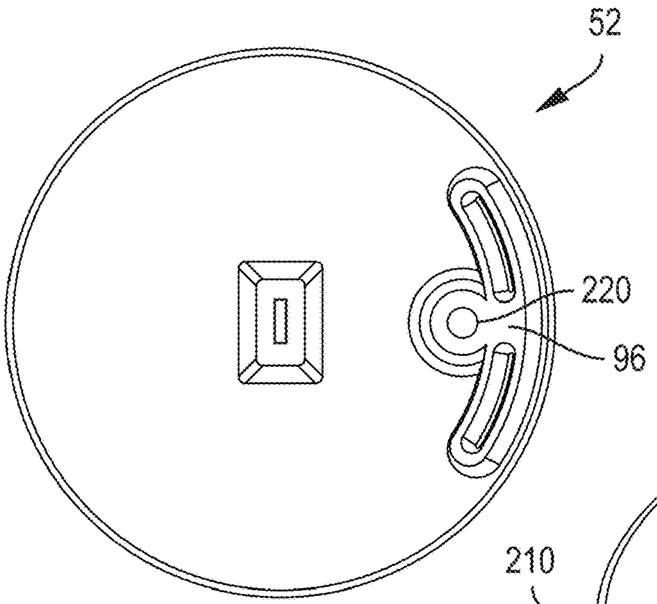
FIG. 34A depicts a bottom plan view of an example reservoir assembly including a septum.
Figure 34B:
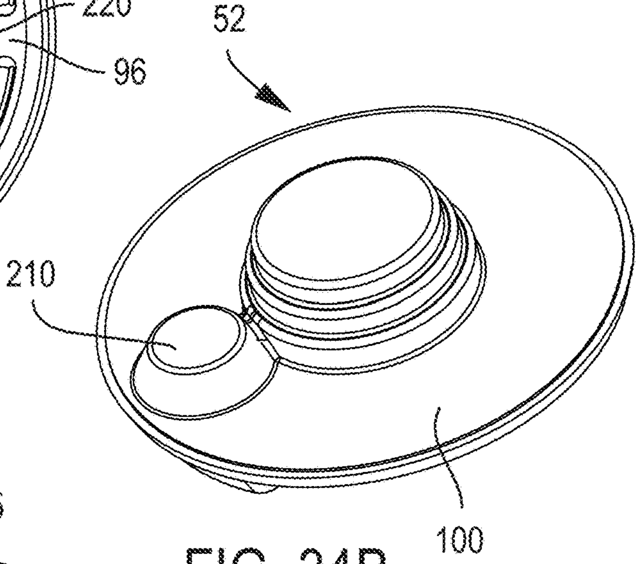
FIG. 34B depicts a perspective view of an example reservoir assembly including a septum.
Figure 34C:
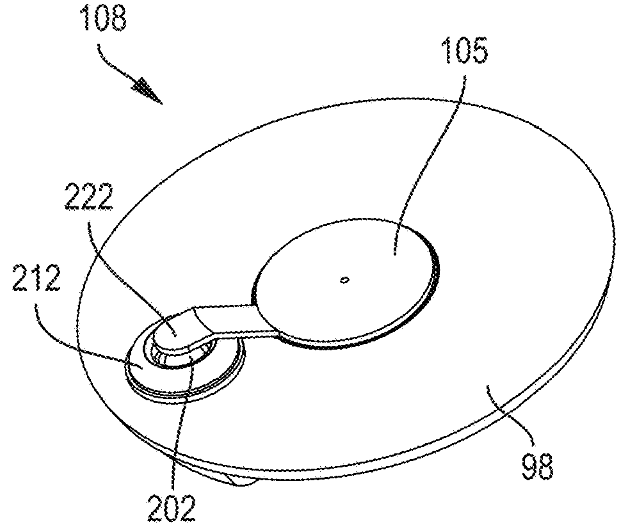
FIG. 34C depicts a perspective view of an example rigid reservoir portion and a flow restrictor including a shield projection.
Figure 34D:
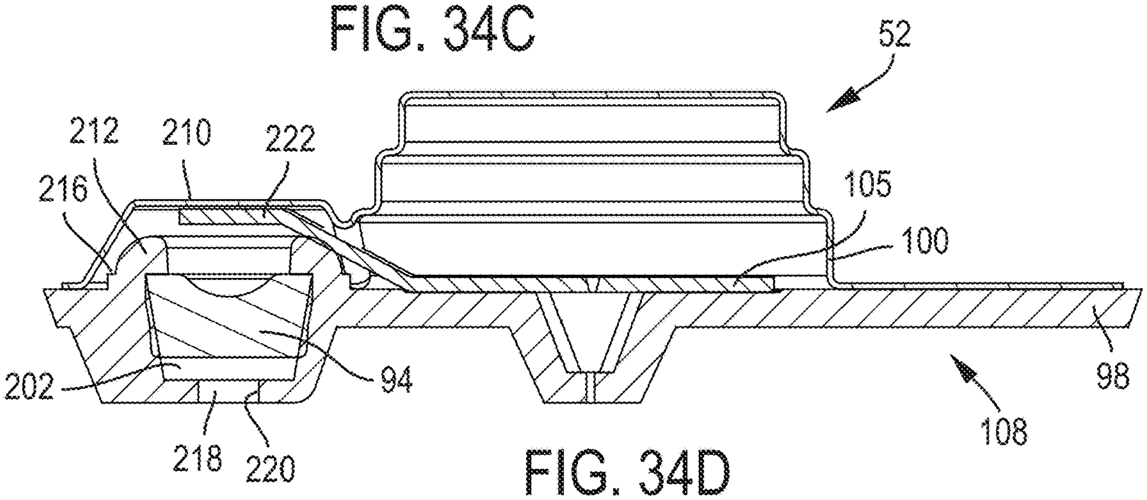
FIG. 34D depicts a cross-sectional view of an example reservoir assembly including a septum.

To fill the example reservoir assembly 52 of FIGS. 33A-33C, a dispensing sharp 302 may puncture the bay receptacle 210 and advance through the sealed volume 214 and septum 94. This may place the tip 116 of the dispensing sharp 302 in communication with the receiving volume 206 of the bay 202. Gas may be sucked out of the reservoir assembly 52 if necessary to collapse the main interior volume 275 and fluid may subsequently be transferred into the reservoir 52.

Referring now to FIG. 34A-34D, another exemplary reservoir assembly 52 including a septum 94 is depicted. The example septum 94 is axially oriented and the sharp access pathway 218 is also axially oriented. As shown, the rigid portion of the reservoir assembly 52 (in this example, the holder 108) includes a bay 202. The wall of the bay 202 opposite the reservoir portion 100 includes a pass-through 220 which forms the sharp access pathway 218 for the reservoir assembly 52. Thus, the interior of the reservoir assembly 52 may be accessed from a delivery sharp 72 bearing side of the reservoir assembly 52. The septum 94 may be installed in the bay 202 and a peripheral wall 212 of the bay 202 may be swaged over a portion of the septum 94 to retain the septum 94 in place within the bay 202.

The reservoir portion 100 may define a tiered main interior volume 275 as described in relation to FIGS. 30A-30B and a bay receptacle 210. These features may, for example, be thermoformed into the reservoir portion 100. The reservoir portion 100 may be heat staked to the holder 108 leaving a region of the reservoir portion 100 surrounding the periphery of the bay 202 uncoupled to the reservoir portion 100. Thus, there may be a flow path 216 around at least a portion of the bay 202.

To fill the example reservoir assembly 52 of FIGS. 34A-34D, a dispensing sharp 302 may be advanced through the pass-through 220 and septum 94 such that the tip 116 of the dispensing sharp 302 is within a receiving space between the septum 94 and the wall of the bay receptacle 210 of the reservoir portion 100. Gas may be sucked out of the reservoir assembly 52 if necessary to collapse the main interior volume 275 and fluid may subsequently be transferred into the reservoir 52.

It may be desirable that guards of reservoir assemblies 52 present a backstop or physical barrier to advancement of a dispensing sharp 302 into a position where it is possible to contact a reservoir portion 100. This may allow for a reservoir assembly 52 to be filled with any desired dispensing sharp 302. Additionally, it may obviate use of an adapter which adjusts the exposed length of a dispensing sharp 302. Additionally a physical barrier may lessen the precision needed when inserting the dispensing sharp 302 into the septum 94. Instead of advancing the tip 116 into a very small recessed channel 128 (see, e.g., FIG. 32), the dispensing sharp 302 may be pierced through a septum 94 at any orientation allowed by the sharp access pathway 218. The example reservoir assembly 52 in FIGS. 34A-34D includes a guard which presents a physical barrier that inhibits the tip 116 from contacting the reservoir portion 100. In the example embodiment, the flow restrictor 105 includes a shield projection 222. In alternative embodiments, a shield projection 222 may be provided as part of another component (e.g. the holder 108) of the reservoir assembly 52 or as a stand-alone component which may be coupled into the reservoir assembly 52 (e.g. attached to the holder 108 during manufacture). The shield projection 222 may include at least a segment that is spaced from but extends over the face of the septum 94 in communication with the main interior volume 275 of the reservoir assembly 52. For example, this segment may extend over or rest on the peripheral wall of the bay 202. Thus, as the dispensing sharp 302 is advanced into the reservoir assembly 52, the tip 116 of the dispensing sharp 302 may be blocked from contacting the reservoir portion 100. In some embodiments, the shield projection 222 may be paired with or include a stiffener (e.g. rib or set or ribs) which strengthen the shield projection 222.

Figure 35A:
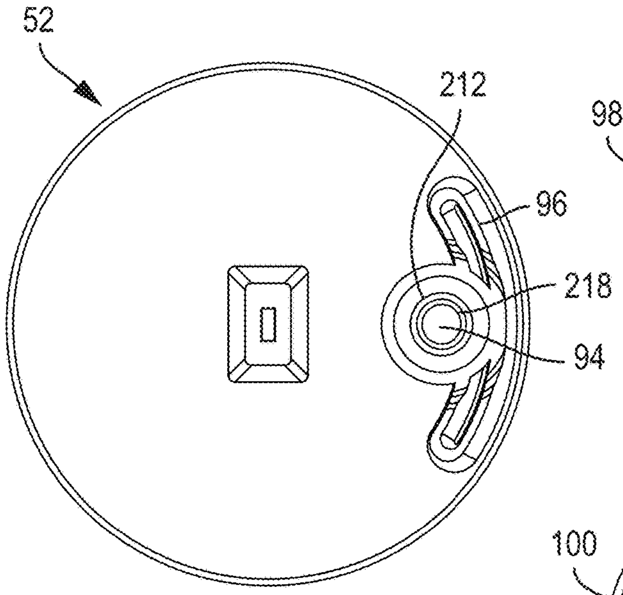
FIG. 35A depicts a bottom plan view of an example reservoir assembly including a septum.
Figure 35B:
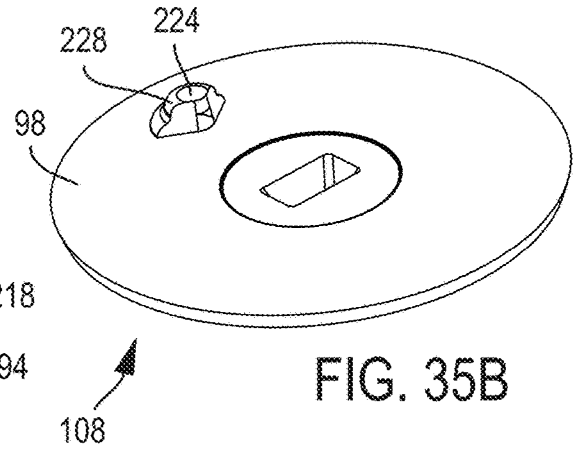
FIG. 35B depicts a perspective view of an example rigid reservoir portion for a reservoir assembly.
Figure 35C:
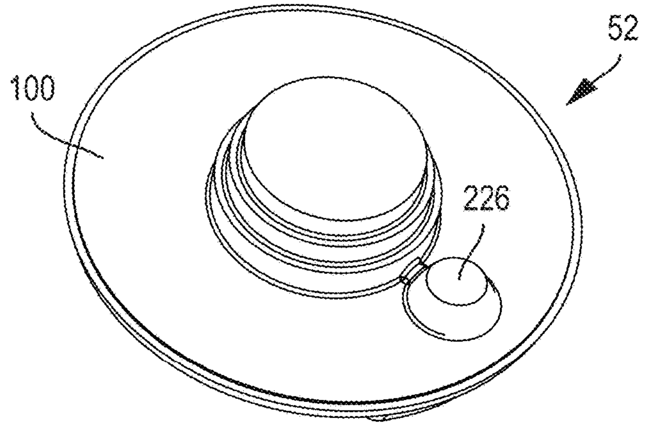
FIG. 35C depicts a perspective view of an example reservoir assembly including a septum.
Figure 35D:
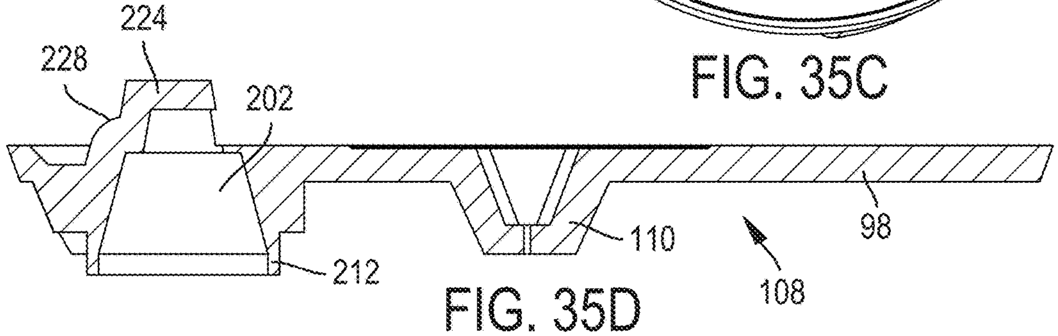
FIG. 35D depicts a cross-sectional view of an example rigid reservoir portion for a reservoir assembly including a bay for installation of a septum.
Figure 35E:
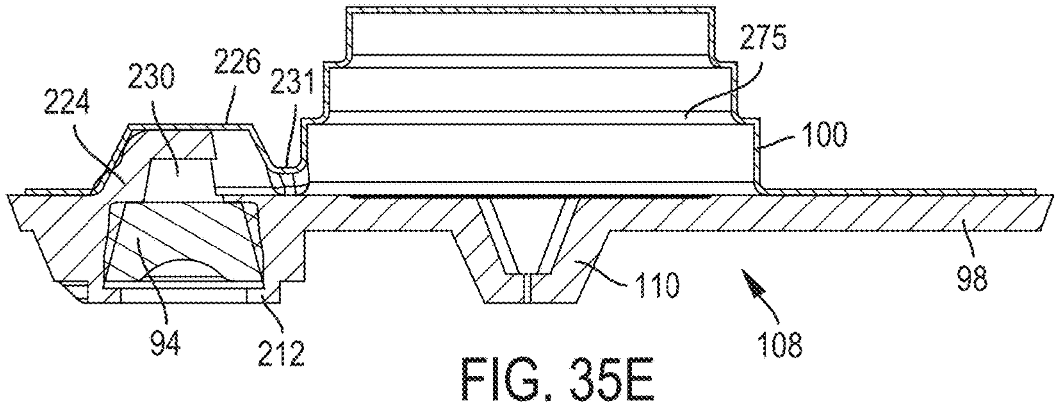
FIG. 35E depicts a cross-sectional view of an example reservoir assembly including a septum.

Referring now to FIGS. 35A-35E, another exemplary embodiment of a reservoir assembly 52 including a septum 94 is depicted. The example septum 94 is axially oriented and the sharp access pathway 218 is also axially oriented. As shown, the rigid portion of the reservoir assembly 52 (in this example, the holder 108) includes a bay 202. As best shown in FIGS. 35D-35E, the peripheral wall 212 of the bay 202 may be disposed on a side of the holder 108 opposite the reservoir portion 100. A septum 94 may be installed in the bay 202 and the peripheral wall 212 may be swaged over the septum 94 as shown in FIG. 35E (shown prior to swage in FIG. 35D). The swaged peripheral wall 212 may form the sharp access pathway 218 for the reservoir assembly 52. Thus, the interior of the reservoir assembly 52 may be accessed from a delivery sharp 72 bearing side of the reservoir assembly 52.

To fill the example reservoir assembly 52 of FIGS. 35A-35E, a dispensing sharp 302 may be advanced through the sharp access pathway 218 and septum 94 such that the tip 116 of the dispensing sharp 302 is within a receiving space 230 in communication with the main interior volume 275 of the reservoir assembly 52 on the side of the septum 94 most proximal the reservoir portion 100. Gas may be sucked out of the reservoir assembly 52 if necessary to collapse the main interior volume 275 and fluid may subsequently be transferred into the reservoir 52.

As with other embodiments described herein, the reservoir assembly 52 of FIGS. 35A-35E may include a guard which presents a physical barrier to the tip 116 of a dispensing sharp 302. In the example shown, the holder 108 of the reservoir assembly 52 includes a protective hood 224 which extends over at least a portion of the face of the septum 94 most proximal the reservoir portion 100. The protective hood 224 may physically block advancement of the tip 116 of a dispensing sharp 302 into contact with the reservoir portion 100. The reservoir portion 100 may include a tiered main interior volume 275 as described in relation to FIGS. 33A-33B as well as a hood receptacle 226. These features may, for example, be thermoformed in the reservoir portion 100. When the reservoir portion 100 is joined to the holder 108, the protective hood 224 may be positioned in the hood receptacle 226 and the reservoir portion 100 may, for example, be heat staked to the holder 108. The hood receptacle 226 may be coupled to the surface of the protective hood 224 as well when the reservoir portion 100 and holder 108 are coupled. At least a portion of the sidewall 228 of the protective hood 224 may be open so as to allow fluid transfer between the receiving space 230 adjacent the septum 94 and the main interior volume 275 of the reservoir assembly 52. A transfer channel 231 may also be formed in the reservoir portion 100 to create a connection between the main interior volume 275 and volume of the hood receptacle 226. In alternative embodiments, a flow recess 254A (see, e.g., FIG. 43B) may be included in the holder 108 to ensure fluid communication between the volume of the hood receptacle 226 and the main interior volume 275.

Referring now to FIGS. 36A-36E, another example embodiment of a reservoir assembly 52 including a septum 94 is depicted. The example septum 94 is axially oriented, however, the sharp access pathway 218 for the reservoir assembly 52 is skew or non-parallel to the axial dimension of the septum 94. As shown, the rigid portion of the reservoir assembly 52 (in this example, the holder 108) includes a bay 202. The bay 202 may be partially surrounded by a peripheral wall 212. The partial peripheral wall 212 may surround a region of the bay 202 most distal the main interior volume 275 of the reservoir assembly 52. The peripheral wall 212 may include a gap 232 along the portion of the bay 202 most proximal the main interior volume 275. A septum 94 may be installed in the bay 202 and the peripheral wall 212 may be swaged over the septum 94 to retain the septum 94 within the bay 202.

The reservoir portion 100 of the reservoir assembly 52 may include a bay receptacle 210. The reservoir portion 100 may also include a wall 104 which defines the main interior volume 275 of the reservoir assembly 52. The wall 104 and bay receptacle 210 may be thermoformed into the reservoir portion 100. When the reservoir portion 100 is coupled to the holder 108, the peripheral wall 212 and gap 232 may be disposed in the bay receptacle 210. The reservoir portion 100 may then be coupled (e.g. heat staked) to the holder 108.

As shown, the wall 104 is formed (e.g. thermoformed on a porous metal or other form) such that the main interior volume 275 of the reservoir assembly 52 is in a collapsed or substantially evacuated state. Thus, withdrawal of gas from the reservoir assembly 52 (or otherwise managing gas in the reservoir assembly 52) may be skipped prior to transferring fluid into the reservoir assembly 52. When the main interior volume 275 of the reservoir assembly 52 is filled, the wall 104 may displace to accommodate the fluid transferred into the reservoir assembly 52. The undulations in the reservoir portion 100 when the main interior volume 275 is in the collapsed state may help to facilitate collapse of the main interior volume 275 after filling. Likewise, the undulations facilitate expansion of the main interior volume 275 as agent is loaded into the main interior volume 275. Thus, the collapsed state may also be referred to as an inflatable or expansible state or state in which the main interior volume 275 is expansile. The undulations may allow the volume of the main interior volume 275 to be varied at least to a target fill volume without elastically deforming the wall 104. Thus, the main interior volume 275 may be brought to a filled, but unpressurized state when loaded with agent. In some embodiments, the shape of reservoir portion 100 when the main interior volume 275 is collapsed may cause it to take on a tiered appearance similar to that shown in FIGS. 35A-35E when the main interior volume 275 is loaded with fluid.

There may be a small amount of gas disposed within the collapsed main interior volume 275 prior to filling of a reservoir assembly 52 with agent. The amount of gas may typically (though need not be) be consistent from reservoir assembly 52 to reservoir assembly 52 and may be determined by the thermoformed (or otherwise formed) shape of the reservoir portion 100. Thus a small amount gas may be maintained in reservoir assemblies 52 when they are loaded with agent. This may be desirable as it provides a compliant volume within the reservoir assembly 52. As pressure is initially applied to the reservoir assembly 52 when a delivery device 12 is transitioned to a delivery state, the small volume of gas may behave as a damper. This may help inhibit bursting of reservoir assemblies 52 and may potentially facilitate use of a greater range of materials for the reservoir portion 100 of the reservoir assembly 52. The volume of gas within the main interior volume 275 when agent is loaded into the reservoir assembly 52 to transition the main interior volume 275 to a full state may be less than 25% (e.g. no more than 15% or 20%) of the main interior volume 275 (when the main interior volume 275 is unpressurized).

Any reservoir portions 52 described herein may be provided with the main interior volume 275 in a collapsed state. Additionally, the undulations defining the wall 104 when the main interior volume 275 is collapsed may differ from that shown when the main interior volume 275 of a reservoir assembly 52 is provided in a collapsed state. In the example, the undulations are formed as substantially straight wall segments (when viewed in cross-section) connected by round or radiused spans of wall 104 material. A central plateau region is also present. Each undulation (and the central plateau) is substantially even in height and of a constant height. Different undulations (and the central plateau region if included) may have different heights. Additionally each individual undulation (and the central plateau region if included) may vary in height. Each undulation in the example shown is substantially concentric (non-concentric arrangements such as a series of nested ovals or ellipses could alternatively be used). Any number of undulations may be included. Certain straight wall segments may extend generally perpendicular to the holder 108 when the reservoir portion 100 is coupled to the holder 108 (though described as perpendicular, a slight draft may be present to facilitated release from a form). In some embodiments, the straight wall segments may be provided in pairs which tilt toward one another at angles that are substantially congruent. In some embodiments, the angle of the straight wall segments in each pair may differ with at least one tilting toward the other of each pair. Though the straight wall sections are connected with rounded spans the rounded spans may be replaced by straight spans. The corners at the transition between the straight wall sections and the straight connecting spans may be rounded. In some embodiments, the straight wall sections may not be included and the wall 104 may instead have a sinusoidal type cross-section.

Different types of undulations may be provided in each wall 104. The height of each undulation formed in a wall 104 may differ. The spacing between undulations may differ. The spacing between straight wall sections across pairs of straight wall sections formed in the wall 104 may differ. In some examples radial or outwardly extending undulations may be present in addition to concentric undulations.

Figure 36A:
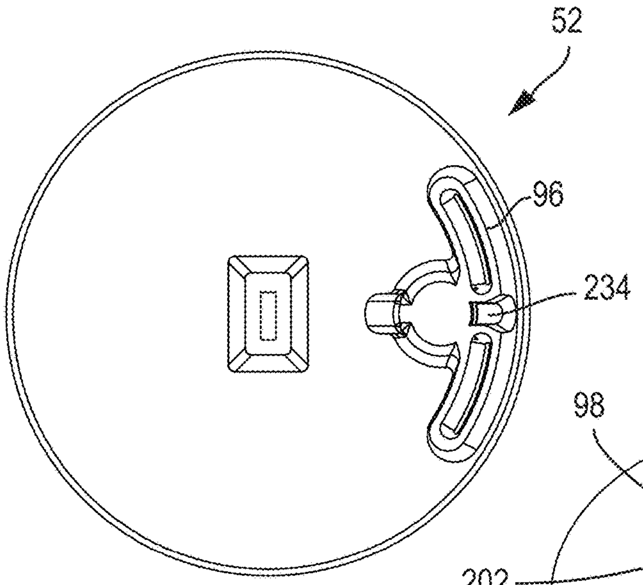
FIG. 36A depicts a bottom plan view of an example reservoir assembly including septum.
Figure 36B:
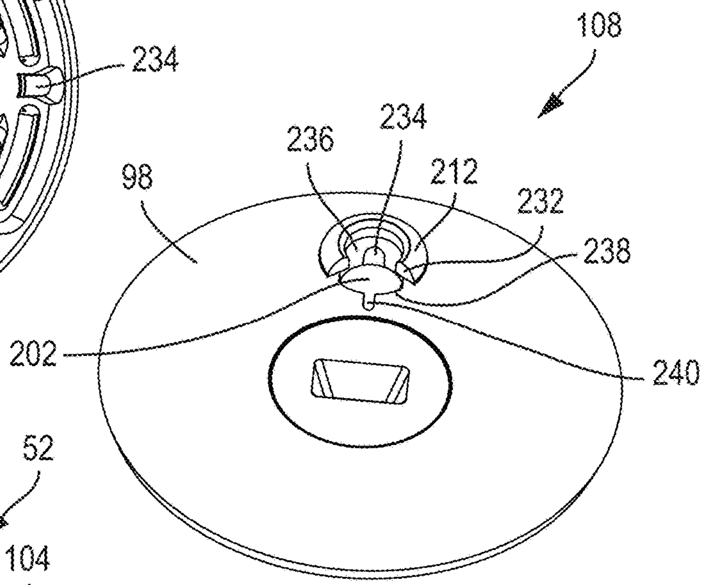
FIG. 36B depicts a perspective view of an example rigid reservoir portion for a reservoir assembly with a bay for installation of a septum.
Figure 36C:
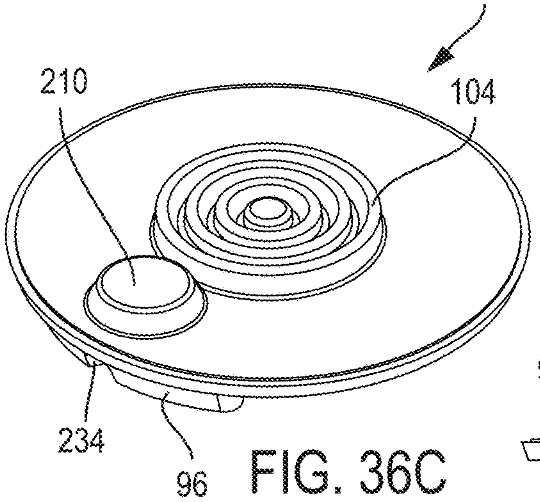
FIG. 36C depicts a perspective of an example reservoir assembly including a septum and with the main interior fluid holding volume of the reservoir assembly depicted in a collapsed state.
Figure 36D:
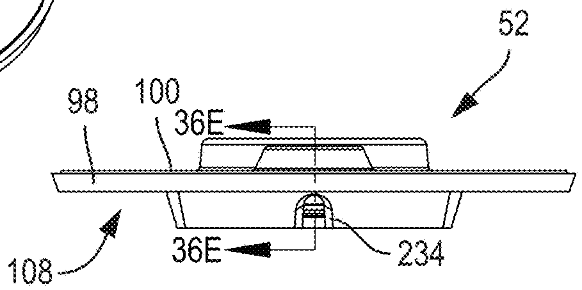
FIG. 36D depicts a side view of an example reservoir assembly including a septum.
Figure 36E:
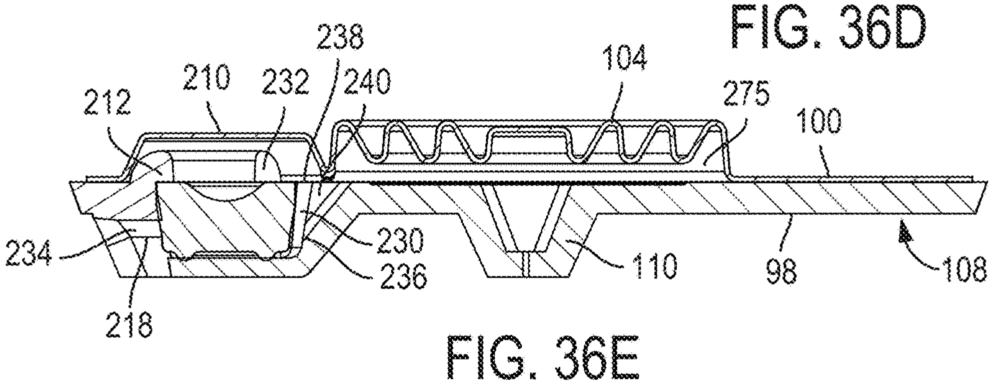
FIG. 36E depicts a cross-sectional view of an example reservoir assembly including a septum.

Still referring to FIGS. 36A-36E, an access passage 234 through at least a sidewall 236 of the bay 202 may be included in the holder 108. The access passage 234 may, in some examples, extend through a rocker member 96 of the holder 108. The access passage 234 may provide the sharp access pathway 218 for the reservoir assembly 52. The bay 202 may be dimensioned such that the bay 202 includes an outcropped region adjacent the gap 232. When installed and retained within the bay 202 the septum 94 may fit snuggly against or be slightly compressed against the sidewall 236 of the bay 202 in at all but the outcropped region 238. As best shown in FIG. 36E, there may be an open space or receiving space 230 between the septum 94 and sidewall 236 of the bay 202 at the location of the outcropped region 238.

To transfer fluid into the example reservoir assembly 52 of FIGS. 36A-36E, a dispensing sharp 302 may be advanced through the sharp access pathway 218 and septum 94 such that the tip 116 of the dispensing sharp 302 is within the receiving space 230 established by the outcropped region 238. The receiving space 230 may be in fluid communication with the main interior volume 275 of the reservoir assembly 52. Fluid may be delivered through the dispensing sharp 302 into the receiving space 230 and may fill the collapsed main interior volume 275. In some examples, a recessed flow channel 240 may be included to facilitate flow of fluid from the receiving space 230 to the main interior volume 275. The position and dimensions of the access passage 234 may be used to create a guard for the reservoir assembly 52. For example, the walls of the access passage 234 may physically block dispensing sharps 302 from being advanced through the septum 94 at angles where the tip 116 may contact the reservoir portion 100. Thus, the access passage 234 may define a sharp guide which ensures the tip 116 of the dispensing sharp 302 is directed into the receiving volume 230.

Referring now to FIGS. 37A-37E, another example embodiment of a reservoir assembly 52 including a septum 94 is depicted. The example septum 94 has an axial dimension which extends in a direction outward from the periphery of the reservoir assembly 52. Specifically, the embodiment in FIGS. 37A-37E includes a radially oriented septum. The sharp access pathway 218 is also radially oriented in the example embodiment. As shown, the rigid portion of the reservoir assembly 52 (in this example, the holder 108) includes thickened region 242 at a portion of its periphery. A bay 202 is defined in the thickened region 242 as a tunnel which extends through the thickened region 242 substantially along a radial dimension of the reservoir assembly 52. The septum 94 may be placed in the bay 202 and may, in some examples, be retained in the bay 202 by a press or interference fit (see, e.g. FIG. 37D). Alternative embodiments of other example reservoir assemblies 52 described herein can include septa 94 which are retained in place in this manner. In alternative embodiments, a peripheral wall 212 (see, e.g., FIG. 37E) surrounding the bay 202 may be included and may be swaged over a portion of the septum 94 to retain the septum 94 in place within the bay 202. The thickened region 242 also includes portions which flank a receiving volume 230 downstream of the bay 202 and adjacent an interior end of the septum 94. Preferably the thickened region 242 does not protrude into the footprint of the main interior volume 275 of the reservoir assembly 52.

The bay 202 may be laterally flanked on each side by ramped portions 244A, B of the thickened region 242. The portions of the thickened region 242 flanking the receiving volume 230 may be formed by ramped portions 244C, D. The ramped portions 244A-D may taper progressively thinner from a thickest portion most proximal the bay 202 down to the thickness of the main portion of the holder 108 as distance from the bay 202 increases. Including the ramped portions 244A-D in a thickened region 242 may allow the bay 202 to be accommodated while providing a relatively gentle transition in thickness of the holder 108 in the region of the bay 202. The ramped portions 244C, D flanking the receiving space 230 may also help to limit dead volume in the reservoir assembly 52. The reservoir portion 100 may define a tiered main interior volume 275 as described in relation to FIGS. 30A-30B and a receptacle 246 for the thickened region 242 of the holder 108. These features may, for example, be thermoformed into the reservoir portion 100. The reservoir portion 100 may be heat staked to the holder 108. The gentle transition provided by the ramped portions 244A, B may facilitate a robust and fluid tight coupling of the reservoir portion 100 to the holder 108. The reservoir portion 100 may also be formed with the main interior volume 275 in a collapsed state as described elsewhere herein.

Figure 37A:
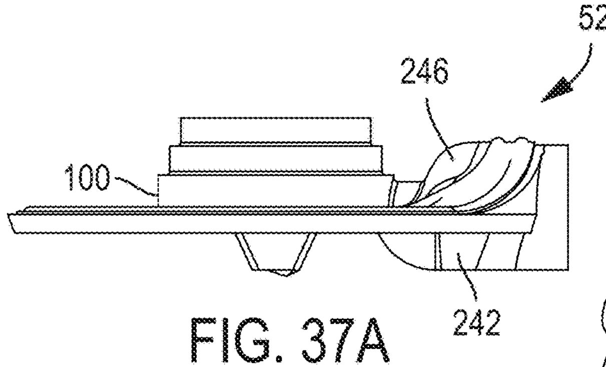
FIG. 37A depicts a side view of an example reservoir assembly including a septum.
Figure 37B:
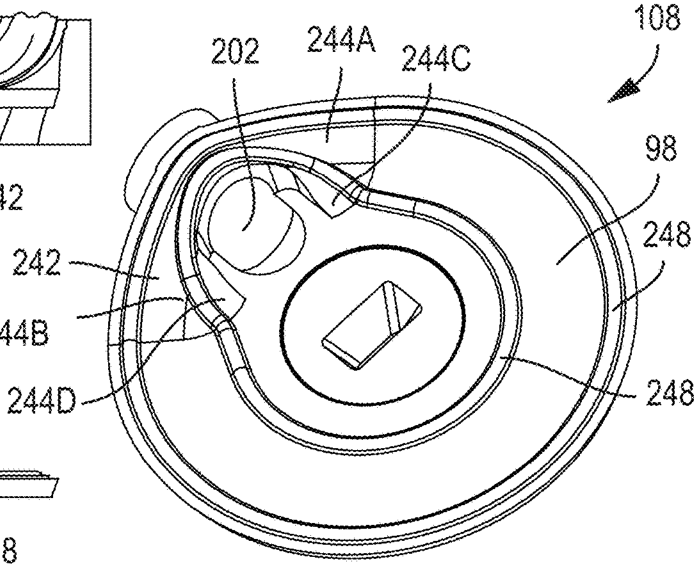
FIG. 37B depicts a perspective view of an example rigid reservoir portion for a reservoir assembly including a thickened region with a bay for installation of a septum.

Additionally, as shown best in FIG. 37B, in various example embodiments of reservoir assemblies 52 described herein, the holder 108 may be formed with a set of ridges 248. Any reservoir assemblies 52 or holders 108 described herein where ridges 248 are absent may include such ridges 248 in alternative embodiments. In the example shown in FIGS. 37A-37E, two ridges 248 are included however, additional ridges 248 or only a single ridge 238 may be included in other embodiments. Each ridge 248 may surround or enclose a region of face of the holder 108 to which the reservoir portion 100 is coupled. As shown, one ridge 248 encompasses the central region of the holder 108 (e.g. the footprint of the main interior volume 275 of the reservoir assembly 52) and extends over the surface of the enlarged region 242. The other ridge 248 extends along the periphery of the holder 108 and over the surface of the enlarged region 242. The ridges 248 may create additional volumes of material in the holder 108 that may tend to easily melt as a reservoir portion 100 is coupled to the holder 108 via a heat stake or the like. Thus, inclusion of such ridges 248 may assist in generating a robust fluid tight coupling between the reservoir portion 100 and holder 108. The ramped portions 244A-B of the holder 108 may be omitted in certain embodiments including a thickened region 242. Instead, the ridges 248 in this region may be stand-alone structures flanking the thickened region 242 and may provide the contour for the gentle transition in the vicinity of the thickened region 242. An example of such and embodiment is depicted in FIGS. 38A-38B.

To fill the example reservoir assembly 52 of FIGS. 37A-37E, a dispensing sharp 302 may be advanced through the sharp access pathway 218 and septum 94 such that the tip 116 of the dispensing sharp 302 is within a receiving space 230 in communication with the main interior volume 275 of the reservoir assembly 52. Gas may be sucked out of the reservoir assembly 52 if necessary to collapse the main interior volume 275 and fluid may subsequently be transferred into the reservoir 52.

Figure 38A:
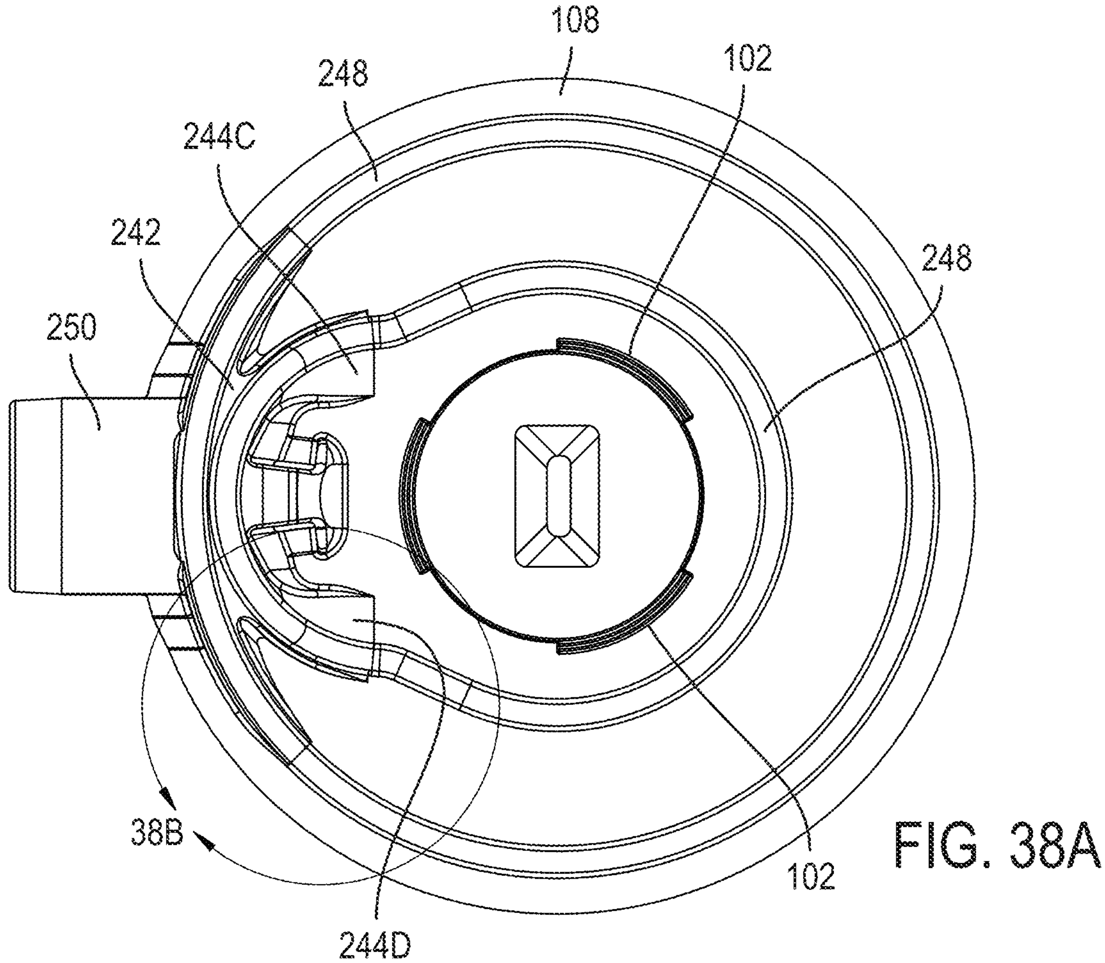
FIG. 38A depicts a top down view of an example rigid reservoir portion for a reservoir assembly including a protruding body with a bay for installation of a septum.
Figure 38B:
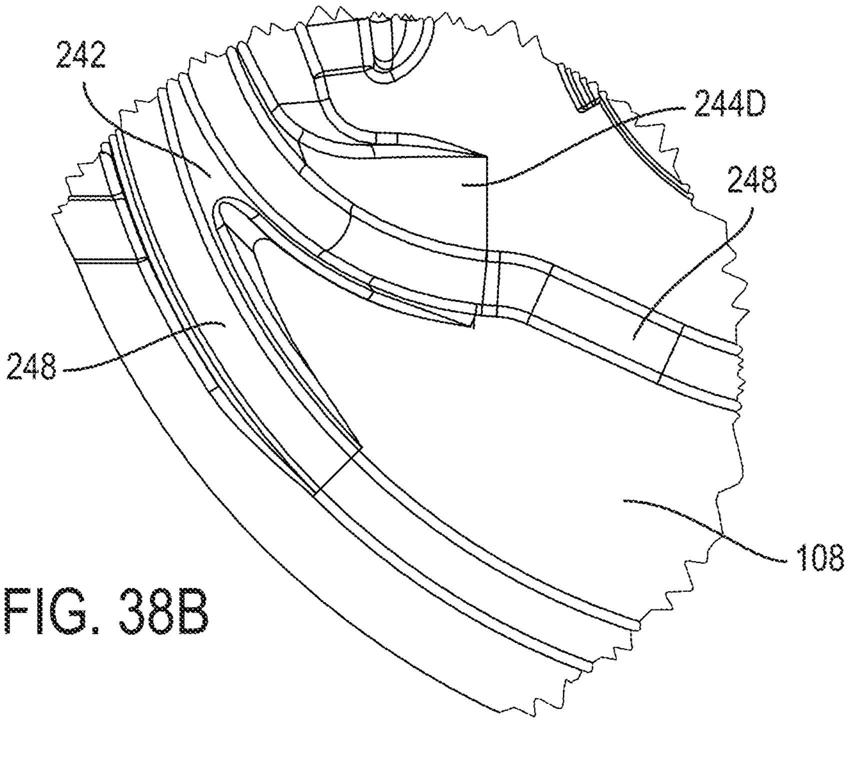
FIG. 38B depicts a detailed view of the indicated region of FIG. 38A.
Figure 39A:
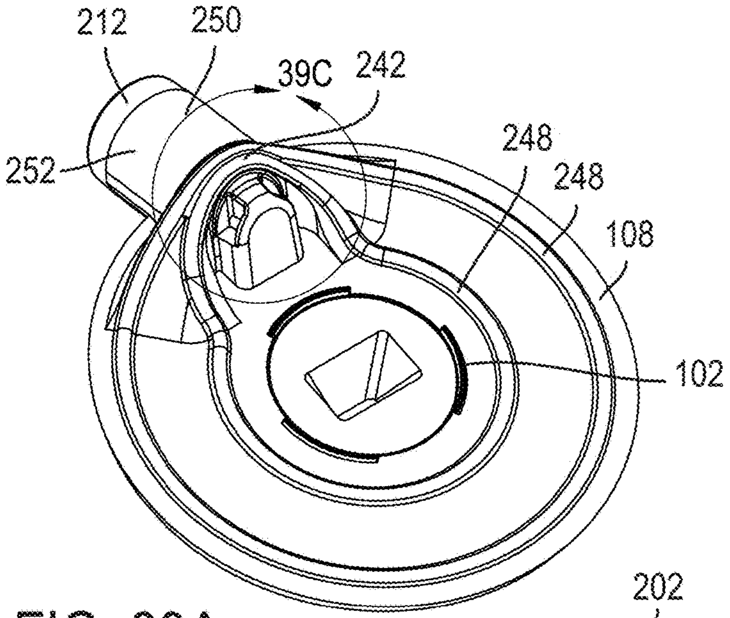
FIG. 39A depicts a perspective view of an example rigid reservoir portion for a reservoir assembly including a tilted protruding body with a bay for installation of a septum.
Figure 39B:
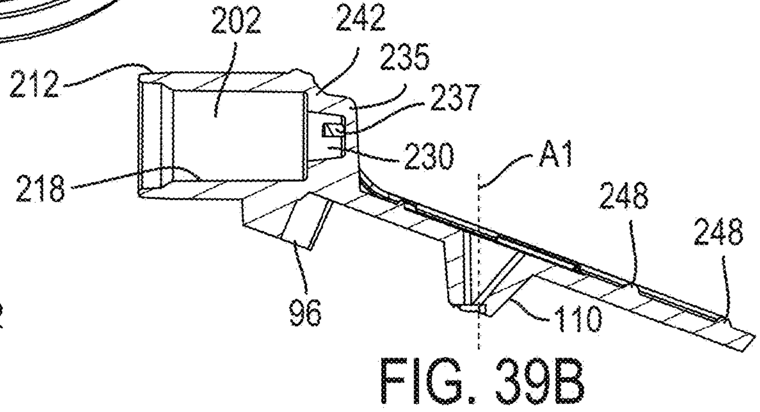
FIG. 39B depicts a cross-sectional view of the example rigid reservoir portion of FIG. 39A.
Figure 39C:
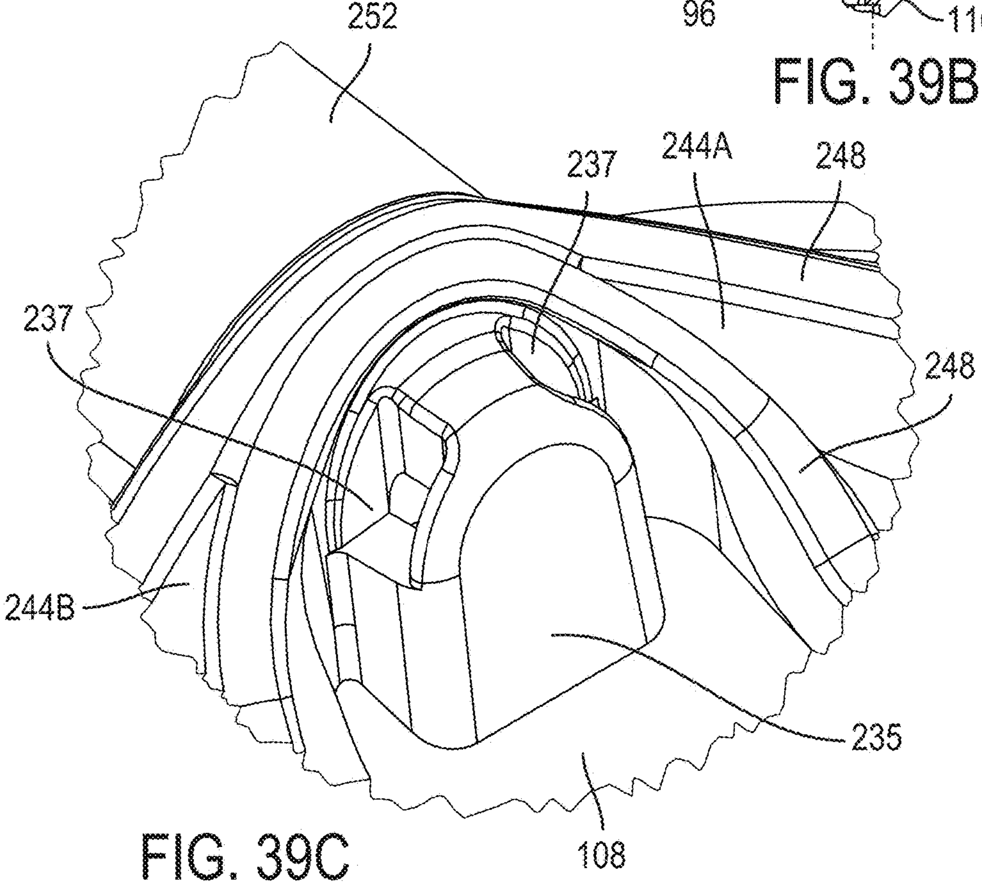
FIG. 39C depicts a detailed view of an example ported backstop which may be included downstream of a septum retaining bay in example reservoir assemblies described herein.

Referring now to FIGS. 39A-39C, another example of a rigid portion of a reservoir assembly 52 is depicted. The rigid portion in the example embodiment is a holder 108 including a thickened region 242 with a bay 202 for receiving a septum 94. As shown, the bay 202 is also partially defined by a barrel 252 in a protruding body 250 extending outwardly from the periphery of the holder 108. A protruding body 250 is also included in the embodiment described in relation to FIGS. 38A-38B. The bay 202 for the septum 94 is oriented at an angle which is neither parallel to the holder 108 nor parallel to the axial dimension of the reservoir assembly 52. Thus, when installed within the holder 108, the axial dimension of the septum 94 may extend outwardly from the periphery of the reservoir assembly 52, but be tilted at an angle (e.g. 20°) with respect to the radial dimension of the holder 108. The sharp access pathway 218 may be oriented in this manner as well. The outer most end of the protruding body 250 may include a peripheral wall 212 which may be swaged over a septum 94 once the septum 94 is installed in the bay 202 to retain the septum 94 in place.

As best shown in FIGS. 39B-39C, a receiving space 230 or receiving volume may be disposed downstream of the bay 202 and may be defined by the walls of a ported backstop 235 included in the holder 108. The ported backstop 235 may have at least one flow passage 237 therethrough which places the receiving space 230 in fluid communication with the main interior volume 275 of the reservoir assembly 52 when the reservoir portion 100 is coupled to the holder 108. To fill a reservoir assembly 52 including a holder 108 of the variety depicted in FIGS. 39A-39C, a dispensing sharp 302 may be advanced through the sharp access pathway 218 and septum 94 such that the tip 116 of the dispensing sharp 302 is within a receiving space 230. Gas may be sucked out of the reservoir assembly 52 if necessary to collapse the main interior volume 275 and fluid may subsequently be transferred into the reservoir 52. The flow passages 237 in the ported backstop 235 may be positioned such that a dispensing sharp 302 may not extend through the flow passages 237 when advanced through the sharp access pathway 218. Thus, the ported backstop 235 may provide a guard which physically prevents contact of the tip 116 of the dispensing sharp 302 with a reservoir portion 100 of a reservoir assembly 52 and the receiving space 230 may be partially defined by this physical barrier.

Including a tilted bay 202 for housing a septum 94 may be particularly desirable in certain reservoir assemblies 52. For example, in reservoir assemblies 52 where the delivery sharps 72 are disposed so as to project at a non-perpendicular angle to the disk body 98 (further described in relation to FIGS. 16A-16D), a tilted bay 202 may facilitate coupling the of delivery sharps 72 to the holder 108 during injection molding. It may be desirable that shut-offs 664A, B (see, e.g., FIG. 24-25) for a mold 660 press against the sharp bearing body 26 along an axis A1 which is normal to the sharp bearing body's 26 sharp bearing face and the face opposing the sharp bearing face (further described in relation to FIGS. 24-25). Thus, the portion of the mold 660 forming the cavity for the disk body 98 may be tilted relative to the direction of the clamping force exerted by the mold shut-offs 664, B (as an illustrative aid, the disk body 98 is depicted in a tilted state in FIG. 39B). The mold 660 would then incorporate a stepped parting line with a parting plane being disposed at an angle relative to the clamping direction. The parting plane angle may be equal to the desired angle of the delivery sharps 72 relative to a plane normal to the disk body 98. For instance, if the delivery sharps 72 are desired to project in a direction 20° from a normal orientation, the parting plane for the mold 660 would be 20° from the clamping force direction. By orienting the protruding body 250 and bay 202 at an angle, the side action in the mold 660 used to form these components may be simplified. The axis of the protruding body 250 and bay 202 may be parallel to the sharp bearing face of the sharp bearing body 26. This may allow the side action in the mold 660 to displace at an angle which is perpendicular to the clamping direction of the mold 660.

Figure 37C:
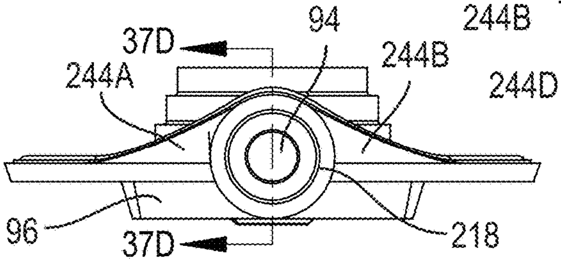
FIG. 37C depicts a front view of an example reservoir assembly including a septum.
Figure 37D:
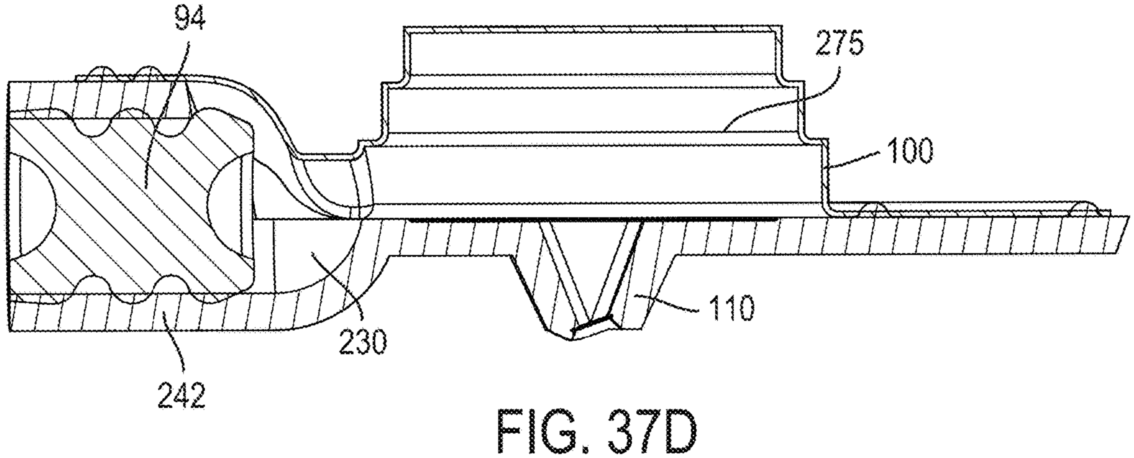
FIG. 37D depicts a cross-sectional view of an example reservoir assembly including a septum.
Figure 37E:
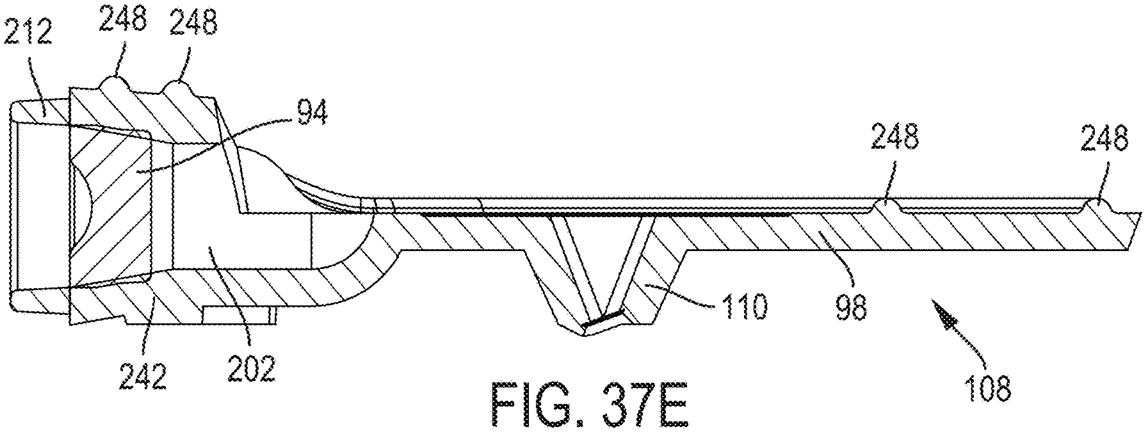
FIG. 37E depicts a cross-sectional view of an example rigid reservoir portion for a reservoir assembly in which a septum is installed.

Referring now to FIGS. 37A-37C, the bay 202 and any protruding body 250 may be aligned with the rocker member 96 of the holder 108. The bay 202 may thus be positioned most proximate the back facing edge 23 of the microneedles coupled to the stage projection 110. The thickness of the rocker member 96 may be leveraged to provide a space for the bay 202 without creating a separate standoff on the proximal face of the holder 108. This may help to limit the required height of the thickened region 242 against which the reservoir portion 100 is coupled. Consequentially, the transition between the main portion of the holder 108 and the thickened region 242 may be kept gentle where the reservoir portion 100 is coupled to the holder 108.

Figure 40A:
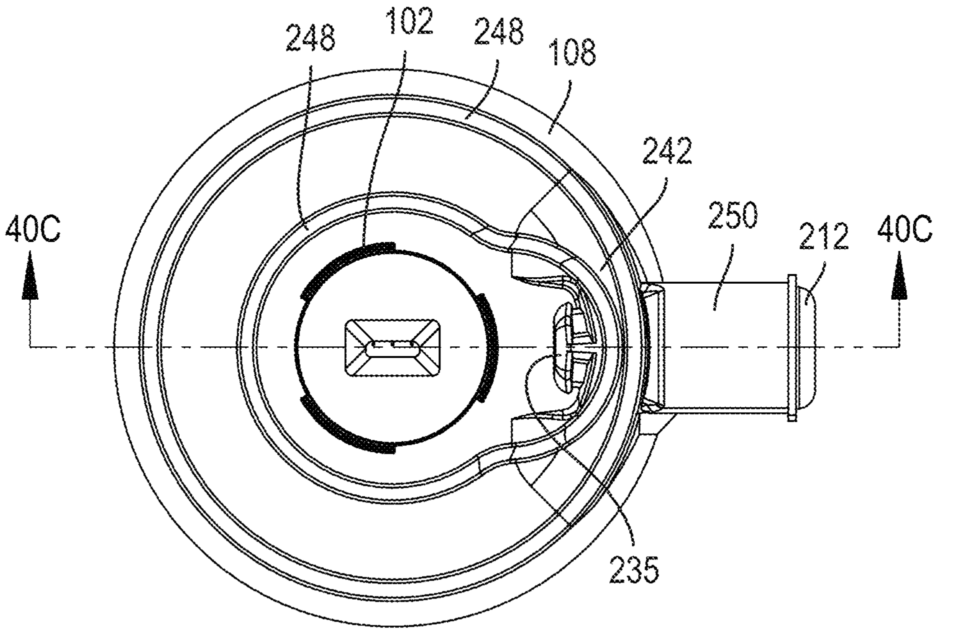
FIG. 40A depicts a top plan view of an example rigid reservoir portion for a reservoir assembly, the rigid reservoir portion including a protruding body with a bay for installation of a septum.
Figure 40B:
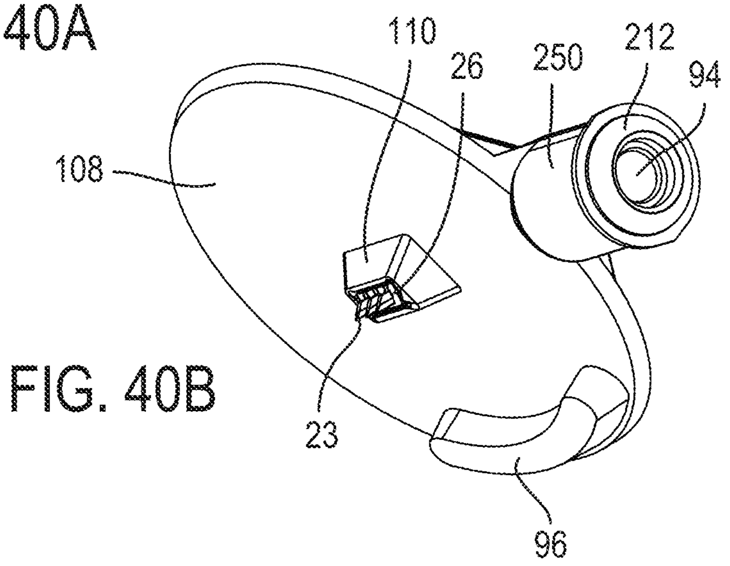
FIG. 40B depicts a perspective view of an example rigid reservoir portion with a protruding body having a bay in which a septum is installed.
Figure 40C:
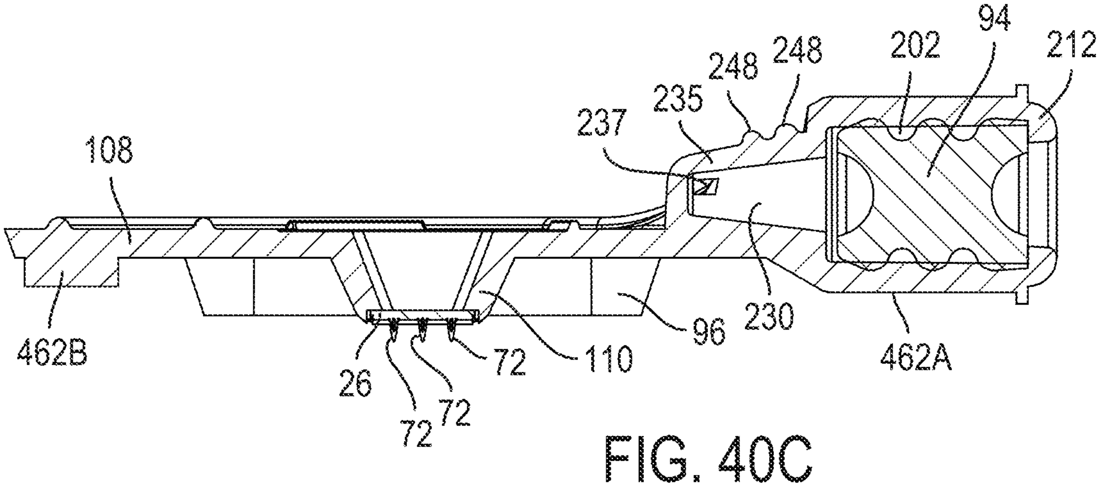
FIG. 40C depicts a cross-sectional view of an example rigid reservoir portion including a protruding body in which a septum is installed.

In alternative embodiments, and referring now to FIGS. 40A-40C, the bay 202 and optionally a protruding body 250 may be provided in a different rotational orientation on the holder 108. In the example shown, a holder 108 including a bay 202 and protruding body 250 which are spaced along the periphery of the holder 108 at a point 90° from the center of the rocker member 96 is depicted. The axes of the bay 202 and protruding body 250 run substantially parallel to two of the sidewalls 27 and the plane of the sharp bearing face of the sharp bearing body 26. The bay 202 and protruding body 250 extend along axes which are substantially parallel to the direction of extent of the row along which the delivery sharps 72 are provided on the sharp bearing body 26. That is, the axes of the bay 202 and protruding body 250 may be parallel to a plane in which the back facing edges 23 of the delivery sharps 72 lay. The bay 202 and protruding body 250 are also disposed in alignment with the stage projection 110 on the holder 108. This may be particularly desirable where the holder 108 is formed with a mold 660 having a parting plane which is not perpendicular to the clamping force. The holder 108 may be formed with a bay 202 which extends in a radial direction while still utilizing a side action which is actuated perpendicular to the direction of clamping force.

The protruding body 250 may project proud of the face of the disk body 98 on which the stage projection 110 is included and may form a nub 462A. In some embodiments, a nub 462B may be included on this face of the disk body 98 opposite nub 462A. This may help to inhibit rolling motion of the delivery device 12 when the delivery device 12 is transitioned from a storage state to a delivery state. The nub 462B may be omitted in some embodiments, particularly if the nub 462A is substantially shorter than the stage projection 110. The nub 462A may have a height no greater than the height of the stage projection 110 in various examples.

Certain reservoir assemblies 52 described herein may be relatively small. In embodiments where reservoir assemblies 52 are especially small, the reservoir assemblies 52 may have a diameter of less than 2 cm (e.g. 17-20 mm). The main interior volume 275 may be disposed in the center of that diameter and span 30-40% of the diameter. Moreover, the rigid portion (e.g. holder 108) of the reservoir assemblies 52 may have a thickness of less than 1 mm (e.g. 0.6-0.7 mm). It may however, be desirable to include a septum 94 in such reservoir assemblies 52 that is comparatively large. This may help to ensure that the increase in percent compression is kept within a desired range upon insertion of a dispensing sharp 302 to fill the reservoir assembly 52. Thus a large septum 94 may help to ensure that the septum 94 does not pass out of its range of elastic compression when a dispensing sharp 302 is advanced through the septum 94. This may help inhibit coring or irreversible deformation of the septum 94. A septum 94 may have an axial dimension 20-25% the diameter of the reservoir assembly 52. Additionally, the septum 94 may be 5-5.5 (or more) times thicker than main portion of the rigid section of the reservoir assembly 108. Where a reservoir assembly 52 is filled by hand (e.g. in a pharmacy) it may be desirable to provide a large diameter septum 94 so as to provide a target for a manually positioned filling implement 42 that may be reliably hit with minimal dexterity. The diameter of the dispensing sharp 302 used to access the septum 94 may have a diameter no greater than 30% of the diameter of the septum 94.

As best shown in FIG. 40C, inclusion of a protruding body 250 in rigid portions of various reservoir assemblies 52 described herein may permit the height of the thickened region 242 against which the reservoir portion 100 is coupled to be kept relatively short. Additionally, the nub 462A may be kept at a height lower than that of the stage 110. At the same time, use of a relatively large diameter septum 94 may be permitted. As shown, the thickened region 242 of the holder 108 is arranged to accommodate the receiving volume 230. The bay 202 in which the septum 94 is installed may be defined entirely within the barrel 252 of the protruding body 250. The receiving volume 230 (which also provides a physical barrier type guard via a ported backstop) has a cross-sectional area that tapers smaller as distance toward the center of the holder 108 decreases. The cross-sectional area of the receiving volume 230 may, however, at all points be smaller than the cross sectional area of the bay 202. This may allow the transition from the main portion of the holder 108 to the thickened region 242 to be kept relatively gentle. In turn, this may help to lower dead space in the reservoir assembly 52. The reservoir portion 100 may be coupled to the thickened region 242 and may not contact, be coupled to, or extend over the protruding portion 250. Thus, the bay 202 and septum 94 may be disposed entirely outside the footprint of the reservoir portion 100 when the reservoir assembly 52 is assembled. The reservoir portion 100 may be coupled to the exterior surface of the receiving volume 230. In some examples, a ridge 248 may extend along the length of this surface to facilitate coupling of the reservoir portion 100 to the exterior of the receiving volume 230.

Figure 41A:
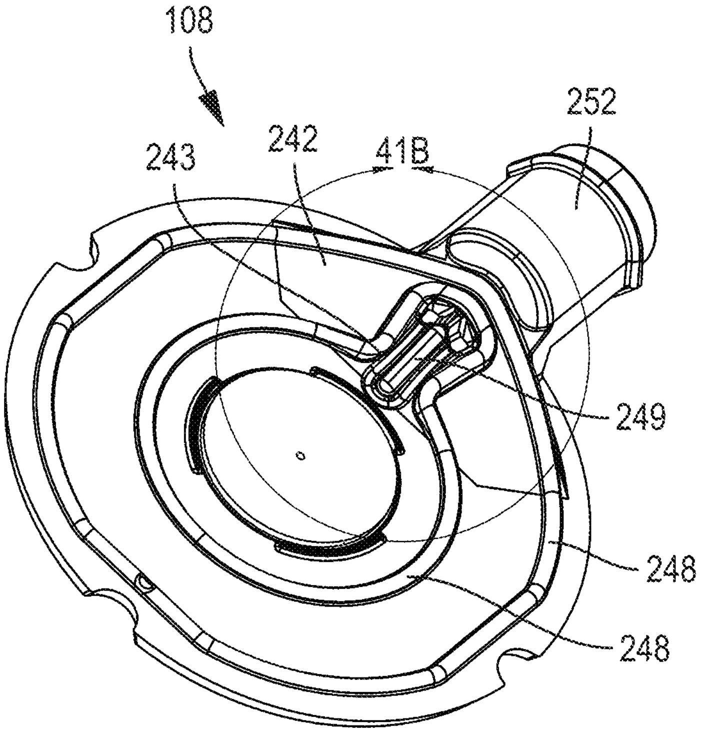
FIG. 41A depicts a perspective view of an example rigid reservoir portion with a protruding body having a bay in which a septum may be installed.
Figure 41B:
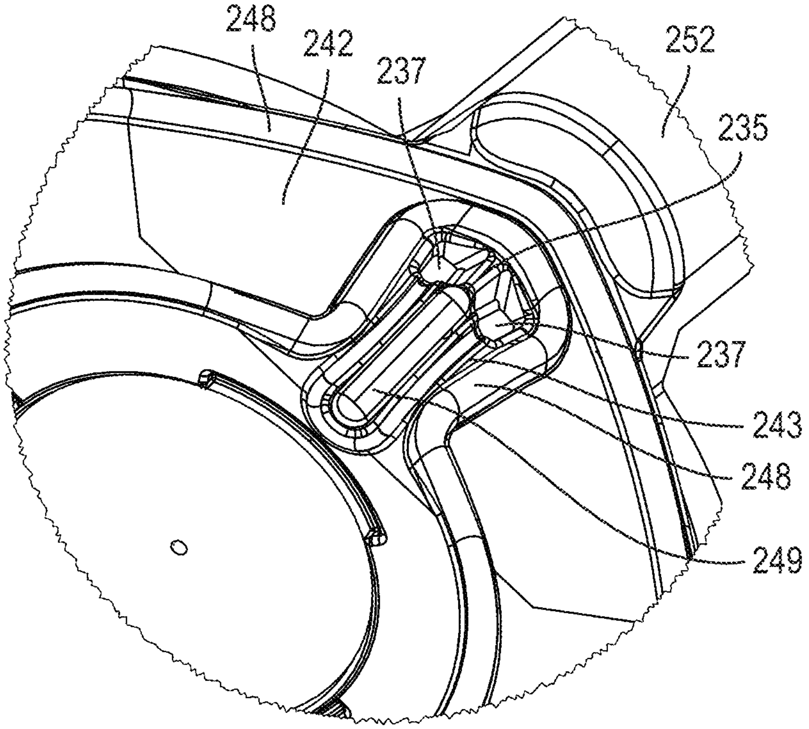
FIG. 41B depicts a detailed view of the indicated region of FIG. 41A.

Referring now to FIGS. 41A-41B, in some embodiments, the thickened region 242 of the holder 108 may include a ramp 243 leading up to the flow passages 237 of the ported backstop 235. A ramp ridge 249 may be provided in the ramp 243 leading to the flow passages 237 of the ported backstop 235. Additionally, one of the ridges 248 of the holder 108 may include spans which closely flank and surround a majority of the ramp ridge 249. When the reservoir portion 100 is coupled to the holder 108, the ramp ridge 249 and surrounding ridge 248 may assist in keeping the reservoir portion 100 held against the reservoir as pressure is applied to dispense fluid out of the interior volume 275 of the reservoir assembly 52.

Referring now to FIGS. 42A-42D, an example embodiment of a reservoir assembly 52 including a septum 94 is depicted. The example reservoir assembly 52 may be used with any of the delivery devices 12 shown and described herein. The example reservoir assembly 52 may also be utilized with any of the delivery device apparatuses, systems, and methods shown or described in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023. Additionally, the example reservoir assembly 52 described in relation to FIG. 42A-42D may be modified to included features of the reservoir assemblies 52 shown and described in herein (and vice versa).

Still referring to FIGS. 42A-42D, the example septum 94 has an axial dimension which extends in outwardly direction from the periphery of the reservoir assembly 52. Specifically, the embodiment in FIGS. 42A-42D includes a radially oriented septum. The sharp access pathway 218, through which a dispensing sharp 302 may access the main interior volume 275, is also radially oriented in the example embodiment. As shown, a rigid portion of the reservoir assembly 52 (in this example, a holder 108) includes a protruding body 250 defining a barrel 252 within which the septum 94 is installed. The outermost end of the protruding body 250 may include a peripheral wall 212 which may, as shown, be swaged over the exterior face of the septum 94 to retain the septum 94 within the protruding body 250.

The protruding body 250 is positioned such that a bay 202 of the protruding body 250 is disposed outside of the footprint of the main portion of the holder 108. Any features raised off the main portion or surface of the holder 108 to accommodate the bay 202 or receiving volume 230 (for the tip 116 of a dispensing sharp 302) are disposed opposite the side of the holder 108 where surfaces defining the main interior volume 275 of the reservoir assembly 52 are located (see, e.g., FIG. 42D). Thus, the reservoir assembly 52 may include a protruding body 250, but be devoid of any thickened region 242 in the holder 108 which presents contours the reservoir portion 100 must conform to when it is coupled to the holder 108.

Figure 42A:
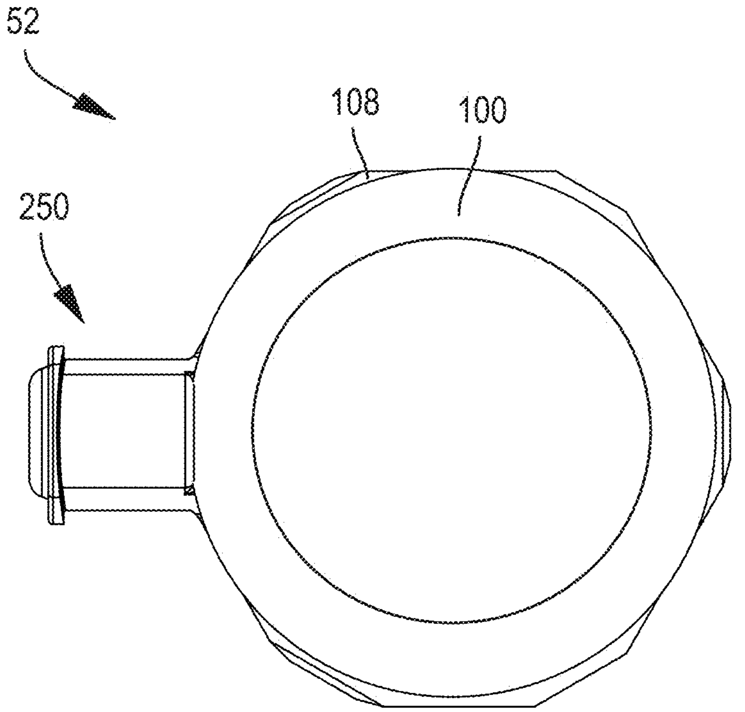
FIG. 42A depicts a top plan view of example reservoir assembly including a septum.
Figure 42B:
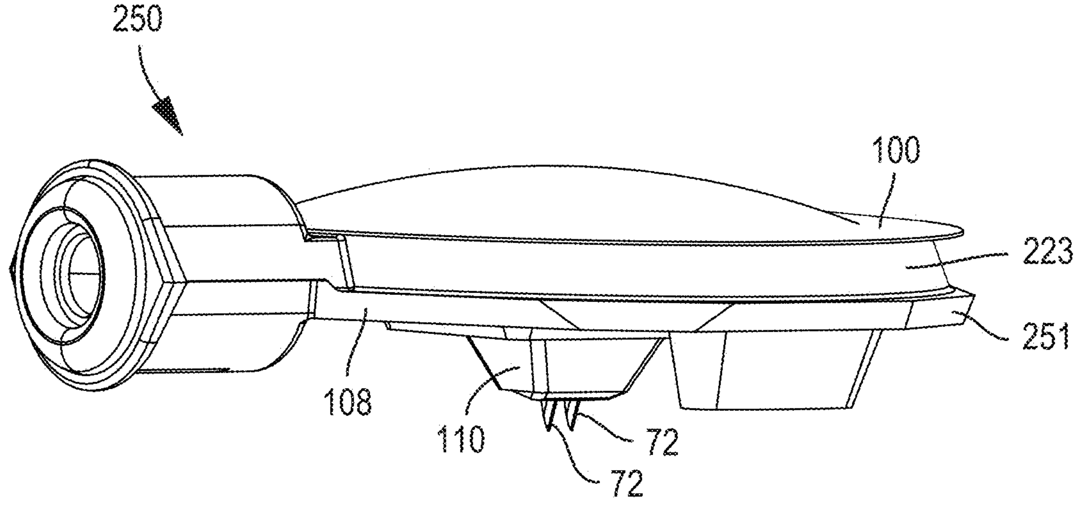
FIG. 42B depicts a perspective view of an example reservoir assembly including a septum.
Figure 42C:
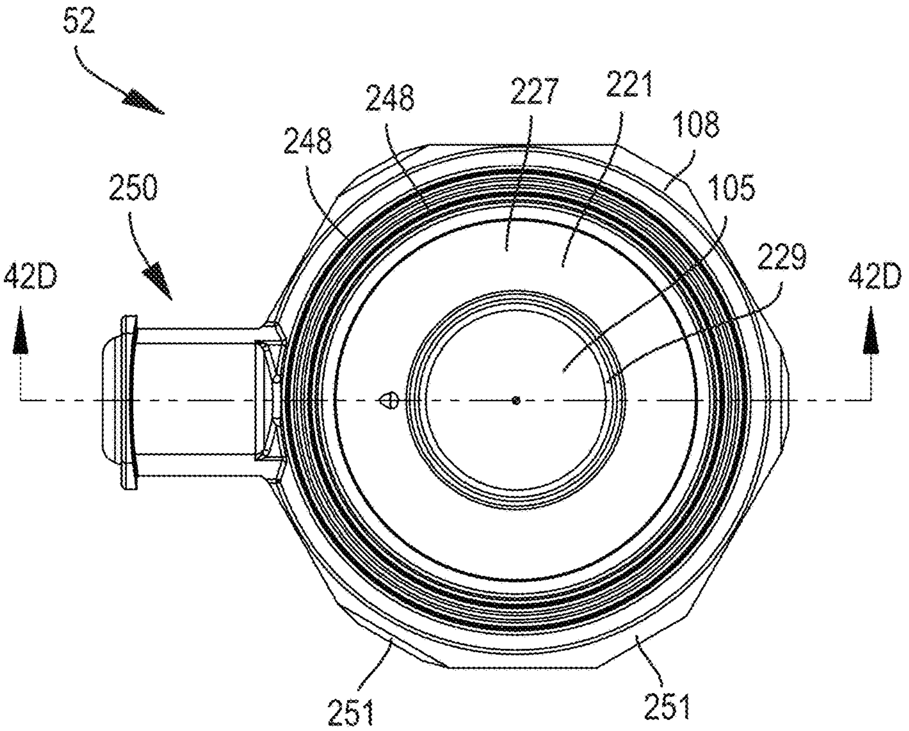
FIG. 42C depicts a top plan view of an example reservoir assembly with a flexible portion of the reservoir which partially defines the main interior volume of the reservoir removed.
Figure 42D:
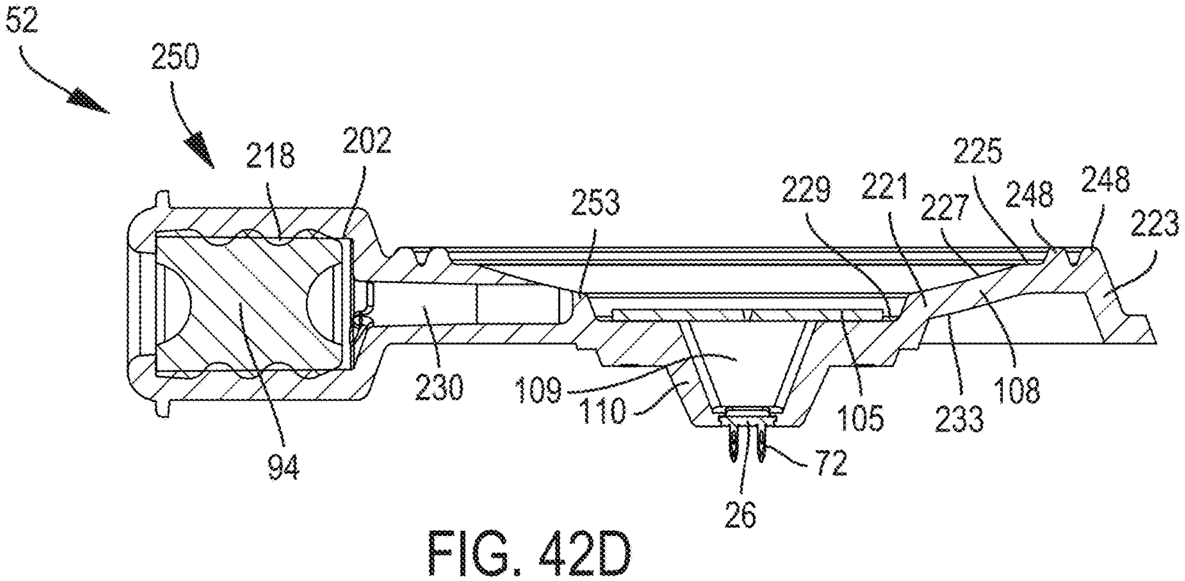
FIG. 42D depicts a cross-sectional view of an example reservoir assembly with a flexible portion of the reservoir which partially defines the main interior volume of the reservoir removed.
Figure 43A:
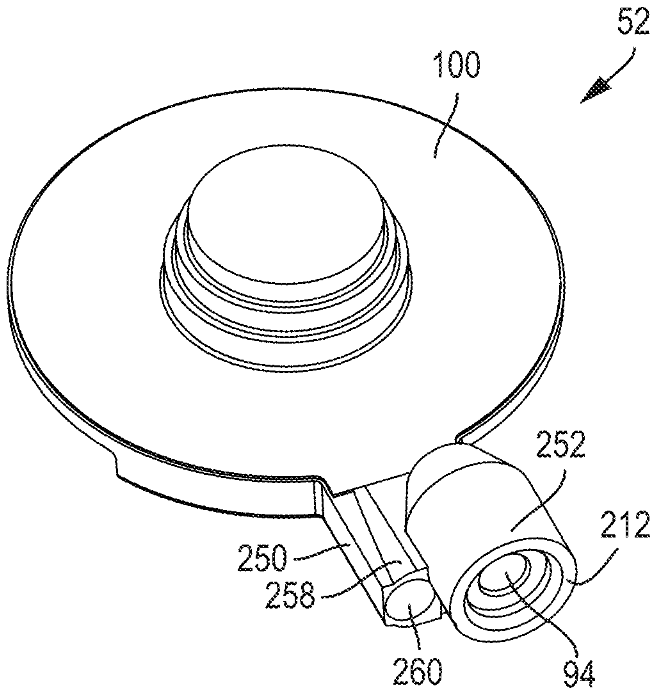
FIG. 43A depicts a perspective view of an example reservoir assembly having a protruding body in which a septum and a vent filter are housed.
Figure 43B:
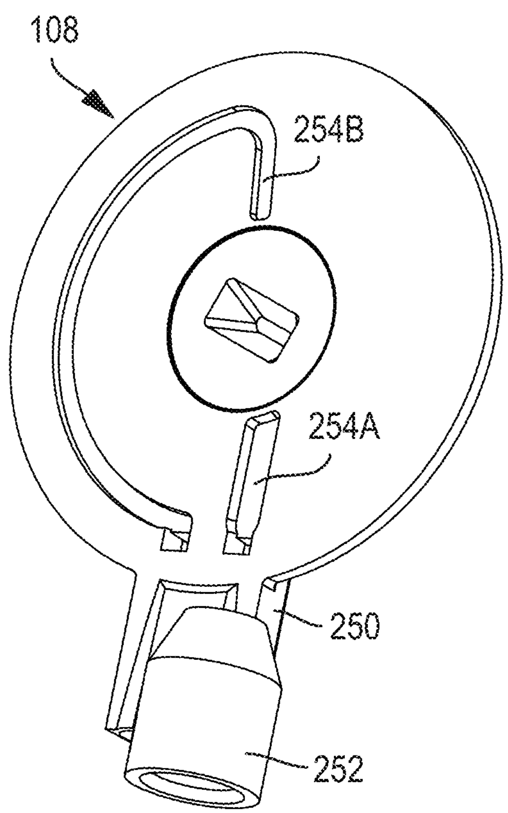
FIG. 43B depicts a perspective view of an example rigid reservoir portion including a number of recessed channels which fluidly communicate with a protruding body of the example rigid reservoir portion.
Figure 43C:
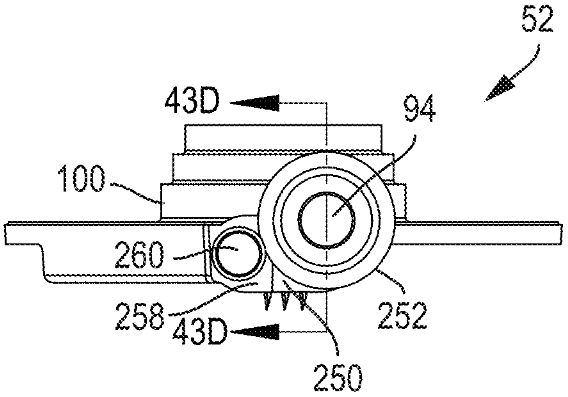
FIG. 43C depicts a front view of an example reservoir assembly including a protruding body in which a septum and a vent filter are housed.
Figure 43D:
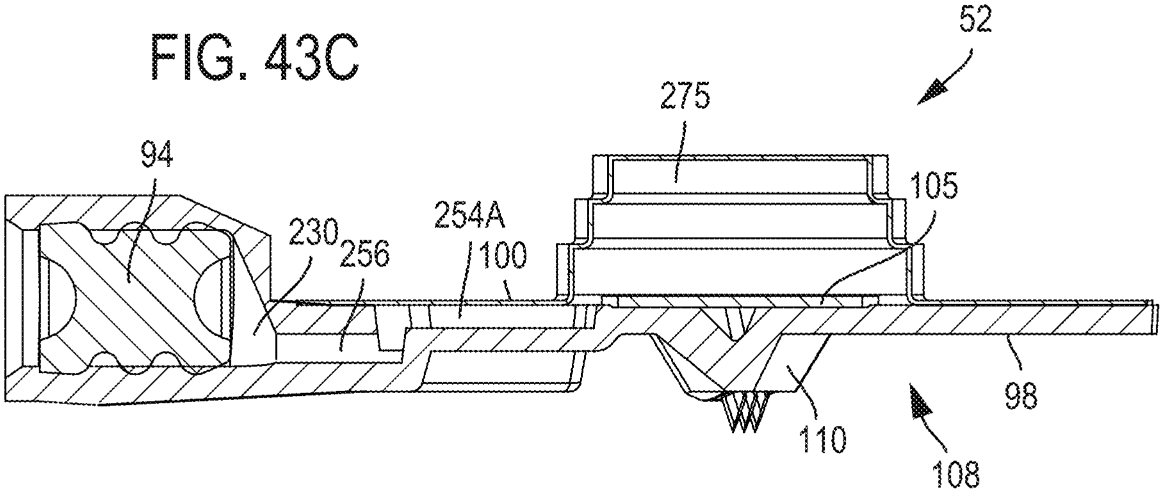
FIG. 43D depicts a cross-sectional view taken at the indicated cut plane of FIG. 43C.
Figure 44A:
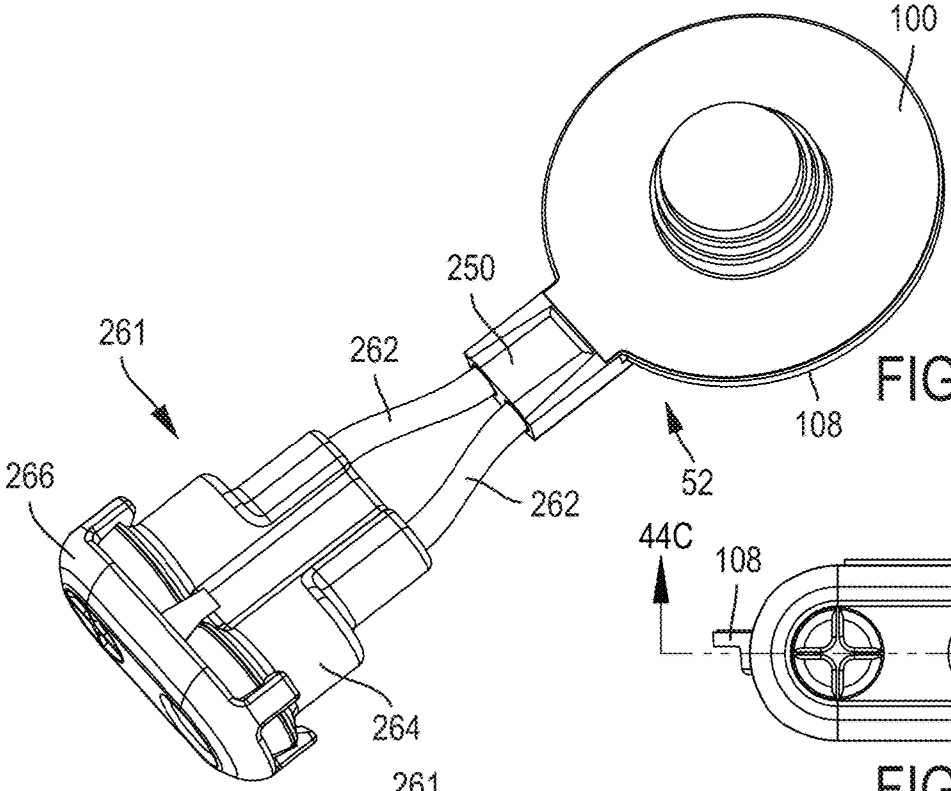
FIG. 44A depicts a perspective view of an example reservoir assembly including a septum housing in fluid communication with the remainder of the reservoir assembly via tubing.
Figure 44B:
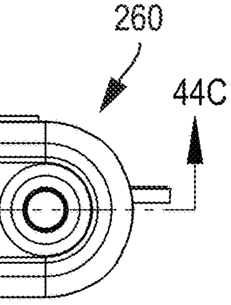
FIG. 44B depicts a front view of the example reservoir assembly of FIG. 44A.
Figure 44C:
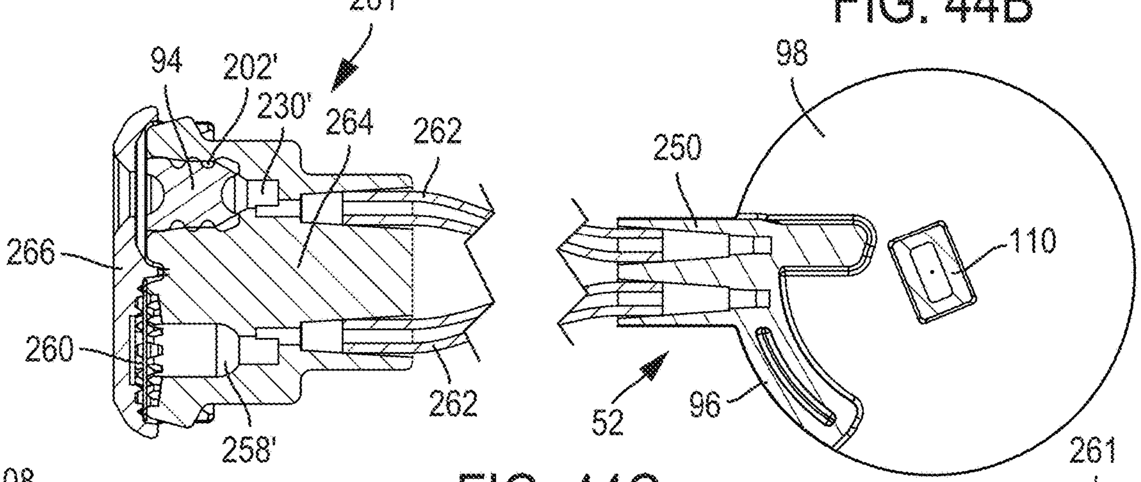
FIG. 44C depicts a cross-sectional view taken at the indicated cut plane of FIG. 44B.
Figure 44D:
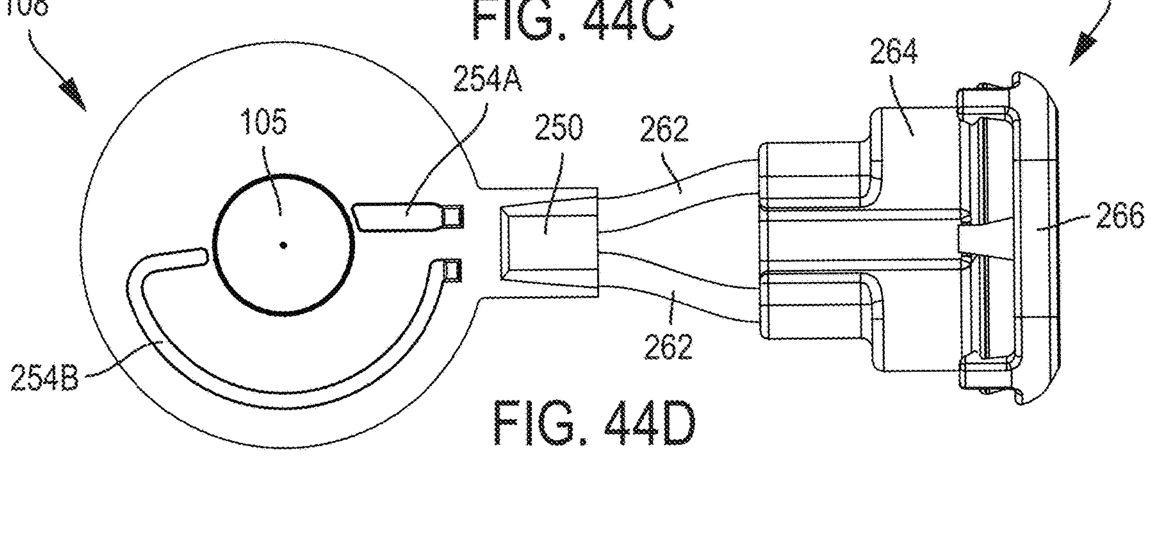
FIG. 44D depicts a top plan view of the example reservoir assembly of FIG. 44A with the flexible reservoir portion of the reservoir assembly removed.
Figure 45A:
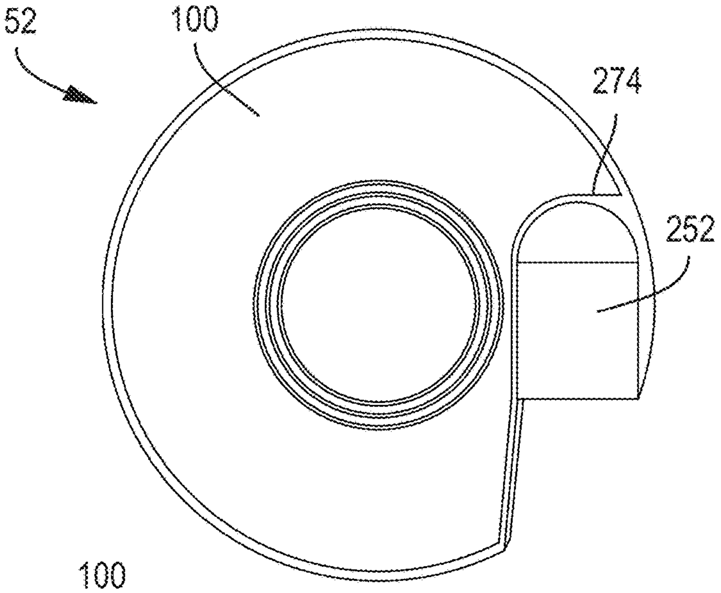
FIG. 45A depicts a perspective view of an example reservoir assembly including a bay for installation of a septum.
Figure 45B:
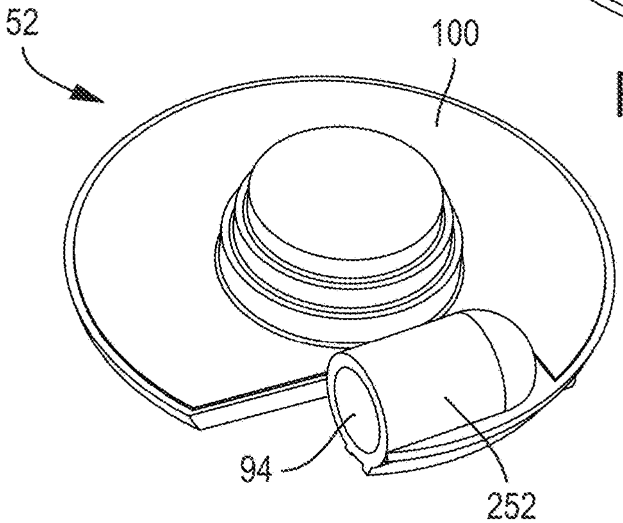
FIG. 45B depicts a top plan view of the example reservoir assembly of FIG. 45A.
Figure 45C:
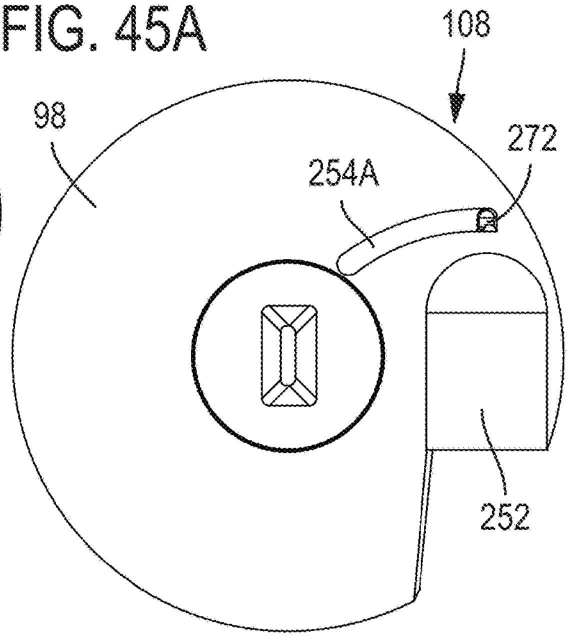
FIG. 45C depicts a perspective view of an example rigid reservoir portion including a bay for installation of a septum.
Figure 45D:
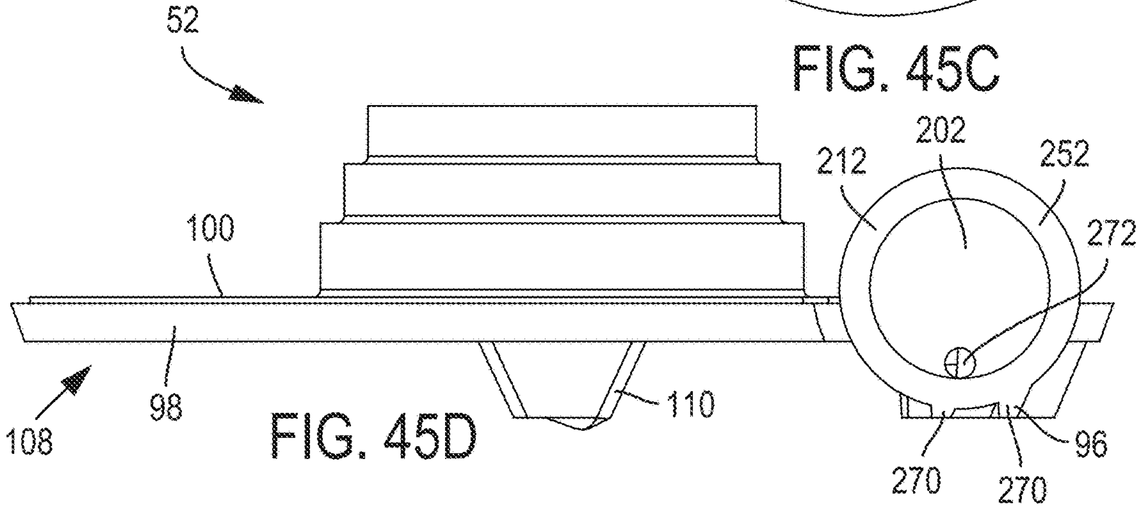
FIG. 45D depicts a side view of an example reservoir assembly including a bay for installation of a septum.

As best shown in FIG. 42D, the example holder 108 includes a dome region 221 surrounded by a brim 223. Intermediate the dome region 221 and the brim 223 is a ridged surface 225 including at least one ridge 248. The ridged surface 225 may be a substantially flat, annular region and, in the example embodiment, includes two ridges 248 projecting therefrom. The ridges 248 may provide material to facilitate coupling of the holder 108 to a reservoir portion 100 during assembly. Thus, the ridged surface 225 may be referred to as an attachment region. A greater or lesser number of ridges 248 may be included in other embodiments. The ridges 248 may for example provide a volume of material which may melt and flow when a reservoir portion 100 is heat staked to the holder 108.

The brim 223 may include a set of flanges 251 spaced about the edge of the brim 223 (see, e.g., FIG. 42C). The flanges 251 may provide catch surfaces to facilitate assembly of a reservoir assembly 52 into a main body 50 of a delivery device 12 via snap fit. The main body 50 may, for example, include tabs which may clip against the underside of respective flanges 251 when a reservoir assembly 52 is pressed into place within a main body 50. The flanges 251 may also help properly orient the reservoir assembly 52 during manufacturing/assembly of a delivery device 12. The reservoir assembly 52 may be coupled to a main body 50 in any other manner described or shown herein.

The domed region 221 may define a convex side and a concave side. The concave side may include a concave surface 227. There may be a central a receptacle 229 in the concave surface 227. The receptacle 229 may be a substantially flat basin in various embodiments. A flow restrictor 105 may be installed within the receptacle 229. The concave side may define the main interior volume 275 of the reservoir assembly 52 in conjunction with the reservoir portion 100. As best illustrated in FIG. 42B, the reservoir portion 100 may be pre-formed (e.g. thermoformed) to have a domed shape which substantially matches that of the domed region 221 of the holder 108. With such a pre-form, the reservoir portion 100 may preferentially take on the domed shape of the domed region 221 or an inverted version of the domed shape (as shown in FIG. 42B). When attached to the holder 108, the reservoir portion 100 may generally sit against the concave side of the domed region 221. The reservoir portion 100 may not conform into the receptacle 229. As fluid is filled into the reservoir assembly 52, the reservoir portion 100 may displace toward the inverted dome shape shown in FIG. 42B. There may be a small amount of gas in the receptacle 229 which remains present when the main interior volume 275 is in the filled state. This may provide a small volume of compressible fluid which may behave as a damper when pressure is applied to the reservoir assembly 52 to expel fluid.

Reservoir assemblies 52 including a reservoir portion 100 pre-formed to mimic a domed region 221 of a holder 108 may be simpler to load with agent. When, for example, agent is dispensed into the reservoir assembly 52 by a dispensing sharp 302 extending through the septum 94, a relatively low pressure may be used while still resulting in a proper fill of the main interior volume 275. This may help minimize or eliminate fluid flow through the flow restrictor 105 into the cavity or well 109 formed by the stage projection 110 as fluid is loaded into the reservoir assembly 52. Additionally, the reservoir assembly 52 may be arranged such that there is at least a slight negative pressure present in the reservoir assembly 52 after it is filled. The slight negative pressure may be less than 1-0.5 p.s.i. or smaller. In some embodiments, there may not be a slight negative pressure but the main interior volume 275 may not be positively pressurized with respect to ambient. Thus, example reservoir assemblies 52 may be at a slight negative or ambient pressure when loaded with a target volume or dose of agent. The volume of agent loaded into the reservoir assembly 52 may be insufficient to drive the reservoir portion 100 fully to the inverted version of the domed pre-form shape. The volume may, however, be sufficient to drive the reservoir portion 100 to a position in which it would shift to the inverted version of the domed pre-form shape if allowed. A cap 280 (see, e.g. FIG. 48) may be included over the stage projection 110 and the delivery sharps 72. In certain examples, the cap 280 may create a gas tight seal which inhibits the reservoir portion 52 from shifting to the inverted version of the pre-form shape. Thus, the tendency of the reservoir portion 100 to take on the inverted version of the pre-form shape may establish a bias which generates a small negative pressure (or at least not positive pressure) within the main interior volume 275. This may avoid a scenario in which the main interior volume 275 is pressurized such that agent is expelled from the delivery sharps 72 when the cap 280 is removed and the pressure is relieved.

The convex side of the domed region 221 may include a convex surface 233. A raised region 241 may be present on the convex surface 233 to accommodate a receiving volume 230 between the main interior volume 275 of the reservoir assembly 52 and the interior face of the septum 94. The tip 116 of a dispensing sharp 302 may, for example, be advanced into the receiving volume 230 when the reservoir assembly 52 is loaded with agent. The axis of the receiving volume 230 may be arranged to extend through a wall 253 before reaching the main interior volume 275 so as to inhibit displacement of the tip 116 into contact with the reservoir portion 100 during filling of the reservoir assembly 52. The concave surface 227 may include a divot or aperture which extends into communication with the receiving volume 230.

Referring now to FIGS. 43A-43D, yet another example embodiment of a reservoir assembly 52 including a septum 94 is depicted. The example septum 94 has an axial dimension which extends in a direction outward from the periphery of the reservoir assembly 52. The sharp access pathway 218 is oriented likewise in the example embodiment. As shown, the rigid portion of the reservoir assembly 52 includes a protruding body 250 which extends outwardly from the periphery of the holder 108. The protruding body 250 includes a barrel portion 252 which defines a bay 202. A septum 94 may be placed in the bay 202 and retained by a press or interference fit or alternatively by swaging a peripheral wall 212 surrounding the bay 202 over a section of the septum 94. An overmolding operation may also be used to couple a septum 94 in place within a bay 202.

The holder 108 of the reservoir assembly 52 may include at least one flow recess 254A, B formed as a depression in the face of the holder 108 to which the reservoir portion 100 is coupled. In combination with the reservoir portion 100, the flow recesses 254A, B may form fluid tight flow pathways within the reservoir assembly 52. Each of the at least one flow recess 254A, B may have a span which is within the footprint of the main interior volume 275 of the reservoir assembly 52. In the example embodiment, two flow recesses 254A, B are included. A first of the flow recesses 254A is in communication with a flow passage 256 included in the protruding body 250 that extends from a receiving space 230 on an interior side of the septum 94. The second of the flow recesses 254B may extend into communication with a filter receptacle 258 portion of the protruding body 250. A filter 260 may be retained within the filter receptacle 258. The filter 260 may be a hydrophobic filter which may be constructed of a membrane material having pores of 0.2 μm or smaller.

Inclusion of flow passages 256 may allow the face of the holder 108 to which the reservoir portion 100 is coupled to be kept flat. Thus a thickened region 242 may not be necessary to accommodate a bay 202 or receiving volume 230. Both the receiving volume 230 and the bay 202 may be disposed beyond the footprint of the reservoir portion 100. Embodiments described herein including a thickened region 242 may be modified to include a flow passage 256 fluidly connecting a septum containing protruding body 250 to the rest of the reservoir assembly 52 in place of the thickened region 242.

To fill the example reservoir assembly 52 of FIGS. 43A-43D, a dispensing sharp 302 may be advanced through the sharp access pathway 218 and septum 94 such that the tip 116 of the dispensing sharp 302 is within the receiving space 230. As shown, the position of the flow passage 256 may establish a guard within the reservoir assembly 52 which physically blocks the tip 116 of a dispensing sharp 302 from contacting the reservoir portion 100. The flow passage 256 itself may also be disposed in an off center position with respect to the axial dimension of the septum 94 limiting the potential for the dispensing sharp 302 to enter and/or be able to advance along the extent of the flow passage 256. In some embodiments, at least one dimension of the flow passage 256 may be smaller than the diameter of a dispensing sharp 302 intended to be used to fill the reservoir assembly 52. This may further guard against inadvertent contact of the tip 116 of the dispensing sharp 302 with the reservoir portion 100. With the tip 116 of a dispensing sharp 302 in the receiving volume 230, agent may be transferred into the reservoir assembly 52 and may transit through the flow passage 256 and flow recess 254A to the main interior volume 275 of the reservoir assembly 52. As agent is transferred into the reservoir assembly 52, any gas within the reservoir assembly 52 may be displaced toward the filter receptacle 258 and through the filter 260. Once the reservoir assembly 52 reaches a filled state, any agent which progresses to the filter 260 may be blocked from exiting the reservoir assembly 52 due to the hydrophobic nature of the filter 260. In alternative examples, the main interior volume 275 may be provided in a collapsed state and the filter 260 and associated flow recess 254B may be omitted.

In various embodiments, the reservoir assembly 52 may positioned in a known orientation within an isolated fill environment 14. As shown, the second flow recess 254B is positioned such that the portion of second flow recess 254B within the footprint of the main interior volume 275 of the reservoir assembly 52 is offset from that of the first flow recess 254A (see, also FIG. 44D). The reservoir assembly 52 may be filled in a position in which the portion of the second flow recess 254B within the footprint of the main interior volume 275 is slightly below a highest portion of the main interior volume 275. This position may be referred to herein as an upright position or orientation of the reservoir assembly 52. Thus, as fluid is delivered into such a reservoir assembly 52, a small volume of gas may tend to remain in the main interior volume 275. By maintaining a small volume of gas within the main interior volume 275 of the reservoir assembly 52, the contents of the reservoir assembly 52 may include at least a small volume of compressible fluid. Thus, as pressure is initially applied to the reservoir assembly 52 when a delivery device 12 is transitioned to a delivery state, the small volume of gas may behave as a damper. In the example shown in FIGS. 43A-43D, the reservoir assembly 52 may be oriented such that the axis of the septum 94 is in a vertical direction during fill and the main interior volume 275 is above the septum 94 during filling.

In alternative embodiments, the filter receptacle 258 and the filter 260 may be omitted and gas in the reservoir assembly 52 may be sucked out via a dispensing sharp 302 before filling of the reservoir assembly 52. Use of a reservoir assembly 52 including a filter 260 may facilitate filling of reservoir assemblies 52 in a parallel manner within a system 10. It should be understood that any systems 10 described herein as filling reservoir assemblies 52 or delivery devices 12 in serial fashion may be modified for parallel filling via inclusion of a filter 260 in the reservoir assemblies 52 or delivery devices 12. Similarly collapsed main interior volumes 275 may be used to modify a system 10 where reservoir assemblies 52 or delivery devices 12 are filled in serial fashion to a system 10 in which they are filled in parallel.

Referring now to FIGS. 44A-44D, an alternative embodiment of the reservoir assembly 52 depicted in FIGS. 43A-43D is shown. In certain embodiments, at least one of a septum 94 and a filter 260 may not be retained within the holder 108 of a reservoir assembly 52. Septa 94 may, for example, be installed within a separate septum housing 261 which may be coupled to the rest of the reservoir assembly 52. The septum housing 261 may, for example, be coupled by at least one run of fluid conduit 262 which is in fluid communication with the main interior volume 275 of the reservoir assembly 52. In the example embodiment, the fluid conduits 262 are plumbed into a protruding body 250 spaced from the periphery of the reservoir assembly 52. As indicated by the break in the fluid conduits 262 shown in FIG. 44C, the fluid conduits 262 may be of any desired length. Typically, any fluid conduits 262 may be kept as short as is practicable so as to minimize the dead volume of the reservoir assembly 52. Including a septum housing 261 coupled to the remainder of a reservoir assembly 52 by fluid conduit(s) 262 may be desirable for a variety of reasons. For example, as the septum housing 261 is spaced from the remainder of the reservoir assembly 52, it may act as a guard mitigating potential for a tip 116 of a dispensing sharp 302 to contact the reservoir portion 100 of the reservoir assembly 52. Such a septum housing 261 may also provide greater flexibility in placement of delivery devices 12 within an isolated fill environment 14 where septa 94 of such delivery devices 12 are provided in a pre-spiked state. Delivery devices 12 could be provided in an upright orientation within an isolated fill environment 14 while allowing the axial dimension of the septum 94 to be independently positioned. The axial dimension of the septum 94 could be placed in any convenient orientation without constraining the position of the rest of the delivery device 12 due to the flexibility of the fluid conduits 262. This may allow for a greater freedom in fluid bus 32 design, for example, within an isolated fill environment 14. Additionally, a septum housing 261 may provide space to include a fill indicator 451 (see, e.g., FIG. 114) in a delivery device 12.

As shown, the septum housing 261 includes a main body 264 and a cap 266. The main body 264 may include a bay 202' into which a septum 94 may be installed. The cap 266 may be coupled to the main body 264 (e.g. via solvent bonding, sonic welding, adhesive, snap fit, etc.) to capture the septum 94 in place within the bay 202'. Any other reservoir assembly 52 embodiments described herein may similarly include a cap 266 which is coupled to the reservoir assembly 52 to capture a septum 94 in place within the reservoir assembly 52. A receiving volume 230' may be disposed adjacent a face of the septum 94 opposite the externally accessible face of the septum 94. A fluid conduit 262 may couple into a recess in the face of the septum housing 261 opposite the cap 266 and may be in fluid communication with the receiving volume 230' (e.g. through a flow path defined in the septum housing 261).

Where a filter 260 is included in the reservoir assembly 52, the filter 260 may optionally be positioned in the septum housing 261. As shown, the septum housing 261 includes a filter receptacle 258'. A filter 260 as described in relation to FIGS. 43A-43D may be installed in the filter receptacle 258' and captured in place by the cap 266. A fluid conduit 262 may be coupled to the septum housing 261 opposite the cap 266 and may be in fluid communication with an interior face of the filter 260 (e.g. via a flow path extending through the septum housing 261). Filters 260 may be omitted where the main interior volume 275 is provided in a collapsed state.

The holder 108 of the reservoir assembly 52 may include a protruding body 250 including ports 268 for each of the fluid conduits 262 extending from the septum housing 261. Alternatively, a thickened region 242 similar to that shown in FIGS. 37A-37E may be included and may accommodate the ports 268. In the example shown, the fluid conduit 262 leading away from the septum 94 is coupled to one of the ports 268 which is in fluid communication with the first flow recess 254A. The fluid conduit 262 leading to the filter 260 is plumbed into a port 268 in fluid communication with the second flow recess 254B. As described in relation to FIGS. 43A-43D, as agent is transferred into the reservoir assembly 52, gas may be evacuated through the filter 260, however, the filter 260 may inhibit passage of agent out of the reservoir assembly 52.

Referring now to FIG. 45A-45D, another example embodiment of a reservoir assembly 52 including a septum 94 is depicted. The example septum 94 has an axial dimension which extends in a direction outward from the periphery of the reservoir assembly 52. In the example embodiment, the axial dimension of the septum 94 is non-parallel (substantially perpendicular) to a radial dimension of the reservoir assembly 52. The sharp access pathway 218 is oriented likewise in the example embodiment. As shown, the rigid portion of the reservoir assembly 52 (the holder 108 in this example) includes a barrel portion 252 which defines bay 202. The barrel portion 252 may include a set of ribs 270 which together with the barrel portion 252 act as a rocker member 96 for the reservoir assembly 52. A septum 94 may be placed in the bay 202 and retained by a press or interference fit or alternatively by swaging a peripheral wall 212 surrounding the bay 202 over a section of the septum 94. There may be a receiving volume 230 (see, e.g., FIG. 43D) adjacent the interiorly disposed end of the septum 94. A flow channel 272 may extend from the receiving volume 230 to a flow recess 254A in the holder 108. A portion of the flow recess 254A may extend within the footprint of the main interior volume 275 of the reservoir assembly 52.

The reservoir portion 100 may define a tiered main interior volume 275 which may be thermoformed into the reservoir portion 100 as described in relation to FIGS. 30A-30B. The reservoir portion 100 may also include a notch 274. During assembly, the barrel portion 252 may be positioned in the notch 274 and the reservoir portion 100 may be coupled to the holder 108 (e.g. via heat stake). The reservoir portion 100 may also form a seal around the flow recess 254A. Inclusion of a bay 202 which is oriented as shown in FIGS. 45A-45D may allow the portion of the holder 108 to which the reservoir portion 100 is coupled to be kept flat.

To fill the example reservoir assembly 52 of FIGS. 45A-45D, a dispensing sharp 302 may be advanced into the bay 202 and through the septum 94 such that the tip 116 of the dispensing sharp 302 is within the receiving space 230 in communication with the main interior volume 275 of the reservoir assembly 52. Gas may be sucked out of the reservoir assembly 52 if necessary to collapse the main interior volume 275 and fluid may subsequently be transferred into the reservoir 52. Alternatively, the main interior volume 275 may be provided in a collapsed state as described elsewhere herein. Fluid delivered to the reservoir assembly 52 may pass from the receiving space 230, through the flow channel 272 and flow recess 254A into the main interior volume 275 of the reservoir assembly 52. The barrel portion 252 and flow channel 272 may form a guard which obstructs a pathway from the dispensing sharp 302 to contact the reservoir portion 52.

Figure 46:
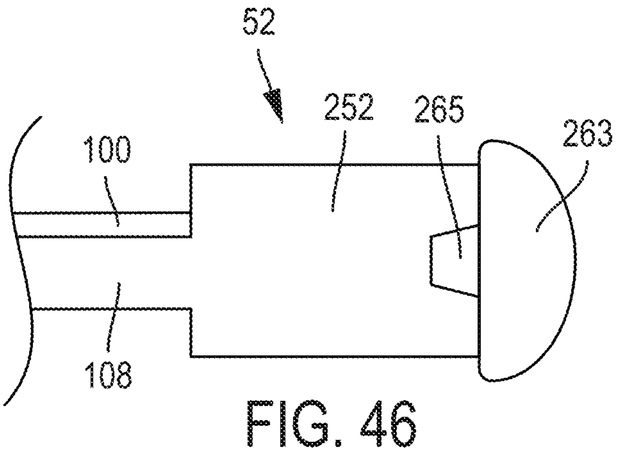
FIG. 46 depicts a diagrammatic view of a portion of an example reservoir assembly having a cap which has been installed to block access to a septum of the reservoir portion.

Referring now to FIG. 46, a diagram of a portion of a reservoir assembly 52 is depicted. Any of the reservoir assemblies 52 including a septum 94 which are shown and described herein may include a cap or cover 263. The cap 263 may be coupled to the reservoir assembly 52 to cover the septum 94 and prevent the interior volume of the reservoir assembly 52 from being accessed after filling. This may help to prevent adulteration of the contents of the reservoir assembly 52 and help to inhibit reuse. The cap 263 may be formed of a puncture resistant material (e.g. suitable plastic) and may couple to the barrel portion 252 of a holder 108. The cap 263 may couple over the septum 94 in any suitable manner (e.g. adhesive, interference fit, sonic welding, snap interface, heat stake, crimped, etc.). As shown, the cap 263 includes a set of snap fit projections 265 which may snap into detents in the exterior of the barrel portion 252. Preferably, the cap 263 may be irreversibly coupled to the reservoir assembly 52 once attached. Removal of the cap 263 may compromise the cap 263 or reservoir assembly 52 preventing the cap 263 from being reinstalled. The delivery device 12 may be visually inspected for the cap 263 prior to use and may not be utilized in the event that cap 263 is determined to be absent.

Figure 47A:
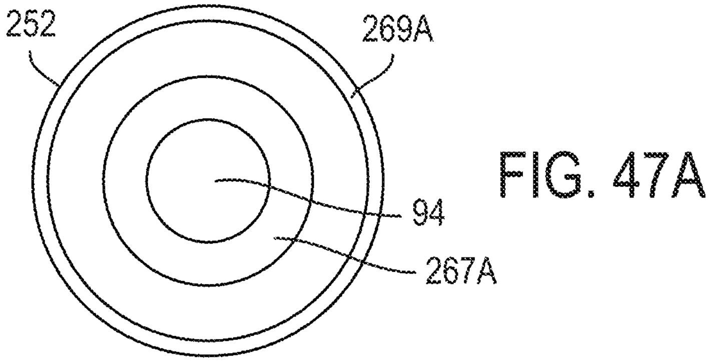
FIG. 47A depicts a view of an example barrel portion of an example reservoir assembly having a set of ribs surrounding a bay in which a septum is disposed.
Figure 47B:
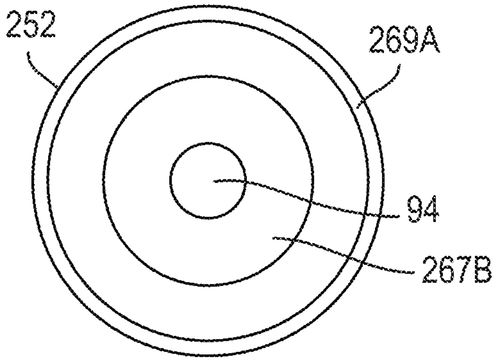
FIG. 47B depicts the example barrel portion of FIG. 47A with a first of the ribs swaged into a retaining position to hold the septum in place within the bay.
Figure 47C:
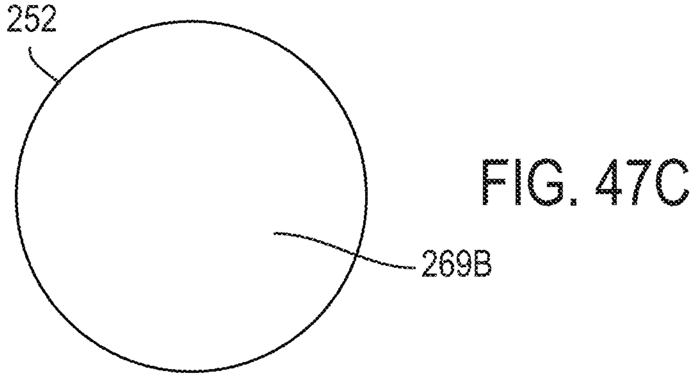
FIG. 47C depicts the example barrel portion of FIG. 47B with a second of the ribs swaged into a covering or capping position to inhibit access to the septum within the bay.

Referring now to FIGS. 47A-47C, in alternative embodiments, a separate cap 263 may not be used. Instead, the septum 94 of the reservoir assembly 52 may be capped or covered via a heat swage operation. For example, the barrel portion 252 of the holder 108 may include a first and second rib 267A, 269A (see, FIG. 47A) of material which surround the bay 202 in which the septum 94 is installed. The first rib 267A may be swaged (e.g. heat swaged) into a retaining body 267B over the periphery of the septum 94 to hold the septum 94 in place within the barrel portion 252 (see FIG. 47B). After the reservoir assembly 52 is filled, the second rib 269A may be swaged (e.g. heat swaged) into a cover 269B over the entire exteriorly accessible face of the septum 94 (see FIG. 47C). Thus access to the septum 94 may be inhibited after the reservoir assembly 52 is loaded with agent.

Figure 48:
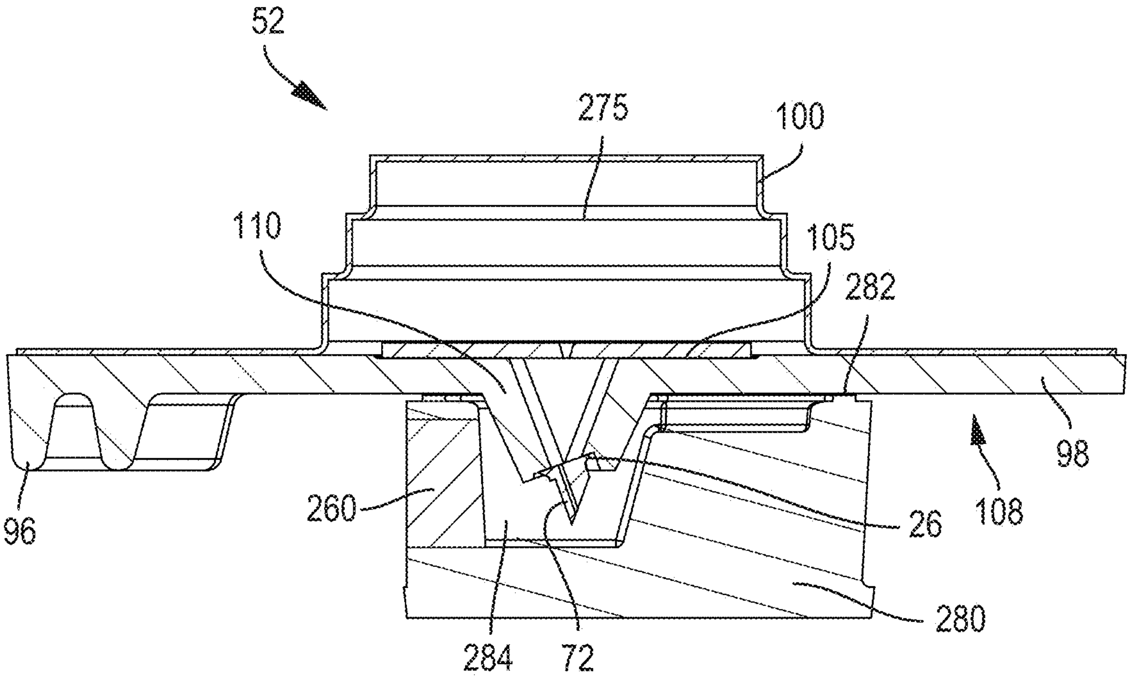
FIG. 48 depicts cross-sectional view of an example reservoir assembly including a cap with a vent filter.

Referring now to FIG. 48, a cross-section of another example embodiment of a reservoir assembly 52 is depicted. The reservoir assembly 52 may include any of the septum 94 arrangements described herein. As shown, the reservoir assembly 52 also includes a filter 260. Depending on the embodiment, a reservoir assembly 52 may include a cap 280. The cap 280 may be coupled to the delivery sharp 72 bearing side of the holder 108 of the reservoir assembly 52. In various embodiments, the cap 280 may be coupled to the holder 108 via an adhesive 282. The cap 280 may include a well 284 which may house the stage projection 110, sharp bearing body 26 and delivery sharp(s) 72 of the reservoir assembly 52. The filter 260 may be included in a wall of the cap 280 in communication with the well 284. As fluid is dispensed into the main interior volume 275 of the reservoir assembly 52, gas within the main interior volume 275 may be displaced through the flow restrictor 105 and into the cap 280 via the delivery sharp(s) 72. The filter 260 may allow the gas to exit the cap 280. The pressure used to fill the main interior volume 275 with agent may be kept relatively low such that agent is not compelled out of the main interior volume 275 through the small orifice in the flow restrictor 105. Such an arrangement may help to lower dead volume in the reservoir assembly 52. No second flow recess 254B, for example, may be needed as an escape path for gas as the reservoir assembly 52 is filled. During fill, the reservoir assembly 52 may be oriented such that the flow restrictor 105 is the highest portion of the main interior volume 275. This may help to encourage full filling of the reservoir assembly 52. Alternatively, the reservoir assembly 52 may be slightly tilted out of this orientation to encourage a small volume of compressible fluid to remain in the main interior volume 275 after filling.

Figure 49A:
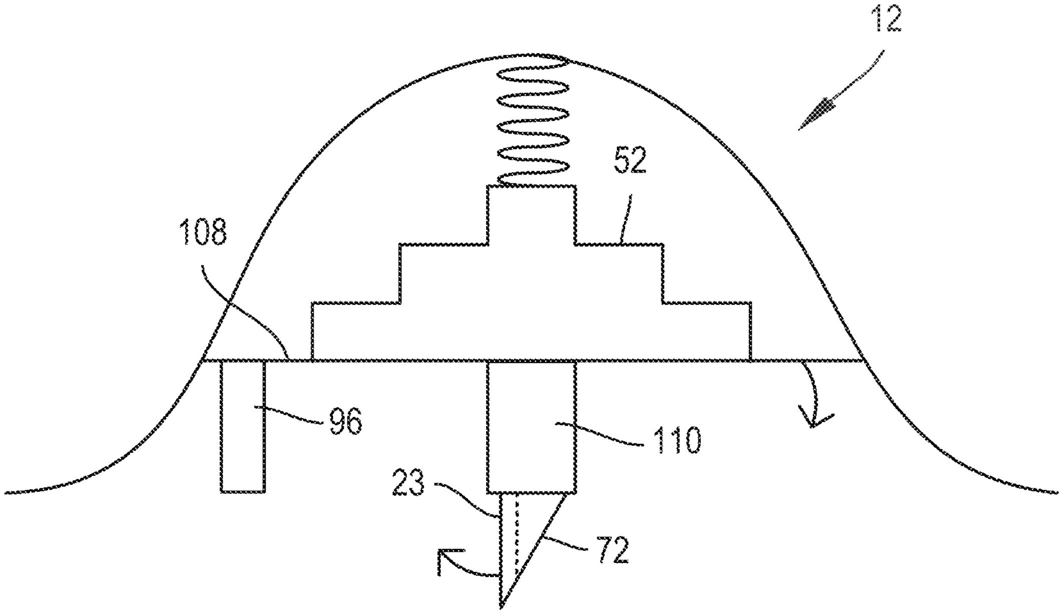
FIG. 49A depicts a block diagram view of an example delivery device with an example rocker member.
Figure 49B:
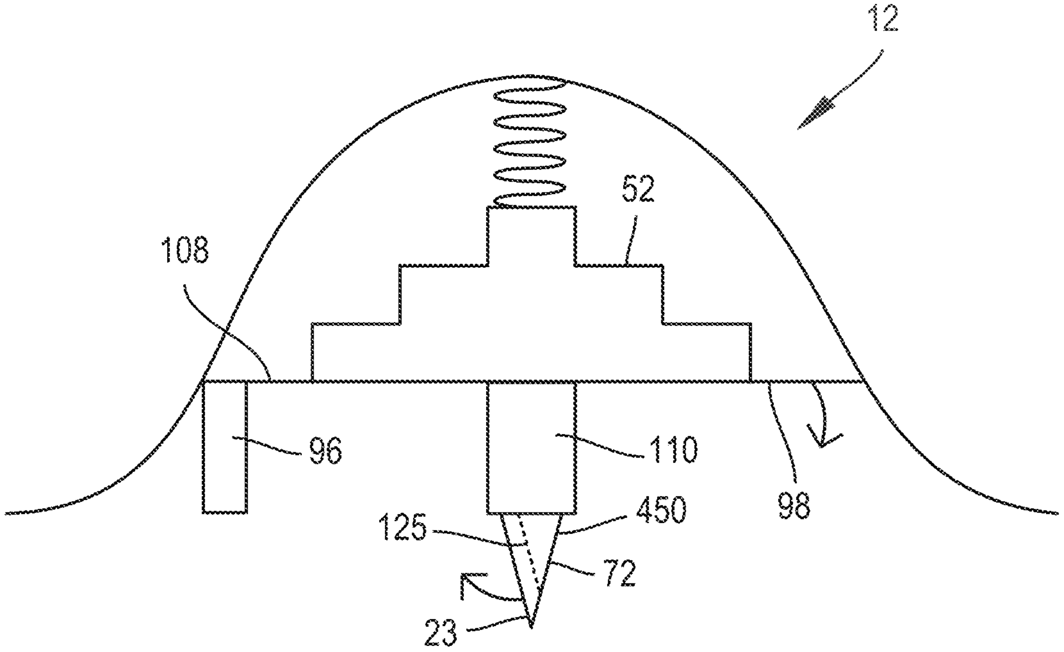
FIG. 49B depicts a block diagram view of an example delivery device with an example rocker member.

Referring now to FIGS. 49A-49B, various embodiments of the delivery devices 12 described herein may include a reservoir assembly 52 with at least one rocker member 96. When such a delivery device 12 is applied to a user and transitioned to a delivery state, skin may be rendered taught due to spreading displacement of portions of the delivery device 12 and the at least one delivery sharp 72 of the delivery device 12 may displace into the stretched skin. Movement of the delivery sharp(s) 72 may generally be in a first direction which is substantially perpendicular to the surface of the skin and the delivery sharp(s) 72 may generally puncture downwardly into the skin. The at least one rocker member 96 may cause the reservoir assembly 52 to tilt or rock as a consequence of the delivery device 12 being transitioned to a delivery state. The at least one rocker member 96 may cause the delivery sharp(s) 72 to displace slightly in a second direction substantially opposite the first direction when pressure is relieved from the delivery device 12. Tilting as well as displacement in the second direction may occur.

In some embodiments, portions of the delivery device 12 may also deform or adjust in response to the rocking of the reservoir assembly 52 in order to accommodate the rocking of the reservoir assembly 52. The tilting of the reservoir assembly 52 may cause the delivery sharp(s) 72 to displace in a non-straight path. For example the delivery sharp(s) 72 may rotate or swing along an arcuate path during at least a portion of the transition of a delivery device 12 to the delivery state. In example embodiments, the tilting may occur automatically as a consequence of the transition of a delivery device 12 to a delivery state. No linkages or interactions with guide elements may be needed in order to achieve the tilting. Example reservoir assemblies 52 may tilt together as a single unit due to the presence of the one or more rocker member 96. Such tilting of a reservoir assembly 96 may lower the pressure at which injection may begin to occur and/or increase delivery flow rate in certain delivery device 12 embodiments. Additionally, the inclusion of one or more rocker member 96 may impact characteristics of bleb formation during delivery. Tilting may also help to facilitate delivery where delivery sharps 72 are initially advanced into skin at an angle substantially perpendicular to the skin.

Still referring to FIGS. 49A-49B, a rocker member 96 may be a protrusion which extends from a proximal face of a holder 108. In various examples, a rocker member 96 may be disposed at or inward of the peripheral edge of the holder 108. A rocker member 108 may have a height which is approximately the height of a stage projection 110. Shorter and taller rocker members 96 are also possible.

When delivery devices 12 including at least one rocker member 96 are transitioned to a delivery state, the rocker member(s) 96 may come into contact with the user and impede further displacement of the portion of the reservoir assembly 52 including the rocker member(s) 96. The opposing side may be free of any rocker members 96 and the reservoir assembly 52 may tilt or rock to accommodate continued displacement of the opposing side toward the user. In certain examples, the delivery sharp(s) 72 (e.g. microneedles) may tilt 3-5° (e.g. 4°) with respect to their initial orientation. In other examples, the delivery sharp(s) 72 may tilt lesser or greater amounts. Height of a rocker member 96 may alter the point at which the delivery sharp(s) 72 begin to rotate or swing during the transition of the delivery device 12 to the delivery state. Rocker members 96 even with the height of a stage 110 may, for example, tend to initiate tilting after the delivery sharp(s) 72 have punctured the skin.

In certain examples, the delivery sharp(s) 72 may be microneedles such as any of those described herein. Where the delivery sharp(s) 72 is/are microneedle(s), the rocker member(s) 96 may be disposed on a side of the reservoir assembly 52 closest the back facing edge 23 of the microneedle(s). The rocker member(s) 96 may be positioned such that back facing edge 23 of the microneedle(s) is the portion of the microneedle(s) most proximal the rocker member(s) 96. As rocking of the reservoir assembly 52 transpires, the displacement path followed by the microneedle(s) may be such that the back facing edge(s) 23 may be driven through the skin. The beveled surfaces leading to the back facing edge 23 may facilitate cutting of the skin as the microneedle(s) are displaced. Thus, the back facing edge 23 may be a cutting edge. Additionally, this may cause a face of each microneedle in which an outlet of the lumen 125 of that microneedle is disposed to be displaced away from skin contacted during the initial puncture. For example, the lumen(s) 125 of any microneedles may be displaced away from skin contacted by the sloped face(s) 450 during the initial puncture. Such displacement of the microneedle(s) may aid in ensuring fluid may easily flow out of the lumen(s) 125 and into the skin as delivery occurs. The above described displacement may also create a small receiving volume in the skin into which fluid may be delivered from the lumen(s) 125. When pressure applied to the delivery device 12 to transition the delivery device 12 to the delivery state is relieved, the delivery sharp(s) 72 may displace slightly in a direction away from the patient. This may create a small receiving volume in the skin and displace the lumen 125 away from skin contacted during initial puncture. The rocker member 96 may help to encourage this.

In some examples (see also, e.g., FIG. 32), delivery sharp(s) 72 may be mounted to a stage 110 having a mounting area (e.g. a pocket 107) which is non-parallel with respect to a disk body 98 of the holder 108. In such examples, the delivery sharp(s) 72 may extend from the stage 110 at a prescribed angle (e.g. 15°) with respect to a plane normal to the disk body 98. The disk body 98 and skin may be generally parallel when various example delivery devices 12 are first applied to a user. Delivery sharp(s) 72 may thus be angled with respect to a plane normal to the skin. As the reservoir assembly 52 tilts, the delivery sharp(s) 72 may be displaced to a position in which they are closer (e.g. 3-5°) to a normal orientation with respect to the skin. Depending on the mounting angle of the delivery sharp(s) 72, the delivery sharp(s) 72 may be brought to or nearly to a normal orientation with respect to the skin as the reservoir assembly 52 tilts. In other embodiments, the delivery sharp(s) 72 may be 10° or more (e.g. 11-12°) away from a normal orientation.

Still referring to FIGS. 49A-49B, in some examples, a reservoir assembly 52 may include at least one marking member. The at least one marking member may contact or press against the skin as the delivery device 12 is dispensing agent to a user. In some embodiments, any rocker member(s) 96 may double as marking members though dedicated marking members may also be present in some embodiments. Marking members may also be used in embodiments which do not include a rocker member 96. When a delivery device 12 is used, one or more marking member may leave a perceptible marking on the skin. This marking may be a temporary impression or depression in the skin resulting from the marking member pressing on the skin as a delivery occurs. Alternatively or additionally, the marking member (e.g. rocker member 96) may bear a marking agent (e.g. ink) which at least partially transfers to the skin when the delivery device 12 is used. As the contact surface of the marking member may be of a known size, the perceptible marking may serve as a fiducial reference. The delivery site may, in some examples, be imaged after a delivery device 12 is removed and an image of the delivery site may be analyzed (e.g. any suitable image processing such as edge detection may be used) by a controller to identify the perceptible marking. In certain examples, it may be required that an image be taken within some preset time after a delivery device 12 is removed. The perceptible marking may aid in confirming a delivery device 12 has been used when identified in an image. Additionally, the perceptible marking could aid in determining, for example, one or more attribute related to the delivery (e.g. bleb presence, size, area, relative location of the bleb to the mark). For example, a controller may analyze an area of an image a defined distance from the marking for the one or more attribute related to the delivery or the controller may ensure that an attribute of interest conforms to an expected relationship with the marking (e.g. is within some range of distances from the marking). The mark left by a marking member or the arrangement of marking members on the delivery device 12 could be selected to leave a perceptible mark having a particular pattern. Any suitable pattern could be used. The pattern could be selected to assist in image analysis or perhaps could be selected to provide a patient friendly delivery confirmation marking (e.g. smiley face or the like).

Figure 50:
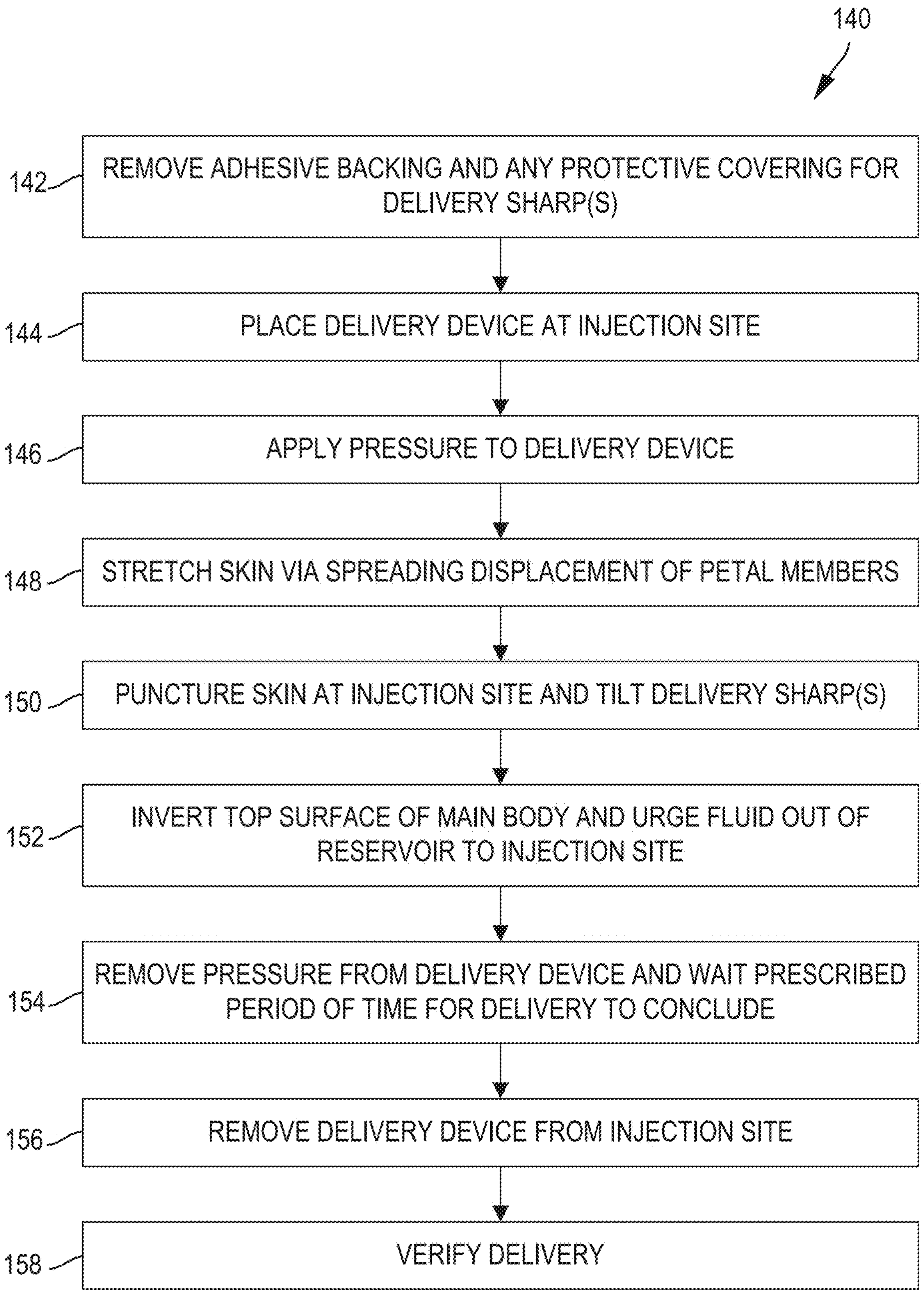
FIG. 50 depicts a flowchart detailing a number of example actions which may be executed to delivery agent with a delivery device.

Referring now to FIG. 50, a flowchart 140 depicting a number of exemplary actions which may be executed to deliver agent from a delivery device 12 to an injection site is shown. A delivery device 12 or reservoir assembly 52 may be filled as described in any of the embodiments shown and/or discussed herein. Once filled, the delivery device 12 may be disassociated from an isolated fill environment 14. If needed, a reservoir assembly 52 may be installed into a delivery device 12. The delivery device 12 may be distributed for use after the delivery device 12 includes a filled reservoir assembly 52.

As shown, in block 142, an adhesive backing 136 (see, e.g., FIG. 6) may be removed from a delivery device 12. Additionally, any covering (e.g. cover 138 of FIG. 6) protecting the delivery sharp(s) 72 may be removed from the delivery device 12 in block 142. In block 144, the delivery device 12 may be placed at a desired injection site.

Figure 51:
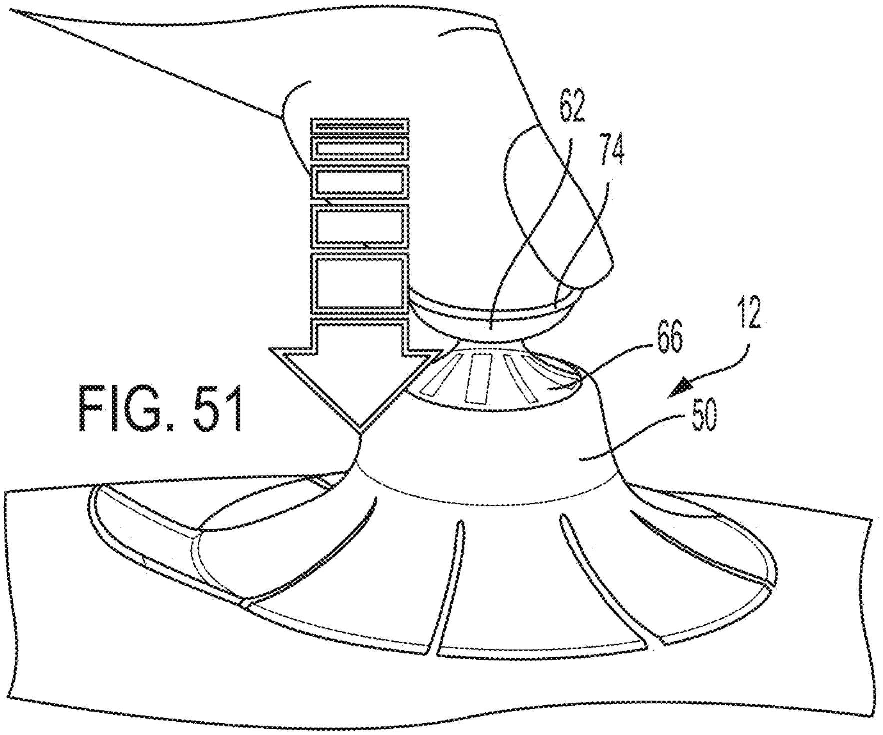
FIG. 51 depicts an illustration of an example delivery device after being applied to a user.

Referring now also to FIG. 51, pressure may be applied to the delivery device 12 in block 146. In some examples, pressure may be applied to the top surface 66 of a main body 50 of a delivery device 12. Alternatively, and as shown in the illustration in FIG. 51, pressure may be applied to a depressor body 62 (e.g. a dish body 74) of the delivery device 12. Pressure may be applied manually, for example, with a single finger of a user.

Figure 52:
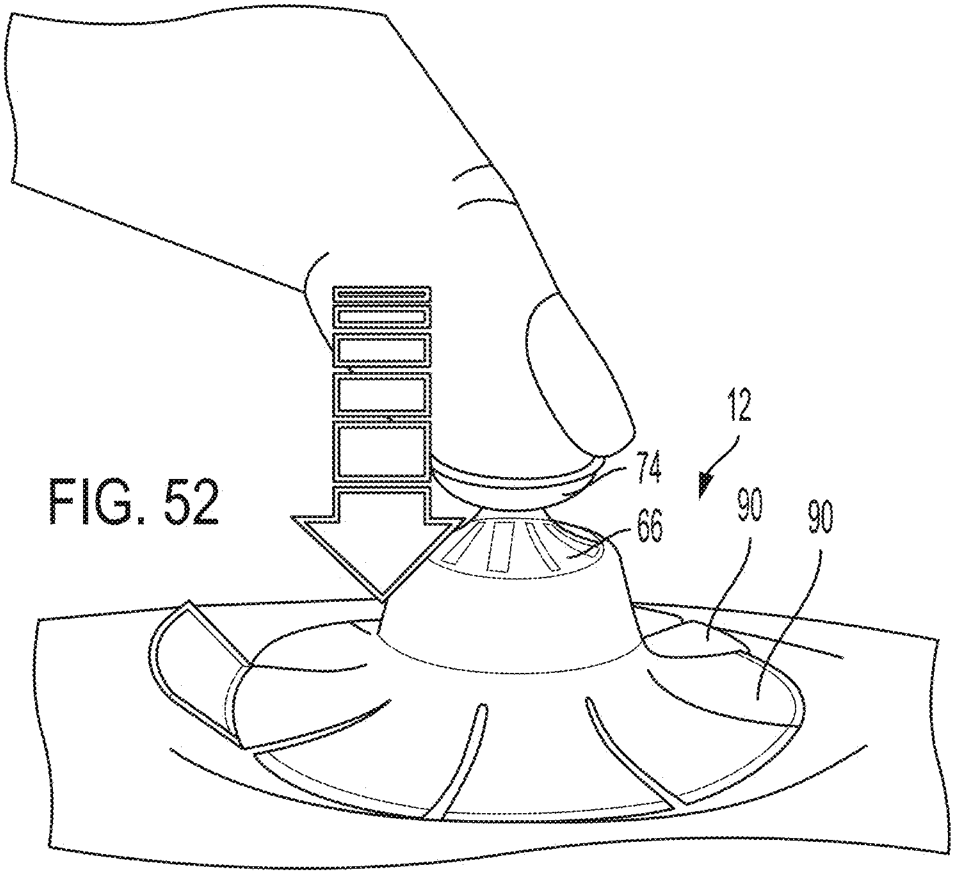
FIG. 52 depicts an illustration of an example delivery device in process of transitioning from a storage state to a delivery state.

Referring now primarily to FIG. 50 in combination with FIG. 52, in block 148, the skin coupled to the delivery device 12 via adhesive 56 of the delivery device 12 may be stretched. At least two portions of the delivery device 12 adhered to the skin may distort from their initial state so as to spreadingly displace and stretch the skin. For example, this may occur as petal members 90 of the main body 50 distort under pressure being applied to the delivery device 12. As described elsewhere herein, when the petal members 90 distort, the reservoir assembly 52 and delivery sharp(s) 72 coupled thereto may displace toward the skin. The delivery sharp(s) 72 may puncture the skin and may optionally tilt (e.g. due to the presence of a rocker member 96) in block 150. As shown in FIG. 52, the top surface 66 of the delivery device 12 may resist deformation at least as the petal members 90 initially begin to spreadingly displace.

The petal members 90 may be constructed to have a stiffness selected to help ensure that this occurs. The petal members 90 may for example be substantially or primarily planar and project from the rest of the delivery device 12 at a constant angle (see, e.g., FIGS. 55A-55B). This may allow the petal members 90 to deflect relatively easily as pressure is applied to the delivery device 12. In alternative embodiments, the petal members 90 may have curvature at least in certain regions. Any curvature in the petal members 90 may be selected to ensure that at least a desired amount of distortion of the petal members 90 occurs prior to deformation of the top surface 66. In preferred embodiments, the main body 50 may be constructed such that the petal members 90 distort an amount sufficient to stretch the skin and allow the delivery sharp(s) 72 to penetrate the skin prior to the top surface 66 substantially deforming.

Figure 53:
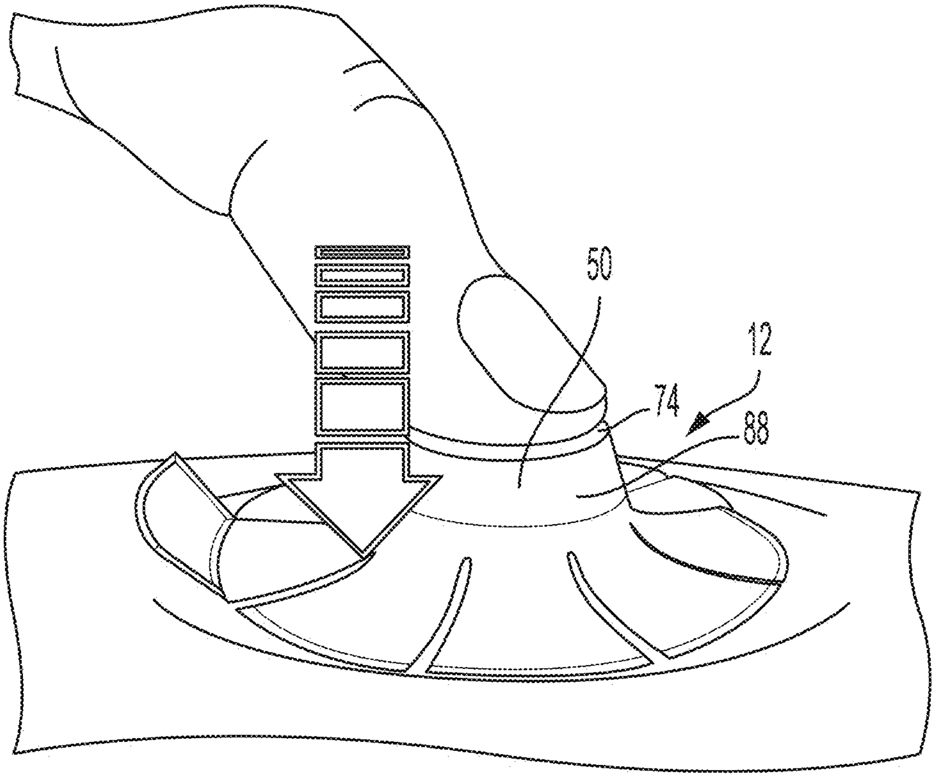
FIG. 53 depicts an illustration of an example delivery device in process of transitioning from a storage state to a delivery state.

Referring now primarily to FIG. 50 in combination with FIG. 53, the top surface 66 of the main body 50 may flip from a protruding state to a depressed state or invert in block 152. Fluid may also be urged out of the reservoir assembly 52 in block 152. In various examples, a bias member 58 may become compressed upon flipping of the top surface 66. Fluid may be driven out of the reservoir assembly 52 into the injection site via the delivery sharp(s) 72 as the bias member 58 restores to less distorted state. As shown in FIG. 53, in embodiments including a depressor body 62 with a dish body 74, the dish body 74 may seat against an end of the supporting structure 88 when the top surface 66 inverts. The dish body 74 may obstruct view of the top surface 66 when the top surface 66 is inverted giving a visual cue the delivery device 12 has been used (see also FIG. 54).

Figure 54:
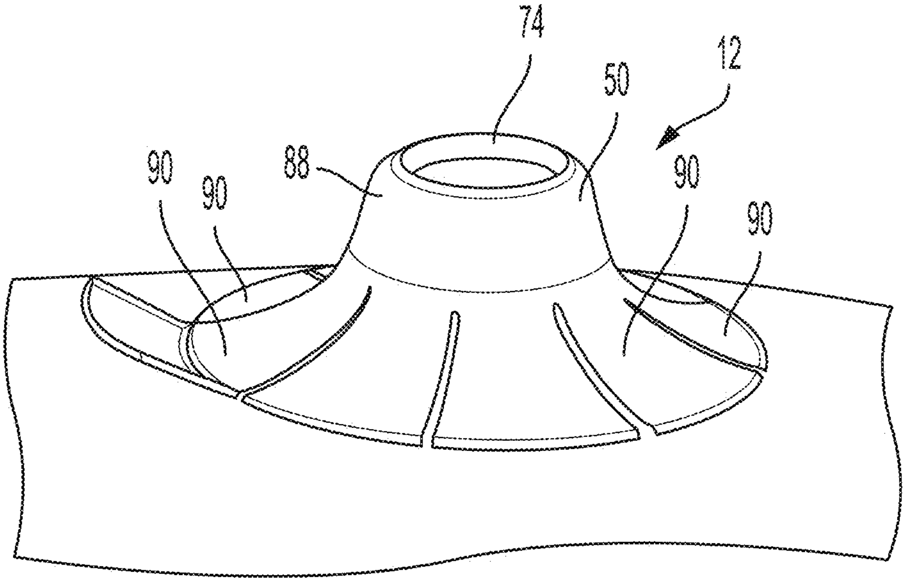
FIG. 54 depicts an illustration of a delivery device in a delivery state.

Referring now primarily to FIG. 50 in combination with FIG. 54, in block 154, pressure may be removed from the delivery device 12 and a predetermined period of time may be allowed to elapse. The period of time may be selected to be at least as long as and preferably greater than an expected delivery time. In certain examples, the wait time may be (1-5 minutes).

In certain examples and as shown in FIG. 54, when pressure is removed, one or more portion of the delivery device 12 may at least partially restore from its distorted state. Thus, the main body 50 may have at least one invertible region, at least one resilient region, and at least one region which elastically deforms as a delivery device 12 is transitioned to a delivery state. The at least one region which elastically deforms may be distorted from an initial state, to an intermediate state, and then elastically restore at least partially from the intermediate state during the course of the transition to the delivery state. The intermediate state may be a state during the transition in which the region is maximally distorted. The region may restore from this state back towards the initial state. The petal members 90 may, for example, at least partially restore from their distorted state. As the petal members 90 of the delivery device 12 are adhered to the skin via the adhesive 56 of the delivery device 12, the skin may be pulled away from the underlying anatomy as the petal members 90 restore. As the petal members 90 restore, the reservoir assembly 52 may also displace slightly in a direction away from the skin (this may be assisted via inclusion of a rocker member 96). Where adhesive 56 is present on portions of the reservoir assembly 52 (e.g. the holder 108) skin may also be pulled away from underlying anatomy as the reservoir assembly 52 displaces. This may relieve some pressure on the injection site which otherwise tends to compress anatomy at the injection site. This decreased compression at the injection site may allow fluid to be more readily be transferred from the delivery sharp(s) 72 into the delivery destination. Additionally, depending on the orientation of the delivery sharp(s) 72, the delivery sharp(s) 72 may tug the skin into which they have punctured upward away from underlying anatomy as the petal members 90 restore. Again, this may help to facilitate delivery as the compactedness of the anatomy at the delivery destination may be reduced. The shape of the petal members 90 and material used to construct the main body 50 may be selected to help encourage this at least partial restoration or recoil of the petal members 90 when pressure is removed.

In block 156, the delivery device 12 may be removed from the injection site. In certain examples, delivery may be verified in block 158. In certain embodiments, this verification may be manual. Staff at a vaccination site or clinic may verify by eye that a bleb or wheal is present after injection and no leaks are seen. In other embodiments, an image of the injection site may be taken, analyzed, and perhaps documented in electronic records. Image analysis may, for example, determine whether an expected marking (bleb, depression from rocker member 96, ink transferred during usages, etc.) is present at the injection site or whether characteristics of interest are present in the image (or have a desired relationship with a fiducial marking, e.g. rocker member 96 depression). In other examples, an image may be analyzed for the presence of a cool region in the skin (via analysis of an infrared image).

Referring now to FIGS. 55A-55B and FIGS. 57A-57B, two exemplary main bodies 50 which may be used in various delivery devices 12 described herein are respectively shown. In various embodiments where delivery devices 12 are or may be injection molded, portions of the main body 50 may be injection molded so as to be in the storage state or in the delivery state. Portions of the main body 50 may transition more easily or tend to restore into the configuration in which they were molded. Such portions may also have a tendency to stay in the configuration in which they were molded. In the examples in FIGS. 55A-55B, the top surface 66 is molded in a delivery state position. The petal members 90 are molded in a storage state position. During assembly of a delivery device 12, the various portions of the main body 50 may be brought into a storage state configuration and remain in that configuration until use. Molding the top surface 66 in the delivery state position may lower the effort needed to transition a delivery device 12 from a storage state to a delivery state. Likewise, molding the petal members 90 in their storage state positions encourages the petal members to 90 to restore toward their storage state positions (see, e.g., FIG. 54 and related description) when a user relieves pressure on the delivery device 12 during use.

As mentioned above, in certain embodiments, petal members 90 may be relatively devoid of curvature. For example, petal members 90 be substantially flat and/or extend from the rest of a main body 50 at an angle or angles thereto. This may assist in making the force required to cause deflection in the petal members 90 relatively low as pressure is applied to the delivery device 12. In turn, this may help to assist in generating spreading displacement of the petal members 90 and help ensure puncture of the skin with the delivery sharp(s) 72 prior to deformation of the top surface 66 of the main body 50.

Figure 55A:
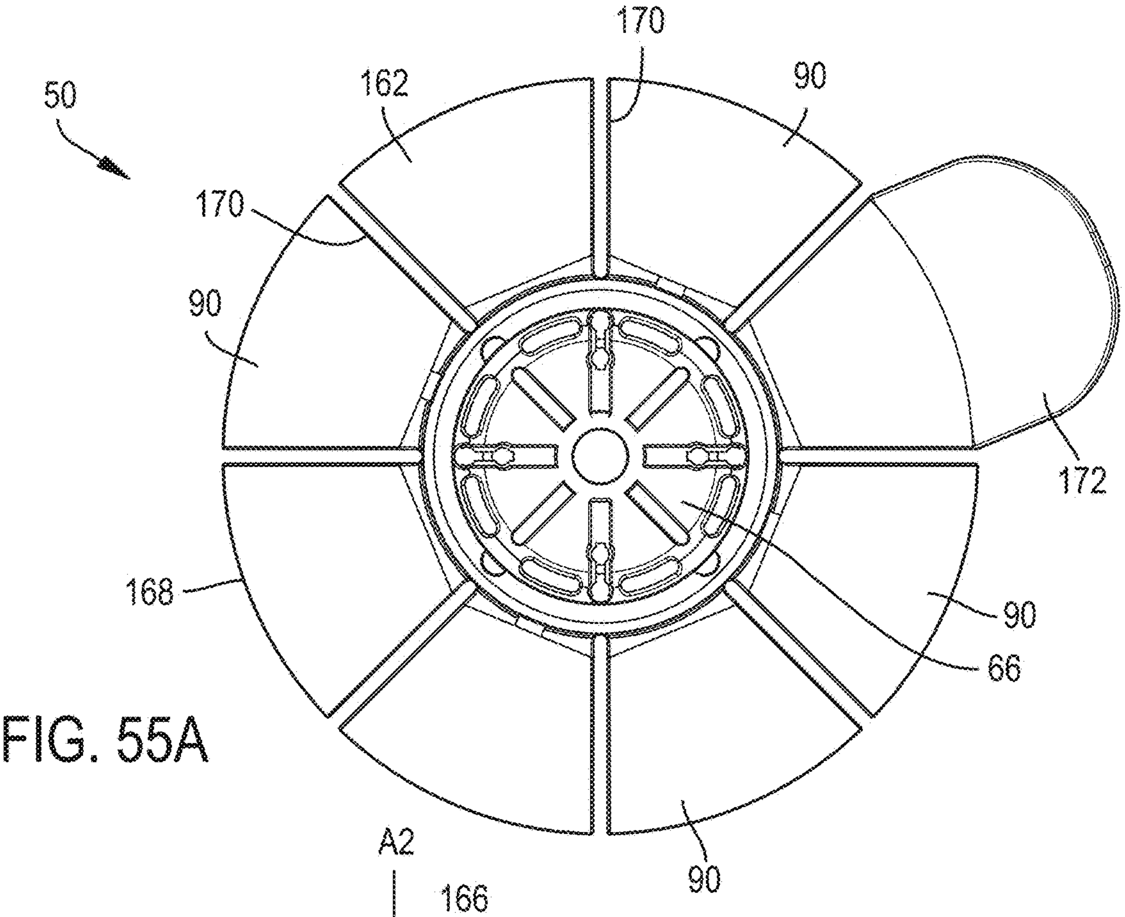
FIG. 55A depicts a view of an example main body which may be included in a delivery device.
Figure 55B:
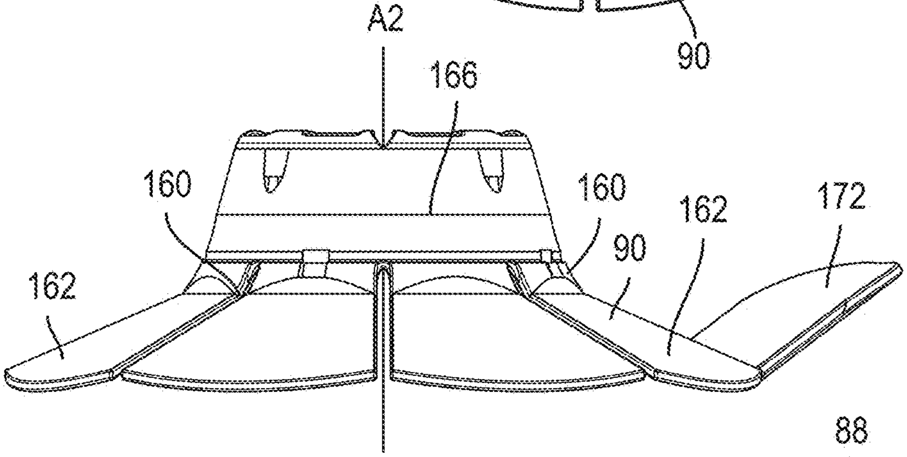
FIG. 55B depicts a side view of an example main body which may be included in a delivery device.
Figure 56:
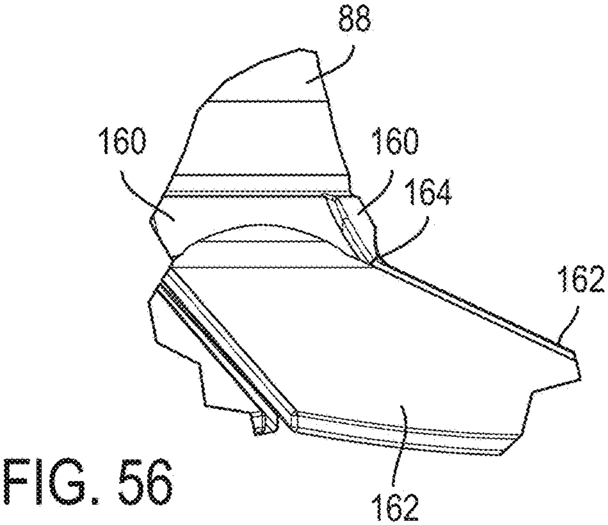
FIG. 56 depicts a detailed view of a portion of an exemplary main body.

As shown in FIGS. 55A-55B, the petal members 90 of example main bodies 50 may each include first regions 160 adjacent the supporting structure 88 and second regions 162 which form the more peripheral portions of the petal members 90. As shown, the first regions 160 may be arced roughly similar to that of the adjacent portion of the supporting structure 88. The second regions 162 may be oriented at a constant angle to the center axis A2 of the main body 50. The second regions 162 may form the majority of the petal members 90. In some examples, the petal members 90 may have a curved region or surface, while being predominantly flat. In various embodiments, a small curved transition 164 between the first and second regions 160, 162 of the petal members 90 may be included (see, e.g., FIG. 56).

A living hinge may be formed at the transition between the first and second regions 160, 162. As pressure is applied to the top surface 88 of a main body 50, the living hinge may allow the second regions 162 of the petal members 90 to displace relative to the first regions 160. The first regions 160 may distort to a lesser degree than the second regions 162 throughout the transition of the delivery device 12 to the delivery state. In some examples, the first regions 160 may resist substantial deformation and remain generally undistorted throughout the transition. Thus, the first regions 160 may behave as stops which may help to limit spreading displacement of the petal members 90 after a desired amount of spreading displacement has been achieved. Curved transitions 164 may be included to assist in encouraging the petal members 90 to at least partially restore once pressure on the delivery device 12 has been relieved. In examples including petal members 90 such as those in FIGS. 55A-55B, it may be preferred that, in the storage state, the base of any stage projection 110 be substantially even with the end of the second region 162 of the petal members 90 most proximal the central region 166.

Figure 57A:
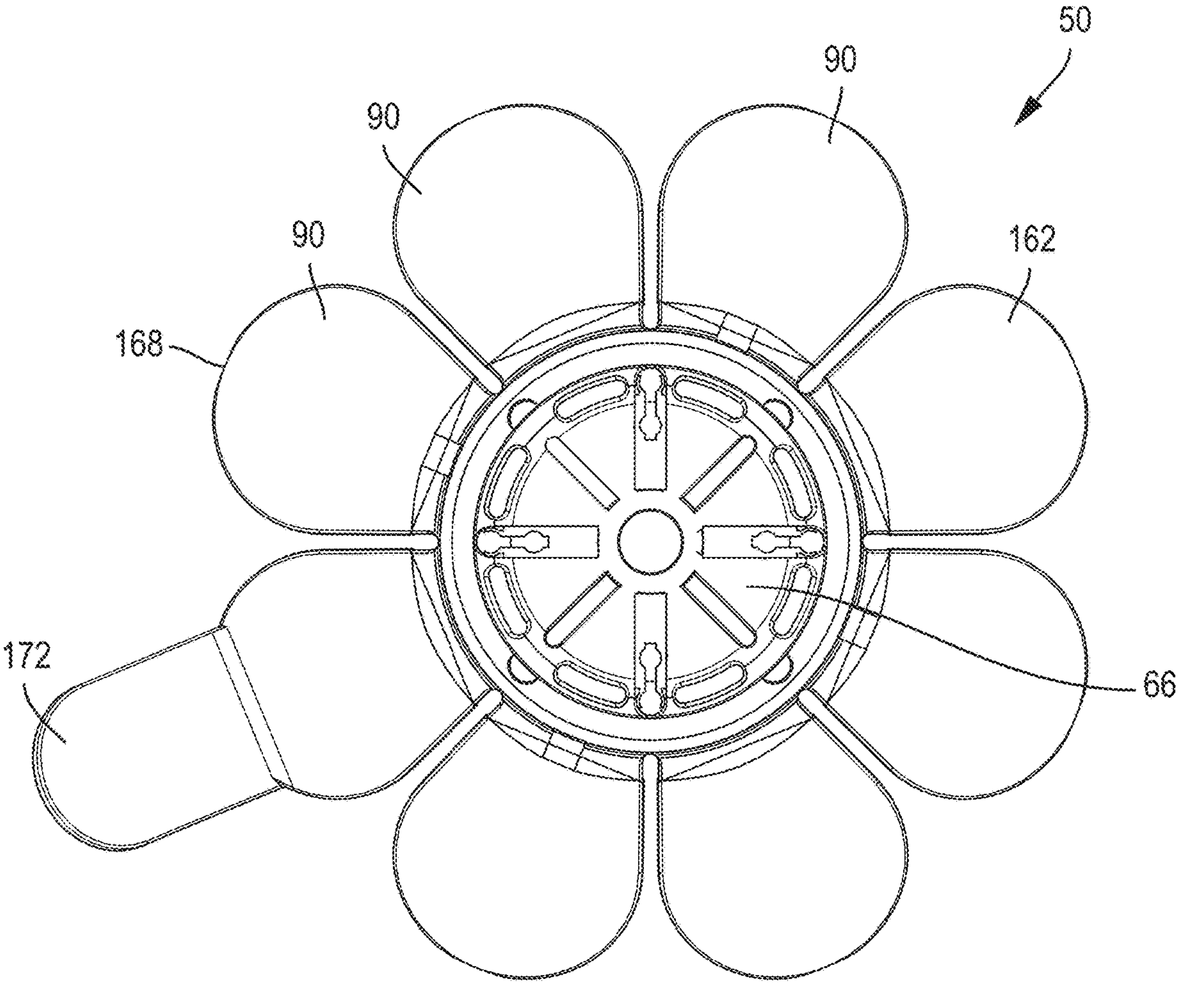
Figure 57B:
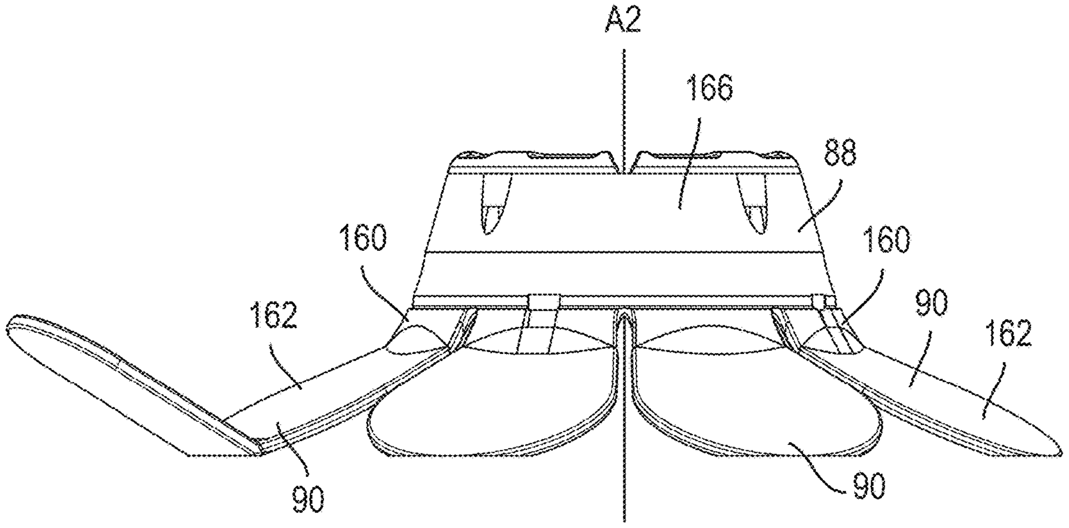
Figure 58A:
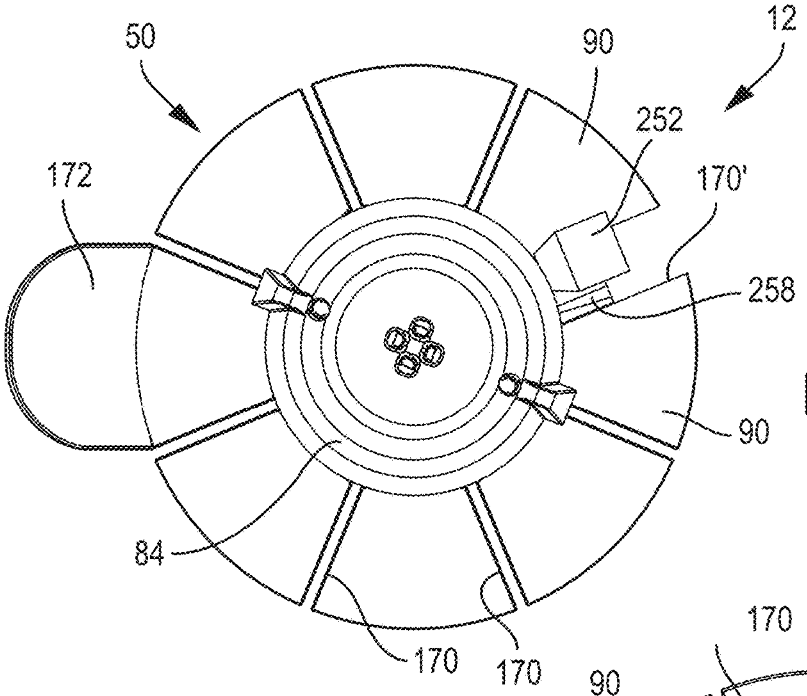
Figure 58B:
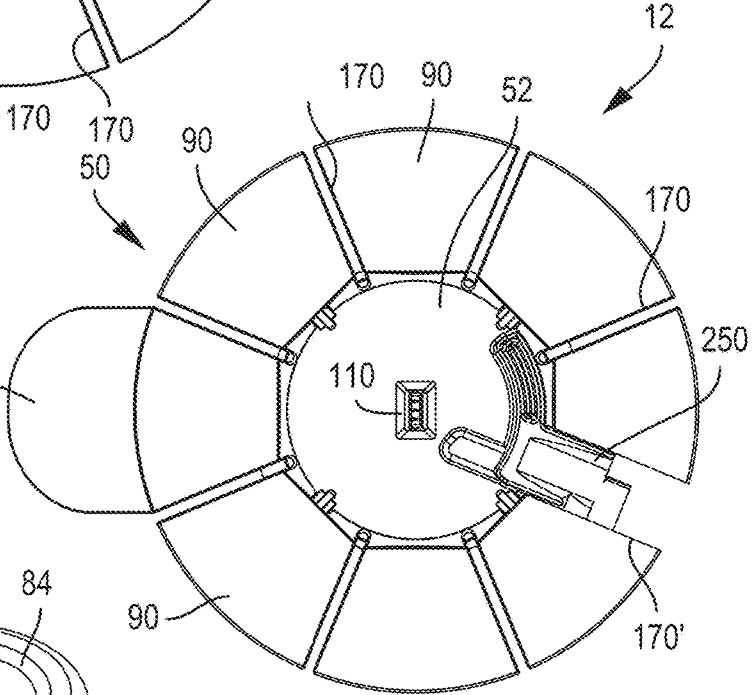
Figure 58C:
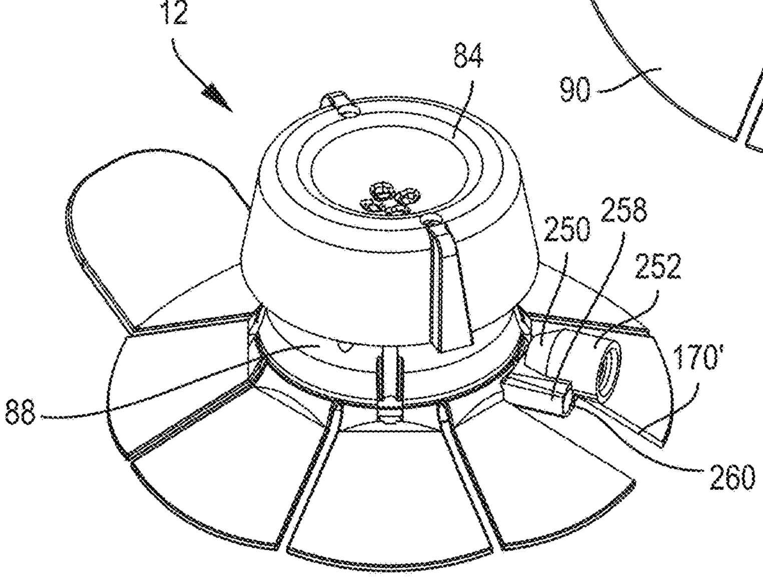
Figure 59A:
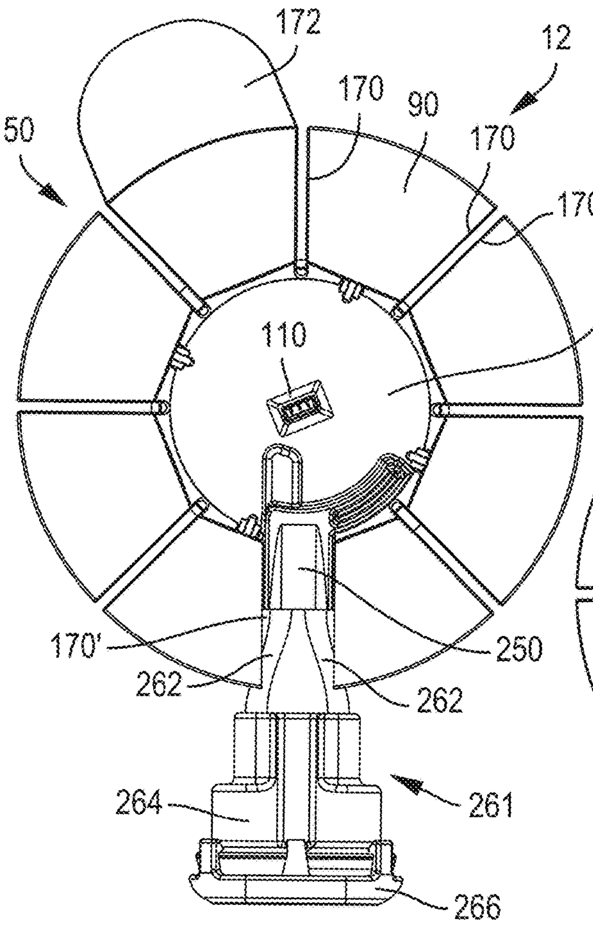
Figure 59B:
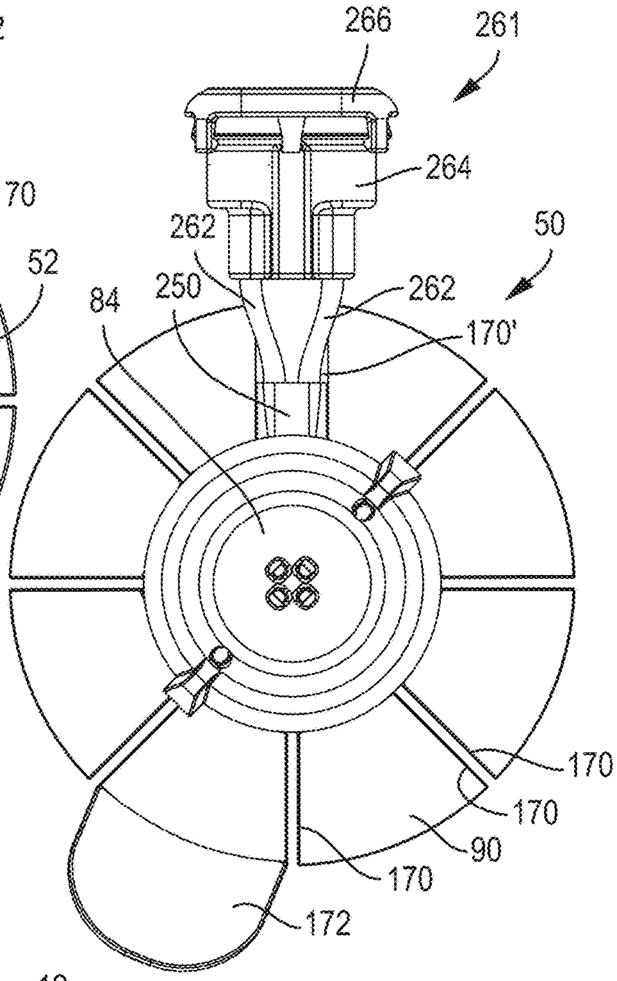
Figure 59C:
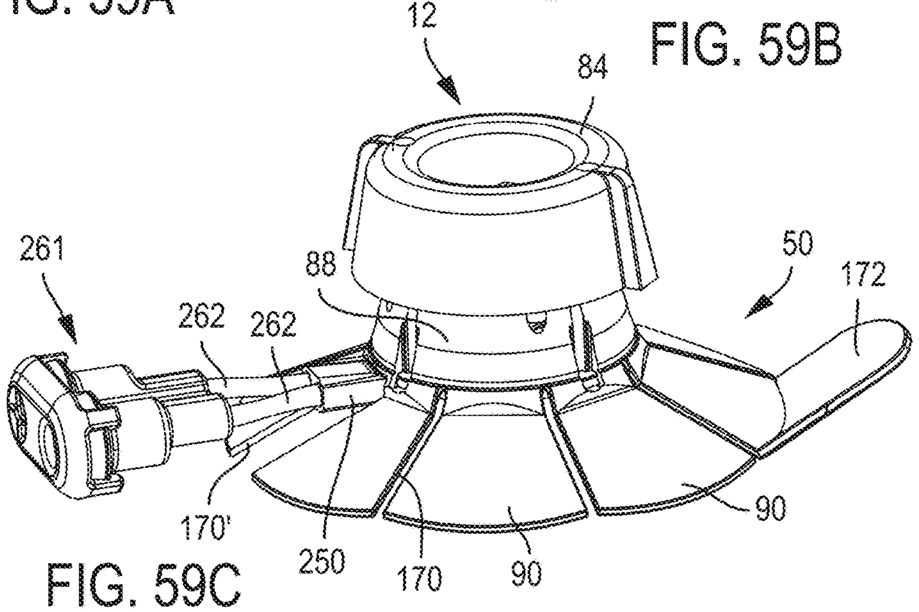

The main body 50 may have a round, substantially circular footprint in examples such as that shown in FIG. 55A-55B. The portion of each petal member 90 at the peripheral edge 168 of the main body 50 may arc along a radius extending from the center axis A2 of the main body 50. In various examples and referring now to FIGS. 57A-57B, the width of the portions of the petal bodies 90 forming the peripheral edge 168 may decrease as distance from the central region 166 of the main body 50 increases. For instance, the portion of the petal members 90 forming the peripheral edge 168 of the main body 50 may be arced other than along a radius extending from a center point within the center axis A2 of the main body 50. For example, a radius defining the curve of the periphery of each petal member 90 may be extended from a center point within the respective petal member 90 or within the second portion 162 of the respective petal member 90. The outermost region of each of the petal members 90 may be disposed more distal the central region 166 than the ends of the slits 170 most distal the central region 166. The outermost regions may decrease in width as distance from the central region 166 increases. In certain examples, the portion of each petal body 90 forming the peripheral edge 168 may taper to a point or be rounded as shown in FIGS. 57A-57B.

This may assist in removal of a delivery device 12 as it may decrease the surface area of adhesive which a user is attempting to dissociate from the skin during initial portions of the removal action. Though each petal member 90 may be described as having the same shape, it should be understood that such description may be inclusive of at least one petal member 90 differing in shape slightly to accommodate a pull tab 172 (see, e.g., FIG. 57B) which may be included to assist in removal of the delivery device 12.

Referring now to FIGS. 58A-59C, in any of the main body 50 embodiments described herein, at least two of the petal members 90 of a main body 50 may be separated by a widened slit 170'. In various embodiments, the petal members 90 adjacent the widened slit 170' may have a smaller surface area than the remaining petal members 90 of the main body 50. The petal members 90 adjacent the widened slit 170' may be substantially identical. In other embodiments, the surface area of each of the petal members 90 may be adjusted to accommodate the widened slit 170' and each of the petal members 90 may have a substantially equal surface area. One petal member 90 may also be completely omitted to create the widened slit 170'. Though only one widened slit 170' is included, alternative embodiments may have two or more widened slits 170' which may, though need not be the same size.

Each widened slit 170' may define a septum 94 and/or filter 260 access. In the example embodiment shown in FIGS. 58A-58C, the widened slit 170' accommodates a protruding body 250 of a reservoir assembly 52 (further described above in relation to FIGS. 43A-43D). In the example shown in FIGS. 59A-59C, the widened slit 170' accommodates a protruding body 250 of a reservoir assembly 52 and also provides a space for the conduits 262 to be routed through if desired. Where multiple widened slits 170' are included, one widened slit 170' may accommodate a protruding body 250 in which a septum 94 is disposed. Another may accommodate a protruding body 250 in which a filter 260 is disposed.

Though the example main bodies 50 in FIGS. 58A-59C are depicted with a widened slit 170', other embodiments may include a port 89 or notch in the supporting structure 88 through which a septum 94 may be accessed to fill the reservoir assembly 52. A port 89 or notch in addition to and in line with a widened slit 170' may be included in some examples and may simplify molding of a main body 50. In examples where a reservoir assembly 52 is filled before installation into a delivery device 12, the main body 50 may be devoid of widened slits 170' or notches/ports in the supporting structure 88. A projection from a reservoir assembly 52 housing a venting filter may also be accommodated in a port 89 as well.

Figure 60A:
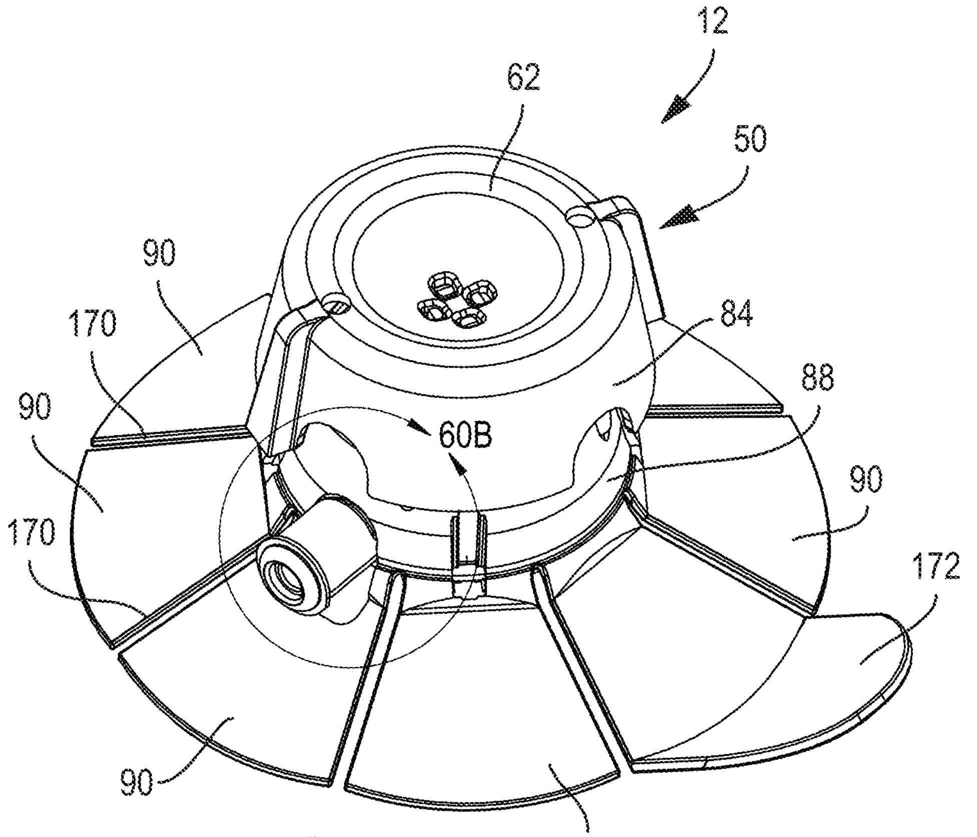
Figure 60B:
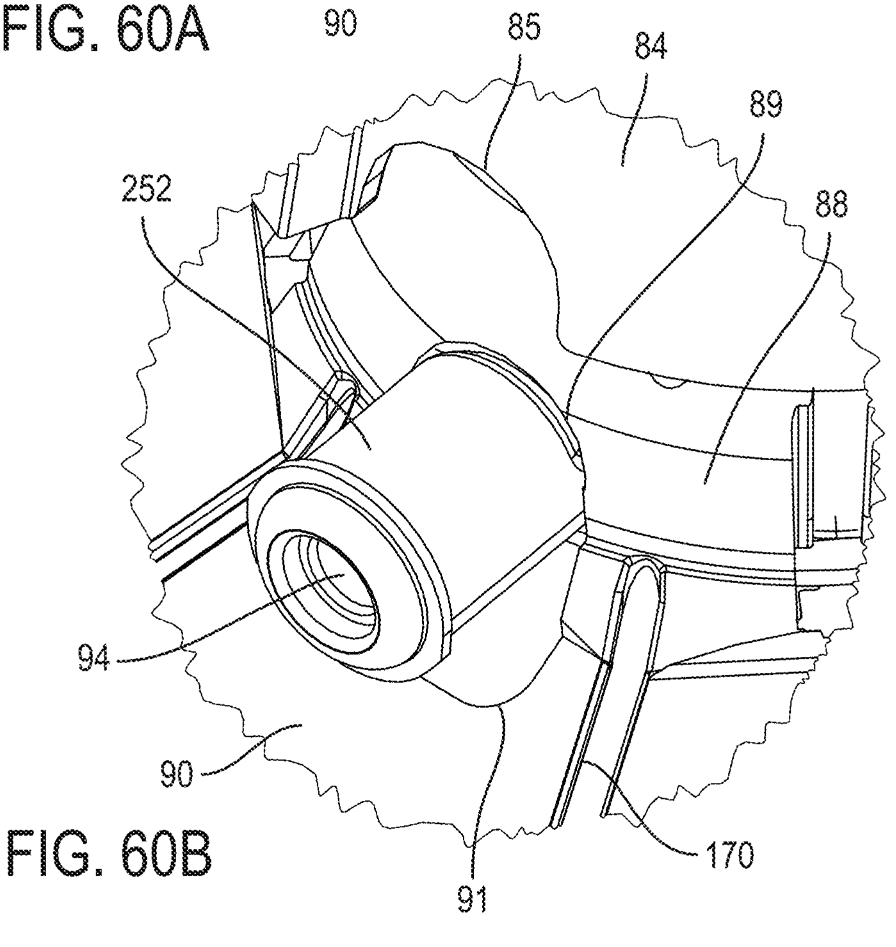

An exemplary embodiment of a delivery device 12 having a main body 50 with a port 89 in the supporting structure 88 is depicted in FIGS. 60A-60B. The delivery device 12 is shown with the reservoir assembly 52 depicted in FIGS. 40A-40C though ports 89 may similarly be included in main bodies 50 to accommodate other septum 94 arrangements described herein. The port 89 is sized such that the barrel 252 of the protruding body 250 defining the bay 202 in which the septum 94 is disposed may extend through the wall of the supporting structure 88. Additionally, in place of a widened slit 170', the petal member 90 in line with the barrel 252 includes an aperture 91 disposed adjacent the central region 68 of the main body 50. The aperture 91 is continuous with the opening defining the port 89 in the supporting structure 88 of the main body 50. The aperture 91 may provide a pass through in the main body 50 for the barrel 252 of the reservoir assembly 52 facilitating assembly of the delivery device 12. The aperture 91 is centrally disposed within the petal member 90, though need not necessarily be so in all examples.

Additionally, where included, the skirt 84 of a depressor body 62 may include at least one indented region 85. The indented region 85 may be sized to accept the barrel 252 of the reservoir assembly 52 when the delivery device 12 is transitioned to the delivery state. In the example embodiment, the depicted skirt 84 includes a set of indented regions 85 disposed at regular angular intervals. This may simplify assembly of the delivery device 12 allowing the depressor body 62 to be installed in a greater variety of orientations.

Figure 61A:
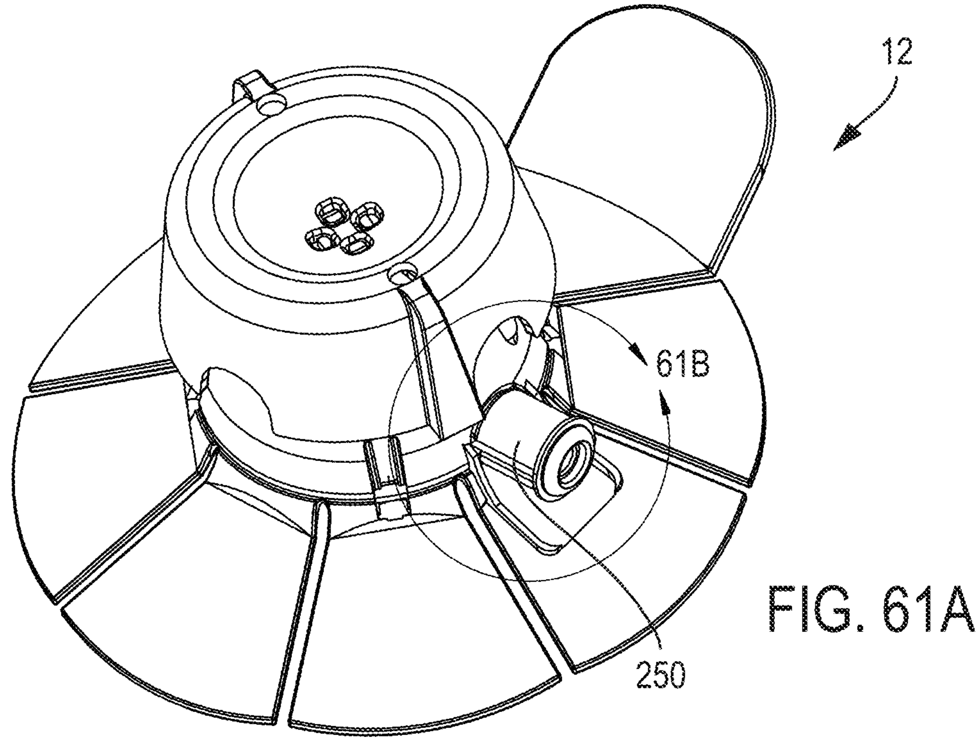
Figure 61B:
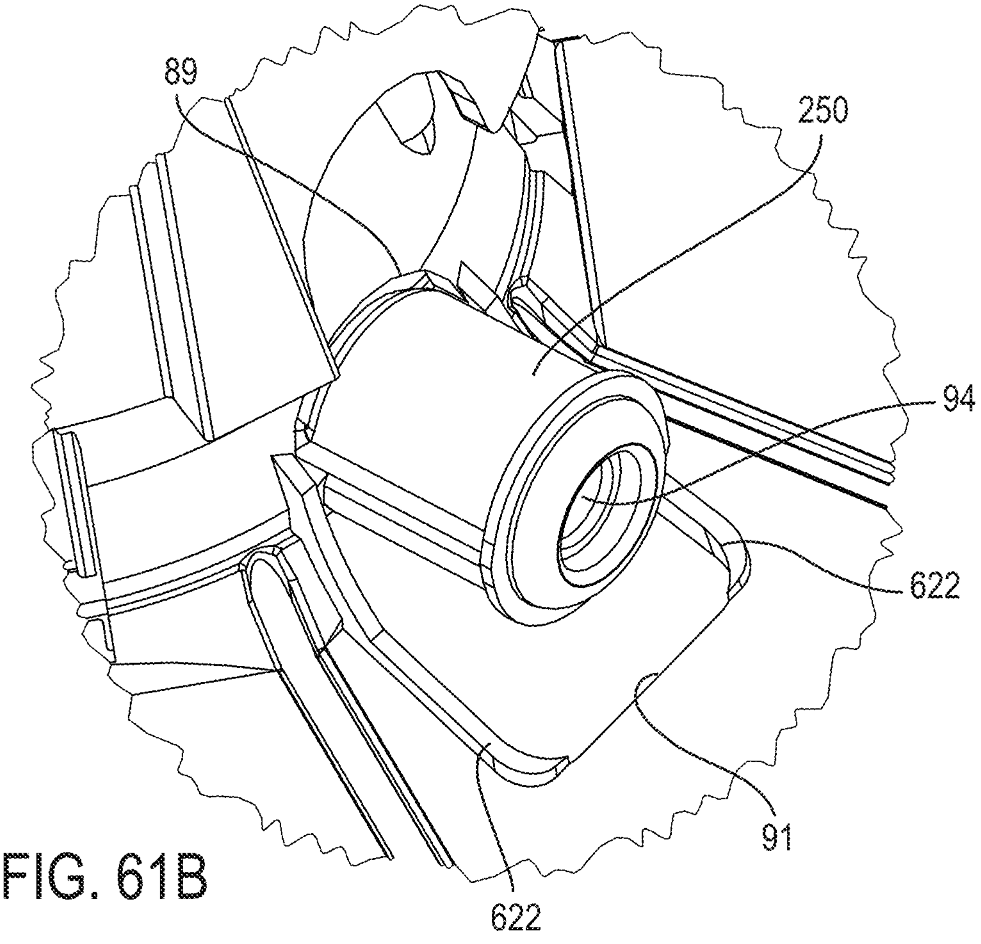

Referring now to FIGS. 61A-61B, in certain examples including a widened slit 170' or aperture 91, the petal members 90 including these features may include strengthened sections. The strengthened sections may, for example be ribs 622. The ribs 622 may span over the portion of the petal member(s) 90 which deflect during transition of the delivery device 12 from a storage state to a delivery state. In the example, the ribs 622 are disposed about at least a portion of the periphery of an aperture 91. The ribs 622 may reinforce the petal member 90 on which they are disposed and make the petal member 90 more difficult to deflect. The amount of material in the ribs 622 may be selected to make the petal member 90 including the aperture 91 or adjacent the widened slit 170' behavior similar to other petal members 90 on the main housing 50. For example, the ribs 622 may make the parent petal member 90 deflect a like amount as other petal members 90 given the same force application. Ribs 622 may also be included on otherwise unadulterated petal members 90 to increase the force necessary to deflect the petal member 90 a given amount.

Other example delivery devices 12 may be used in various embodiments. For example, any of the devices shown or described in U.S. Publication No. US 2023/0264006A1, filed Dec. 22, 2022, and entitled "Delivery Device Apparatuses, Systems, and Methods", which is hereby incorporated by reference in its entirety may be used.

Referring now to FIG. 62, in some examples, delivery devices 12 may include a delivery unit 850 and a trigger unit 852. The delivery unit 850 may be formed of a first set of components and the trigger unit 852 may at least include a trigger body 854 and may include a second set of components in some embodiments. The trigger body 854 may displace relative to the delivery unit 850 to transition the delivery device 12 from its storage state to a delivery state. The delivery unit 850 may, for example, include a main body 50, reservoir assembly 52, adhesive 56, bias member 58, and a reservoir interface member 64. The trigger unit 852 may, for example, include the trigger body 854 and a deformable spacer 856 (though the spacer 856 may form part of the delivery unit 850 in certain examples).

The trigger body 854 may be a button and may include or be coupled to at least one barrier 858A, B which may block displacement of a portion of the delivery unit 850 until the trigger body 854 is displaced by a user. For example, the at least one barrier 858A, B may impede movement of the reservoir interface member 64 in the direction of the reservoir assembly 52. In some embodiments, there may be a set of barriers 858A, B which displace in tandem and block movement of different sections of a reservoir interface member 64 (e.g. sections on opposite sides of the reservoir interface member 64 or sections spaced about the reservoir interface member 64 perhaps at regular angular intervals). The deformable spacer 856 may hold the trigger body 854 in a blocking position and may deform upon application of pressure to make way for the trigger body 854 and barrier(s) 858A, B to displace to a trigger position. The deformable spacer 856 may be a spring, elastomeric body, gas bladder, or any other compliant member in various examples. Alternatively, the deformable spacer 856 may be a flexure formed integral to the trigger body 854 or a portion of the main body 50. The deformable spacer 856 may also be a frangible in certain implementations which may permanently distort or break upon application of pressure. Once the trigger unit 852 has reached the trigger position, the bias member 58 may propel the reservoir interface member 64 in the direction of the reservoir assembly 52 to expel the contents of the reservoir assembly 52.

In some embodiments, a series of barriers 858A, B may divide displacement of the reservoir interface member 64 into a number of stages. For example, a first barrier 858A (or set of first barriers 858A) may inhibit displacement of the reservoir interface member 64 until the trigger body 854 is displaced to the triggered position. A second barrier 858B (or set of second barriers 858B) may be displaced to a blocking position as the trigger unit 852 is driven to the trigger position. The reservoir interface member 64 may partially displace to an intermediate point in its displacement range due to the presence of the second barrier 858B (or set of second barriers 858B). As pressure upon the trigger unit 852 is released, the deformable spacer 856 may restore to a less distorted state and the second barrier 858B (or set thereof) may be urged to an unobstructing position. This may free the reservoir interface member 64 to displace to a second end of its displacement range allowing the reservoir interface member 64 to bring the reservoir assembly 52 to its depleted state under the urging of the bias member 58.

Referring now to FIGS. 63A-63F, a number of diagrams of portions of an example delivery device 12 of the variety described in relation to FIG. 62 are depicted. With reference to FIG. 63A, a portion of a delivery unit 850 is depicted alone. As shown, certain exemplary delivery units 850 may include at least one guide track 860. Each of the at least one guide track 860 may be defined as a recess or ledge included in a side wall of a portion of the main body 50. Each guide track 860 may generally slope or ramp from a first end of the main body 50 toward an end of the main body 50 including the peripheral region 830. A barrier channel 866 may be disposed somewhere in the intermediate region of each guide track 860 and may accept the barrier 858A when the barrier 858A is in the trigger position. The reservoir interface member 64 may be propelled by a bias member 58 to displace along the guide track(s) 860 upon triggering of the delivery device 12. As mentioned above, and as shown in FIGS. 63A-63F, the reservoir interface member 64 may be blocked from fully displacing along each guide track 860 by a second barrier 858B when the trigger unit 852 is in a trigger position. As pressure on the trigger unit 852 is relieved, the second barrier 858B may retract allowing the reservoir interface member 64 to continue displacement to a terminal point in its displacement range. Thus, such a delivery device 12 may be triggered over two stages. In the first stage, the reservoir interface member 64 may traverse an upstream portion of each guide track 860 and in the second stage the reservoir interface member 64 may proceed to the end of its displacement range along a downstream region of each guide track 860.

In the embodiment depicted in FIGS. 63A-63F, the guide track 860 shown includes an initial region 862 which is separated from a knoll region 864 of the guide track 860 by the barrier channel 866. The exemplary guide track 860 may also include a terminal region downstream of the knoll region 864. The initial region 862 may be sloped so as to form a ramp. Upstream of the initial region 862 may be a wall or backstop 861 which blocks motion of the reservoir interface member 64 in that direction. The portion of the knoll region 864 most proximal the initial region 862 may be positioned substantially at a point falling on a line at the same angle as the initial region 862 which bridges the barrier channel 866 (line shown in phantom in FIG. 63A). Alternatively, the portion of the knoll region 864 most proximate the initial region 862 may be below this point (that is, closer to the bottom of the barrier channel 866). The terminal region 868 may be a track which extends at a sharp angle or is substantially parallel to the barrier channel 866. The terminal region 868 may also act as a barrier channel for a respective second barrier 858B included in the delivery device 12. The knoll region 864 may be at a constant angle or, as shown, may transition from the angle of the initial portion 862 (or some other angle) to the angle of the terminal portion 868. Though the knoll region 864 displays a rounded transition in the example, the transition may be formed of a series of increasingly steeply angled guide track segments 860 in alternative embodiments.

Referring now primarily to the progression of FIGS. 63B-63F, the portion of the delivery device 12 is shown as the delivery device 12 is transitioning from a storage state to a delivery state. As shown in FIG. 63B, in the storage state, the reservoir interface member 64 of the delivery unit 850 may be positioned over the initial region 862 of the example guide track 860. Where multiple guide tracks 860 are included, each may be identical and a portion of the reservoir interface member 64 may be positioned in the initial region 862 of each guide track 860.

The bias member 58 (represented by an arrow in FIG. 63B) may supply a bias against the reservoir interface member 64 which tends to drive the reservoir interface member 64 along the guide track 860 in the direction of the terminal portion 868. A first barrier 858A may be partially within the barrier channel 866 of each guide track 860 and inhibit displacement of the reservoir interface member 64 along the guide track 860 under the urging of the bias member 58. As shown in FIG. 63B, the barrier(s) 858A may be held in a blocking position by the deformable spacer 856. In FIG. 63B, an arrow representing force exerted by a spring type deformable spacer 856 is shown within each barrier 858A, B.

Referring now primarily to FIG. 63C, the reservoir interface member 64 may remain static relative to the guide track(s) 860 as a user begins to apply pressure to the trigger unit 852. The pressure exerted through the trigger body 852 may cause the main body 50 to press against an injection site. As this occurs at least two adhesive bearing portions (e.g. petal member 90) of the main body 50 may be displaced with respect to one another so as to stretch or spread a surface anchored to the main body 50 via the adhesive 56. As these portions may be adhered to the skin surface, the skin may be stretched as the adhesive bearing portions are displaced with respect to one another rendering it taut for piercing by the delivery sharp(s) 72 of the delivery device 12. The delivery sharp(s) 72 may also displace toward and pierce the skin (or other surface) as this occurs.

Referring now to FIG. 63D, the trigger unit 852 may displace at least until the first barrier 858A reaches an unobstructing or stowed position. This may be a guide track completing position in which a ramp surface 870 of each first barrier 658A is advanced to a position in which it is at least even with initial region 862 of the respective guide track 860. Thus, in the trigger position, the first barrier(s) 858A may not present an interference to displacement of the reservoir interface member 64 along the guide track 860 under urging of the bias member 58. As shown, a second barrier 858B (where included) may be displaced into the terminal portion 868 of each guide track 860 when the trigger unit 852 is in the trigger position. With the first barrier(s) 858A in their trigger position(s), the bias member 58 may drive the reservoir interface member 64 over the ramp surface(s) 870 of the first barrier(s) 858A and along the guide track 860 toward the terminal region 868. Though in the example embodiment the ramped portion 870 is displaced even with the guide track 860 it could be displaced to a position in which it is recessed with respect to the initial portion 862 in certain examples.

Referring now primarily to FIG. 63E, in embodiments where second barriers 858B are included, the reservoir interface member 64 may progress to an intermediate point in its displacement range at which it contacts the second barrier(s) 858B. At some point after the reservoir interface member 64 has progressed beyond the initial region 862 of the guide track(s) 860, the reservoir interface member 64 may come into contact with the reservoir assembly 52. Further progress of the reservoir interface member 64 along the guide track(s) 860 may cause a reservoir portion 100 of the reservoir assembly 52 to collapse expelling fluid from the reservoir assembly 52 and out of the delivery sharp(s) 72 of the delivery device 12. When the reservoir interface member 64 reaches the terminal region 868 of the guide track 860 (see FIG. 63F), the reservoir portion 100 may be fully collapsed and the reservoir assembly 52 may be substantially empty or depleted. In embodiments including second barriers 858B, the intermediate point at which the reservoir interface member 64 encounters the second barriers 858B may be a point at which the reservoir interface member 64 comes into contact with the reservoir portion 100. Pressure may need to be relieved on the trigger unit 852 allowing the second barrier(s) 858B to retract before the reservoir interface member 64 may pass to the terminal region 868 of the guide track 860.

Use of such a delivery device 12 may provide a number of potential advantages. For example, the guide track 860 may prevent the full force of the bias member 58 from being exerted on the reservoir assembly 52 in a binary manner. Thus, the pressure applied on the reservoir assembly 52 via the bias member 58 may be decreased during an initial portion of the delivery by inclusion of a guide track 860. The steepness or angle of the guide track 860 may be adjusted to increase or decrease the component of force exerted by the bias member 58 which is aligned with the direction of motion of the reservoir interface member 64 toward the reservoir assembly 52. Thus, the pressure exerted by the bias member 58 upon commencement of delivery may be altered. Such a guide track 860 may also be used in conjunction with a flow restrictor 105 (see, e.g., FIG. 6) in certain implementations.

Such a delivery device 12 may also facilitate positioning the reservoir interface member 64 in spaced relation to the reservoir assembly 52 when the delivery device 12 is in a storage state. Upon transition of the trigger unit 852 to the trigger position, the reservoir interface member 64 may be brought into contact with the reservoir portion 100, but prevented from aggressively driving into and impacting the reservoir assembly 52 by the presence of the second barrier(s) 858B. This may assist in initiating the expulsion of fluid from the reservoir assembly 52 in a more gentle manner. Additionally, it may allow for a greater range of reservoir portion 100 materials or material thicknesses to be used in a delivery device 12.

Referring now to FIGS. 64A-64B, exploded views of an example embodiment of a delivery device 12 are depicted. The delivery device 12 may include a delivery unit 850 and a trigger unit 852. The main body 50 of the delivery unit 850 may include a peripheral region 830 and a central region 68. The peripheral region 830 may include a plurality of petal members 90. Any of the petal members 90 shown or described herein may be used. The central region 68 may include a rigid guide body 872. The rigid guide body 872 may include a sidewall 874 extending from a base 861 of the central region 68. As best shown in FIG. 64B, the interior face of the sidewall 874 may include a number of guide tracks 860. The guide tracks 860 are depicted as cam type tracks, thus the reservoir interface member 64 will rotate as it progresses through its displacement range along the tracks 860. The face of the rigid guide body 872 most distal the peripheral region 830 may include a central depression or cup 876. The cup 876 may be a locating recess which may assist in locating the deformable spacer 856 of the trigger unit 852 (a compression spring in the example depicted). The trigger body 854 may also include a locating projection 878 for the deformable spacer 856. A number of apertures may be included to allow for passage of the barriers 858A, B of the trigger body 854 into the interior of the rigid guide body 872.

The delivery unit 850 may include a bias member 58 (e.g. compression spring as shown). The opposing side of the cup 876 may provide a projection which may help locate the bias member 58 within the delivery unit 850. The reservoir interface member 64 may be a plunger having a number of outwardly (e.g. radially) extending protrusions 880. Each of the protrusions 880 may interface with one of the guide tracks 860 defined on the sidewall 874 of the rigid guide body 872. The guide tracks 860 and the protrusions 880 may be spaced at regular angular intervals.

Referring now also to FIG. 64C, a cross-sectioned view of the main body 50 and trigger body 854 of FIGS. 64A-64B are depicted. The portion of the rigid guide body 872 most distal to the base 861 of the central region 28 has also been removed for illustrative purposes. As shown, the barriers 858A, B of the trigger body 854 may be formed monolithically with the trigger body 854. The barriers 858A, B depicted in the example embodiment are formed as peg like projections extending from an end surface of the trigger body 854. In the example, each barrier 858A, B is defined as a region of the same projection though discrete projections for each barrier 858 A, B could be included in alternative embodiments. The barriers 858A, B may be aligned with the barrier channel 866 and terminal region 868 of a respective guide track 860 such that they may displace into these features when the trigger body 854 is brought to a trigger position. Additionally, the trigger body 854 may include at least one guide fin 882. The guide fin 882 may displace along a slot 884 defined in the rigid guide body 872. This may assist in directing displacement of the trigger body 854 during operation and may inhibit rotational displacement of the trigger body 854. The guide fin(s) 882 may also assist in retaining the trigger body 854 in relation with the main body 50 and may thus be referred to as a retention fin or projection herein.

An alternative embodiment a delivery device 12 including a delivery unit 850 and a trigger unit 852 is shown in FIGS. 65A-67. As shown, the example delivery device 12 shown in FIG. 65A includes a lock 890 (shown in isolation in FIG. 66). The lock 890 may preferably be formed of a single piece of injection molded material. In the example embodiment, the lock 890 includes a base portion 892 from which a set of arm members 894 extend. The base portion 892 may include a first segment 896 having a protuberance 898. The base portion 892 may also include a second segment 900. The second segment 900 may include a peripheral wall 899 along its edges. The second segment 900 may also include a passage 902 defined therein which extends from an exterior face of the base portion 892, through the lock 890, to an interior face of the base portion 892. The passage 902 may taper from a first cross-sectional area to a second cross-sectional area smaller than the first as distance from the exterior face increases. In the example, the first and second segments 896, 900 are connected by a living hinge 904.

As best shown in FIG. 65B, the second segment 900 may include a receptacle 905. The receptacle 905 may accept a protruding body 907 of the reservoir assembly 52 in which a septum 94 is retained. When the lock 890 is engaged with the delivery device 12 and the protruding body 907 is in the receptacle 905, the passage 902 may be aligned with the septum 94. The passage 902 may thus form a sharp guide which may direct a dispensing sharp 302 (e.g. a needle attached to a syringe or automated filling station) into alignment with the septum 94. The receptacle 905 may also help ensure that the delivery device 12 is placed into the lock 890 in a prescribed orientation.

Still referring to FIGS. 65A-67, as shown the height of the arm members 894 may be selected such that the trigger unit 852 rests on or is in close proximity to a face of the lock 890. The opposite side of lock 890 may rest on the peripheral region 830 of the main body 50 which may support the lock 890. With the lock 890 supported by the peripheral region 830, the trigger unit 852 may be blocked from displacing due to the interference presented by the lock 890. As shown, the base portion 892 may also include a wall which blocks displacement of the trigger unit 852 relative to the delivery unit 850. As the lock 890 may prevent displacement of the trigger unit 852, the lock 890 may inhibit inadvertent actuation of the delivery device 12 during handling or shipping. It may be required that the lock member 890 be removed from the delivery device 12 before use.

The arm members 894 may be displaceable relative to one another so as to alter the gap between the arm members 894. When the arm members 894 are in a home position, the shape of the arm members 894 may cradle the central region 68 of the main body 50 of the delivery device 12 retaining it in place between the arm members 894. The arm members 894 may be displaced to a spread state in which the delivery device 12 is released from the lock 890. When the arm members 894 are in a spread position, the arm members 894 may be biased toward the home position (shown in FIG. 65A and FIG. 66). In the example embodiment, a user may press on the protuberance 898 and displace it toward the most proximal face of the peripheral wall 899 of the second segment 900. This may distort the base member 890 at the living hinge 904 spreading the arm members 894 apart from one another. The material forming the lock 890 may be selected so as to elastically distort as this occurs. When force is relieved, the material may restore to a resting state and the arm members 894 may return to a home position. Alternatively, the lock 890 may be formed of multiple pieces and the living hinge 904 may be replaced by a hinge coupling the first and second segments 896, 900 of the base portion 892.

The protuberance 898 may include a serif 906 at its unsupported end. The serif 906 may collide with the wall 899 of the second segment 900 when the user pinches the protuberance 898 towards the second segment 900. Thus the serif 906 may provide a stop which inhibits excess deformation of the lock 890 when the arm members 894 are spread. The unsupported ends of the arm members 894 may form a lead in feature which assists in installing the lock 890 on the delivery device 12 during manufacture or packaging. In the example, the interior faces 910 of the end regions 908 of the arm members 894 are angled such that the gap between the arm members 894 increases as proximity to the ends of the arms members 894 increases. Thus, the end regions 908 of the arm members 894 may guide the delivery device 12 into place as it is pressed into the lock 890.

Referring now primarily to FIG. 67, an exploded view of the example delivery device 12 depicted in FIG. 65A is shown. As mentioned above, the example delivery device 12 includes a delivery unit 850 and a trigger unit 852. The central region 68 of the main body 50 may define a housing 912. Referring now also to FIG. 68, a guide insert 914 may also be included in the delivery unit 850. The interior face of the guide insert 914 may include a number of guide tracks 860. The guide tracks 860 are depicted as cam type tracks, thus the reservoir interface member 64 will rotate as it progresses through its displacement range along the tracks 860. The guide insert 914 may include a number of cantilevered latch projections 916. When the guide insert 914 is advanced into the housing 912 during assembly, the latch projections 916 may deflect toward the longitudinal axis of the guide insert 914. Referring now also to FIG. 69, after the guide insert 914 has been advanced beyond a certain distance into the housing 912, the latch projections 916 may reach respective fenestrations 918 in the housing 912 allowing them to restore outward from their deflected states. The latch projections 916 may each include a step 920 which may latch into place against a ledge 922 defined in the wall of the fenestration 918. This may retain the guide insert 914 in place within the housing 912. Use of a guide insert 914 in place of a rigid guide body of the type described in FIGS. 64A-C may simply manufacture of the delivery device 12. The delivery device 12 described in relation to FIGS. 64A-C may be modified to include a guide insert 914 instead or a rigid guide body.

Referring now also to FIG. 69, the main body 50 may include a number of swaged posts 924. The swaged posts 924 may be molded as pegs and the reservoir assembly 52 may be inserted into the main body 50. The molded pegs may be disposed at various positions around the periphery of the reservoir assembly 52. With the reservoir assembly 52 in place, the molded pegs may then be swaged (e.g. heat swaged) over a face of the reservoir assembly 52. Once this is completed, the swaged posts 924 may retain the reservoir assembly 52 in place within the delivery device 12.

The end of the housing 912 most distal the peripheral region 830 includes a central depression or cup 876. The cup 876 may be a locating recess which may assist in locating the deformable spacer 856 of the trigger unit 852 (a compression spring in the example depicted). As with embodiments described in relation to FIGS. 64A-C, the trigger body 854 may also include a locating projection 878 for the deformable spacer 856. A number of apertures may be included in the housing 912. Barriers 858A, B of the trigger body 854 (further described in relation to FIGS. 62-64C) may displace into the interior of the housing 912 through the apertures. The trigger body 854 may additionally include at least one guide fin 882 which may displace along a slot 884 defined in the housing 912. This guide fin 882 may assist in directing displacement of the trigger body 854 relative to the delivery unit 850 and prevent rotational displacement of the trigger body 854.

Still referring to FIG. 69, the opposing side of the cup 876 in the housing 912 may provide a projection 926. The projection 926 may help locate a bias member 58 of the delivery unit 850 in place. In some embodiments, the end of the main body 50 defining the cup 876 may be constructed of a material which differs from the rest of the main body 50. The main body 50 may, for example, be formed using multi-shot molding. The end including the cup 876 may be formed of a more rigid material than the remainder of the main body 50. In some examples, the end including the cup 876 may be formed of a polycarbonate material while the remainder of the main body 50 may be a polypropylene material. In some embodiments, the main body 50 may be formed of one material, however, the end region including the cup 876 may be formed with greater wall thicknesses or otherwise buttressed with additional material. In alternative embodiments, a rigid member (e.g. metallic or steel body) may be placed against or molded into the end region including the cup 876. This inhibit any creep or deformation of the material during storage and may facilitate use of a greater range of bias members 58 and deformable spacers 856.

The example delivery device 12 includes a plunger as the reservoir interface member 64. The plunger includes a number of outwardly extending protrusions 880 which may interface with one of the guide tracks 860 of the guide insert 914. The example embodiment shown in FIGS. 65A-67 includes a plunger with three outwardly extending protrusions 880 at regular angular intervals. In other examples, such as those shown in FIGS. 64A-C, four evenly spaced protrusions 880 may be included. The bias member 58 may press the protrusions 880 against respective guide tracks 860. This in turn, may prevent the guide insert 914 from advancing further into the housing 912.

As the trigger body 854 is displaced toward the delivery unit 850, the barriers 858A, B of the trigger body 854 may move relative to the guide tracks 860. This may allow the plunger to advance toward the reservoir assembly 52 along the guide tracks 860 as further described in to FIGS. 63A-64C. When the user releases the trigger body 854, the deformable spacer 856 may urge the trigger body 854 and barrier 858A, B to again displace in relation to the guide tracks 860. This may allow the plunger to further advance toward the reservoir assembly 52 and expel fluid from the delivery device 12 as further described in relation to FIGS. 63A-64C.

As shown best in FIG. 67, the main body 50 may include at least one reservoir fill verification aperture 928. The aperture(s) 928 may be positioned so as to provide a line of sight to the reservoir portion 100 of the reservoir assembly 52. When the reservoir assembly 52 is in a filled state, the reservoir portion 100 may be in a raised state. After the reservoir assembly 52 is loaded with agent, the delivery device 12 may be positioned such that an imager may view the reservoir portion 100 via a fill verification aperture 928. An image may be taken of the delivery device 12 through the fill verification aperture 928. A controller may analyze the image to determine whether the reservoir portion 100 is in a position consistent with the reservoir assembly 52 being in an appropriate filled state. The delivery device 12 may be associated with a unique identifier (e.g. data matrix) on an exterior of the delivery device 12. The image from the imager and a pass/fail determined by the controller may be associated with a record of the unique identifier for that delivery device 12 which is stored in a database (e.g. cloud database). In the event the image analysis performed by the controller indicates that the reservoir assembly 52 is not properly filled, an alert may be generated by the controller and the delivery device 12 may be segregated to prevent its use. Other sensing hardware may be used in alternative embodiments. For example, a beam break sensor could utilized to monitor for the raising of the reservoir portion 100 when the reservoir assembly 52 is brought to a filled state.

Referring now also to FIG. 70, a diagrammatic representation of an example trigger body 852 is depicted. As shown, the trigger body 852 includes only a single first barrier 858A. This is merely illustrative, the trigger body 852 may include a first barrier 858A for each respective guide track 860 within a delivery device 12. The first barriers 858A may gate displacement of the reservoir interface member 58 as described in relation to FIGS. 63A-64C. The trigger body 852 may be devoid of second barrier members 858B. The trigger body 852 may also include at least one integral deformable spacer 856. In the example embodiment, the deformable spacer 856 is a cantilevered latch projection. The latch projection includes a step 930 at the unsupported end thereof. The latch projection is disposed at a non-parallel angle to the long axis of the trigger body 852.

When the trigger body 852 is displaced toward a delivery unit 850, the cantilevered projection may collide with a wall of the main body 50 and deflect. For example, the cup 876 of the housing 912 may have a chamfered or filleted opening (see, e.g. FIG. 67) which guides the deflection such that the cantilevered latch projection is directed into the cup 876. As the trigger body 852 reaches the end of its displacement range, the step 930 of the cantilevered latch projection may reach a ledge defined on the main body 50 and the latch projection may restore to a less deflected state and into engagement with the ledge. There may be an opening in the wall of the cup 876 and a sidewall of the opening may serve as the ledge 876 for instance. With the latch projection in the engaged position, the first barriers 858A may be in unobstructing states and the reservoir interface member 64 of the delivery device 12 may be driven along the guide tracks 860 and against the reservoir assembly 52 by the bias member 58. The trigger body 852 may be held in a depressed state by the engagement of the step 930 with the ledge. Additionally, the force required to deflect the cantilevered latch projection may ensure that the petal members 90 spreadingly displace before the trigger body 852 is pressed to the end of its displacement range and the first barriers 858A reach an unobstructing position. This may prevent reuse and serve as an indicator that a delivery device 12 has already been consumed.

Though the cantilevered latch projection is shown extending from the trigger body 852 it could be included as part of the main body 50 in other embodiments. In such examples, the trigger body 852 would define the ledge on which the step 930 engages.

Referring now to FIGS. 71A-72B, in some embodiments, a delivery device 12 may include an indicator which communicates whether the delivery device 12 has been used. An example delivery device 12 with a trigger unit 852 and delivery unit 850 is depicts in FIGS. 72A-72B. As with the embodiments described in FIGS. 63A-64C and FIGS. 65A-69, example delivery devices 12 may include a reservoir interface member 64 such as a plunger. The reservoir interface member 64 may include regions of contrasting appearance 855A, B as shown in FIGS. 71A-71B. For example, a first portion of the reservoir interface member 64 may be a first color and another region may be a second color. In some embodiments, the contrasting appearance may be accomplished through use of an applique, paint, or the like which is applied after the reservoir interface member 64 is manufactured. Alternatively, the reservoir interface member 64 may be given regions of contrasting appearance 855A, B during molding. For example, a different color material may be overmolded onto a precursor reservoir interface member 64 to complete the reservoir interface member 64. Multi-shot molding or any other suitable method may be used.

As mentioned above, when the delivery device 12 is used, the reservoir interface member 64 may translationally displace against the reservoir assembly 52 and may rotationally displace along the guide tracks 860. The main body 50 of the delivery device 12 may include one or more window 859 in the central region 68. In some examples, a fill verification aperture 928 may serve as the window 859. When the delivery device 12 is in the storage state, a portion of the reservoir interface member 64 having a first appearance may be in alignment with the window(s) 859. As the reservoir interface member 64 is displaced to its post usage position, a portion of the reservoir interface member 64 having a second appearance may displace into alignment with the window(s) 859. In some examples, a bottom region of the reservoir interface member 64 may have the first appearance and the top region may have a second appearance. The translational displacement of the reservoir interface member 64 may cause the bottom region to displace out of the field of view of the window 859 while the top region displaces into the field of view of the window 859. Alternatively and as shown in FIGS. 71A-71B, the side wall of the reservoir interface member 64 may have a least one strip or section having a second appearance while the remainder of the side wall has the first appearance. As the reservoir interface member 64 rotates while it travels along the guide tracks 860, the section(s) having the second appearance may rotate into alignment with the window(s) 859. Thus the portion of the reservoir interface member 64 with the second appearance may be revealed once a delivery device 12 is used. In still other embodiments, the indicator may be a stripe or line (see, e.g., FIG. 67) included on the reservoir interface member 64 which passes into alignment with a window 859 when the reservoir interface member 64 displaces. Regardless of the indicator used, a user or caregiver may look at the window(s) 859 to quickly determine if a particular delivery device 12 has been used. A user or caregiver may also monitor the window 859 when a delivery device 12 is applied to a user and triggered. This may allow a user to verify that the delivery device 12 properly actuated and that agent should have been delivered from the reservoir assembly 52.

Figure 73A:
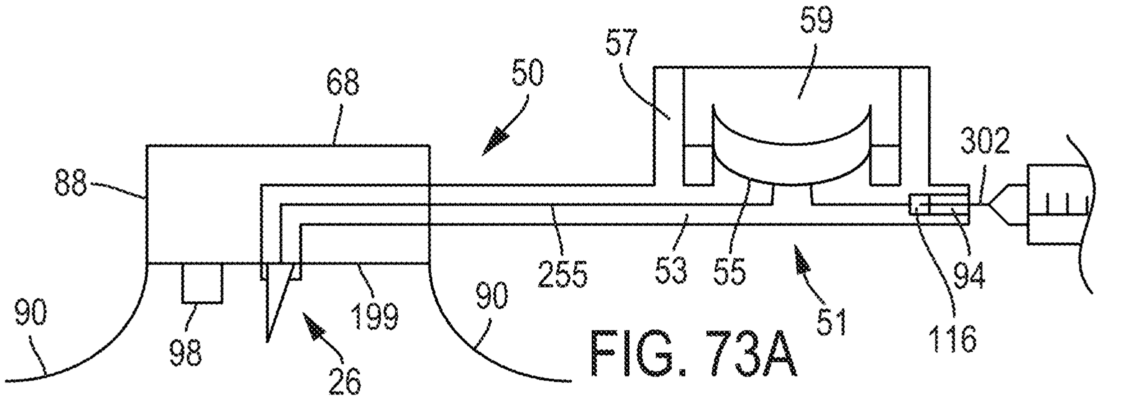
Figure 73B:
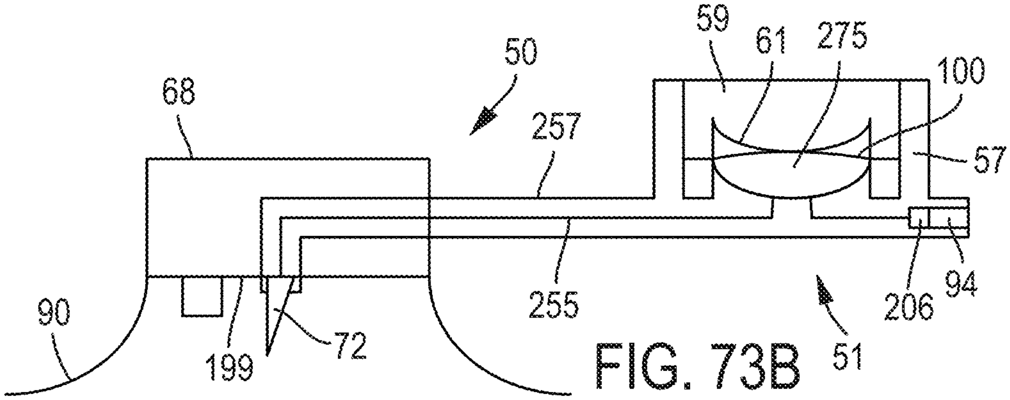

Referring now to FIGS. 73A-73B, a diagram of an example embodiment of a delivery device 12 is depicted. As shown, the delivery device 12 may include a main body 50. The main body 50 may include a central region 68 with a supporting region 88 and petal members 90. The main body 50 and portions thereof may be any of those shown or described in herein or in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023 which is hereby incorporated herein by reference in its entirety.

In certain examples, the central region 68 may be modified. The central region 68 may not be deformable or invertible. Instead, the central region 68 may be a resilient pressure application surface and may remain substantially undistorted when the delivery device 12 is actuated. The central region 68 may form a slight bowl or thumb depression to facilitate ergonomic application of force on the central region 68.

The example delivery device 12 includes an outboard reservoir 51 that is disposed outside of the main body 50. In place of the reservoir assemblies 52 shown with respect to various other delivery device 12 embodiments described herein, a platform 199 may be coupled to the main body 50. A sharp bearing body 26 may be coupled to platform 199 (e.g. via adhesive or overmolding). The sharp bearing body 26 may be disposed on or molded into a stage projection 110 extending from the platform 199 for example. The platform 199 may also include a rocker member 92. As the delivery device 12 includes an outboard reservoir 51, no bias member 58 or reservoir interface member 64 may be present within the receptacle formed by the central region 68. Additionally room for the filled main interior volume 275 of a reservoir assembly 52 may not be needed in the receptacle formed by the central region 68. The supporting structure 88 height may thus be truncated.

The platform 199 may be coupled to the outboard reservoir 51 via a flow path 255 so as to place the main interior volume 275 of the outboard reservoir 51 in fluid communication with the lumens 125 of the sharp bearing body 26. The flow path 255 may be created in any number of suitable manners. A conduit 262 may, for example, span between the platform 199 and the outboard reservoir 51. In other examples, the platform 199 may be integrally connected to a rigid portion of the outboard reservoir 51 and be formed monolithically therewith. There may, for example, be a bridge 257 of material running between the platform 199 and the rigid portion of the outboard reservoir 51. A recessed channel may extend from an outlet of the main interior volume 275 along the bridge 257, across the platform 199, and into communication with the sharp bearing body 26. A rigid or flexible piece of material may be coupled over the recess to sealingly enclose the recess and create the flow path 255. In such embodiments, the piece of material may be coupled over the recessed channel by heat stake, laser weld, or in any other suitable manner. The main body 50 may include an aperture 91 or widened slot 170' to allow passage of the flow path 255 through the wall of the main body 50.

Exemplary outboard reservoirs 51 may include a base portion 53 which may be rigid. The base portion 53 may be formed as a single injection molded part or may be formed of an assembly of parts which are coupled to one another. The base portion 53 may include a bay 202 in which a septum 94 is retained (e.g. by swaging a peripheral wall 212 of the bay 202 over the septum 94). The base portion 53 may also include a depression 55. A reservoir portion 100 may be coupled to the base portion 53 surrounding the depression 55 in a fluid tight manner. The depression 55 and reservoir portion 100 may together define the main interior volume 275 of the outboard reservoir 51. The reservoir portion 100 may be displaceable and formed of a sheet of flexible material such that the main interior volume 275 may be variable. As shown, the main interior volume 275 may be provided substantially empty. The main interior volume 275 may be filled by inserting a delivery sharp 302 through the septum 94. With the tip 116 of the delivery sharp 302 placed into fluid communication with a receiving volume 206 intermediate the interior face of the septum 94 and the main interior volume 275, fluid may be dispensed into the outboard reservoir 51 through the delivery sharp 302. The reservoir portion 100 may displace to accommodate the fluid until a desired volume has been transferred into the main interior volume 275 as shown in FIG. 73B. The length and cross-sectional area of the flow path 255 may inhibit fluid from reaching the lumens 125 in the sharp bearing body 26 as the outboard reservoir 51 is loaded with fluid. The example septum arrangement shown in FIGS. 73A-73D is merely exemplary. Any reservoir assembly 52 including a septum 94 shown or described herein may be modified into an outboard reservoir 52. That is, any of the septum 94 arrangements described herein may be included in an outboard reservoir 51.

The base portion 53 may also include a guide 57. The guide 57 may at least partially surround the depression 55. The guide 57 may confine displacement of a delivery body 59 which may be driven against the reservoir portion 100 to expel fluid from the outboard reservoir 51 toward the sharp bearing body 26. The delivery body 59 may include a contact face 61 which is dimensioned to mimic the shape of the depression 55. Thus as the delivery body 59 is driven into the reservoir portion 100, the main interior volume 275 of the outboard reservoir 51 may be substantially emptied. Such an arrangement may be utilized in any outboard reservoir described herein to facilitate maximal emptying of the main interior volume 275.

The guide 57 may constrain the delivery body 59 such that the contact 61 face is aligned and centered over the depression 55 to help facilitate a complete emptying of the main interior volume 275. The delivery body 59 may include retention members (e.g. bard or snap fit features) which may couple into receiving features on the base portion 53 when the delivery body 59 is displaced. Additionally, the delivery body 59 may be held in a raised state by one or more frangible in certain examples. As a user applies force to the delivery body 59, the frangibles may break allowing displacement of the delivery body 59. Though shown displacing within the guide 57, in certain examples the delivery body 59 may have a portion which at least partially surrounds the guide 57 in alternative embodiments of the outboard reservoirs 51 described herein.

Figure 73C:
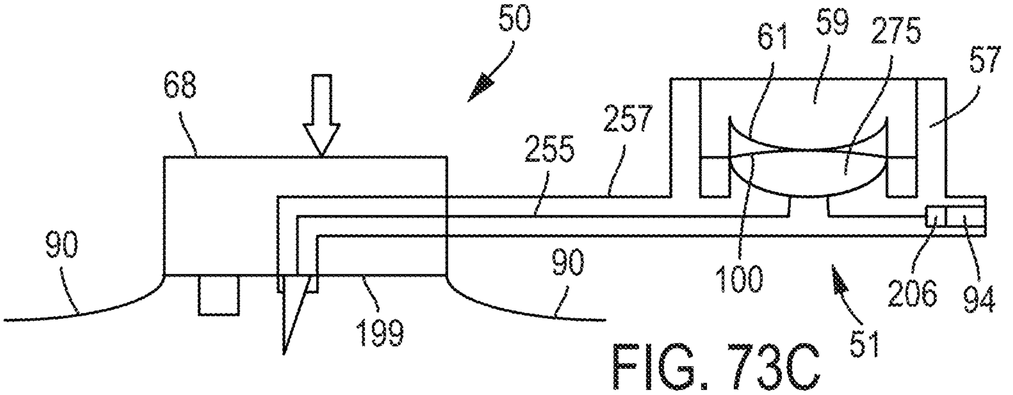
Figure 73D:
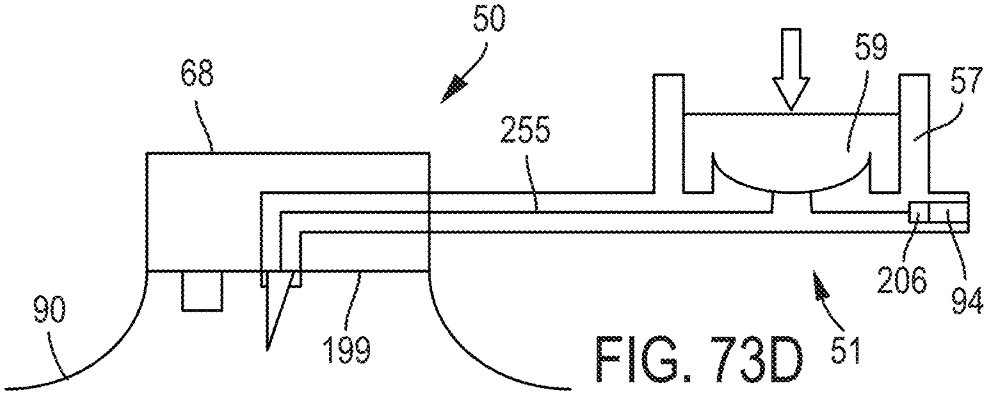

As shown in the progression of FIGS. 73A-73D, the outboard reservoir 51 may be filled, for example, shortly prior to use. The delivery device 12 may then be placed over a delivery destination on a patient. The delivery device 12 may include an adhesive pad such that at least the petal members 90 of the delivery device 12 are adhesive bearing. A user may press the central region of the main body 50 toward the delivery destination as depicted in FIG. 73C. This may cause a spreading displacement of the petal members 90 and the skin coupled thereto via the adhesive. The delivery sharps 72 on the sharp bearing body 26 may puncture the skin as this occurs. When force is relieved, the petal members 90 may be arranged such that the main body

50 restores or recoils from its maximally distorted state at least partially toward its undistorted state as further described elsewhere herein. The delivery body 59 may then be driven from a ready state to an actuated state (see FIG. 73D) to dispense fluid from the outboard reservoir 51 through the delivery sharps 72 and into the delivery destination. The delivery device 12 may be removed after delivery is completed. In some implementations, delivery may be verified as shown and described in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023 which is hereby incorporated herein by reference in its entirety.

Referring now to FIGS. 74A-74C, an exemplary embodiment of a delivery device 12 with an outboard reservoir 51 is depicted. As shown, the delivery device 12 includes a main body 50 with a number of petal members 90. The central region 68 of the main body 50 is a rigid structure. A flow path 255 defined in a bridge 257 of material running from the outboard reservoir 51 to a platform 199 (see, e.g., FIGS. 73A-73D) is included. The delivery body 59 (best shown in FIG. 74C) may displace within a guide 57. In some embodiments, the delivery body 59 may include a set of rails 259 that may interface with the guide 57 to assist in directing movement of the delivery body 59 within the guide 57. In some embodiments, the guides 259 may displace along tracks defined in the guide 57. Alternatively, the guide 57 may include rails that interface with tracks recessed into the delivery body 59. The reservoir portion 100 may have any suitable shape and that shown in FIG. 74C is merely exemplary. Any reservoir portion 100 shown or described herein may be used. As shown in FIGS. 74A-74C, the outboard reservoir 51 may be provided pre-filled with agent. In alternative examples, and as mentioned above with respect to FIGS. 73A-73D a septum 94 may be included.

Referring now to FIG. 75, a block diagram of an example outboard reservoir 51 is depicted. In certain examples, an outboard reservoir 51 may include a dispensing assembly 60. The dispensing assembly 60 may include at least a bias member 58. Any bias member 58 shown or described herein or in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023 which is hereby incorporated herein by reference in its entirety may be used. The bias member 58 may be disposed intermediate the delivery body 59 and the reservoir portion 100 of the outboard reservoir 51. In FIG. 75, the dispensing assembly 60 also includes a reservoir interface member 64. The delivery body 59 may include a set of catches 281. As a user applies force to displace the delivery body 59 toward the base 53, bias member 58 may become stressed. The catches 281 may engage with respective retention features 283 (e.g. ledges) defined in the guide 57 holding the delivery body 59 in place. As the bias member 58 restores to a less stressed state, the reservoir interface member 64 may be driven against the reservoir portion 100. This may expel fluid from the main interior volume 275 until the reservoir portion 100 bottoms out against the base 53. Though not depicted, a septum 94 arrangement may be included in the outboard reservoir 51 depicted in relation to FIG. 75.

Referring now to FIG. 76, another block diagram of an example outboard reservoir 51 is depicted. The outboard reservoir 51 again includes a dispensing assembly 60. The dispensing assembly 60 includes a bias member 58 and a reservoir interface member 64. In place of a delivery body 59, a toggle region 285 is included at the top of the guide 57. Force may be applied to the toggle region 285 to flip the toggle region 285 from a protruding state (shown) to a depressed state (see, e.g. progression of FIG. 52 to FIG. 53. The top surfaces 66 of delivery devices shown or described herein or in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023 which is hereby incorporated herein by reference in its entirety may be incorporated into an outboard reservoir 51 as the toggle region 285 of the outboard reservoir 51. When force is applied to the toggle region 285, the toggle region 285 may flip from the protruding state to a depressed state. The distance from the reservoir portion 100 to the most proximal surface of the toggle region 285 may decrease as this occurs. In turn the bias member 58 may become stressed. The toggle region 285 may resist a return to the protruding state under the urging of the distorted bias member 58. The reservoir interface member 64 may be driven against the reservoir portion 100 as the bias member 58 restores to a less stressed state depleting the main interior volume 275 of the outboard reservoir 51. Fluid may be expelled from the main interior volume 275 of the outboard reservoir 51 until the reservoir portion 100 bottoms out against the base 53. Though not depicted, a septum 94 arrangement may be included in the outboard reservoirs 51 depicted in relation to FIG. 76.

Referring now to FIG. 77, a block diagram example embodiment of an example filling portion 17 of a system 10 is shown. The filling portion 17 may include a cartridge 304 or tray which may hold a number of reservoir assemblies 52. Any filling portions 17 having trays 304 filled with reservoir assemblies 52 may alternatively include trays 304 filled with assembled delivery devices 12. The filling portion 17 may also include a filling manifold 300 including a fluid bus 32. The fluid bus 32 may include a number of dispensing sharps 302 which may puncture into communication with the main interior volume 275 of respective reservoir assemblies 52 via septa 94 included in those reservoir assemblies 52. The filling manifold 300 and cartridge 304 may be sterilized within an overpack 306. The overpack 306 may be removed by a user when the filling portion 17 is readied for use. The sealed volume of the fluid bus 32 and main interior volumes 275 of the reservoir assemblies 52 the fluid bus 32 communicates with may provide the isolated fill environment for the system 10.

As shown, the filling manifold 300 may include a fluid introduction port 16. The fluid introduction port 16 may include an introduction port septum which may be pierced to establish access between the fluid bus 32 and a medicament supply 18. In some embodiments, the fluid introduction port 16 may be pierced by the delivery sharp of a syringe filled from a medication vial. Alternatively, a filling sharp coupled to an output line from a pumping portion 15 of a system 10 may gain access to the fluid bus 32 via the fluid introduction port 16. Where the example filling portion 17 of FIG. 77 is utilized with a pumping portion 15, the pumping portion 15 may be any of those shown and described herein.

The filling manifold 300 may include a number of variable volume fill chambers 308 disposed along the fluid bus 32. An end of the fluid bus 32 opposite the fluid introduction port 16 may include a vent 310. The vent 310 may be hydrophobic sterile filtering membrane which may allow for gas to leave the fluid bus 32 but inhibit passage of liquid agent. Each of the fill chambers 308 may, for example, include a flexible or elastomeric wall or membrane 309 which may displace or elastically distend as the fill chamber

308 is loaded with agent. The fill chambers 308 may each be separated by a fill chamber valve 312. Each of the fill chamber valves 312 may be open as the fill manifold 300 is loaded with agent. Once the fill chambers 308 have been filled with agent, the fill chamber valves 312 may be closed to isolate each of the fill chambers 308. Though four fill chambers 308 are depicted, any number may be included in a fill manifold 300.

The fill manifold 300 may also include a set of reservoir valves 314. A reservoir valve 314 may be intermediate each fill chamber 308 and the delivery sharp 302 associated with that fill chamber 308. As the fill manifold 300 is loaded with agent, the reservoir valves 314 may remain closed. Each of the reservoir valves 314 may be opened and the fill chambers 308 may be collapsed to drive agent loaded into the fill chambers 308 through the dispensing sharps 302 and into the reservoir assemblies 52.

In some embodiments, a dispenser plate 316 may be included with the filling portion 17. The example dispenser plate 316 includes a set of protrusions 318 which may be spaced and formed complimentarily to the fill chambers 308. The dispenser plate 316 may be aligned upon the filling manifold 300 (guide rails or other features may be included) and driven against the filling manifold 300. The protrusions 318 may displace into the fill chambers 308 and press the membrane 309 of the fill chambers 308 against the fill chamber 308 walls defined in the filling manifold 300. This in turn will evacuate the agent out of the fill chambers 308 and into the reservoir assemblies 52. The reservoir assemblies 52 may be provided in a collapsed state and inflate as agent is transferred into each reservoir assembly 52. Alternatively, the reservoir assemblies 52 may be elastomeric or sufficiently robust to allow gas within the reservoir assemblies 52 to pressurize as fluid is transferred thereto. In the latter arrangement, upon removal of application of pressure on the fill chambers 308, at least some of the pressurized gas may be allowed to exit the reservoir assemblies 52 through the dispensing sharps 302. The reservoir assemblies 52 may subsequently be removed and installed in delivery devices 12 for use.

In other embodiments, the reservoir assemblies 52 may be provided in a gas filled state. The fill manifold 300 may be provided with both the fill chamber valves 312 and the fill chamber valves 314 in an open state (a fill chamber value 312 between the vent 310 and an adjacent fill chamber 308 may be closed). A syringe may be placed into communication with the fluid bus 32 and gas may be aspirated from the reservoir assemblies 52 through the fluid bus 32 and fluid introduction port 16 to collapse the reservoir assemblies 52. A syringe may then be filled with agent and the agent may be loaded into the fill chambers 308. The reservoir assemblies 52 may then be filled as described above. In other embodiments, the reservoir assemblies 52 may each fluidically communicate with a filter 260 as described in various embodiments above (see, e.g., FIG. 43C). In such examples, gas may exit the main interior volumes 275 via the filters 260 as the main interior volumes 275 are loaded with agent.

Referring now to FIG. 78, another block diagram exemplary filling portion 17 of a system 10 is depicted. In some embodiments, a filling portion 17 may include a filling manifold 300 and a tray 304 which may be sterilized in a removable overpack 306. The example filling manifold 300 in FIG. 78 is devoid of fill chambers 308 and valves 312, 314 and instead includes a fluid bus 32. The reservoir assemblies 52 may be provided in the tray 304 with septa 94 prespiked by dispensing sharps 302. The filling manifold 300 and main interior volumes 275 of the reservoir assemblies 52 may provide the isolated fill environment 14 for the system 10. In alternative embodiments, the dispensing sharps 302 may be replaced with blunt filling cannulas and the septa 94 may be split septa. It should be noted that embodiments of delivery devices 12 and reservoir assemblies 52 described herein may be outfitted with split septa 94 instead of pierceable septa 94 to facilitate use of a blunt cannula for access. Likewise, any of the filling portions 17 described herein as including dispensing sharps 302 may be modified to replace the dispensing sharps 302 with blunt cannulas.

The reservoir assemblies 52 may be provided in a collapsed state and fluid communication from a medicament supply 18 to the reservoir assemblies 52 may be established by piercing the fluid introduction port 16 (e.g. a septum). The filling portion 17 may be coupled to any of the pumping portions 15 described herein or the medicament supply 18 may be a manually operated filling implement 42 depending on the embodiment. Agent may be transferred into the fluid bus 32 and delivered into the reservoir assemblies 52 through the dispensing sharps 302. The dispensing sharps 302 may be removed from the septa 94 and the reservoir assemblies 52 may be assembled into a delivery device 12 for use. In some embodiments, the reservoir assemblies 52 may be filled with gas when the overpack 306 if doffed. In such examples, a syringe or a pumping portion 15 of a system 10 may access the fluid bus 32 via the fluid introduction port 16 and a vacuum may be drawn to collapse the reservoir assemblies 52. A syringe (or other medicament supply 18) may then be used to transfer agent into the reservoir assemblies 52 via the fluid bus 32. The reservoir assemblies 52 may alternatively include filters 260 through which gas in the main interior volumes 275 may escape as the reservoir assemblies 52 are filled. Reservoir assemblies 52 may also be provided within the overpack 306 in a collapsed state in certain examples.

Referring now to FIG. 79, another block diagram example filling portion 17 of a system 10 is depicted. As shown, the filling portion 17 includes a filling manifold 300 and a tray or cartridge 304 filled with reservoir assemblies 52. The filling manifold 300, tray 304, and reservoir assemblies 52 may be sterilized within an overpack 306 which is discarded before use. Respective dispensing sharps 302 and vent sharps 320 may be in fluid communication with the interior volume 275 of each of the reservoir assemblies 52 when received in the overpack 306. The reservoir assemblies 52 may be provided in a gas filled state. A medicament supply 18 (e.g. manually operated filling implement 42 or any of the pumping portions 15 herein) may be placed into fluid communication with a first fluid bus 332 via the fluid introduction port 16. Agent may be delivered into the first fluid bus 332 and transferred into each of the reservoir assemblies 52 via the fluid bus 332 and the dispensing sharps 302. Gas in the interior volume 275 of each reservoir assembly may displace through the respective vent sharp 320 as the interior volume 275 of that reservoir assembly 52 fills with agent. The gas may exit the filling manifold through a second fluid bus 334 which includes a terminally disposed sterile filter 322 (e.g. 0.2 μm filter). The reservoir assemblies 52 are connected to the first fluid bus 332 in parallel. As a reservoir assembly 52 fills with agent, the respective vent sharp 320 may be wetted with agent. The impedance of the vent sharp 320 may cause fluid being delivered into the first fluid bus 332 to preferentially flow into any unfilled reservoir assemblies 52 until each of the reservoir assemblies 52 has reached a filled state. The vent sharps 320 and perhaps flow paths forming the second fluid bus 334 may be constructed with fluid flow passages having a relatively small cross-sectional area compared to the first fluid bus 332 and delivery sharp 302. This would increase the impedance of the second fluid bus 334 and vent sharp 320 helping to ensure that agent is delivered into each reservoir assembly 52 until they are filled.

Referring now to FIG. 80, a block diagram of an exemplary system 10 is depicted. The example system 10 includes a filling portion 17 having filling manifold 300 and a tray or cartridge 304 filled with reservoir assemblies 52. The filling manifold 300 is arranged such that the reservoir assemblies 52 may be filled in series. As with other embodiments described herein, the filling manifold 300, tray 304 and reservoir assemblies 52 may be sterilized within an overpack 306 (see, e.g., FIG. 79) which may be removed before use. The filling manifold 300 may be sealed at one end via a fluid introduction port 16 and sealed at the opposing end by a vent 310 (e.g. hydrophobic sterile filtering membrane). Each of the reservoir assemblies 52 may include a septum 94 which may be provided in a pierced state. A dispensing sharp 302 may extend from the filling manifold 300 into each of the reservoir assemblies 52. Additionally a series connecting sharp 324 may project from the filling manifold 300 and into fluid communication with the interior volume 275 of each reservoir assembly 52 via the septum 94. In certain embodiments, the flow lumens provided by the dispensing sharp 302 and the series connecting sharp 324 may be incorporated into a dual lumen sharp. Thus, both the delivery flow path and series connection may be provided by a single sharp extending through each septum 94 in certain alternative embodiments. Any reservoir assembly 52 embodiments including a filter 260 described herein may alternatively be filled with such a dual lumen sharp and the filter 260 may be omitted.

Agent may be delivered into the filling manifold 300 through the fluid introduction port 16 and may flow into a reservoir assembly 52 most proximal the fluid introduction port 16. As this reservoir assembly 52 fills, the series connecting sharp 324 in fluid communication with that reservoir assembly 52 may provide a pathway to a downstream portion of the filling manifold 300. The series connecting sharp 324 may act as a venting sharp which allows gas to be displaced out of the reservoir assembly 52 as agent is transferred in. In alternative embodiments, the reservoir assemblies 52 may be provided in a collapsed state. Once a reservoir assembly 52 is filled, agent may be transferred through the filled reservoir assembly 52 and into the downstream portion of the filling manifold 300. Agent may then travel into the next reservoir assembly 52 via the delivery sharp 302 in communication with the interior volume 275 of the next reservoir assembly 52. This may continue until all reservoir assemblies 52 have been filled and agent reaches the vent 310 at the terminal end of the filling manifold 300.

Agent may be dispensed into the filling manifold 300 in any suitable manner (e.g. via a syringe). In the example shown in FIG. 80, the system 10 includes a pumping portion 15 with a medicament container 28 (vial in the example shown). The medicament container 28 may be accessed (via a closure septum 398) by a filling spike 336 on a fill line 328. The fill line 328 may also be spiked or otherwise coupled into communication with the filling manifold 300 via the fluid introduction port 16 of the filling manifold 300. The medicament container 28 may also be accessed through a pressure line spike 326 in fluid communication with a pressure source 330. The pressure source 330 may be a hand pump, pressurized disposable cartridge, pump feed accumulator, etc. The medicament container 28 may be brought to a pressurized state and the pressure in the medicament container 28 may drive agent through the filling spike 336 and fill line 328 into the filling manifold 300 to fill the reservoir assemblies 52 in series. The pressure source 330 may be controlled to a preset pressure value with a regulator of the like to maintain a target pressure in the medicament container 28. Gas from the pressure source may be sterile filtered air in certain examples. Other pumping portions 15 described herein may be used in place of the example pumping portion 15 included in FIG. 80.

Referring now to FIGS. 81A-81B, an example embodiment of a number of reservoir assemblies 52 is depicted. As shown, the reservoir assemblies 52 are septum free and are coupled to a filling manifold 300 which is integrally formed with the reservoir assemblies 52. As shown, the filling manifold 300 may include a rigid base member 340 to which a film 342 is coupled. The rigid base member 340 may also form the rigid portion (e.g. holder 108) of each of the reservoir assemblies 52. The film 342 may be the same piece of material which forms the reservoir portion 100 of each reservoir assembly 52. As shown, the film 342 includes a number of flow channels 344 formed therein. The flow channels 344 may be thermoformed into the film 342 at the same time as the wall 104 defining the interior volume 275 of the reservoir assembly 52 is created. The film 342 may be heat staked to the rigid base member 340 to form the reservoir assemblies 52 and filling manifold 300. The holders 108 for each of the reservoir assemblies 52 may be formed at a terminal portion of respective branches 346 off a main trunk 348 of the rigid base member 340. The interior volume 275 of each reservoir assembly 52 may be in fluid communication with two flow channels 344 which extend along the branch 346 on which the reservoir assembly 52 is located. One of the flow channels 344 may provide for fluid flow into a respective reservoir assembly 52. The other of the flow channels 344 may a form path for agent to flow in serial fashion to an adjacent downstream reservoir assembly 52. A medicament supply 18 may be brought into fluid communication with the filling manifold 300 via a septum in a fluid introduction port 16 (see, e.g., FIG. 80). Agent may then be dispensed through the filling manifold 300 to fill each of the reservoir assemblies 52 serially. An end of the filling manifold 300 opposite the fluid introduction port 16 may include a vent 310 (see, e.g., FIG. 80). As with other embodiments described herein, the filling manifold 300 and reservoir assemblies 52 may be provided sterilized within an over pack 306 (see, e.g., FIG. 79) which is removed before use.

Once the reservoir assemblies 52 are filled, the reservoir assemblies 52 may be sealed. As shown, each of the branches 346 may include a hinge 350. In the example embodiment, each branch 346 includes a living hinge at which the trunk 348 may be folded over upon the branch 346. The base member 340 may include respective occluder tabs 352 for each of the branches 346 of the filling manifold 300. The occluder tabs 352 may extend from a side of the main trunk 348 opposite the branches 346. The occluder tabs 352 may include an occluder 354 which in the example shown is a raised rib or bar extending along the face of each occluder tab 352. Each occluder tab 352 may also include at least one coupling barb 356. When the trunk 348 is folded over upon the branches 346, the coupling barb(s) 356 of each occluder tab 352 may enter an engaging state with receptacles 358 defined in the branches 346. This may hold main trunk 348 and occluder tabs 352 firmly against the branches 346. The filling manifold 300 may be referred to as being in a folded state in this configuration. The occluder 354 of each occluder tab 352 may press against and collapse the flow channels 344 along the branch 346 inhibiting transfer of agent from the reservoir assemblies 52 via the flow channels 344. Additionally, the fold at the hinge 350 in the branch 346 may crush the flow channels 344 creating a redundant obstruction in the flow channels 344 which inhibits fluid flow. The main trunk 348 may include a number of weakened separation points 360. Once the reservoir assemblies 52 have been filled and the filling manifold 300 is in the folded state, the reservoir assemblies 52 may be singulated by breaking the filling manifold 300 at each of the separation points 360. This may be done by cutting the filling manifold 300 at the separation points 360. The reservoir assemblies 52 may then be installed in a delivery device 12 for use on a patient. A port 89 (see, e.g., FIG. 60B) in the supporting structure 88 of the main body 50 of the delivery device 12 and or a widened slot 170' (see, e.g., FIG. 58B) between two of the petal members 90 may be included to accommodate the branch 346 extending from the holder 108.

Referring now to FIGS. 82-84, an example reservoir assembly 52 and filling manifold 300 are depicted. As shown in FIG. 82, the reservoir assembly 52 may include a holder 108 and a reservoir portion 100. The holder 108 may include a protruding body 250 including a set of ports 362A, B. One of the ports 362A, B may be a filling port and the other of the ports 362A, B may be a series connection port. A septum 94 may be installed in the ports 362A, B to fluidically seal the ports 362A, B. The example septum 94 includes a main body 364 from which a set of plug bodies 366 for sealing each port 362A, B extend. In alternative embodiments, discrete septa 94 may be individually disposed within each port 362A, B. The holder 108 of the reservoir assembly 52 may include a set of flow recesses 254A, B formed as depressions in the face of the holder 108 to which the reservoir portion 100 is coupled. In combination with the reservoir portion 100, the flow recesses 254A, B may form fluid tight flow pathways within the reservoir assembly 52. Each of the flow recess 254A, B may have a span which is within the footprint of the main interior volume 275 of the reservoir assembly 52. Each flow recess 254A, B may be in communication with one of the ports 362A, B.

Referring primarily to FIGS. 83-84, the filling manifold 300 may include pairs of sharps spaced along the filing manifold 300. Each pair of spikes may include a dispensing sharp 302 and a series connecting sharp 324. The sharps 302, 324 may be in communication with a fluid bus 32 extending through the filling manifold 300 as described above in relation to FIG. 80. A reservoir assembly 52 may be installed onto each pair of sharps 302, 324 in the filling manifold 300 (see, FIG. 84) such that the interior volume 275 of each reservoir assembly 52 is in fluid communication with the fluid bus 32. Filling manifold 300 and reservoir assemblies 52 may be provided sterilized within an over pack 306 (see, e.g., FIG. 79) which is removed and discarded before use. The filling manifold 300 may include a fluid introduction port 16 (see, e.g., FIG. 80) and vent 310 (see, e.g., FIG. 80) as described elsewhere herein. Agent may be dispensed into the filling manifold 300 to fill the reservoir assemblies 52 in series. Reservoir assemblies 52 may be removed from the filling manifold 52 once filled and subsequently installed in a delivery device 12.

Referring now to FIG. 85, an example block diagram of a filling manifold 300 and number of delivery devices 12 is depicted. In the example, each of the delivery devices 12 is shown with a septum 94 spiked onto an access sharp 368 in fluid communication with a fluid bus 32. The example fluid bus 32 is arranged for serial filling of delivery devices 12 in spiked onto the access sharps 368. The fluid bus 32 together with the main interior volumes 275 of the reservoir assemblies 52 may provide an isolated fill environment 14 for the delivery devices 12. A filling implement 42 (see, e.g., FIG. 89) may be placed into fluid communication with the fluid bus 32 via a fluid introduction port 16 (e.g. septum) coupled to the filling manifold 300. Agent may be transferred out of the filling implement 42 and into the delivery devices 12 through the fluid bus 32.

As best shown in FIG. 86, the filling manifold 300 may be created from one or more piece of a sheeting 343. For example, two pieces of sheeting 343 may be coupled to one another or a single piece of sheeting 343 may be folded upon itself to form the walls of the filling manifold 300. The access sharps 368 may include body 345 which extends radially outward from the each access sharp 368. The body 345 may be overmolded onto the access sharp 368 in certain examples. The sheeting 343 may be bonded to the body 345 to create a fluid tight coupling between the body 345 and the sheeting 343. The body 345 may have a boat like cross-sectional shape to facilitate coupling of the sheeting 343 to the body 345. The sheeting 343 may be heat staked to the body 345 in certain examples. The fluid introduction port 16 may be similarly coupled to the sheeting 343 of the filling manifold 300. Use of sheeting 343 and access sharps 368 (and fluid introduction ports 16) with bodies 345 may facilitate construction of a cost effective, rapidly producible, and robust, filling manifold 300.

As shown in FIG. 87, the sheeting 343 may also be coupled to itself when the filling manifold 300 is formed. This may, for example, be done by heat staking the sheeting 343 together. When the sheeting 343 is coupled to itself, flow pathways 347 may be formed by leaving certain regions of the sheeting 343 uncoupled. A main pathway and branches to each of the access sharps 368 may be included. When the sheeting 343 is coupled together to form the flow pathways 347, the flow pathways 347 may be substantially collapsed with minimal air volume. As agent is delivered into the filling manifold 300, the flow pathways 347 may inflate providing a pathway for the agent. Where the reservoir assemblies 52 are provided with the interior volumes 275 in a collapsed state, venting of gas in the filling manifold 300 and reservoir assemblies 52 may be avoided simplifying the filling manifold 300.

Referring now primarily to FIG. 88, in certain embodiments, the filling manifold 300 of FIGS. 85-87 may be placed into a container 38 (see, e.g., FIGS. 95-96). The filling manifold 300 may, for example, replace the filling manifold 300 shown in FIG. 99. In such embodiments, the body 345 overmolded onto each access sharp 368 may include retention features which facilitate coupling of the bodies 345 into a locating tray 410 in the container 38. As depicted in FIG. 88, each body 345 may include a portion which extends proud of the sheeting 343. An end of this section of the bodies 345 include barb projections 349. The locating tray 410 may include receiving apertures 351. The bodies 345 may be advanced into respective receiving apertures 351 until their barb projections 349 pass entirely through the apertures 351 and overhang a surface of the locating tray 410. This may prevent the bodies 345 from being displaced back through the receiving apertures 351 in the locating tray 410. The bodies 345 may also have a taper which interfaces with a taper of the receiving apertures 351 to prevent the bodies 345 from be inadvertently pulled through the receiving apertures 351. Delivery devices 12 (or reservoir assemblies 52) may be spiked onto the access sharps 368 as shown in FIG. 102.

Referring now to FIG. 89, another example block diagram of a system 10 is depicted. As shown, the system 10 may include a sealed container 38 in which an isolated fill environment 14 and a number of delivery devices 12 (or alternatively reservoir assemblies 52) are disposed. Certain containers 38 (or other portions of systems 10) depicted herein, including that shown in FIG. 89, are illustrated with a break to indicate any desired number of delivery devices 12 may be included depending on the embodiment.

The container 38 may be sterilized with the delivery devices 12 in a spiked state and provide a sterile barrier until use. The container 38 may be partitioned into a first portion 370 and a second portion 372. The first portion 370 may optionally be removed before the delivery devices 12 are filled if desired. The second portion 372 may include any of the filling manifold 300 embodiments described herein (see, e.g., FIGS. 77-80). In the example, each of the delivery devices 12 is shown with a septum 94 spiked onto an access sharp 368 in fluid communication with a fluid bus 32 defined in the second portion 372 of the container 38. As described above in relation to FIG. 80, the fluid bus 32 is arranged for serial filling of delivery devices 12 included in the container 38 and the access sharps 368 are dual lumen sharps with a filling lumen and serial fill connecting lumen. The fluid bus 32 together with the main interior volumes 275 of the reservoir assemblies 52 may provide the isolated fill environment 14 for the delivery devices 12.

A filling implement 42 (depicted as a syringe) may be coupled to a fluid introduction port 16 included in the second portion 372. In some embodiments, the fluid introduction port 16 may include a luer lock which may be covered by a cap or cover. The cover may be removed and a cooperating luer on a syringe or other filling implement 42 may be coupled to the luer lock. Agent may then be transferred out of the filling implement 42 and into the delivery devices 12 through the fluid bus 32. Gas in the fluid bus 32 and reservoir assemblies 52 of the delivery devices 12 may be displaced out of the container 38 via a vent 310 at an end of the fluid bus 32 as the reservoir assemblies 52 are filled.

Referring now to the progression of FIGS. 90-94, an example system 10 is depicted being utilized to fill a number of example delivery devices 12. With reference primarily to FIG. 90, a system 10 may include a container 38. As shown, containers 38 may include a first portion 370 and second portion 372 as described in relation to FIG. 89. The example container 38 also includes a third portion 374. The isolated fill environment 14 may be provided by the interior volumes 275 of the reservoir assemblies 52 and the fluid bus 32 with which they are in communication. Any filling manifold 300 described herein may be used in the system 10, however, the example includes a fluid bus 32 arranged for serially filling the delivery devices 12 included in the container 38. Each delivery device 12 may include a septum 94 spiked by a dual lumen sharp with a fill lumen and a serial connection lumen.

The third portion 374 may form a compartment with a pressure source and a vial spiking assembly 376. Any suitable pressure source may be used. For example, the pressure source may be a pre-pressurized accumulator, hand pump, etc. The pressure source in the example is a filling implement 42 and is depicted as a syringe. A spacer 386 may be included on the syringe and may hold the plunger 388 of the syringe in a raised position such that the syringe is maintained in a state in which it is filled with sterile gas. A cap 390 may also be disposed on over the outlet of the syringe.

The vial spiking assembly 376 may include a pressurizing spike 378 and a delivery spike 380. The spiking assembly 376 may be protected by a guard 392. The pressurizing spike 378 may be in fluid communication with a pressure port 382. The pressure port 382 may be capped by a removable port cover 384. The pressure source or the pressure port 382 may be associated with a sterile filter such as a 0.2 μm filtration membrane in certain examples to ensure fluid delivered to the pressurizing spike meets certain biological content criteria. The delivery spike 380 may be in fluid communication with the fluid bus 32 through which agent may be delivered to the delivery devices 12 included in the container 38.

As shown in FIG. 91, a user may access the third portion 374 of the container 38, for example, by removing a peelable lid or housing panel 394. The filling implement 42 may be retrieved and the guard 392 may be disengaged from the vial spiking assembly 376. As shown in FIG. 92, a vial 396 of agent may be spiked onto the vial spiking assembly 376 such that each of the pressurizing spike 378 and the delivery spike 380 extend through a closure septum 398 of the vial 396 and into the interior volume of the vial 396. The pressurizing spike 378 may have a length greater than the delivery spike 380. The pressurizing spike 378 may typically have an outlet disposed in a gas filled head space within the vial 396 when the vial 396 is spiked. This may help to prevent aeration of the agent in the vial 396 as the vial 396 is pressurized with gas. The delivery spike 380 may have a length which positions the inlet to the delivery spike 380 adjacent the closure septum 398 of the vial 396 when the vial 396 is spiked. Thus, the delivery spike 380 may be positioned to provide a pathway for agent out of the vial 396 even when the amount of agent in the vial 396 has been substantially depleted.

Referring now to FIG. 93, the cover 384 on the pressure port 382 may be removed. The cap 390 may be removed from the syringe or other filling implement 42 and the syringe may be coupled to the pressure port 384. The spacer 386 may be disassociated from the syringe and the plunger 388 of the syringe may be displaced to drive sterile gas out of the syringe and into the vial 396 via the pressurizing spike 378 as shown in FIG. 94. As indicated by the depleted vial 396 in FIG. 94, the pressure established within the vial 396 may act to drive agent of the vial 396 and through fluid bus 32 in order to fill the delivery devices 12 included within the container 38. Once filled, the portion of the container 38 including the delivery devices 12 may be opened (if it has not already been accessed) and the delivery devices 12 may be removed for use. Pressure may also be supplied to the vial 396 via any other suitable pressure source. In some embodiments, a sterile filter may be disposed intermediate the pressure port 382 and pressurizing spike 378.

Referring now to FIG. 95 an example container 38 which may be used with various systems 10 described herein is depicted. As shown, the container 38 may include a main housing 400 which may be a rigid or hard walled enclosure. The container 38 may also include a peelable lid 36 which may be coupled over an opening in the main housing 400. In the example shown, the peelable lid 36 forms a side of the container 38. The peelable lid 36 may be constructed of a sheet of a flashspun high-density polymer (e.g. polyethylene) fiber material such as Tyvek. The peelable lid 36 may be removed from the container 38 to gain access to the interior of the container 36.

Referring now also to FIG. 96, a cover tray 402 may be included within the container 38. The cover tray 402 may include a depression 404 within which a filling implement 42 may be disposed. In the example embodiment, the filling implement 42 is depicted as a syringe. The cover tray 402 may also include a number of cover receptacles 406 which may accommodate a portion of a package 408 (see, e.g., FIG. 112) for a delivery device 12. The cover tray 402 may be interference fit in place within the container 38. As shown in FIG. 97, the filling implement 42 may be collected from the depression 404 and manually filled with fluid from a medicament container 28 such as a vaccine vial. The cover tray 402 may be disassociated from the container 38.

Referring now to FIGS. 98-99, views of the container 38 with the peelable lid 36 and cover tray 402 removed are shown. The container 38 may include a locating tray 410. The locating tray 410 may include a number of locating receptacles 426. Each locating receptacle 426 may receive a portion of a respective package 408. The locating receptacles 426 may cooperate with the cover receptacles 406 in the cover tray 402 to hold the packages 408 in place within the container 38 during shipping and handling. The locating tray 410 may be retained in place via interference fit within the container 38 or may potentially be coupled in place via adhesive, sonic welding, heat stake, or some other generally permanent attachment method. The locating tray 410 may cover a fluid bus 32 of a filling manifold 300 of the container 38. Though the example filling manifold 300 is arranged such that each of the reservoir assemblies 52 is filled in parallel, it should be understood the container 38 may be modified to include any of the filling manifolds 300 described herein.

The receptacles 406, 426 may be arranged in any desired number of rows and columns. Depending on the embodiment, a greater or lesser number of packages 408 may be accommodated within the container 38. The fluid bus 32 may include a number of branches 469A, B which service each of the rows and/or columns of packages 408 within the container 38.

Referring now also to FIG. 100, a cross-sectional view taken at the indicated cut plane of FIG. 98 is depicted. As shown, a fluid introduction port 16 may be included in the container 38. In the example shown, the fluid introduction port 16 includes a fluid introduction septum 412. In other embodiments, the fluid introduction port 16 may include a fitting (e.g. luer lock) to which a filling implement 42 or pumping portion 15 with a cooperating fitting may be coupled. In such examples, the fitting of the fluid introduction port 16 may be sealed with a removable cover to separate the isolated fill environment 14 from the ambient surroundings. The downstream side of the fluid introduction port 16 may form the isolated fill environment 14 in systems 10 utilizing the example container 38.

The example fluid introduction port 16 includes a port housing 416 which is formed as a raised protrusion defined in the material of the locating tray 410 and an insert 414 which is coupled (e.g. via adhesive) to the port housing 416. The insert 414 may include a main body 420 having a bore 422 in which the fluid introduction septum 412 may be placed. The main body 420 of the insert 414 may also include a filling channel 424 into which an inlet to the fluid bus 32 is plumbed. The inlet 472 may be a common portion of the fluid bus 32 from which any branches 469A, B in the fluid bus 32 may stem. The fluid introduction septum 412 may be sized such that a downstream volume of the bore 422 is open and may act as a receiving space for the tip of a sharp of a delivery implement 42. As shown, the port housing 416 may also define a guide 418 which may surround the periphery of the fluid introduction septum 412 when the insert 414 is coupled to the port housing 416. The guide 418 may be a funnel shaped surface of the port housing 416 which may assist in directing a sharp into the fluid introduction septum 412 when piercing the fluid introduction septum 412.

Referring now primarily to FIGS. 101-102, cross-sectional views of packages 408 in place within locating receptacles 426 of the locating tray 410 are depicted. FIG. 101 is taken at the indicated cut plane of FIG. 98 and FIG. 102 is an enlarged view of the indicated region of FIG. 101. Each of the delivery devices 12 include reservoir assemblies 52 of the type depicted in FIGS. 44A-44D though any of the reservoir assemblies 52 described herein may be included within a container 38.

As best shown in FIG. 102, each of the locating receptacles 426 may include a spiking aperture 428. Spiking apertures 428 may be placed in line with dispensing sharps 302 included on the fluid bus 32. In some examples, the dispensing sharps 302 may project through the spiking apertures 428, though in alternative embodiments, the tips of the dispensing sharp 302 may be disposed on a side of the locating tray 410 opposite the packages 408. This may help to inhibit inadvertent contact with the dispensing sharps 302. The example spiking aperture 428 is sized to accept a septum housing 261 of the reservoir assembly 52. In alternative embodiments, the spiking aperture 328 may accept any protruding body 250, barrel 252 in which a septum 94 is disposed, thickened region of a reservoir assembly 52, etc. The locating receptacles 426 may be defined by sloped walls which tend to guide the septum 94 containing portion of the delivery device 12 onto the dispensing sharp 302 as the package 408 is displaced into the locating receptacle 426.

Referring now to FIG. 103, to load agent into each of the delivery devices 12, a filling implement 42 (or pumping portion 15) may be placed into fluid communication with the fluid bus 32 via the fluid introduction port 16. A sharp of the filling implement 42 may, for example, puncture through the fluid introduction septum 412 and fluid may be transferred from the filling implement 42 into each of the reservoir assemblies 52 via the fluid bus 32. Each branch of the fluid bus 32 may terminate in a vent 310 (see, e.g., FIG. 100) which may include a hydrophobic filter. This may assist in evacuating any gas out of the fluid bus 32 as agent is compelled into the fluid bus 32. Once filled, each of the packages 408 may be disassociated from the respective locating receptacle 426 and disseminated to a user. Alternatively, the container 38 may be stored with the reservoir assembly 52 in each of the packages 408 in a filled state.

Referring now to FIG. 104 and FIG. 105, in certain alternative examples, the container 38 may be provided with a filling aid 590. The filling aid 590 may, for example, be held in a depression 404 in the cover tray 402 (see, e.g., FIG. 95) when the container 38 is distributed. The filling aid 590 may include a medicament container dock 592 and a filling implement receptacle 594. A medicament container 28 (e.g. vial) may be seated into the medicament container dock 592 and the interior volume of the medicament container 28 may be accessed via a first and second spike 602, 604 of the filling aid 590. The first spike 602 may be in fluid communication with a vent filter 606. The vent filter 606 may be a 0.2 μm filter through which gas may enter the medicament container 28 to replace agent withdrawn from the medicament container 28 via the second spike 604. The second spike 604 may be in fluid communication with a filling implement coupling 608 in the filling implement receptacle 594. There may also be an outlet sharp 600 in fluid communication with the filling implement coupling 608. When a filling implement 42 is engaged with the filling implement coupling 608, agent may be drawn from the medicament container 28 and transferred into the filling implement 42. This may, for instance, be accomplished by withdrawing a plunger of a syringe where the filling implement 42 is a syringe. A check valve 610 is included intermediate the filling implement coupling 608 and outlet sharp 600 to inhibit flow of fluid from the outlet sharp 600 toward the filling implement coupling 608. Once filled with agent, the filling implement 42 may be operated to drive the agent out of the outlet sharp 600. A check valve 612 may be included to inhibit flow of agent back to the medicament container 28.

The filling aid 590 may include a housing 596. The fluid paths of the filling aid 590 may be disposed within the housing 596. Additionally, the housing 596 may include a recess 614. The outlet sharp 600 may extend into, but not out of the recess 614 such that the tip off the outlet sharp 600 is protected against inadvertent contact. The housing 596 may also include a set of slots 616, 618. The slots 616, 618 extend from opposing sides of the recess 614. Each of the recess 614 and slot 616, 618 may include a span which tapers wider adjacent the exterior surface of the housing 596.

Referring now also to FIGS. 106A-106B, a guide 598 may be provided in the container 38 in the vicinity of the fluid introduction port 16. The guide 598 may accept the housing 596 and assist in ensuring that the housing 596 is advanced along a desired displacement path as an outlet sharp 600 of the filling aid 590 pierces the fluid introduction septum 412. Additionally, the fluid introduction port 16 may include a set of wings 620. The leading faces of the fluid introduction port 16 and wings 620 may be tapered (best shown in FIG. 106A). As the filling aid 590 is advanced into the guide 598, the fluid introduction port 16 and the wings 620 may respectively enter the recess 614 and slots 616, 618. The tapered portions of the recess 614 and slots 616, 618, as well as the fluid introduction port 16 and wings 620 may assist in directing the outlet sharp 600 along the desired displacement path. An audible and/or tactile feedback may be created when the filling aid 590 is advanced fully into the guide 598 such that the outlet sharp 600 is in fluid communication with the fluid bus 32 in the container 38. This may be generated by a snap projection on either of the guide 598 or housing 596 entering into a detent in the other of the guide 598 and housing 596.

Referring to FIG. 107, an example apparatus 950 for reconstituting a medical agent is depicted. The medical agent may be any suitable medical agent which may be supplied in dried formulation. Such dried formulations may, for non-limiting example, include spray dried formulations, lyophilized formulations, vacuum dried formulations, convective dried formulations, microwave dried formulations, and formulations which have dried by some combination of the above. The medical agent may be any of a variety of agents which may be supplied in a desiccated, powdered, or otherwise dried form. In certain examples the medical agent may be a vaccine. In such examples, a dried vaccine may be particularly useful in scenarios where cold chain infrastructure is minimal or non-existent. For example, low/middle income countries or relatively isolated terrain (e.g. forward operating bases in conflict scenarios) may find vaccine access via dried formulation particularly attractive. Thus, the apparatus 10 may be useful in expanding vaccine (or other medical agent) access in challenging regions of the world As shown, the medical agent may be provided in a container 952. The container 952 in the example embodiments, is depicted as a vial. Other example containers 952 may include bags, partially flexible reservoirs, blister packs, etc. The medical agent container 952 may be spiked onto an access sharp 954 included on a fluid bus 956 of the apparatus 950. The access sharp 954 may be disposed within a medical container dock 958 defined in a surface of a housing 960 of the apparatus 950. In any embodiments described herein as having a housing 960, the housing 960 may be optional. In such examples, the fluid bus 956 may be nude or unhoused. The spikes 954, 964, syringe port 976, and selection valve 972 (or other valves, clamps, and occluders described herein) may be coupled to tubing portions which form the fluid bus 956. When the medical agent container 952 is spiked, the medical container dock 958 may accept at least a portion of the medical agent container 952. A diluent container 966 may be spiked onto a diluent sharp 964 included on the fluid bus 956 of the apparatus 950. The housing 960 may also include a diluent container dock 962 which is defined in a surface of the housing 960. The diluent sharp 964 may be disposed within the diluent container dock 962. When the diluent container 966 is spiked, the diluent container dock 962 may accept at least a portion of the diluent container 966. The diluent container 966 may be any of the containers described herein. The diluent may be any suitable diluent and may be differ depending on the medical agent contained in the medical agent container 952. In certain example, the diluent may be a monograph quality water (e.g. Water for Injection). In certain other embodiments, the diluent may be a solution such as a salt solution (e.g. Normal Saline). Other diluents are possible. Though spikes are described, capped luer lock (or other fittings) may replace one or each of the sharps 954, 964. The containers 952, 966 may be provided with a cooperating fitting which is capped. The medical agent and diluent containers 952, 966 may be aseptically brought into fluid communication with the fluid bus 956 when installed into the apparatus 950.

As shown, a syringe 968 may also be brought into communication with a port 976 of the fluid bus 956. For example, the syringe 968 may include a luer lock fitting which may engage with a cooperating fitting of the port of the fluid bus 956. Alternatively, a sharp may be coupled to the syringe 968 and the fluid bus 956 may include a self-sealing septum through which the syringe 968 may be placed into communication with the fluid bus 956. The housing 960 may include a syringe dock 970 which accepts at least a portion of the syringe 968. The septum or fitting with which the syringe 968 engages may be disposed within the syringe dock 970.

As shown, the fluid bus 956 may include a selection valve 972. In certain examples, the selection valve 972 may be manually controlled. In some such embodiments, the selection valve 972 may be stopcock. In alternative embodiments, the apparatus 950 may include a battery or other power source and the selection valve 972 may be electromechanical. The apparatus 950 may also include a power cord and electrical adapters allowing the apparatus 950 to be plugged into a wall outlet for power. The selection valve 972 may have a first state in which the diluent sharp 964 is in fluid communication with the syringe port 976 and the syringe port 976 is out of fluid communication with the medical agent container spike 954 and an outlet line 974 of the apparatus 950. The selection valve 972 may have a second state in which the syringe port 976 is in fluid communication with the medical agent spike 954 and out of fluid communication with the outlet line 974 and the diluent spike 964. The selection valve 972 may have a third state in which the syringe port 974 is in fluid communication with the outlet line 974 and out of fluid communication with the spikes 954, 964.

With the selection valve 972 in the first state, a user may draw diluent from the diluent container 966 through the fluid bus 956 and into the syringe 968. The amount of fluid drawn into the syringe 968 may be monitored by a user to ensure it is appropriate to reconstitute the medical agent in the medical agent container 952. The selection valve 972 may then be transition from the first state to the second state. Diluent may be ejected from the syringe 968 through the fluid bus 956 and into the medical agent container 952. Fluid from the medical agent container 952 may be drawn back into the syringe 968. Optionally, fluid may be retransferred to the medical agent container 952 and drawn back into the syringe 968 at least once. This may help to ensure that the reconstituted medical agent is thoroughly mixed and all of the dried agent has been reconstituted. The selection valve 972 may then be transitioned to the third state and reconstituted medical agent may be ejected from the syringe and through the outlet line 974 of the apparatus 950. The outlet line 974 may be in fluid communication with a delivery device 978 or a fluid bus via which interior fluid holding volumes of a number of delivery devices 978 may be accessed. Thus, as fluid is dispensed through the outlet line 974 it may be transferred into at least one delivery device 12 filling the delivery device(s) 12 for use. The delivery devices 12 may subsequently be distributed to patients and consumed. This may allow for heat labile medical agents to be utilized in regions with inadequate cold chain infrastructure. The delivery devices 12 may be any of those shown and described herein. Any of the containers having a plurality of delivery devices 12 in fluid communication with fluid buses described herein may also be used with the apparatuses 950 described herein.

Referring now FIG. 108, another example embodiment of an apparatus 950 is depicted. As shown the apparatus 950 includes a second syringe port 980. The syringe port 980 may be disposed within a second syringe dock 982 defined in the housing 960. A second syringe 984 may be engaged with the second syringe port 982 to place the second syringe 984 into fluid communication with the fluid bus 956. A luer fitting or septum may for example be used for the second syringe port 980. The second syringe 984 may be different than the first syringe 968. For example, the first syringe 968 may be a smaller volume syringe with markings which allow for more granular resolution as to the volume of fluid drawn into the syringe 968. The second syringe 984 may be a larger syringe 984. The first syringe 968 may be referred to as a metering syringe and the second syringe 984 may be referred to as a reconstituting syringe.

The diluent spike 964 may be at a first end of the fluid bus 956. Immediately downstream of the diluent spike 964 may be the first syringe port 976. Immediately downstream of the first syringe port 36 may be the second syringe port 980. The fluid bus 956 may branch downstream of the second syringe port 980. One branch may include the medical agent spike 954. The second branch may be the outlet line 974 of the fluid bus 956.

The apparatus 950 depicted in FIG. 108 does not include a selection valve 972. The fluid bus 956 includes a check valve 986 intermediate the diluent sharp 964 and the first syringe port 976. There may be a first clamp or occluder 988A intermediate the first syringe port 976 and second syringe port 982. There may be a second clamp or occluder 988B on the first branch disposed intermediate the second syringe port 982 and the medical agent spike 954. There may be a third clamp or occluder 988 C on the outlet line 974. Any the clamps or occluders 988A-C may be any suitable clamp or occluder. In certain embodiments, pinch clamps may be used.

In use, the clamps 988A-C of the apparatus 950 may begin in a closed state which blocks flow through the fluid bus 956. A user may act on the metering syringe 968 to draw an appropriate amount of diluent from the diluent container 966. The check valve 986 may prevent back flow to the diluent container 966. The first clamp 988A may be opened and the diluent may be transferred from the metering syringe 968 to the reconstituting syringe 984. In some embodiments, the first clamp 988A may be closed and more diluent may be drawn into the metering syringe 968 if less than the desired amount could be collected in the initial fill stroke for the metering syringe 28. The first clamp 988A may be opened and the diluent may again be transferred to the reconstituting syringe 984. This may be repeated as needed to shuttle the appropriate amount diluent to the reconstituting syringe 984. The first clamp 988A may be closed and the second clamp 988B may be opened. Diluent in the reconstituting syringe 984 may be driven out of the reconstituting syringe 984, through the fluid bus 956 and into the medical agent container 952. The fluid in the medical agent container 952 may be withdrawn back into the reconstituting syringe 984. In some embodiments, the fluid may be transferred back and forth between the reconstituting syringe 984 and the medical agent container a number of times to ensure appropriate mixing and reconstitution. The second clamp 988B may then be closed and the third clamp 988C may be opened. The reconstituted medical agent may then be dispensed out of the apparatus 950 and to a delivery device 12 (or fluid bus on which a number of delivery devices 12 are engaged).

Referring now to FIG. 109, in certain example apparatuses, the check valve 986 and the clamps or occluders 988A-C may be replaced by valves 990A-D. Any suitable valves 990A-D may be used. The valves 990A-D may be ball valves in certain examples (see, e.g., FIG. 110). Other varieties of valves 990A-D may be utilized. Volcano valves may for example be used.

An example embodiment of an apparatus 950 including volcano valves 992A-992D instead of the check valves 986 and clamps 988A-C is depicted in FIG. 111A. An example volcano valve 992E shown in isolation is depicted in FIG. 111B. As shown, each of the volcano valves 992A-D may include a body 993. The body 993 may include side walls 994 which surround a valve seat 995 which projects from a midbody 996. The midbody 996 may separate the first side of the volcano valve 992E with which a first inlet/outlet 997 communicates from a second side of the volcano valve 992E with which a second inlet/outlet 998 communicates. The valve seat 995 may provide a passage through the midbody 996. The first side of the volcano valve 992E may be overlaid with a first membrane or diaphragm 991. The diaphragm 991 may seal the first side of the valve. The second side of the volcano valve 992E may be covered by a second diaphragm 999 or a rigid plate which seals the second side of the volcano valve 992E.

As shown, an actuator 985 may be coupled to the first side of the volcano valve 992E. The actuator 985 may include a plunger 987. The plunger 987 may be displaceable toward and away from the first diaphragm 991. The plunger 987 may be displaced into the first diaphragm 991 to press the first diaphragm 991 against the valve seat 995 blocking flow through the volcano valve 992E to close the volcano valve 922E. When the volcano valve 992E is closed, the plunger 987 may be displaced away from the first diaphragm 991 to transition the valve to an open, flow permitting state. The plunger 987 may be biased to a home position (in which the valve is closed or open depending on the embodiment) by a bias member such as a spring. The plunger may include a set of fins 989. The channel 983 within the actuator 985 in which the plunger 987 displaces may have passages in which the fins 989 may travel. The passages may include respective detent features into which the fins 989 may be rotated to lock the plunger 987 in a position. Thus, the volcano valve 992E may for example be held closed or open. The plunger 987 may include a flange or similar projection which inhibits the plunger 987 from being disassociated from the actuator 985 by virtue of it being too large to pass through some portion of the channel 983 within which the plunger 987 displaces. Referring to FIG. 111A in conjunction with FIG. 111B, a user may manually operate the volcano valves 992A-D and syringes 968, 984 to reconstitute medical agent in the medical agent container 952 and dispense it through the outlet line 974 of the apparatus 950.

Referring now to FIG. 109-111B, the example apparatuses 950 are shown as utilizing two syringes 968, 984 as described in relation to FIG. 108. It should be appreciated that the embodiment of FIG. 107 may be modified to include individual valves (any suitable valves such as those shown and described herein) in place of the selector valve 972. In such examples, a valve would be placed on the fluid bus 956 intermediate the diluent spike 964 and the syringe port 976. Another valve would be placed on the fluid bus 956 intermediate the medical agent spike 954 and the syringe port 976. An additional valve would be placed on the fluid bus 956 on the outlet line 974. In FIGS. 108, the clamps or occluders 988A-C could be replaced by a selector valve 972 (e.g. stopcock). In FIGS. 109-111A certain of the valves 990B-D and volcano valves 992B-D could be replaced by a selector valve 972 (e.g. stopcock).

Referring now to FIG. 112 and FIG. 113, a perspective view of an example package 408 and a partial cut away view of a package 408 are respectively shown. The package 408 depicted is that shown in FIGS. 97-103. As shown, packages 408 may include an exterior sleeve or jacket 432 which surrounds an interior shell 430. The sleeve 432 may be constructed of a single piece of folded material (paper or cardstock type material) which may include flap members 446A, B at opposing terminal ends. When the interior shell 430 is deposited in the sleeve 432 the flap members 446A, B may be coupled to one another (e.g. via adhesive). The sleeve 432 may be printed with logos, instructions for use, various indicators (in the example a fill indicator 451 is shown), etc.

The interior shell 430 may be formed from a shell basin 434 and a shell cover 436. Alternatively, the two portions may be formed in clamshell arrangement as monolithic body. The shell basin 434 and shell cover 436 would be connected by a piece of material serving as a living hinge. As shown, the shell basin 434 and shell cover 436 include cooperating pockets 442 and protuberances 444 which may be interference fit into one another to couple the shell basin 434 and cover 436 in place around a delivery device 12. As shown, the shell basin 434 may define a tub or depression against which the petal members 90 of the delivery device 12 rest. As shown in FIG. 112, the shell cover 436 may include a dome region 438 which accepts the raised central region 68 and any depressor body 62 of the delivery device 12. The jacket 432 may include an aperture 449 through which the dome region 438 may project. The interior shell 430 or at least the cover shell 436 may be constructed of a rigid plastic. Thus the dome region 438 may be a protective shield which may inhibit the delivery device 12 from inadvertently being transitioned to a delivery state due to impacts or other abrupt handling of the package 408. This may be particularly desirable where delivery devices 12 is filled at a hub and transported, potentially over rough terrain in challenging circumstances (e.g. a conflict scenario), to a point of use.

In certain examples, the interior shell 430 may also include a retention channel 453. The retention channel 453 may hold or capture at least a portion of a protruding body 250 or septum housing 261 (as shown) of a reservoir assembly 52 when a package 408 is assembled. The retention channel 453 may help to support and immobilize the section of the reservoir assembly 52 including the septum 94. For example, the retention channel 453 shown in FIG. 113 includes a ledge 455 against which a portion of the reservoir assembly 52 (in this case the septum housing 261) rests. The ledge 455 may prevent the reservoir assembly 52 and septum 94 from displacing as the septum 94 is spiked onto a dispensing sharp 302 within a container 38 (see, e.g., FIG. 102). The sleeve 432 may include a notch 457 within which a wall of the retention channel 453 may be located.

Referring now to FIG. 114, as mentioned above the package 408 may include a fill indicator 451 in certain examples. In some embodiments, the exterior of the package 408 may be opaque or translucent and include a window 710. A float 712 may be disposed within a portion of the filling flow paths of the delivery device 12. When the delivery device 12 is in an unfilled state, the float 712 may be in a home position in which it is out of alignment with the window 710. In the home position, view of the float 712 is blocked or obscured. The density of the float 712 may be selected that the float 712 will rise into alignment with the window 710 when agent has been transferred into the portion of filling flow path in which the float 712 is disposed. The float 712 may have a color which contrasts starkly with surrounding material in the delivery device 12 and package 408 such that its presence may be easily discerned on a cursory inspection if aligned with the window 710. When within a container 38, packages 408 may be installed into an orientation in which the float 712 will rise into alignment with the window 710 as agent is filled into each delivery device 12.

The window 710 may, for example, be formed in or coupled onto a portion of the retention channel 453 in the interior shell 430. Alternatively, the sleeve 432 may surround or cover the retention channel 453 and the window 710 may be formed as a cut-out in the sleeve 432 material. In the example embodiment, the float 712 is positioned in the filter receptacle 258' of the septum housing 261. The septum housing 261 may be at least partially formed of a see-through (e.g. transparent or highly translucent material). As agent is loaded into the reservoir assembly of the delivery device 12, gas may be expelled past the float and through the filter 712. Agent may fill into the filter receptacle 258' causing the float 712 to rise into alignment with the window 710. Preferably the float 712 may be positioned at a terminal region of the filling flow path or a region downstream of the main interior volume 275 of the reservoir assembly 52. Thus, the float 712 may indicate that the reservoir assembly 52 has been fully filled.

Referring now to FIG. 115, an exemplary system 10 including a filling portion 17 and a pumping portion 15 is depicted. The filling portions 17 in the forthcoming figures are that shown and described in relation to FIG. 79, however, this is merely exemplary and any filling portions 17 described herein may be used. Each of the pumping portion 15 and filling portion 17 may include a cooperating luer lock 459A, B or other fluid fitting. The luer locks 459 A, B may be provided capped and may be coupled together following proper aseptic technique to place the pumping portion 15 and filling portion 17 into fluid communication with one another. The example medicament supply 18 of the pumping portion 15 includes a medicament container 28 and a pump 30. The medicament container 28 may be any suitable container such as a vial, bag, syringe, or other reservoir. The pump 30 may be any of the example pumps 30 described herein. As shown, the pumping portion 15 is a benchtop module 462 which may be placed or affixed to a table or other surface during use.

In alternative embodiments, and referring now to FIG. 116, the pumping portion 15 may be incorporated into a handheld module 464. Where a handheld module 464 is used, the handheld module 464 may be arranged for use with a single hand and may include a grip 496 (e.g. pistol grip) to facilitate wielding of the module 464 by a user. The handheld module 464 may include a pump 30 which may be any of the pumps shown or described herein. The handheld module 464 may include a user interface 492 which may include one or more buttons (e.g. for commanding powering of the pump 30), display, lights, and tactile feedback assemblies (e.g. vibratory motors). The handheld module 464 may also include a holster 465 into which a medicament container 28 (a vial in the example embodiment) may be placed. An access spike 463 may be provided in the holster 465. The access spike 463 may ensure that fluid communication between the fluid handling components of the handheld module 464 and the contents of the medicament container 28 is established when the medicament container 28 is placed in the hostler 465. Fluid may be compelled by the pump 30 to be transferred from the medicament container 28 in the holster 465 to an outlet 468 of the handheld module 464. As shown, the outlet 468 of the handheld module 464 is a delivery sharp.

The fluid introduction port 16 of the filling portion 17 may include a receptacle 466 into which a portion of the handheld module 464 including the outlet 468 may be advanced. The receptacle 466 may be a raised wall or the like and may in some embodiments include a tapered segment which helps to guide the handheld module 464 into place within the receptacle 466. The fluid introduction septum 412 of the fluid introduction port 16 may be disposed at a bottom of the receptacle 466. The outlet 468 of the handheld module 464 may pierce through the fluid introduction septum 412 when the handheld module 464 is docked in the receptacle 466. Once the fluid introduction septum 412 has been pierced, the pump 30 may be powered to drive fluid from the medicament container 28 into the reservoir assemblies 52 via the fluid bus 32 of the filling portion 17.

Referring now to FIG. 117, a block diagram of an example system 10 including a filling portion 17 and a pumping portion 15 is depicted. As shown, the pumping portion 15 in FIG. 117 includes a pump housing 470. The pump housing 470 includes a raceway 474 into which a fluid handling set 476 may be loaded. The fluid handling set 476 may include an inlet spike 478A which may be retained in receptacle defined in the housing 470. The fluid handling set 476 may additionally include an outlet spike 478B which may also be retained within a respective receptacle defined on the housing 470. A span of tubing 475 may span between the inlet and outlet spikes 478A, B.

The pump 30 in the example shown is a rotary peristaltic type pump though finger type peristaltic type pumps may also be used in alternative embodiments. The fluid handling set 476 is loaded into the raceway 474, the raceway 474 may route a segment of the tubing 475 by a rotor 480 of the pump 30. The raceway 474 may also place the tubing 475 adjacent a senor assembly 490 (e.g. pressure sensor) of the pumping portion 15.

The contents of a medicament container 28 (shown as a vial in FIG. 117) may be placed into fluid communication with the fluid handling set 476. As shown, a vial septum 398 may, for example, be pierced by the inlet spike 478A of the fluid handling set 476. With the medicament container 28 in fluid communication with the fluid handling set 476, a user may command transfer of agent from the medicament container 28. Prior to piercing of the fluid introduction septum 412 of the filling portion 17, the pump 30 may be powered to prime the fluid handling set 476 with agent. The prime volume may be based on a nominal interior volume of the fluid handling set 476. The fluid introduction septum 412 may then be pierced and the user may command powering of the pump 30 to transfer agent to the filling portion 17 of the system 10. Commands to transfer fluid may be conveyed via a user interface 492 on the housing 470. Upon receipt of a signal indicative of a request to transfer fluid, a controller 488 in the housing 470 may power a drive motor 482 of the pump 30 to rotate the rotor 480. As this occurs, rollers 484 on the rotor 480 may pass over the tubing 475 in the adjacent raceway 474 to compel fluid to displace through the fluid handling set 476. The controller 488 may monitor the amount of volume dispensed based on a data signal output from a rotation sensor 486 (e.g. rotary encoder) monitoring the position of the rotor 488. Additionally, the controller 488 may monitor pressure in the fluid handling set 476 via a data signal output from the sensor assembly 490. The fluid bus 32 and reservoir assemblies 52 in the filling portion 17 may have a known volume and the controller 488 may dispense fluid into the filling portion 17 until the data signal from the rotation sensor 486 indicates that a volume of fluid equal to the known volume has been transferred from the medicament container 28. In some examples, the controller 488 may also monitor for a spike in pressure in the fluid handling set 476. This may indicate that all reservoir assemblies 52 in the filling portion 17 have been filled and that the pump 30 is attempting to drive agent through the vent 310 at the downstream end of the fluid bus 32.

Referring now to FIG. 118, another block diagram of an exemplary system 10 including a pumping portion 15 and a filling portion 17 is depicted. The pumping portion 15 in FIG. 118 includes a pump housing 470 in which a fluid handling set 476 may be loaded. The fluid handling set 476 includes inlet and outlet spikes 478A, B in fluid communication with one another via a span of tubing 475 as described in relation to FIG. 117. The fluid handling set 476 in FIG. 118 also includes a diaphragm pumping chamber 494. A raceway 474 is included on the pump housing 470 adjacent the rotor 480 of a diaphragm chamber fill pump 485. A motor 482 of the diaphragm chamber fill pump 485 may be powered to drive agent from a medicament container 28 into the diaphragm pumping chamber 494. A rotation sensor 486 of the diaphragm chamber fill pump 485 may be monitored by a controller 488 of the pumping portion 15 and may halt delivery of agent when a target fill volume for the diaphragm pumping chamber 494 has been transferred. The pumping portion 15 in FIG. 118 includes a plunger actuator 496 which may be powered to govern displacement of a plunger 498. The plunger 498 may be driven into a diaphragm of the diaphragm pumping chamber 494 and may urge the diaphragm against an opposing wall of the diaphragm pumping chamber 494. This may drive fluid out of the diaphragm pumping chamber 494 and out of the outlet spike 478B of the fluid handling set 476. At least one load cell 500 may be associated with the plunger 498 to monitor the force being exerted by the plunger 498 against the diaphragm pumping chamber 494. This force may be indicative of the delivery pressure being exerted against the agent in the diaphragm pumping chamber 494. Delivery pressure may spike as the agent reaches the vent 310 as agent may not readily pass through the vent 310. Thus, the controller 488 may monitor for a spike in the force data being output by the load cell 500 as this may be indicative of agent having filled into the fluid bus 32 and each of the reservoir assemblies 52 of the filling portion 17. As shown, the example system 10 also includes a plunger displacement sensor 502 (e.g. linear potentiometer). The controller 488 may monitor data from the plunger displacement sensor 502 to track when a target volume of fluid has dispensed from the diaphragm pumping chamber 494 into the filling portion. The controller 488 may halt delivery of fluid from the pumping portion 15 when the load cell 500 data, plunger displacement sensor 502 data or data from a combination of these sensors is indicative that the filling portion 17 has been fully filled with agent.

Referring now to FIG. 119, another example embodiment of a system 10 including a pumping portion 15 and a filling portion 17 are depicted. As shown, the fluid handling set 476 in FIG. 119 may include a pumping cassette 504 which may be inserted into a dock on the pump housing 470. The pumping cassette 504 may include a rigid cassette body 506. One side of the cassette body 506 may include a set of valves 508A, B and at least one pumping chamber 510. An opposing side of the cassette body 506 may defined a fluid bus 512. Each side of the cassette body 506 may be overlaid by a respective flexible sheet or membrane 514A, B. When the pumping cassette 504 is installed in the pump housing 470, the membranes 514A, B may be pressed against walls defined on the cassette body 506 to fluidically seal the valves 508A, B, pump chamber 510, and fluid bus 512. For example, the dock in which the pumping cassette 504 is installed may close against and exert pressure on the pumping cassette 504 to hold the membranes 514A, B against the walls of the cassette body 506.

The valves 508 may each be volcano type valves and include a valve seat 516 disposed within a well surrounded by a set of walls. The valve seat 516 may include a passage which connects the valve well volume to the fluid bus 512. The passages of each valve 508A, B may be blocked by pressing a portion of the membrane 514A over the valve 508A, B against the valve seat 516 to seal off the passage through the valve 508A, B. The passages may be opened by displacing the portion of the memberane 514A over the respective valve 508A, B away from its valve seat 516. The first valve 508A may be an inlet valve to the pumping cassette 504 and may be opened to allow fluid flow from the medicament container 28 to the pumping cassette 504 through the tubing 475. The second valve 508B may be an outlet valve of the pumping cassette 504 and may be opened to provide a flow path out of the cassette 504 to the filling portion 17.

The pumping chamber 510 may include a pump chamber wall 518 which defines a depression in the cassette body 506. The pumping chamber 518 may be in fluid communication with the fluid bus 512 via an aperture in the cassette body 506. The section of the membrane 514A overlaying the pumping chamber 510 may be drawn away from the cassette body 506 to create a vacuum in the pump chamber 510 which draws fluid into the pump chamber 510. The section of the member 514A overlaying the pumping chamber 510 may be driven against the pump chamber wall 518 to decrease the interior volume of the pumping chamber 510 and displace fluid out of the pump chamber 510. In the example shown, with the inlet valve 508A open and the outlet valve closed 508B, the membrane 514A over the pumping chamber 510 may be drawn away from the cassette body 506. This will pull agent into the pumping chamber 510 from the medicament container 28. The inlet valve 508A may then be closed and the outlet valve 508B may be opened. The membrane 514A over the pumping chamber 510 may be driven against the pump chamber wall 518 to transfer fluid out of the pumping chamber 510 to the filling portion 17.

In the example shown, the pumping portion 15 includes a pneumatic assembly 520. The pneumatic assembly 520 includes a pneumatic pump 536 which may communicate with a first pressure reservoir 532 and second pressure reservoir 534. Valves 522 may be included intermediate the pneumatic pump 536 and the pressure reservoirs 532, 534. The first pressure reservoir 532 may be maintained at a positive (with respect to ambient) pressure by the pneumatic pump 536. The second pressure reservoir 534 may be maintained at a negative (with respective to ambient) pressure by the pneumatic pump 536. Pressure sensors may be associated with the pressure reservoirs 532, 524. The data signals from these pressure sensors may be monitored by the controller 488 as the controller 488 powers the pneumatic pump 536 to keep the pressure reservoirs 532, 534 within a range of respective target values.

The pneumatic assembly 520 also includes a set of valve control chambers 538A, B and a pump control chamber 540. The valve control chambers 538A, B and pump control chamber 540 may respectively be disposed adjacent the valves 508A, B and pumping chamber 510 of the pumping cassette 504 when the pumping cassette 504 is installed in the pump housing 470. The membrane 514A and a control membrane 544 may be interposed between the control chambers 538A, B, 540 and the valves 508A, B and pumping chamber 510. Pressure from the pressure reservoirs 532, 534 may selectively be applied to the control volumes by opening pneumatic distribution valves 542 on pressure supply paths in the pneumatic assembly 520. Positive pressure may drive the membrane 514A in the direction of the cassette body 506 to close valves 508A, B and dispense fluid from the pumping chamber 510. Negative pressure may draw the membrane 514A away from the cassette body 506 to open valves 508A, B and pull fluid into the pumping chamber 510. The volume of fluid transferred via the pump chamber 510 may, for example, be tracked by a fluid measurement system of the type described in described in U.S. Publication No. US 2019/0316948 A1, filed Apr. 15, 2019, entitled "Medical Treatment System and Method Using a Plurality of Fluid Lines" which is hereby incorporated by reference in its entirety.

Referring now to the progression of FIGS. 120-123, a number of block diagrams showing reservoir assemblies 52 being filled by an example embodiment of a system 10 with a pumping portion 15 and filling portion 17 are depicted. Referring primarily to FIG. 120, a fluid handling set 476 may be loaded into a pump housing 470. The fluid handling set 476 may include a syringe 564 which may be coupled to the tubing 475 of the fluid handling set 476 intermediate a set of check valves 558A, B. A syringe pump 562 is included in the pumping portion 15. The syringe pump 562 may be may include any of those shown or described in U.S. Patent No. U.S. Pat. No. 10,391,241 B2, filed Feb. 20, 2015, Issued Aug. 27, 2019, and entitled "Syringe Pump Having a Pressure Sensor Assembly" which is hereby incorporated by reference in its entirety.

When readying the pumping portion 15 for use, a barrel 568 of the syringe 564 of the fluid handling set 476 may be placed within a barrel clamp 566 of the syringe pump 562. Additionally, the plunger 572 of the syringe 564 may be coupled to a plunger driver 570 of the syringe pump 562.

The plunger driver 570 may interface with a motor 571 driven leadscrew 573 of the syringe pump 562 which may be rotated to displace the plunger driver 570 and syringe plunger 572 relative to the barrel 568 of the syringe 564. Thus, fluid may be expelled from or drawn into the syringe 564. The check valves 558A, B are arranged such that fluid is transferred from the upstream portion of the fluid handling set 476 when the plunger 572 is displaced to draw fluid into the syringe 564 (see, e.g., FIG. 122). Thus, agent would be transferred from a medicament container 28 in communication with the fluid handling set 476 when the plunger 572 is withdrawn. Additionally, the check valves 558A, B ensure that fluid may only be expelled from the syringe 564 in a downstream direction toward the outlet spike 478B of the fluid handling set 476 (see, e.g., FIG. 123).

As shown, pumping portion 15 may include a spiking assembly 546 which may be operated to establish fluid communication with a filling portion 17 in an automated manner. The spiking assembly 546 may include an imager 548 such as a CCD or CMOS camera assembly. The container 38 of the filling portion 17 may include a fiducial indicator 554. The fiducial indicator 554 may be placed in a predefined position relative to the fluid introduction port 16 of the container 38. The container 38 may be placed in a datum tray 556 which is positioned in a known location relative to the pumping portion 15. With the container 38 positioned in the datum tray 556, the imager 548 may be commanded to capture an image of the container 38. For example, the controller 488 may orchestrate capture of an image upon receipt of an input via the user interface 492 that the container 38 is in position within the datum tray 556. The controller 488 may then perform an analysis of the image to determine the location of the fiducial indicator 554 on the container 38. This information may then be used by the controller 488 to determine the position of the fluid introduction port 16 of the container 38 relative to the pumping portion 15. In some embodiments, a unique identifier may be included on the container 38 near the fiducial indicator 554 (or the fiducial indicator 554 may be a unique identifier). The unique identifier may document various information about the container 38. For example, the unique identifier may include any of a serial number for the container 38, a lot number for the container 38, a "use by" date for the container 38, a target fill volume for the container 38, etc. The unique identifier may be a machine readable indicia such as a bar code, QR code, data matrix, etc.

The outlet spike 478B of the fluid handling set 476 may be disposed in a cradle 552 of a sled 551 included in the spiking assembly 546. The sled 551 may be displaceable by a sled actuation assembly 550. The sled actuation assembly 550 may include at least a linear actuator which may drive the sled 551 in a direction parallel to the axis of the outlet spike 478B. The sled actuation assembly 550 may also include actuators for displacement of sled 551 along other displacement axes. For example, the sled actuation assembly 550 may be displaceable along X, Y, and Z axes. Based on the location of the fluid introduction port 16 determined from the image analysis, the controller 488 may generate commands to the sled actuation assembly 550. The commands may power the sled actuation assembly 550 to displace the sled 551 such that the outlet spike 478B pierces a fluid introduction septum 412 of the fluid introduction port 16 (see, e.g., FIG. 121). The controller 448 may also generate commands to the sled actuation assembly 550 which align the outlet spike 478B with the fluid introduction port 16 prior to advancement of the outlet spike 478B into the fluid introduction septum 412.

Once the fluid handling set 476 is in fluid communication with the filling portion 17, the controller 488 may command the syringe pump 562 to draw agent from a medicament container 28 in a holster 560 on the pump housing 470 to fill the syringe 564 (see, e.g., FIG. 122). The syringe pump 562 may then be commanded by the controller 488 to dispense agent in the syringe 564 into the filling portion 17 to load agent into the reservoir assemblies 52 in the container 38 (see, e.g., FIG. 123). The syringe pump 562 may include one or more sensor 567 which may monitor the position of the plunger driver 570. In the example embodiment the depicted sensor 567 is a motor encoder. The controller 488 may, for example, operate the syringe pump 562 to transfer a target volume of fluid (perhaps specified and read from the unique identifier) based on data from the sensor 567. In some examples, pressure in the fluid handling set 476 may be monitored by a pressure sensor 490. The controller 488 may monitor the data signal from the pressure sensor 490 for a pressure spike to confirm that the reservoir assemblies 52 have been filled with agent. As mentioned elsewhere herein, agent may not readily pass through a vent 310 for the container 38 and a pressure spike may indicate that the syringe pump 562 is attempting to drive agent through the vent 310.

Referring now to FIG. 124, an exemplary embodiment of a cartridge 304 or tray which may be used to store and fill reservoir assemblies 52 is depicted. As shown, the cartridge 304 includes a set of troughs 630. The troughs 630 in the example embodiment span the length of the cartridge 304 and are arranged in two rows. Any number of rows may be included in alternative embodiments. Each of the troughs 630 include sets of niches 632 recessed into the side walls of the troughs 630.

As shown in FIGS. 125-126, each set of niches 632 may receive a reservoir assembly 52. The troughs 630 and niches 632 may be shaped such that each reservoir assembly 52 is supported in a prescribed orientation within the cartridge 304. In the example, the troughs 630 pinch inward at their bottommost span to a width that is approximately the width of the rocker member 92 on a reservoir assembly 52. This may inhibit the reservoir assembly 52 from rotating within the cartridge 304 and help to assist in keeping a septum 94 of the reservoir assembly 52 in a target position within the cartridge 304.

In some examples, and referring now to FIG. 127, a cartridge 304 may hold assembled delivery devices 12 instead of reservoir assemblies 52. A portion of a cartridge 304 in which a number of delivery devices 12 are held is depicted in FIG. 127. The cartridge 304 may include a trough 630 which includes niches 632 in its sidewall. The bottommost part of the trough 630 may include repeating sets of cradle divots 634. Each cradle divot 634 may be shaped to accommodate and support the main body 50 and depressor body 62 of the delivery device 12. As shown, a niche 632 on one side of each cradle divot 634 may accept a portion of at least one petal member 90 of the main body 50. A niche 632 on the opposing side of each petal member 90 may accept at least the petal member 90 on which the pull tab 172 is included. This may assist in ensuring that delivery devices 12 may be installed in the cartridge 304 in a prescribed orientation. In the example, the delivery devices 12 depicted include a reservoir assembly 52 of the variety shown in FIG. 40A-40C. The cradle divots 634 and niches 632 are arranged to ensure that the septum 94 of each delivery device 12 is positioned in an upward facing orientation.

Referring now to FIGS. 128-129, an exemplary filling gantry 640 and fill head 638 are depicted. The filling gantry 640 may include X, Y, and Z axis displacement assemblies 636A-C which may be electromechanical, hydraulic, pneumatic, etc. The fill head 638 may be displaced about a coordinate system by a controller 644 which governs powering of the displacement assemblies 636A-C. A cartridge 304 filled with delivery devices 12 or reservoir assemblies 52 (as shown) may be placed on a platform 642 coupled to the filling gantry 640. The platform 642 may include a set of guides or a datum tray 556 (see, e.g., FIG. 120) which may retain the cartridge 304 in a known location on the platform 642. As the position of the cartridge 304 and the spacing of the reservoir assemblies 52 within the cartridge 304 may be known, the controller 644 may displace the fill head 638 to coordinates associated with each reservoir assembly 52 in order to fill the reservoir assemblies 52.

As best shown in FIG. 129, the fill head 638 may include a set of opposing graspers 646. The graspers 646 may each include a reservoir contact finger 648. The graspers 646 may be closed about a reservoir assembly 52 (e.g. a protruding body 250 of a reservoir assembly 52) to support the reservoir assembly 52 during spiking of the septum 94 and filling. A dispensing sharp 302 may also be included in the fill head 638. The contact fingers 648 may be shaped to help center the septum 94 along the axis of the dispensing sharp 302 as the graspers 646 are driven (e.g. pneumatically) closed. This may correct any minor misalignment of the reservoir assembly 52 within the cartridge 304 prior to piercing of the septum 94. The fill head 638 may include a dispensing sharp actuator 650. With the reservoir assembly 52 grasped, the dispensing sharp actuator assembly 650 may drive the dispensing sharp 302 a target displacement distance along its axis and through a septum 94. A pump 652 in the fill head 638 may be powered by a controller 644 to transfer agent from a medicament container 28 into a reservoir assembly 52 via the dispensing sharp 302.

In some embodiments, an imager in data communication with a controller 644 may be included. The controller 644 may analyze data from the imager and may halt dispensing of fluid into each reservoir assembly 52 when the image data indicates that a threshold volume of fluid has been transferred to the reservoir assembly 52. This may be done by monitoring the fluid level in the reservoir assembly 52 as it increases. Alternatively, where a reservoir assembly 52 is provided in a collapsed state, a beam break sensor may be included and may be in data communication with a controller 644. Fluid transfer to the reservoir assembly 52 may halt when the flexible portion of the reservoir assembly 52 is displaced to a position indicative of the reservoir assembly 52 having been loaded with a desired amount of fluid. The controller 644 may monitor data from the beam break sensor and halt delivery when the beam has been broken. In some embodiments, pressure in the flow path to the dispensing sharp 302 may be monitored by a pressure sensor in data communication with a controller 644. Fluid transfer into the reservoir assembly 52 may be halted by a controller 644 when a pressure spike in data from a pressure sensor is observed by the controller 644. In other embodiments, a flow sensor in data communication with a controller 644 may be included. Data from the flow sensor may be monitored by the controller 644 to determine when a target volume of fluid has been transferred into the reservoir assembly 52. The controller 644 may halt delivery of fluid when the target volume has been delivered. In various examples, multiple of the above fill sensing arrangements may be included in a fill head 638.

In the example shown, the fill head 638 includes a medicament container holster 465. The medicament container holster 465 may provide a receptacle for a medicament container 28 (a vial in the example shown). The fill head 638 may also include a medicament container spike dock 654. The medicament container spike dock 654 may accept an inlet spike 478A of a fluid handling set 476 which may be installed in the fill head 638. The fluid handling set 476 may be placed into fluid communication with the pump 652 such that fluid may be pulled from the medicament container 28 once the medicament container 28 has been spiked by the inlet spike 478A. As shown, the example spike dock 654 includes a support channel 656 shaped to snugly accept the inlet spike 478A. The support channel 656 may prevent the inlet spike 478A from displacing (e.g. include a shelf or rib that supports the spike 478A) as the medicament container 28 is pressed into the holster 465 and into the inlet spike 478A.

In the example embodiment, the fill head 638 pneumatically pressurizes the medicament container 28 with a pressurizing spike 479. The pressurizing spike 479 may receive clean (e.g. appropriately filtered) air from a pressure supply port 481 and may be in fluid communication with the pressure supply port 481 via a fluid conduit (not shown). A supply line (not shown) may extend from the inlet spike 478A to an agent receiving port 483 for the dispensing sharp 302 upstream of an in fluid communication with the dispensing sharp 302. A valve for controlling transfer of fluid out of the dispensing sharp 302 may be included and may be pneumatically driven. In such examples, pneumatic pressure to the valve may be supplied via a line extending from a pneumatic supply port 487 to a pneumatic pressure input port 489 for the valve.

The delivery devices 12 shown and described herein may be modified to include features of other delivery devices 12 shown and described herein. The sharp bearing bodies 26 or delivery sharps 72 of any embodiment described herein may be substituted with any other embodiments shown or described herein. Any of the petal members 90 shown and described herein may be used in any of the delivery devices 12 of the present disclosure. The delivery devices 12 shown and described herein may be modified to utilize any of the reservoir assemblies 52 shown and described herein. Portions of reservoir assemblies 52 described herein may be interchanged with the corresponding components of other reservoir assemblies 52 shown and described herein. The delivery devices 12 described herein may be modified to use the bias members shown or described in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023 which is hereby incorporated herein by reference in its entirety.

Additionally, inventory control, use verification, delivery verification, etc, methods described or shown in U.S. patent application Ser. No. 18/087,058, filed Dec. 22, 2022 and entitled Delivery Device Apparatuses, Systems, and Methods, now U.S. Publication No. US-2023-0264006A1, published Aug. 24, 2023 which is hereby incorporated herein by reference in its entirety may be used with the delivery devices 12 described in the present disclosure.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A method of overmolding a component to a sharp bearing body from which at least one microneedle projects comprising:

depositing each of the at least one microneedle in a respective pocket defined in a first shut-off of a mold, each of the at least one microneedle being self-centered by the geometry of the respective pockets as the microneedles are deposited;

enclosing the sharp bearing body within first and second blocks of a mold;

clamping the sharp bearing body, with a resting clamping force, between the first shut-off and a second shut-off of the mold with a sharp bearing face of the sharp bearing body disposed normal to the force of gravity;

exerting pressure against the mold with clamping platens in a direction normal to the sharp bearing face;

forming the component with an axial dimension which extends in a direction other than normal to the sharp bearing face while overmolding material to a sidewall around the periphery of the sharp bearing body and a portion of the face of the sharp bearing body opposite the sharp bearing face;

venting gas through vents abreast an interface between the sidewall and overmolded material; and retaining the second block of the mold against a base during orchestration of a portion of an ejection sequence in which the first block and component are ejected from the mold.

2. The method of claim 1, wherein the method further comprises embedding cleats of ejector pins for the component in the material injected into the cavity.

3. The method of claim 1, wherein clamping the sharp bearing body comprises attracting the first block of the mold to the second block via magnets.

4. The method of claim 1, wherein retaining the second block against the base comprises attracting the second block to the base with magnets disposed in the second block.

5. The method of claim 1, wherein the method further comprises displacing a knockout subassembly including a number of part side ejector pins with a set of hydraulically driven ejector pins.

6. The method of claim 5, wherein the method further comprises returning the knockout subassembly to a home state with at least one bias member.

7. The method of claim 1, wherein the method further comprises automatically degating the component by ejecting a runner plate of the mold.

8. The method of claim 1, wherein the method further comprises holding the component and sharp bearing body against the first block as the first block is disassociated from the first block along an ejection axis.

9. The method of claim 1, wherein overmolding material to the side wall comprises overmolding material over at least one step in the sidewall.

10. The method of claim 1, wherein overmolding material to the sidewall comprises encasing a tier formed in the sidewall in overmolded material.

11. The method of claim 1, wherein overmolding material to the sidewall comprises encasing at least one constant cross-section portion of the sharp bearing body and at least part of a chamfered section of the sidewall of the sharp bearing body in overmolded material.

12. The method of claim 1, wherein overmolding material to the portion of the face of the sharp bearing body opposite the sharp bearing face comprises blocking flow of the overmolded material to lumen associated with each of the at least one microneedle with the second shut-off.

13. The method of claim 1, wherein the method further comprises inhibiting contact of kerf regions associated with each of the at least microneedle with the first shut-off.

14. The method of claim 1, wherein inhibiting contact of the kerf regions associated with each of the at least one microneedle with the first shut-off comprises self-centering each of the at least one microneedle before the kerf regions are advanced into the respective pockets.

15. The method of claim 1, wherein depositing each of the at least one microneedle in a respective pocket comprises guiding each of the at least one microneedle via tapered sidewalls of the respective pocket.

16. The method of claim 1, wherein depositing each of the at least one microneedle in a respective pocket comprises contacting a sloped face of each of the at least one microneedle with a ramped sidewall section of the respective pocket.

* * * * *